United States Patent
Shukla et al.

(10) Patent No.: US 9,464,063 B2
(45) Date of Patent: Oct. 11, 2016

(54) BENZO [B] [1,4] OXAZIN DERIVATIVES AS CALCIUM SENSING RECEPTOR MODULATORS

(75) Inventors: Manojkumar Ramprasad Shukla, Maharashtra (IN); Sarde Gangaram Ankush, Maharashtra (IN); Pachpute Dilip Vipul, Maharashtra (IN); Majid Bashir Sayyed, Maharashtra (IN); Mahadeo Bhaskar Tryambake, Maharashtra (IN); Chetan Sanjay Pawar, Maharashtra (IN); Ganesh Navinchandra Gote, Maharashtra (IN); Sanjeev Anant Kulkarni, Maharashtra (IN); Venkata P. Palle, Maharashtra (IN); Rajender Kumar Kamboj, Maharashtra (IN)

(73) Assignee: LUPIN ATLANTIS HOLDINGS SA, Schaffhausen (CH)

( * ) Notice: Subject to any disclaimer, the term of this patent is extended or adjusted under 35 U.S.C. 154(b) by 241 days.

(21) Appl. No.: 14/005,944

(22) PCT Filed: Mar. 16, 2012

(86) PCT No.: PCT/IB2012/051268
§ 371 (c)(1),
(2), (4) Date: Sep. 18, 2013

(87) PCT Pub. No.: WO2012/127388
PCT Pub. Date: Sep. 27, 2012

(65) Prior Publication Data
US 2014/0018358 A1    Jan. 16, 2014

(30) Foreign Application Priority Data
Mar. 18, 2011  (IN) .............................. 367/KOL/2011

(51) Int. Cl.
*C07D 265/36* (2006.01)
*C07D 413/04* (2006.01)
*A61K 31/538* (2006.01)

(52) U.S. Cl.
CPC ........... *C07D 265/36* (2013.01); *A61K 31/538* (2013.01); *C07D 413/04* (2013.01)

(58) Field of Classification Search
CPC . C07D 265/36; C07D 413/04; A61K 31/538
See application file for complete search history.

(56) References Cited

U.S. PATENT DOCUMENTS

| | | |
|---|---|---|
| 5,550,125 A | 8/1996 | George et al. |
| 2003/0199497 A1 | 10/2003 | Ruat et al. |
| 2010/0029687 A1 | 2/2010 | Hachiya et al. |
| 2011/0028452 A1 | 2/2011 | Didiuk et al. |

FOREIGN PATENT DOCUMENTS

| | | |
|---|---|---|
| EP | 1 882 684 | 1/2008 |
| WO | WO 01/90069 | 11/2001 |
| WO | WO 02/12181 | 2/2002 |
| WO | WO 2004/069793 | 8/2004 |
| WO | WO 2004/106280 | 12/2004 |
| WO | WO 2006/123725 | 11/2006 |
| WO | WO 2008/059854 | 5/2008 |
| WO | WO 2009/065406 | 5/2009 |
| WO | WO 2010/038895 | 4/2010 |
| WO | WO 2010/042642 | 4/2010 |
| WO | WO 2010/136037 | 12/2010 |
| WO | WO 2010/150837 | 12/2010 |

OTHER PUBLICATIONS

Bourlot et al., "New Substituted 1,4-Benzoxazine Derivatives with Potential Intracellular Calcium Activity", *J. Med. Chem.*, vol. 41, 1998, pp. 3142-3158.

International Search Report and Written Opinion from International Application No. PCT/IB2012/051268 mailed May 31, 2013.

Kessler et al., "$N^1$-Benzoyl-$N^2$-[1-(1-naphthypethyl]-*trans*-1,2-diaminocyclohexanes: Development of 4-Chlorophenylcarboxamide (Carlhex 231) as a New Calcium Sensing Receptor Ligand Demonstrating Potent Calcilytic Activity", *J. Med. Chem.*, vol. 49, 2006, pp. 5119-5128.

Mayer et al., "Attempted Synthesis of Ethyl 3,4-Dihydro-2*H*-1,4-benzoxazine-3-carboxylate and 3-Acetate Derivatives", *J. Heterocyclic Chem.*, vol. 38, 2001, pp. 221-225.

Tsutomu Teitei, "The Synthesis of (3'-Oxo-3',4'-dihydro-2' H-1',4'-benzothiazin-2'-yl)acetic Acid and (3'-Oxo-3',4'-dihydro-2' H-1',4'-benzoxazin-2'-yl)acetic Acid Derivatives", *Aust. J. Chem.*, vol. 39, 1986, pp. 503-510.

*Primary Examiner* — Sarah Pihonak
*Assistant Examiner* — Jason A Deck
(74) *Attorney, Agent, or Firm* — Merchant & Gould P.C.

(57) ABSTRACT

Compounds of Formula (I) along with processes for their preparation that are useful for treating, managing and/or lessening the diseases, disorders, syndromes or conditions associated with the modulation of calcium sensing (CaSR) receptors. Methods of treating, managing and/or lessening the diseases, disorders, syndromes or conditions associated with the modulation of calcium sensing (CaSR) receptors of Formula (I).

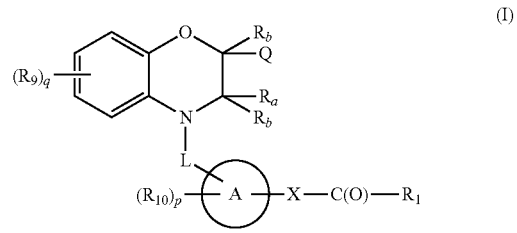

22 Claims, No Drawings

BENZO [B] [1,4] OXAZIN DERIVATIVES AS CALCIUM SENSING RECEPTOR MODULATORS

RELATED APPLICATIONS

This application is a National Stage Application of PCT/IB2012/051268, filed Mar. 16, 2012, which claims the benefit of Indian patent application no. 0367/KOL/2011 filed on Mar. 18, 2011 which applications are hereby incorporated by reference in their entirety. To the extent appropriate, a claim of priority is made to each of the above disclosed applications.

FIELD OF THE INVENTION

The present invention relates to substituted heterocyclic compounds, pharmaceutically acceptable salts thereof and pharmaceutical compositions for the treatment, management, and/or lessening the severity of diseases, disorders, syndromes or conditions associated with the modulation of calcium sensing receptors (CaSR). The invention also relates to methods of treating, managing and/or lessening the severity of diseases disorders, syndromes or conditions associated with the modulation of calcium sensing receptors (CaSR). The invention also relates to processes for the preparation of the compounds of the invention.

BACKGROUND OF THE INVENTION $Ca^{2+}$ is known to be an intracellular second messenger, with the molecular identification of an extracellular calcium sensing receptor (CaSR), it has further opened the possibility that $Ca^{2+}$ might also function as a messenger outside the cells. Information about the local changes in extracellular concentration of $Ca^{2+}$ is conveyed to the interior of many types of cells through this unique receptor.

Calcium-sensing receptor (CaSR) is a G-protein-coupled receptor (GPCR) that signals through the activation of phospholipase C, increasing levels of inositol 1,4,5-triphosphate and cytosolic calcium. The CaSR belongs to the subfamily C of the GPCR superfamily. Structurally, CaSR has an exceptionally large amino-terminal extracellular (ECD) domain (about 600 aminoacids), a feature that is shared by all of the members of the family C GPCRs.

In mammals, the expression of CaSR is quite ubiquitous and its presence in the parathyroid gland plays an important role in the secretion of parathyroid hormone (PTH). The reduction in serum calcium leads to the secretion of PTH. Consequently, PTH secretion leads to conservation of serum $Ca^{2+}$ by increasing kidney retention and intestinal absorption of $Ca^{2+}$. This happens indirectly through the PTH-induced synthesis of the active vitamin D metabolite, 25-dihydroxyvitamin D. In addition, the pulsatile action of PTH has anabolic effects on bone development and its sustained levels can lead to catabolic effects, in which the bones breakdown releasing $Ca^{2+}$ as in the case of osteoporosis. All these systems converge in maintenance of baseline serum $Ca^{2+}$ and it involves a tight regulation between serum PTH and extracellular calcium which is mediated by the remarkable receptor CaSR.

In conditions such as primary and secondary hyperparathyroidism, there is excessive secretion of parathyroid hormone due to hyperplasia of the glands. The most common cause of primary hyperparathyroidism (PHPT) is parathyroid adenoma resulting from clonal mutations (~97%) and associated hypercalcemia. In the case of secondary hyperparathyroidism (SHPT), it is most commonly seen in patients with chronic renal failure. The kidneys fail to convert enough vitamin D to its active form and also does not adequately excrete phosphorous. Excess phosphorous further depletes serum calcium forming calcium phosphate (kidney stones) leading to hypocalcemia.

Small molecules that are positive allosteric modulators called calcimimetics modulate and improve the receptors sensitivity to the already existing milieu of extracellular ionic calcium. This would eventually translate in lowering plasma PTH levels thereby improving conditions of hyperparathyroidism, calcium homeostasis and bone metabolism. US 2011/0028452, WO 2010/150837, WO 2010/136037, WO 2010/042642, WO 2010/038895, WO 2009/065406, WO 2008/059854, WO 2006/123725, WO 2004/106280, WO 2004/069793, WO 2002/012181 and US 2003/0199497 applications disclose the compounds related to calcium sensing receptors (CaSR) for the treatment of various diseases mediated by CaSR. And also J. Med. Chem. (2006), 49, 5119-5128 discloses the compounds related to calcium sensing receptors (CaSR).

SUMMARY OF THE INVENTION

In accordance with one aspect, the invention provide compounds having the structure of Formula (I),

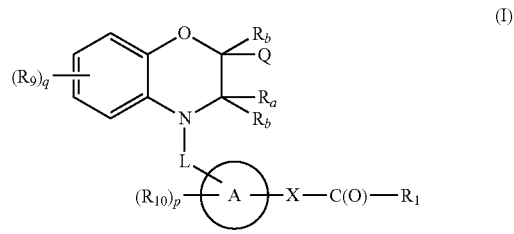

(I)

wherein,

Q is hydrogen or

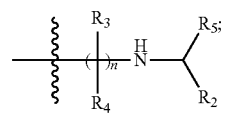

$R_a$ is selected from

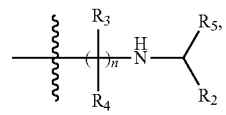

hydrogen, halogen, cyano, substituted or unsubstituted alkyl, substituted or unsubstituted cycloalkyl and substituted or unsubstituted haloalkyl;

$R_b$ is selected from hydrogen, halogen, cyano, substituted or unsubstituted alkyl, substituted or unsubstituted cycloalkyl and substituted or unsubstituted haloalkyl;

or $R_a$ and $R_b$ together attached on the same carbon form C(O) or C(S);

provided that,
when Q is then

R$_a$ is selected from hydrogen, halogen, substituted or unsubstituted alkyl, cyano, substituted or unsubstituted cycloalkyl and substituted or unsubstituted haloalkyl; or R$_a$ and R$_b$ together attached on the same carbon atom form C(O) or C(S);

when Q is hydrogen then R$_a$ is

L is selected from a bond, —(CR$_c$R$_d$)$_m$—, —C(O)—, —C(S)—, —C(O)NR$_7$—, —S(O)$_2$—, —S(O)$_2$—NR$_7$, —C(O)CH$_2$—, —CH$_2$C(O)— and —C(O)O—;

ring A is aryl;

R$_c$ and R$_d$, which may be same or different at each occurrence, are independently selected from hydrogen, halogen, substituted or unsubstituted alkyl and substituted or unsubstituted haloalkyl;

X is selected from a bond, —(CR$_e$R$_f$)$_m$—, —O—, —O(CR$_e$R$_f$)$_m$—, —(CR$_e$R$_f$)$_m$O—, —C(O)(CR$_e$R$_f$)$_m$—, —C(O)NR$_7$—, —C(O)NR$_7$(CR$_e$R$_f$)$_m$—, -cycloalkylene-, and —O-cycloalkylene-;

R$_e$ and R$_f$, which may be same or different at each occurrence, are independently selected from hydrogen, halogen, hydroxy, cyano, nitro, substituted or unsubstituted alkyl, substituted or unsubstituted haloalkyl and substituted or unsubstituted cycloalkyl; or R$_e$ and R$_f$ together with the carbon atom to which they are attached, form a substituted or unsubstituted 3 to 7 membered saturated carbocyclic ring;

R$_1$ is —OR$_6$ or —NR$_7$R$_8$;

R$_2$ is selected from substituted or unsubstituted aryl, substituted or unsubstituted heteroaryl and substituted or unsubstituted heterocyclyl;

R$_3$ and R$_4$, which may be same or different at each occurrence, are independently selected from hydrogen, halogen, substituted or unsubstituted alkyl, substituted or unsubstituted haloalkyl, substituted or unsubstituted alkenyl, substituted or unsubstituted alkynyl, substituted or unsubstituted alkoxy, substituted or unsubstituted haloalkoxy and substituted or unsubstituted cycloalkyl;

R$_5$ is substituted or unsubstituted alkyl or substituted or unsubstituted haloalkyl;

R$_6$, which may be same or different at each occurrence, is independently selected from hydrogen, substituted or unsubstituted alkyl, substituted or unsubstituted haloalkyl, substituted or unsubstituted alkenyl and substituted or unsubstituted alkynyl;

R$_7$ and R$_8$, which may be same or different at each occurrence, are independently selected from hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; or R$_7$ and R$_8$, together with the nitrogen atom to which they are attached, form a substituted or unsubstituted 3 to 12 membered cyclic ring, where the cyclic ring may be heteroaryl or heterocyclyl;

R$_9$, which may be same or different at each occurrence, is independently selected from halogen, nitro, cyano, substituted or unsubstituted alkyl, substituted or unsubstituted haloalkyl, substituted or unsubstituted alkenyl, substituted or unsubstituted alkynyl, substituted or unsubstituted cycloalkyl, aryl, —OR$_6$, —C(O)R$_6$, —C(O)OR$_6$, —(CH$_2$)$_r$—C(O)OR$_6$, —O(CH$_2$)$_r$—C(O)OR$_6$, —NR$_7$R$_8$, —C(O)NR$_7$R$_8$, —NR$_7$C(O)R$_6$, —S(O)$_{0-2}$R$_6$, —S(O)$_2$NR$_7$R$_8$, and —NR$_7$S(O)$_2$R$_6$;

R$_{10}$, which may be same or different at each occurrence, is independently selected from halogen, nitro, cyano, substituted or unsubstituted alkyl, substituted or unsubstituted alkenyl, substituted or unsubstituted alkynyl, substituted or unsubstituted haloalkyl, substituted or unsubstituted hydroxyalkyl, —OR$_6$, —C(O)R$_6$, —NR$_7$R$_8$, —NR$_7$C(O)R$_6$, —S(O)$_{0-2}$R$_6$, —S(O)$_2$NR$_7$R$_8$, and —NR$_7$S(O)$_2$R$_6$;

'm' is an integer ranging from 1 to 3, both inclusive;

'n' is an integer ranging from 1 to 3, both inclusive;

'p' is an integer ranging from 0 to 3, both inclusive;

'q' is an integer ranging from 0 to 4, both inclusive; and

'r' is an integer ranging from 1 to 3, both inclusive;

or pharmaceutically acceptable salt thereof.

According to one embodiment, there are provided compounds of the formula (II):

or pharmaceutically acceptable salt thereof;

wherein,

L is selected from a bond, —(CR$_c$R$_d$)$_m$—, —C(O)—, —C(O)NR$_7$—, —C(O)CH$_2$—, and —CH$_2$C(O)—;

Aryl is substituted or unsubstituted phenyl or substituted or unsubstituted naphthyl;

R$_c$, R$_d$, X, R$_1$, R$_7$, R$_9$, R$_{10}$, 'm', 'p' and 'q' are as defined in Formula (I).

According to another embodiment, there are provided compounds of the Formula (III):

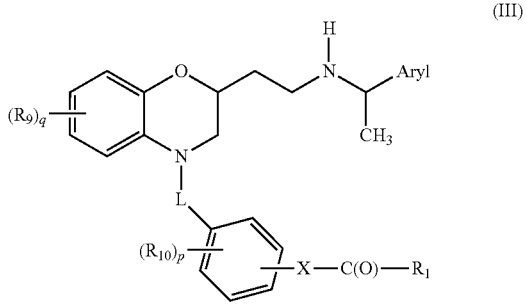

(III)

or pharmaceutically acceptable salt thereof;
wherein,

L is selected from a bond, $-(CR_cR_d)_m-$, $-C(O)-$, $-C(O)NR_7-$, $-C(O)CH_2-$, and $-CH_2C(O)-$;

Aryl is substituted or unsubstituted phenyl or substituted or unsubstituted naphthyl;

$R_c$, $R_d$, X, $R_1$, $R_7$, $R_9$, $R_{10}$, 'm', 'p' and 'q' are as defined in Formula (I).

It should be understood that the compounds of Formula (I) Formula (II) Formula and (III) structurally encompasses all tautomers, stereoisomers, enantiomers and diastereomers, including isotopes wherever applicable and pharmaceutically acceptable salts that may be contemplated from the chemical structure of the genera described herein.

The details of one or more embodiments of the invention set forth in the below are illustrative in nature only and not intended to limit to the scope of the invention. Other features, objects and advantages of the inventions will be apparent from the description and claims.

According to one sub embodiment, there are provided compounds of Formula (I) in which L is selected from a bond, $-(CR_cR_d)_m-$, $-C(O)-$, $-C(S)-$, $-C(O)NR_7-$, $-S(O)_2-$, $-S(O)_2-NR_7$, $-C(O)CH_2-$, $-CH_2C(O)-$ and $-C(O)O-$.

According to one sub embodiment, there are provided compounds of formulae (II) and/or (III) in which X is selected from a bond, $-(CR_eR_f)_m-$, $-O-$, $-O(CR_eR_f)_m-$, $-(CR_eR_f)_mO-$, $-C(O)(CR_eR_f)_m-$, $-C(O)NR_7-$, $-C(O)NR_7(CR_eR_f)_m-$, -cycloalkylene-, and $-O-$cycloalkylene-; wherein $R_e$ and $R_f$ may be same or different and are independently selected from hydrogen, halogen, hydroxy, cyano, nitro, substituted or unsubstituted alkyl, substituted or unsubstituted haloalkyl and substituted or unsubstituted cycloalkyl; or $R_e$ and $R_f$ together with the carbon atom to which they are attached, form a substituted or unsubstituted 3 to 7 membered saturated carbocyclic ring; $R_7$ is hydrogen, alkyl, cycloalkyl or aryl; and 'm' is 1 or 2.

According to another sub embodiment, there are provided compounds of Formulae (II) and/or (III) in which $R_1$ is $-OR_6$ wherein $R_6$ is hydrogen or substituted or unsubstituted alkyl.

According to another sub embodiment, there are provided compounds of Formulae (II) and/or (III) in which $R_1$ is $-NR_7R_8$ wherein $R_7$ and $R_8$ are hydrogen, substituted or unsubstituted alkyl or substituted or unsubstituted cycloalkyl.

According to another sub embodiment, there are provided compounds of Formulae (II) and/or (III) in which $R_9$ is selected from halogen, nitro, cyano, substituted or unsubstituted alkyl, substituted or unsubstituted haloalkyl, substituted or unsubstituted cycloalkyl, substituted or unsubstituted aryl, $-OR_6$, $-C(O)R_6$, $-C(O)OR_6$, $-(CH_2)_r-C(O)OR_6$, $-O(CH_2)_r-C(O)OR_6$, $-NR_7R_8$, $-C(O)NR_7R_8$, $-NR_7C(O)R_6$, $-S(O)_{0-2}R_6$, $-S(O)_2NR_7R_8$, and $-NR_7S(O)_2R_6$; $R_6$ is selected from hydrogen, substituted or unsubstituted alkyl and substituted or unsubstituted haloalkyl; $R_7$ and $R_8$ are independently selected from hydrogen, substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; 'r' is 1 to 3 and 'q' is 0 to 3.

According to another sub embodiment, there are provided compounds of Formulae (II) and/or (III) in which $R_{10}$, which may be same or different at each occurrence, is independently selected from halogen, nitro, cyano, substituted or unsubstituted alkyl, substituted or unsubstituted haloalkyl, substituted or unsubstituted hydroxyalkyl, $-OR_6$, $-C(O)R_6$, $-NR_7R_8$, $-NR_7C(O)R_6$, $-S(O)_{0-2}R_6$, $-S(O)_2NR_7R_8$, and $-NR_7S(O)_2R_6$; $R_6$ is selected from hydrogen, substituted or unsubstituted alkyl, and substituted or unsubstituted haloalkyl; $R_7$ and $R_8$ are independently selected from hydrogen, substituted or unsubstituted alkyl, substituted or unsubstituted cycloalkyl, substituted or unsubstituted cycloalkylalkyl, substituted or unsubstituted aryl, substituted or unsubstituted arylalkyl, substituted or unsubstituted heteroaryl, substituted or unsubstituted heteroarylalkyl, substituted or unsubstituted heterocyclyl, and substituted or unsubstituted heterocyclylalkyl; and 'p' is 0 to 2.

According to another sub embodiment, there are provided compounds of Formulae (II) and/or (III) in which Aryl is substituted or unsubstituted phenyl or substituted or unsubstituted naphthyl, wherein the substituents are one or more, same or different and independently selected from halogen, substituted or unsubstituted alkyl, substituted or unsubstituted alkoxy or substituted or unsubstituted haloalkoxy.

According to another sub embodiment, there are provided compounds of Formula (I) in which Q is

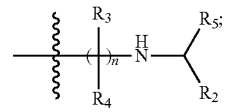

$R_a$ is hydrogen; $R_b$ is hydrogen or substituted or unsubstituted alkyl;

L is selected from a bond, $-(CR_cR_d)_m-$, $-C(O)-$, $-C(O)NR_7-$, $-C(O)CH_2-$, and $-CH_2C(O)-$;

ring A is aryl;

$R_c$ and $R_d$ which may be same or different at each occurrence, are independently selected from hydrogen, halogen, substituted or unsubstituted alkyl and substituted or unsubstituted haloalkyl;

X is selected from a bond, $-(CR_eR_f)_m-$, $-O-$, $-O(CR_eR_f)_m-$, $-(CR_eR_f)_mO-$, $-C(O)(CR_eR_f)_mO-$, $-C(O)NR_7-$, $-C(O)NR_7(CR_eR_f)_mO-$, -cycloalkylene-, and $-O$-cycloalkylene-;

$R_e$ and $R_f$ which may be same or different at each occurrence, are independently selected from hydrogen, halogen, hydroxy, cyano, nitro, substituted or unsubstituted alkyl, substituted or unsubstituted haloalkyl and substituted or unsubstituted cycloalkyl; or $R_e$ and $R_f$ together with the carbon atom to which they are attached, form a substituted or unsubstituted 3 to 7 membered saturated carbocyclic ring;

$R_1$ is —$OR_6$ or —$NR_7R_8$;

$R_2$ is substituted or unsubstituted aryl, wherein the aryl is substituted with one or more substitutents and independently selected from halogen, substituted or unsubstituted alkyl, substituted or unsubstituted haloalkyl, substituted or unsubstituted alkoxy and substituted or unsubstituted haloalkoxy;

$R_3$ and $R_4$ are hydrogen;

$R_5$ is substituted or unsubstituted alkyl or substituted or unsubstituted haloalkyl;

$R_6$ is hydrogen, substituted or unsubstituted alkyl and substituted or unsubstituted haloalkyl;

$R_7$ and $R_8$ are hydrogen or substituted or unsubstituted alkyl;

$R_9$, which may be same or different at each occurrence, is independently selected from halogen, nitro, cyano, substituted or unsubstituted alkyl, substituted or unsubstituted haloalkyl, substituted or unsubstituted cycloalkyl, substituted or unsubstituted aryl, —$OR_6$, —$C(O)R_6$, —$C(O)OR_6$, —$(CH_2)_r$—$C(O)OR_6$, —$O(CH_2)_r$—$C(O)OR_6$, —$NR_7R_8$, —$C(O)NR_7R_8$, —$NR_7C(O)R_6$, —$S(O)_{0-2}R_6$, —$S(O)_2NR_7R_8$, and —$NR_7S(O)_2R_6$;

$R_{10}$, which may be same or different at each occurrence, is independently selected from halogen, nitro, cyano, substituted or unsubstituted alkyl, substituted or unsubstituted haloalkyl, substituted or unsubstituted hydroxyalkyl, —$OR_6$, —$C(O)R_6$, —$NR_7R_8$, —$NR_7C(O)R_6$, —$S(O)_{0-2}R_6$, —$S(O)_2NR_7R_8$, and —$NR_7S(O)_2R_6$;

'm' is 1 to 3; 'n' is 1 to 3; 'p' is 0 to 3; 'q' is 0 to 3; and 'r' is 1 to 2; or pharmaceutically acceptable salt thereof.

According to another sub embodiment, there are provided compounds of Formula (I) in which $R_a$ is

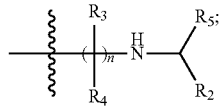

Q is hydrogen; $R_b$ is hydrogen or substituted or unsubstituted alkyl;

L is selected from a bond, —$(CR_cR_d)_m$—, —$C(O)$—, —$C(O)NR_7$—, —$C(O)CH_2$—, and —$CH_2C(O)$—;

ring A is aryl;

$R_c$ and $R_d$ which may be same or different at each occurrence, are independently selected from hydrogen, halogen, substituted or unsubstituted alkyl and substituted or unsubstituted haloalkyl;

X is selected from a bond, —$(CR_eR_f)_m$—, —$O$—, —$O(CR_eR_f)_m$—, —$(CR_eR_f)_mO$—, —$C(O)(CR_eR_f)_m$—, —$C(O)NR_7$—, —$C(O)NR_7(CR_eR_f)_m$—, -cycloalkylene-, and —O-cycloalkylene-;

$R_e$ and $R_f$ which may be same or different at each occurrence, are independently selected from hydrogen, halogen, hydroxy, cyano, nitro, substituted or unsubstituted alkyl, substituted or unsubstituted haloalkyl and substituted or unsubstituted cycloalkyl; or $R_e$ and $R_f$ together with the carbon atom to which they are attached, form a substituted or unsubstituted 3 to 7 membered saturated carbocyclic ring;

$R_1$ is —$OR_6$ or —$NR_7R_8$;

$R_2$ is substituted or unsubstituted aryl, wherein the aryl is substituted with one or more substitutents and independently selected from halogen, substituted or unsubstituted alkyl, substituted or unsubstituted haloalkyl, substituted or unsubstituted alkoxy and substituted or unsubstituted haloalkoxy;

$R_3$ and $R_4$ are hydrogen;

$R_5$ is substituted or unsubstituted alkyl or substituted or unsubstituted haloalkyl;

$R_6$ is hydrogen, substituted or unsubstituted alkyl and substituted or unsubstituted haloalkyl;

$R_7$ and $R_8$ are hydrogen or substituted or unsubstituted alkyl;

$R_9$, which may be same or different at each occurrence, is independently selected from halogen, nitro, cyano, substituted or unsubstituted alkyl, substituted or unsubstituted haloalkyl, substituted or unsubstituted cycloalkyl, substituted or unsubstituted aryl, —$OR_6$, —$C(O)R_6$, —$C(O)OR_6$, —$(CH_2)_r$—$C(O)OR_6$, —$O(CH_2)_r$—$C(O)OR_6$, —$NR_7R_8$, —$C(O)NR_7R_8$, —$NR_7C(O)R_6$, —$S(O)_{0-2}R_6$, —$S(O)_2NR_7R_8$, and —$NR_7S(O)_2R_6$;

$R_{10}$, which may be same or different at each occurrence, is independently selected from halogen, nitro, cyano, substituted or unsubstituted alkyl, substituted or unsubstituted haloalkyl, substituted or unsubstituted hydroxyalkyl, —$OR_6$, —$C(O)R_6$, —$NR_7R_8$, —$NR_7C(O)R_6$, —$S(O)_{0-2}R_6$, —$S(O)_2NR_7R_8$, and —$NR_7S(O)_2R_6$;

'm' is 1 to 3; 'n' is 1 to 3; 'p' is 0 to 3; 'q' is 0 to 3; and 'r' is 1 to 2; or pharmaceutically acceptable salt thereof.

According to another sub embodiment, there are provided compounds of Formula (I) in which the compounds are used as either the free base or a pharmaceutically acceptable salt.

According to another sub embodiment, the provided compounds of Formula (I) structurally encompasses stereoisomers including enantiomers and diastereomers.

Below are the representative compounds, which are illustrative in nature only and are not intended to limit to the scope of the invention.

Methyl4-(2-((((R)-1-(3-methoxyphenyl)ethyl)amino) methyl)-2H-benzo[b][1,4]oxazin-4(3H)-yl)benzoate hydrochloride;

Methyl4-(2-((((R)-1-(naphthalene-1-yl)ethyl)amino) methyl)-2H-benzo[b][1,4]oxazin-4(3H)-yl)benzoate hydrochloride;

Methyl3-(2-((((R)-1-(3-methoxyphenyl)ethyl)amino) methyl)-2H-benzo[b][1,4]oxazin-4(3H)-yl)benzoate hydrochloride;

Methyl 3-(2-((((R)-1-(naphthalen-1-yl)ethyl)amino) methyl)-2H-benzo[b][1,4]oxazin-4(3H)-yl)benzoate hydrochloride;

4-(2-((((R)-1-(3-Methoxyphenyl)ethyl)amino)methyl)-2H-benzo[b][1,4]oxazin-4(3H)-yl)benzoic acid;

4-(2-((((R)-1-(Naphthalen-1-yl)ethyl)amino)methyl)-2H-benzo[b][1,4]oxazin-4(3H)-yl)benzoic acid hydrochloride;

4-(2-((((R)-1-(3-Methoxyphenyl)ethyl)amino)methyl)-2H-benzo[b][1,4]oxazin-4(3H)-yl)-N,N-dimethylbenzamide;

N,N-Dimethyl-4-(2-((((R)-1-(naphthalen-1-yl)ethyl)amino) methyl)-2H-benzo[b][1,4]oxazin-4(3H)-yl)benzamide;

3-(2-((((R)-1-(3-Methoxyphenyl)ethyl)amino)methyl)-2H-benzo[b][1,4]oxazin-4(3H)-yl)benzoic acid hydrochloride;

Methyl-3-(3-(2-((((R)-1-(naphthalen-1-yl)ethyl)amino) methyl)-2H-benzo[b][1,4]oxazin-4(3H)-yl)phenyl)propanoate;

Methyl 3-(4-(2-((((R)-1-(naphthalen-1-yl)ethyl)amino) methyl)-2H-benzo[b][1,4]oxazin-4(3H)-yl)phenyl)propanoate;

Methyl 2-(3-(2-((((R)-1-(naphthalen-1-yl)ethyl)amino) methyl)-2H-benzo[b][1,4]oxazin-4(3H)-yl)phenoxy)acetate;

Methyl 2-fluoro-5-(2-((((R)-1-(naphthalen-1-yl)ethyl) amino)methyl)-2H-benzo[b][1,4]oxazin-4(3H)-yl)benzoate;

Methyl 2-(2-((((R)-1-(naphthalen-1-yl)ethyl)amino) methyl)-2H-benzo[b][1,4]oxazin-4(3H)-yl)benzoate;

Methyl 3-methoxy-5-(2-((((R)-1-(naphthalen-1-yl)ethyl) amino)methyl)-2H-benzo[b][1,4]oxazin-4(3H)-yl)benzoate;

Methyl 4-methoxy-3-(2-((((R)-1-(naphthalen-1-yl)ethyl) amino)methyl)-2H-benzo[b][1,4]oxazin-4(3H)yl)benzoate;

Methyl 2-methoxy-3-(2-((((R)-1-(naphthalen-1-yl)ethyl) amino)methyl)-2H-benzo[b][1,4]oxazin-4(3H)-yl)benzoate;

2-chloro-5-(2-((((R)-1-(naphthalen-1-yl)ethyl)amino) methyl)-2H-benzo[b][1,4]oxazin-4(3H)-yl)benzoate;

Methyl 2-methyl-3-(2-((((R)-1-(naphthalen-1-yl)ethyl) amino)methyl)-2H-benzo[b][1,4]oxazin-4(3H)-yl)benzoate;

Methyl 2-(2-methyl-4-(2-((((R)-1-(naphthalen-1-yl)ethyl) amino)methyl)-2H-benzo[b][1,4]oxazin-4(3H)-yl)phenoxy)acetate;

Methyl 5-(2-((((R)-1-(naphthalen-1-yl)ethyl)amino) methyl)-2H-benzo[b][1,4]oxazin-4(3H)-yl)-2-(trifluoromethyl)benzoate;

Methyl 3-methyl-5-((R)-2-((((R)-1-(naphthalen-1-yl)ethyl) amino)methyl)-2H-benzo[b][1,4]oxazin-4(3H)-yl)benzoate;

Ethyl 2,6-dimethyl-3-(2-((((R)-1-(naphthalen-1-yl)ethyl) amino)methyl)-2H-benzo[b][1,4]oxazin-4(3H)-yl)benzoate;

Methyl 4-(2-((((R)-1-(naphthalen-1-yl)ethyl)amino) methyl)-2H-benzo[b][1,4]oxazin-4(3H)-yl)-2-(trifluoro methyl)benzoate;

Ethyl 2-methyl-5-(2-((((R)-1-(naphthalen-1-yl)ethyl)amino) methyl)-2H-benzo[b][1,4]oxazin-4(3H)-yl)benzoate hydrochloride;

Methyl 2-hydroxy-5-(2-((((R)-1-(naphthalen-1-yl)ethyl) amino)methyl)-2H-benzo[b][1,4]oxazin-4(3H)-yl)benzoate;

Methyl 2-methoxy-5-(2-((((R)-1-(naphthalen-1-yl)ethyl) amino)methyl)-2H-benzo[b][1,4]oxazin-4-(3H)-yl)benzoate;

Methyl 2-isopropyl-5-(2-((((R)-1-(naphthalen-1-yl)ethyl) amino)methyl)-2H-benzo[b][1,4]oxazin-4(3H)-yl)benzoate;

Methyl 2-(3-(2-((((R)-1-(naphthalen-1-yl)ethyl)amino) methyl)-2H-benzo[b][1,4]oxazin-4(3H)-yl)phenyl)acetate;

Methyl 2-methyl-5-(2-((((R)-1-(naphthalen-1-yl)ethyl) amino)methyl)-2H-benzo[b][1,4]oxazin-4(3H)-yl)benzoate;

3-Fluoro-5-(2-((((R)-1-(naphthalen-1-yl)ethyl)amino) methyl)-2H-benzo[b][1,4]oxazin-4(3H)-yl)benzoate;

Methyl 2-(4-(2-((((R)-1-(naphthalen-1-yl)ethyl)amino) methyl)-2H-benzo[b][1,4]oxazin-4(3H)-yl)phenoxy)acetate;

Methyl 2-methyl-4-(2-((((R)-1-(naphthalen-1-yl)ethyl) amino)methyl)-2H-benzo[b][1,4]oxazin-4(3H)-yl)benzoate;

Methyl 2-(2-methyl-5-(2-((((R)-1-(naphthalen-1-yl)ethyl) amino)methyl)-2H-benzo[b][1,4]oxazin-4(3H)-yl)phenoxy)acetate;

Methyl 2-methyl-2-(2-methyl-5-(2-((((R)-1-(naphthalen-1-yl)ethyl)amino)methyl)-2H-benzo[b][1,4]oxazin-4(3H)-yl)phenoxy)propanoate;

Methyl 3-(2-methyl-5-(2-((((R)-1-(naphthalen-1-yl)ethyl) amino)methyl)-2H-benzo[b][1,4]oxazin-4(3H)-yl)phenyl)propanoate;

Methyl 2-fluoro-3-(2-((((R)-1-(naphthalen-1-yl)ethyl) amino)methyl)-2H-benzo[b][1,4]oxazin-4(3H)-yl)benzoate;

Methyl 5-(2-((((R)-1-(3-methoxy phenyl)ethyl)amino) methyl)-2H-benzo[b][1,4]oxazin-4(3H)-yl)-2-methyl benzoate;

Methyl 2-methyl-5-(2-((((R)-1-(naphthalen-1-yl)ethyl) amino)methyl)-3-oxo-2H-benzo[b][1,4]oxazin-4(3H)-yl) benzoate;

3-(2-((((R)-1-(Naphthalen-1-yl)ethyl)amino)methyl)-2H-benzo[b][1,4]oxazin-4(3H)-yl)benzoic acid hydrochloride;

4-(2-((((R)-1-(3-methoxyphenyl)ethyl)amino)methyl)-2H-benzo[b][1,4]oxazin-4(3H)-yl)-N-methyl benzamide;

N-methyl-4-(2-((((R)-1-(naphthalen-1-yl)ethyl)amino) methyl)-2H-benzo[b][1,4]oxazin-4(3H)-yl)benzamide;

3-(2-((((R)-1-(3-methoxyphenyl)ethyl)amino)methyl)-2H-benzo[b][1,4]oxazin-4(3H)-yl)-N-methyl benzamide;

N-methyl-3-(2-((((R)-1-(naphthalen-1-yl)ethyl)amino) methyl)-2H-benzo[b][1,4]oxazin-4(3H)-yl)benzamide;

3-(2-((((R)-1-(3-methoxyphenyl)ethyl)amino)methyl)-2H-benzo[b][1,4]oxazin-4(3H)-yl)-N,N-dimethyl benzamide hydrochloride;

N,N-dimethyl-3-(2-((((R)-1-(naphthalen-1-yl)ethyl)amino) methyl)-2H-benzo[b][1,4]oxazin-4(3H)-yl)benzamide hydrochloride;

3-(4-(2-((((R)-1-(naphthalen-1-yl)ethyl)amino)methyl)-2H-benzo[b][1,4]oxazin-4(3H)-yl)phenyl)propanoic acid;

2-(4-(2-((((R)-1-(naphthalen-1-yl)ethyl)amino)methyl)-2H-benzo[b][1,4]oxazin-4(3H)-yl)phenoxy)aceticacid hydrochloride;

2-(3-(2-((((R)-1-(naphthalen-1-yl)ethyl)amino)methyl)-2H-benzo[b][1,4]oxazin-4(3H)-yl)phenoxy)acetic acid hydrochloride;

2-Fluoro-5-(2-((((R)-1-(naphthalen-1-yl)ethyl)amino) methyl)-2H-benzo[b][1,4]oxazin-4(3H)-yl)benzoic acid hydrochloride;

5-(2-((((R)-1-(3-methoxy phenyl)ethyl)amino)methyl)2H-benzo[b][1,4]oxazin-4(3H)-yl)-2-methyl benzoic acid hydrochloride;

2-(2-((((R)-1-(Naphthalen-1-yl)ethyl)amino)methyl)-2H-benzo[b][1,4]oxazin-4(3H)-yl)benzoic acid hydrochloride;

3-Methoxy-5-(2-((((R)-1-(naphthalen-1-yl)ethyl)amino) methyl)-2H-benzo[b][1,4]oxazin-4(3H)-yl)benzoic acid hydrochloride;

4-Methoxy-3-(2-((((R)-1-(naphthalen-1-yl)ethyl)amino) methyl)-2H-benzo[b][1,4]oxazin-4(3H)-yl)benzoic acid hydrochloride;

Methyl 4-methoxy-3-(2-((((R)-1-(naphthalen-1-yl)ethyl) amino)methyl)-2H-benzo[b][1,4]oxazin-4(3H)-yl)benzoate hydrochloride;

2-Methoxy-3-(2-((((R)-1-(naphthalen-1-yl)ethyl)amino) methyl)-2H-benzo[b][1,4]oxazin-4(3H)-yl)benzoic acid hydrochloride;

2-Methyl-3-(2-((((R)-1-(naphthalen-1-yl)ethyl)amino) methyl)-2H-benzo[b][1,4]oxazin-4(3H)-yl)benzoic acid hydrochloride;

2-(2-Methyl-4-(2-((((R)-1-(naphthalen-1-yl)ethyl)amino) methyl)-2H-benzo[b][1,4]oxazin-4(3H)-yl)phenoxy)acetic acid hydrochloride;

5-(2-((((R)-1-(Naphthalen-1-yl)ethyl)amino)methyl)-2H-benzo[b][1,4]oxazin-4(3H)-yl)-2-(trifluoro methyl)benzoic acid hydrochloride;

3-Methyl-5-(2-((((R)-1-(naphthalen-1-yl)ethyl)amino) methyl)-2H-benzo[b][1,4]oxazin-4(3H)-yl)benzoic acid hydrochloride;

2,6-Dimethyl-3-(2-((((R)-1-(naphthalen-1-yl)ethyl)amino) methyl)-2H-benzo[b][1,4]oxazin-4(3H)-yl)benzoic acid hydrochloride;
4-(2-((((R)-1-(Naphthalen-1-yl)ethyl)amino)methyl)-2H-benzo[b][1,4]oxazin-4(3H)-yl)-2-(trifluoro methyl)benzoic acid hydrochloride;
2-Isopropyl-5-(2-((((R)-1-(naphthalen-1-yl)ethyl)amino) methyl)-2H-benzo[b][1,4]oxazin-4(3H)-yl)benzoic acid hydrochloride;
2-Hydroxy-5-(2-((((R)-1-(naphthalen-1-yl)ethyl)amino) methyl)-2H-benzo[b][1,4]oxazin-4(3H)-yl)benzoic acid hydrochloride;
2-Methoxy-5-(2-((((R)-1-(naphthalen-1-yl)ethyl)amino) methyl)-2H-benzo[b][1,4]oxazin-4(3H)-yl)benzoic acid hydrochloride;
3-(3-(2-((((R)-1-(Naphthalen-1-yl)ethyl)amino)methyl)-2H-benzo[b][1,4]oxazin-4(3H)-yl)phenyl)propanoic acid hydrochloride;
2-(3-(2-((((R)-1-(Naphthalen-1-yl)ethyl)amino)methyl)-2H-benzo[b][1,4]oxazin-4(3H)-yl)phenyl)acetic acid hydrochloride;
2,6-Dimethyl-3-(2-((((R)-1-(naphthalen-1-yl)ethyl)amino) methyl)-2H-benzo[b][1,4]oxazin-4(3H)-yl)benzoic acid hydrochloride;
2-Methyl-5-(2-((((R)-1-(naphthalen-1-yl)ethyl)amino) methyl)-2H-benzo[b][1,4]oxazin-4(3H)-yl)benzoic acid hydrochloride;
3-Fluoro-5-(2-((((R)-1-(naphthalen-1-yl)ethyl)amino) methyl)-2H-benzo[b][1,4]oxazin-4(3H)-yl)benzoic acid hydrochloride;
2-Methyl-4-(2-((((R)-1-(naphthalen-1-yl)ethyl)amino) methyl)-2H-benzo[b][1,4]oxazin-4(3H)-yl)benzoic acid hydrochloride;
2-fluoro-3-(2-((((R)-1-(naphthalen-1yl)ethyl)amino) methyl)-2H-benzo[b][1,4]oxazin-4(3H)-yl)benzoic acid hydrochloride;
2-chloro-5-(2-((((R)-1-(naphthalen-1-yl)ethyl)amino) methyl)-2H-benzo[b][1,4]oxazin-4(3H)-yl)benzoic acid hydrochloride;
2-(2-Methyl-5-(2-((((R)-1-(naphthalen-1-yl)ethyl)amino) methyl)-2H-benzo[b][1,4]oxazin-4(3H)-yl)phenoxy)acetic acid hydrochloride;
2-Methyl-2-(2-methyl-5-(2-((((R)-1-(naphthalen-1-yl)ethyl) amino)methyl)-2H-benzo[b][1,4]oxazin-4(3H)-yl)phenoxy)propanoic acid hydrochloride;
3-(2-Methyl-5-(2-((((R)-1-(naphthalen-1-yl)ethyl)amino) methyl)-2H-benzo[b][1,4]oxazin-4(3H)-yl)phenyl)propanoic acid hydrochloride;
2-(2-Methyl-5-(2-((((R)-1-(naphthalen-1-yl)ethyl)amino) methyl)-2H-benzo[b][1,4]oxazin-4(3H)-yl)benzamido) acetic acid hydrochloride;
Methyl 2-methyl-5-(2-(2-(((S)-1-(naphthalen-1-yl)ethyl) amino)ethyl)-2H-benzo[b][1,4]oxazin-4(3H)-yl)benzoate;
Methyl 3-((2-((((R)-1-(naphthalen-1-yl)ethyl)amino) methyl)-2H-benzo[b][1,4]oxazin-4(3H)-yl)methyl)benzoate;
3-((2-((((R)-1-(Naphthalen-1-yl)ethyl)amino)methyl)-2H-benzo[b][1,4]oxazin-4(3H)-yl)methyl)benzoic acid hydrochloride;
Methyl5-(7-fluoro-2-((((R)-1-(naphthalen-1-yl)ethyl) amino)methyl)-2H-benzo[b][1,4]oxazin-4(3H)-yl)-2-methylbenzoate;
5-(7-Fluoro-2-((((R)-1-(naphthalen-1-yl)ethyl)amino) methyl)-2H-benzo[b][1,4]oxazin-4(3H)-yl)-2-methyl benzoic acid hydrochloride;

Methyl 2-methyl-5-(2-methyl-2-((((R)-1-(naphthalen-1-yl) ethyl)amino)methyl)-2H-benzo[b][1,4]oxazin-4(3H)-yl) benzoate;
2-Methyl-5-(2-methyl-2-((((R)-1-(naphthalen-1-yl)ethyl) amino)methyl)-2H-benzo[b][1,4]oxazin-4(3H)-yl)benzoic acid hydrochloride;
2-Methyl-5-(2-((((R)-1-(naphthalen-1-yl)ethyl)amino) methyl)-3-oxo-2H-benzo[b][1,4]oxazin-4(3H)-yl)benzoic acid hydrochloride;
Methyl 2-methyl-5-(2-(2-(((R)-1-(naphthalen-1-yl)ethyl) amino)ethyl)-2H-benzo[b][1,4]oxazin-4(3H)-yl)benzoate;
Methyl-3-(2-(2-(((R)-1-(naphthalen-1-yl)ethyl)amino) ethyl)-2H-benzo[b][1,4]oxazin-4(3H)-yl)benzoate;
Methyl2-methyl-4-(2-(2-(((R)-1-(naphthalen-1-yl)ethyl) amino)ethyl)-2H-benzo[b][1,4]oxazin-4(3H)-yl)benzoate;
Methyl 5-(2-(2-(((R)-1-(naphthalen-1-yl)ethyl)amino) ethyl)-2H-benzo[b][1,4]oxazin-4(3H)yl)-2-(trifluoro methyl)benzoate;
Methyl2-(2-methyl-5-(2-(2-(((R)-1-(naphthalen-1-yl)ethyl) amino)ethyl)-2H-benzo[b][1,4]oxazin-4(3H)-yl)phenoxy)acetate;
Methyl 2-isopropyl-5-(2-(2-(((R)-1-(naphthalen-1-yl)ethyl) amino)ethyl)-2H-benzo[b][1,4]oxazin-4(3H)-yl)benzoate;
Methyl 2-(3-(2-(2-(((R)-1 (naphthalen-1-yl)ethyl)amino) ethyl)-2H-benzo[b][1,4]oxazin-4(3H)-yl)phenoxy) acetate;
Methyl 3-(4-(2-(2-(((R)-1-(naphthalen-1-yl)ethyl)amino) ethyl)-2H-benzo[b][1,4]oxazin-4(3H)-yl)phenyl)propanoate;
Methyl2-methyl-3-(2-(2-(((R)-1-(naphthalen-1-yl)ethyl) amino)ethyl)-2H-benzo[b][1,4]oxazin-4(3H)-yl)benzoate;
Methyl 2-methoxy-5-(2-(2-(((R)-1-(naphthalen-1-yl)ethyl) amino)ethyl)-2H-benzo[b][1,4]oxazin-4(3H)-yl)benzoate;
Methyl 2-hydroxy-5-(2-(2-(((R)-1-(naphthalen-1-yl)ethyl) amino)ethyl)-2H-benzo[b][1,4]oxazin-4(3H)-yl)benzoate;
Methyl 2-(4-(2-(2-(((R)-1-(naphthalen-1-yl)ethyl)amino) ethyl)-2H-benzo[b][1,4]oxazin-4(3H)-yl)phenyl)acetate;
Methyl 2-(2-methyl-4-(2-(2-(((R)-1-(naphthalen-1-yl)ethyl) amino)ethyl)-2H-benzo[b][1,4]oxazin-4(3H)-yl)phenoxy)acetate;
Methyl 4-(2-(2-(((R)-1-(naphthalen-1-yl)ethyl)amino) ethyl)-2H-benzo[b][1,4]oxazin-4(3H)-yl)benzoate;
Methyl 2-(4-(2-(2-(((R)-1-(naphthalen-1-yl)ethyl)amino) ethyl)-2H-benzo[b][1,4]oxazin-4(3H)-yl)phenoxy)acetate;
Methyl 2,6-dimethyl-3-(2-(2-(((R)-1-(naphthalen-1-yl) ethyl)amino)ethyl)-2H-benzo[b][1,4]oxazin-4(3H)-yl) benzoate;
Methyl 3-(3-(2-(2-(((R)-1-(naphthalen-1-yl)ethyl)amino) ethyl)-2H-benzo[b][1,4]oxazin-4(3H)-yl)phenyl)propanoate;
Methyl 3-methyl-5-(2-(2-(((R)-1-(naphthalen-1-yl)ethyl) amino)ethyl)-2H-benzo[b][1,4]oxazin-4(3H)-yl)benzoate;
Methyl 2-fluoro-5-(2-(2-(((R)-1-(naphthalen-1-yl)ethyl) amino)ethyl)-2H-benzo[b][1,4]oxazin-4(3H)-yl)benzoate;
Methyl 4-methyl-3-(2-(2-(((R)-1-(naphthalen-1-yl)ethyl) amino)ethyl)-2H-benzo[b][1,4]oxazin-4(3H)-yl)benzoate;

Methyl 2-(2-fluoro-3-(2-(2-(((R)-1-(naphthalen-1-yl)ethyl)amino)ethyl)-2H-benzo[b][1,4]oxazin-4(3H)-yl)phenoxy)acetate;
Ethyl 2-(2-fluoro-5-(2-(2-(((R)-1-(naphthalen-1-yl)ethyl)amino)ethyl)-2H-benzo[b][1,4]oxazin-4(3H)-yl)phenoxy)acetate;
Methyl 2-fluoro-3-(2-(2-(((R)-1-(naphthalen-1-yl)ethyl)amino)ethyl)-2H-benzo[b][1,4]oxazin-4(3H)-yl)benzoate;
Methyl 2-(4-fluoro-3-(2-(2-(((R)-1-(naphthalen-1-yl)ethyl)amino)ethyl)-2H-benzo[b][1,4]oxazin-4(3H)-yl)phenoxy)acetate;
Methyl 3-fluoro-5-(2-(2-(((R)-1-(naphthalen-1-yl)ethyl)amino)ethyl)-2H-benzo[b][1,4]oxazin-4(3H)-yl)benzoate;
Ethyl 2-(3-fluoro-5-(2-(2-(((R)-1-(naphthalen-1-yl)ethyl)amino)ethyl)-2H-benzo[b][1,4]oxazin-4(3H)-yl)phenoxy)acetate;
Methyl 2-methyl-5-(2-methyl-2-(2-(((R)-1-(naphthalen-1-yl)ethyl)amino)ethyl)-2H-benzo[b][1,4]oxazin-4(3H)-yl)benzoic acid hydrochloride;
Methyl 5-(7-fluoro-2-(2-(((R)-1-(naphthalen-1-yl)ethyl)amino)ethyl)-2H-benzo[b][1,4]oxazin-4(3H)-yl)-2-methylbenzoate;
Methyl 5-(8-fluoro-2-(2-(((R)-1-(naphthalen-1-yl)ethyl)amino)ethyl)-2H-benzo[b][1,4]oxazin-4(3H)-yl)-2-methyl benzoate;
Methyl3-(8-fluoro-2-(2-(((R)-1-(naphthalen-1-yl)ethyl)amino)ethyl)-2H-benzo[b][1,4]oxazin-4(3H)-yl)benzoate;
Methyl 2-(4-(8-fluoro-2-(2-(((R)-1-(naphthalen-1-yl)ethyl)amino)ethyl)-2H-benzo[b][1,4]oxazin-4(3H)-yl)phenoxy)acetate;
Methyl 2-(3-(8-fluoro-2-(2-(((R)-1-(naphthalen-1-yl)ethyl)amino)ethyl)-2H-benzo[b][1,4]oxazin-4(3H)-yl)phenoxy)acetate;
Methyl 2-(4-(7-fluoro-2-(2-(((R)-1-(naphthalen-1-yl)ethyl)amino)ethyl)-2H-benzo[b][1,4]oxazin-4(3H)-yl)phenoxy)acetate;
Methyl 2-(3-(7-fluoro-2-(2-(((R)-1-(naphthalen-1-yl)ethyl)amino)ethyl)-2H-benzo[b][1,4]oxazin-4(3H)-yl)phenoxy)acetate;
Methyl 2-fluoro-5-(7-fluoro-2-(2-(((R)-1-(naphthalen-1-yl)ethyl)amino)ethyl)-2H-benzo[b][1,4]oxazin-4(3H)-yl)benzoate;
Methyl 5-(7-fluoro-2-(2-(((R)-1-(naphthalen-1-yl)ethyl)amino)ethyl)-2H-benzo[b][1,4]oxazin-4(3H)-yl)-2-methyl benzoate;
Methyl 5-(6-fluoro-2-(2-(((R)-1-(naphthalen-1-yl)ethyl)amino)ethyl)-2H-benzo[b][1,4]oxazin-4(3H)-yl)-2-methyl benzoate;
Methyl 3-(6-fluoro-2-(2-(((R)-1-(naphthalen-1-yl)ethyl)amino)ethyl)-2H-benzo[b][1,4]oxazin-4(3H)-yl)benzoate;
Methyl 2-(4-(6-fluoro-2-(2-(((R)-1-(naphthalen-1-yl)ethyl)amino)ethyl)-2H-benzo[b][1,4]oxazin-4(3H)-yl)phenoxy)acetate;
Methyl 2-(4-(6-fluoro-2-(2-(((R)-1-(naphthalen-1-yl)ethyl)amino)ethyl)-2H-benzo[b][1,4]oxazin-4(3H)-yl)phenoxy)acetate;
Methyl 2-(3-(6-fluoro-2-(2-(((R)-1-(naphthalen-1-yl)ethyl)amino)ethyl)-2H-benzo[b][1,4]oxazin-4(3H)-yl)phenoxy)acetate;
Methyl 2-fluoro-5-(6-fluoro-2-(2-(((R)-1-(naphthalen-1-yl)ethyl)amino)ethyl)-2H-benzo[b][1,4]oxazin-4(3H)-yl)benzoate;
Methyl 2-fluoro-5-(5-fluoro-2-(2-(((R)-1-(naphthalen-1-yl)ethyl)amino)ethyl)-2H-benzo[b][1,4]oxazin-4(3H)-yl)benzoate;
Methyl 2-(3-(5-fluoro-2-(2-(((R)-1-(naphthalen-1-yl)ethyl)amino)ethyl)-2H-benzo[b][1,4]oxazin-4(3H)-yl)phenoxy)acetate;
Methyl 2-(4-(5-fluoro-2-(2-(((R)-1-(naphthalen-1-yl)ethyl)amino)ethyl)-2H-benzo[b][1,4]oxazin-4(3H)-yl)phenoxy)acetate;
2-Methyl-5-(2-(2-(((R)-1-(naphthalen-1-yl)ethyl)amino)ethyl)-2H-benzo[b][1,4]oxazin-4(3H)-yl)benzoic acid hydrochloride;
2-Methyl-4-(2-(2-(((R)-1-(naphthalen-1-yl)ethyl)amino)ethyl)-2H-benzo[b][1,4]oxazin-4(3H)-yl)benzoic acid hydrochloride;
5-(2-(2-(((R)-1-(Naphthalen-1-yl)ethyl)amino)ethyl)-2H-benzo[b][1,4]oxazin-4(3H)-yl)-2-(trifluoro methyl)benzoic acid hydrochloride;
2-(2-Methyl-5-(2-(2-(((R)-1-(naphthalen1yl)ethyl)amino)ethyl)2Hbenzo[b][1,4]oxazin-4(3H)-yl)phenoxy)acetic acid hydrochloride;
2-Isopropyl-5-(2-(2-(((R)-1-(naphthalen-1-yl)ethyl)amino)ethyl)-2H-benzo[b][1,4]oxazin-4(3H)-yl)benzoic acid hydrochloride;
2-(3-(2-(2-(((R)-1-(Naphthalen-1-yl)ethyl)amino)ethyl)-2H-benzo[b][1,4]oxazin-4(3H)-yl)phenoxy)aceticacid hydrochloride;
3-(4-(2-(2-(((R)-1-(Naphthalen-1-yl)ethyl)amino)ethyl)-2H-benzo[b][1,4]oxazin-4(3H)-yl)phenyl)propanoic acid hydrochloride;
2-Methyl-3-(2-(2-(((R)-1-(naphthalen-1-yl)ethyl)amino)ethyl)-2H-benzo[b][1,4]oxazin-4(3H)-yl)benzoic acid hydrochloride;
2-Methoxy-5-(2-(2-(((R)-1-(naphthalen-1-yl)ethyl)amino)ethyl)-2H-benzo[b][1,4]oxazin-4(3H)-yl)benzoic acid hydrochloride;
2-Hydroxy-5-(2-(2-(((R)-1-(naphthalen-1-yl)ethyl)amino)ethyl)-2H-benzo[b][1,4]oxazin-4(3H)-yl)benzoic acid hydrochloride;
2-(4-(2-(2-(((R)-1-(Naphthalen-1-yl)ethyl)amino)ethyl)-2H-benzo[b][1,4]oxazin-4(3H)-yl)phenyl)acetic acid hydrochloride;
2-(2-Methyl-4-(2-(2-(((R)-1-(naphthalen-1-yl)ethyl)amino)ethyl)-2H-benzo[b][1,4]oxazin-4(3H)-yl)phenoxy)aceticacid hydrochloride;
4-(2-(2-(((R)-1-(Naphthalen-1-yl)ethyl)amino)ethyl)-2H-benzo[b][1,4]oxazin-4(3H)-yl)benzoicacid hydrochloride;
3-(2-(2-(((R)-1-(Naphthalen-1-yl)ethyl)amino)ethyl)-2H-benzo[b][1,4]oxazin-4(3H)-yl)benzoic acid hydrochloride;
2-(4-(2-(2-(((R)-1-(Naphthalen-1-yl)ethyl)amino)ethyl)-2H-benzo[b][1,4]oxazin-4(3H)-yl)phenoxy)aceticacid hydrochloride;
2,6-Dimethyl-3-(2-(2-(((R)-1-(naphthalen-1-yl)ethyl)amino)ethyl)-2H-benzo[b][1,4]oxazin-4(3H)-yl)benzoic acid hydrochloride;
3-(3-(2-(2-(((R)-1-(Naphthalen-1-yl)ethyl)amino)ethyl)-2H-benzo[b][1,4]oxazin-4(3H)-yl)phenyl)propanoicacid hydrochloride;
2-Methyl-5-(2-methyl-2-(2-(((R)-1-(naphthalen-1-yl)ethyl)amino)ethyl)-2H-benzo[b][1,4]oxazin-4(3H)-yl)benzoicacid hydrochloride;
3-Methyl-5-(2-(2-(((R)-1-(naphthalen-1-yl)ethyl)amino)ethyl)-2H-benzo[b][1,4]oxazin-4(3H)-yl)benzoicacid hydrochloride;

2-Fluoro-5-(2-(2-(((R)-1-(naphthalen-1-yl)ethyl)amino)ethyl)-2H-benzo[b][1,4]oxazin-4(3H)-yl)benzoic acid hydrochloride;
4-Methyl-3-(2-(2-(((R)-1-(naphthalen-1-yl)ethyl)amino)ethyl)-2H-benzo[b][1,4]oxazin-4(3H)-yl)benzoic acid hydrochloride;
2-(2-Fluoro-3-(2-(2-(((R)-1-(naphthalen-1-yl)ethyl)amino)ethyl)-2H-benzo[b][1,4]oxazin-4(3H)-yl)phenoxy)acetic acid hydrochloride;
2-(2-Fluoro-5-(2-(2-(((R)-1-(naphthalen-1-yl)ethyl)amino)ethyl)-2H-benzo[b][1,4]oxazin-4(3H)-yl)phenoxy)acetic acid hydrochloride;
2-Fluoro-3-(2-(2-(((R)-1-(naphthalen-1-yl)ethyl)amino)ethyl)-2H-benzo[b][1,4]oxazin-4(3H)-yl)benzoic acid hydrochloride;
2-(4-Fluoro-3-(2-(2-(((R)-1-(naphthalen-1-yl)ethyl)amino)ethyl)-2H-benzo[b][1,4]oxazin-4(3H)-yl)phenoxy)acetic acid hydrochloride;
3-Fluoro-5-(2-(2-(((R)-1-(naphthalen-1-yl)ethyl)amino)ethyl)-2H-benzo[b][1,4]oxazin-4(3H)-yl)benzoic acid hydrochloride;
5-(8-Fluoro-2-(2-(((R)-1-(naphthalen-1-yl)ethyl)amino)ethyl)-2H-benzo[b][1,4]oxazin-4(3H)-yl)-2-methylbenzoic acid hydrochloride;
3-(8-Fluoro-2-(2-(((R)-1-(naphthalen-1-yl)ethyl)amino)ethyl)-2H-benzo[b][1,4]oxazin-4(3H)-yl)benzoic acid hydrochloride;
2-(4-(7-Fluoro-2-(2-(((R)-1-(naphthalen-1-yl)ethyl)amino)ethyl)-2H-benzo[b][1,4]oxazin-4(3H)-yl)phenoxy)aceticacid hydrochloride;
2-(3-(7-Fluoro-2-(2-(((R)-1-(naphthalen-1-yl)ethyl)amino)ethyl)-2H-benzo[b][1,4]oxazin-4(3H)-yl)phenoxy)aceticacid hydrochloride;
5-(7-Fluoro-2-(2-(((R)-1-(naphthalen-1-yl)ethyl)amino)ethyl)-2H-benzo[b][1,4]oxazin-4(3H)-yl)-2-methylbenzoic acid hydrochloride;
2-(4-(8-Fluoro-2-(2-(((R)-1-(naphthalen-1-yl)ethyl)amino)ethyl)-2H-benzo[b][1,4]oxazin-4(3H)-yl)phenoxy)aceticacid hydrochloride;
2-(3-(8-Fluoro-2-(2-(((R)-1-(naphthalen-1-yl)ethyl)amino)ethyl)-2H-benzo[b][1,4]oxazin-4(3H)-yl)phenoxy)aceticacid hydrochloride;
5-(6-Fluoro-2-(2-(((R)-1-(naphthalen-1-yl)ethyl)amino)ethyl)-2H-benzo[b][1,4]oxazin-4(3H)-yl)-2-methylbenzoicacid hydrochloride;
3-(6-Fluoro-2-(2-(((R)-1-(naphthalen-1-yl)ethyl)amino)ethyl)-2H-benzo[b][1,4]oxazin-4(3H)-yl)benzoic acid;
2-(4-(6-Fluoro-2-(2-(((R)-1-(naphthalen-1-yl)ethyl)amino)ethyl)-2H-benzo[b][1,4]oxazin-4(3H)yl)phenoxy)acetic acid;
2-(3-(6-Fluoro-2-(2-(((R)-1-(naphthalen-1-yl)ethyl)amino)ethyl)-2H-benzo[b][1,4]oxazin-4(3H)-yl)phenoxy)aceticacid hydrochloride;
2-Fluoro-5-(5-fluoro-2-(2-(((R)-1-(naphthalen-1-yl)amino)ethyl)-2H-benzo[b][1,4]oxazin-4(3H)-yl)benzoicacid hydrochloride;
2-(3-(5-Fluoro-2-(2-(((R)-1-(Naphthalen-1-yl)ethyl)amino)ethyl)-2H-benzo[b][1,4]oxazin-4(3H)-yl)phenoxy)aceticacid hydrochloride;
2-(4-(5-Fluoro-2-(2-(((R)-1-(naphthalen-1-yl)ethyl)amino)ethyl)-2H-benzo[b][1,4]oxazin-4(3H)-yl)phenoxy)aceticacid hydrochloride;
Methyl 2-methyl-5-((2-(2-(((R)-1-(naphthalen-1-yl)ethyl)amino)ethyl)-2H-benzo[b][1,4]oxazin-4(3H)-yl)methyl)benzoate;
Methyl2-methyl-3-((2-(2-(((R)-1-(naphthalen-1-yl)ethyl)amino)ethyl)-2H-benzo[b][1,4]oxazin-4(3H)-yl)methyl)benzoate;
Methyl 3-((2-(2-(((R)-1-(naphthalen-1-yl)ethyl)amino)ethyl)-2H-benzo[b][1,4]oxazin-4(3H)-yl)methyl)benzoate;
Methyl 4-((2-(2-(((R)-1-(naphthalen-1-yl)ethyl)amino)ethyl)-2H-benzo[b][1,4]oxazin-4(3H)-yl)methyl)benzoate;
2-Methyl-5-((2-(2-(((R)-1-(naphthalen-1-yl)ethyl)amino)ethyl)-2H-benzo[b][1,4]oxazin-4(3H)-yl)methyl)benzoic acid hydrochloride;
2-Methyl-3-((2-(2-(((R)-1-(naphthalen-1-yl)ethyl)amino)ethyl)-2H-benzo[b][1,4]oxazin-4(3H)-yl)methyl)benzoic acid hydrochloride;
3-((2-(2-(((R)-1-(Naphthalen-1-yl)ethyl)amino)ethyl)-2H-benzo[b][1,4]oxazin-4(3H)-yl)methyl)benzoic acid hydrochloride;
4-((2-(2-(((R)-1-(Naphthalen-1-yl)ethyl)amino)ethyl)-2H-benzo[b][1,4]oxazin-4(3H)-yl)methyl)benzoic acid hydrochloride;
2-Methyl-5-(2-(2-(((S)-1-(naphthalen-1-yl)ethyl)amino)ethyl)-2H-benzo[b][1,4]oxazin-4(3H)-yl)benzoicacid hydrochloride;
2-Fluoro-5-(6-fluoro-2-(2-(((R)-1-(naphthalen-1-yl)amino)ethyl)-2H-benzo[b][1,4]oxazin-4(3H)-yl)benzoic acid hydrochloride;
2-Fluoro-5-(7-fluoro-2-(2-(((R)-1-(naphthalen-1-yl)amino)ethyl)-2H-benzo[b][1,4]oxazin-4(3H)-yl)benzoic acid hydrochloride;
6-Fluoro-2-methyl-3-(2-(2-(((R)-1-(naphthalen-1-yl)amino)ethyl)-2H-benzo[b][1,4]oxazin-4(3H)-yl)benzoic acid hydrochloride;
2-Fluoro-6-methyl-3-(2-(2-(((R)-1-(naphthalen-1-yl)amino)ethyl)-2H-benzo[b][1,4]oxazin-4(3H)-yl)benzoic acid hydrochloride;
2,6-Difluoro-3-(2-(2-(((R)-1-(naphthalen-1-yl)ethyl)amino)ethyl)-2H-benzo[b][1,4]oxazin-4(3H)-yl)benzoic acid hydrochloride;
3-Fluoro-5-(2-(2-(((R)-1-(naphthalen-1-yl)ethyl)amino)ethyl)-2H-benzo[b][1,4]oxazin-4(3H)-yl)benzoic acid hydrochloride;
2,3-Difluoro-5-(2-(2-(((R)-1-(naphthalen-1-yl)ethyl)amino)ethyl)-2H-benzo[b][1,4]oxazin-4(3H)-yl)benzoic acid hydrochloride;
2-Methyl-2-(4-(2-(2-(((R)-1-(naphthalen-1-yl)ethyl)amino)ethyl)-2H-benzo[b][1,4]oxazin-4(3H)-yl)phenyl)propanoic acid hydrochloride;
2,4-Difluoro-5-(2-(2-(((R)-1-(naphthalen-1-yl)ethyl)amino)ethyl)-2H-benzo[b][1,4]oxazin-4(3H)-yl)benzoic acid hydrochloride;
3-(2-Fluoro-5-(2-(2-(((R)-1-(naphthalen-1-yl)ethyl)amino)ethyl)-2H-benzo[b][1,4]oxazin-4(3H)-yl)phenyl)propanoic acid hydrochloride;
3-(2-Fluoro-3-(2-(2-(((R)-1-(naphthalen-1-yl)ethyl)amino)ethyl)-2H-benzo[b][1,4]oxazin-4(3H)-yl)phenyl)propanoic acid hydrochloride;
3-(3-Fluoro-5-(2-(2-(((R)-1-(naphthalen-1-yl)ethyl)amino)ethyl)-2H-benzo[b][1,4]oxazin-4(3H)-yl)phenyl)propanoic acid hydrochloride;
3-(4-Fluoro-3-(2-(2-(((R)-1-(naphthalen-1-yl)ethyl)amino)ethyl)-2H-benzo[b][1,4]oxazin-4(3H)-yl)phenyl)propanoic acid hydrochloride;
2-(3-Fluoro-4-(2-(2-(((R)-1-(naphthalen-1-yl)ethyl)amino)ethyl)-2H-benzo[b][1,4]oxazin-4(3H)-yl)phenoxy)acetic acid hydrochloride;

2-(2-Fluoro-4-(2-(2-(((R)-1-(naphthalen-1-yl)ethyl)amino)ethyl)-2H-benzo[b][1,4]oxazin-4(3H)-yl)phenoxy)acetic acid hydrochloride;
2-(3-Methyl-4-(2-(2-(((R)-1-(naphthalen-1-yl)ethyl)amino)ethyl)-2H-benzo[b][1,4]oxazin-4(3H)-yl)phenoxy)acetic acid hydrochloride;
2-(2-Methyl-5-(2-(2-(((R)-1-(naphthalen-1-yl)ethyl)amino)ethyl)-2H-benzo[b][1,4]oxazin-4(3H)-yl)phenoxy)acetic acid hydrochloride;
2-(2-Methyl-3-(2-(2-(((R)-1-(naphthalen-1-yl)ethyl)amino)ethyl)-2H-benzo[b][1,4]oxazin-4(3H)-yl)phenoxy)acetic acid hydrochloride;
2-(3-Methyl-5-(2-(2-(((R)-1-(naphthalen-1-yl)ethyl)amino)ethyl)-2H-benzo[b][1,4]oxazin-4(3H)-yl)phenoxy)acetic acid hydrochloride;
2-(4-Methyl-3-(2-(2-(((R)-1-(naphthalen-1-yl)ethyl)amino)ethyl)-2H-benzo[b][1,4]oxazin-4(3H)-yl)phenoxy)acetic acid hydrochloride;
2-Methyl-2-(3-(2-(2-(((R)-1-(naphthalen-1-yl)ethyl)amino)ethyl)-2H-benzo[b][1,4]oxazin-4(3H)-yl)phenyl)propanoic acid hydrochloride;
1-(3-(2-(2-(((R)-1-(Naphthalen-1-yl)ethyl)amino)ethyl)-2H-benzo[b][1,4]oxazin-4(3H)-yl)phenyl)cyclopropanecarboxylic acid hydrochloride;
1-(4-(2-(2-(((R)-1-(Naphthalen-1-yl)ethyl)amino)ethyl)-2H-benzo[b][1,4]oxazin-4(3H)-yl)phenyl)cyclopropanecarboxylic acid hydrochloride;
6-Fluoro-3-(8-fluoro-2-(2-(((R)-1-(naphthalen-1-yl)ethyl)amino)ethyl)-2H-benzo[b][1,4]oxazin-4(3H)-yl)-2-methylbenzoic acid hydrochloride;
2-Fluoro-3-(8-fluoro-2-(2-(((R)-1-(naphthalen-1-yl)ethyl)amino)ethyl)-2H-benzo[b][1,4]oxazin-4(3H)-yl)-6-methylbenzoic acid hydrochloride;
2,6-Difluoro-3-(8-fluoro-2-(2-(((R)-1-(naphthalen-1-yl)ethyl)amino)ethyl)-2H-benzo[b][1,4]oxazin-4(3H)-yl)benzoic acid hydrochloride;
3-Fluoro-5-(8-fluoro-2-(2-(((R)-1-(naphthalen-1-yl)ethyl)amino)ethyl)-2H-benzo[b][1,4]oxazin-4(3H)-yl)benzoic acid hydrochloride;
2-Fluoro-5-(8-fluoro-2-(2-(((R)-1-(naphthalen-1-yl)ethyl)amino)ethyl)-2H-benzo[b][1,4]oxazin-4(3H)-yl)benzoic acid;
2,6-Difluoro-3-(7-fluoro-2-(2-(((R)-1-(naphthalen-1-yl)ethyl)amino)ethyl)-2H-benzo[b][1,4]oxazin-4(3H)-yl)benzoic acid hydrochloride;
3-Fluoro-5-(7-fluoro-2-(2-(((R)-1-(naphthalen-1-yl)ethyl)amino)ethyl)-2H-benzo[b][1,4]oxazin-4(3H)-yl)benzoic acid hydrochloride;
6-Fluoro-3-(6-fluoro-2-(2-(((R)-1-(naphthalen-1-yl)ethyl)amino)ethyl)-2H-benzo[b][1,4]oxazin-4(3H)-yl)-2-methylbenzoic acid hydrochloride;
2-Fluoro-3-(6-fluoro-2-(2-(((R)-1-(naphthalen-1-yl)ethyl)amino)ethyl)-2H-benzo[b][1,4]oxazin-4(3H)-yl)-6-methylbenzoic acid hydrochloride;
2,6-Difluoro-3-(6-fluoro-2-(2-(((R)-1-(naphthalen-1-yl)ethyl)amino)ethyl)-2H-benzo[b][1,4]oxazin-4(3H)-yl)benzoic acid hydrochloride;
3-Fluoro-5-(6-fluoro-2-(2-(((R)-1-(naphthalen-1-yl)ethyl)amino)ethyl)-2H-benzo[b][1,4]oxazin-4(3H)-yl)benzoic acid hydrochloride;
6-Fluoro-3-(5-fluoro-2-(2-(((R)-1-(naphthalen-1-yl)ethyl)amino)ethyl)-2H-benzo[b][1,4]oxazin-4(3H)-yl)-2-methylbenzoic acid hydrochloride;
2-Fluoro-3-(5-fluoro-2-(2-(((R)-1-(naphthalen-1-yl)ethyl)amino)ethyl)-2H-benzo[b][1,4]oxazin-4(3H)-yl)-6-methylbenzoic acid hydrochloride;
2,6-Difluoro-3-(5-fluoro-2-(2-(((R)-1-(naphthalen-1-yl)ethyl)amino)ethyl)-2H-benzo[b][1,4]oxazin-4(3H)-yl)benzoic acid hydrochloride; and
3-Fluoro-5-(5-fluoro-2-(2-(((R)-1-(naphthalen-1-yl)ethyl)amino)ethyl)-2H-benzo[b][1,4]oxazin-4(3H)-yl)benzoic acid hydrochloride;

or pharmaceutically acceptable salts thereof or stereoisomers thereof.

In another aspect of the invention, there is provided a compound of Formula (I) useful in treating, managing or lessening the severity of diseases, disorders, syndromes or conditions associated with calcium sensing receptor (CaSR) modulators.

In another aspect, the invention provides a pharmaceutical composition comprising at least one compound of Formula (I) and at least one pharmaceutically acceptable excipient.

In another aspect, the invention provides a pharmaceutical composition of compound of Formula (I) useful in treating, managing or lessening the severity of the diseases disorders, syndromes or conditions associated with calcium sensing receptor (CaSR) modulators in a subject, in need thereof, by administering to the subject, one or more compounds described herein in a therapeutically effective amount to cause modulation of such receptor.

In another aspect, the invention provides a pharmaceutical composition comprising a compound of Formula (I) or a pharmaceutically acceptable stereoisomer, salt, or in vivo hydrolysable ester thereof together with a pharmaceutically acceptable excipient.

In another aspect, there are provided processes for the preparation compounds of Formula (Ia) and (Ic):

(Ia)

(Ic)

wherein ring A, L, $R_b$, X, $R_1$, $R_2$, $R_5$, $R_9$, $R_{10}$, 'p' and 'q' are as defined in Formula (I);

the process comprising:

a) coupling of compound of Formula (5) with Formula (b) where L' is leaving group, to get compound of Formula (6);

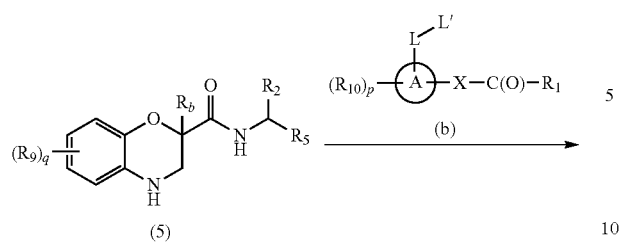
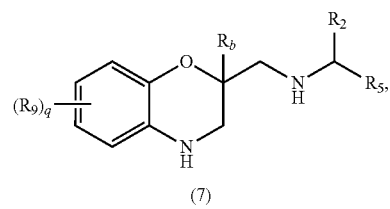

b) reducing a compound of Formula (6) using suitable reducing agents to get compound of Formula (Ia);

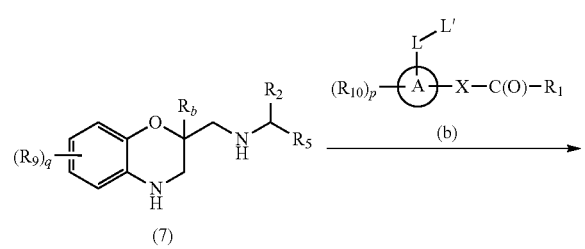

d) coupling of compound of Formula (7) with Formula (b) where L' is leaving group, to give compound of Formula (Ia);

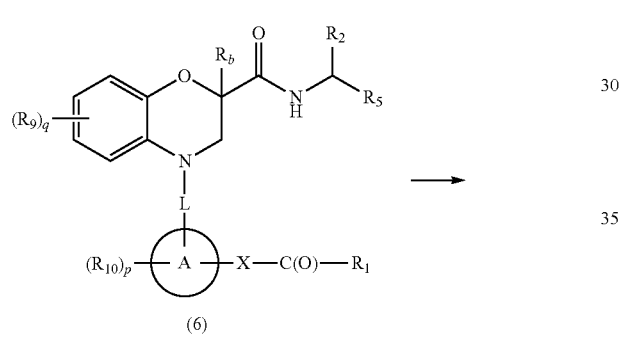

or c) reducing a compound of Formula (5) using suitable reducing agent to get compound of Formula (7);

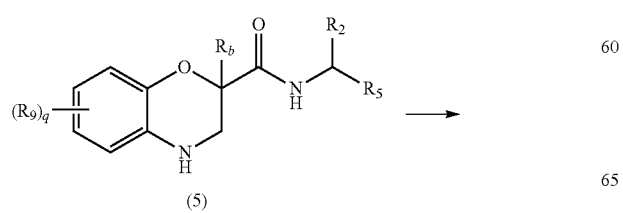

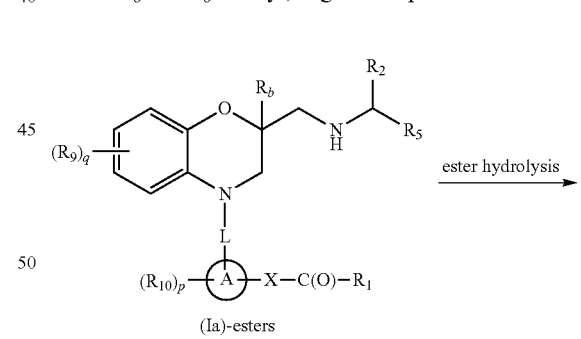

e) hydrolyzing the compound of Formula (Ia) when $R_1$ is $OR_6$ and $R_6$ is alkyl, to give compound of Formula (Ic);

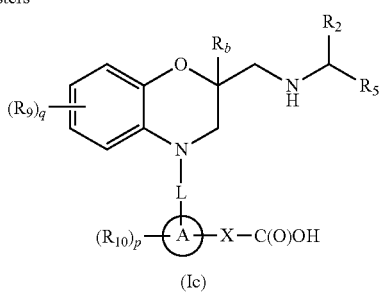

f) reacting acid compound of Formula (Ic) with suitable amine to give compound of Formula (Id)

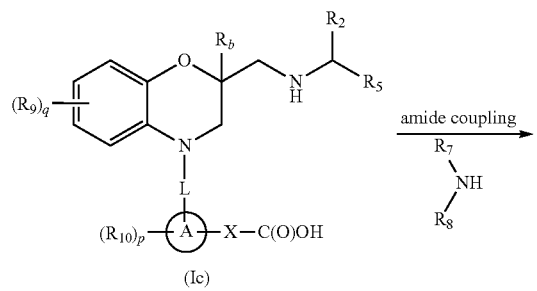

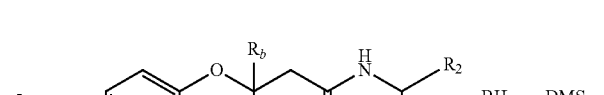

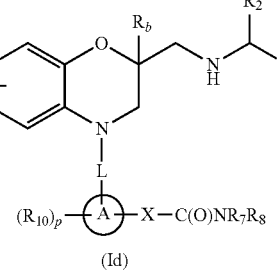

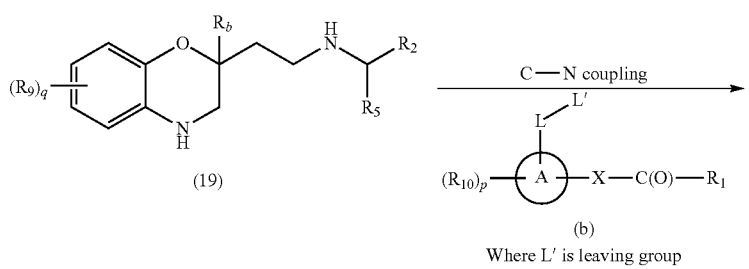

b) coupling of compound of Formula (19) with Formula (b) where L' is leaving group, to give compound of Formula (Ii);

In another aspect, there are provided processes for the preparation compounds of Formula (Ii):

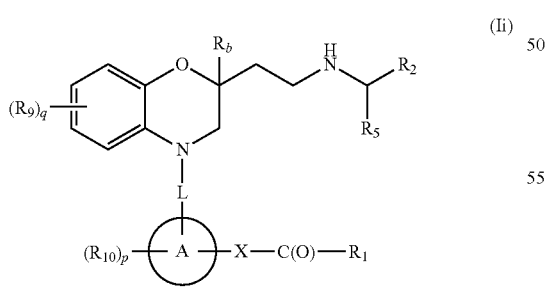

wherein ring A, L, $R_b$, X, $R_1$, $R_2$, $R_5$, $R_9$, $R_{10}$, 'p' and 'q' are as defined in Formula (I);

a) reducing the compound of Formula (18) to give compound of Formula (19) using suitable reducing agent c) hydrolyzing the compound of Formula (Ii) when $R_1$ is $OR_6$ and $R_6$ is alkyl, to give corresponding acid and further coupling with suitable amine to give corresponding amide.

DETAILED DESCRIPTION OF THE INVENTION

Definitions and Abbreviations

Unless otherwise stated, the following terms used in the specification and claims have the meanings given below.

For purposes of interpreting the specification, the following definitions will apply and whenever appropriate, terms used in the singular will also include the plural and vice versa.

The terms "halogen" or "halo" means fluorine, chlorine, bromine, or iodine.

Unless otherwise stated, in the present application "oxo" means C(=O) group. Such an oxo group may be a part of either a cycle or a chain in the compounds of the present invention.

The term "alkyl" refers to an alkane derived hydrocarbon radical that includes solely carbon and hydrogen atoms in the backbone, contains no unsaturation, has from one to six carbon atoms, and is attached to the remainder of the molecule by a single bond, e.g., methyl, ethyl, n-propyl, 1-methylethyl (isopropyl), n-butyl, n-pentyl, 1,1-dimethylethyl (t-butyl) and the like. Unless set forth or recited to the contrary, all alkyl groups described or claimed herein may be straight chain or branched, substituted or unsubstituted.

The term "alkenyl" refers to a hydrocarbon radical containing from 2 to 10 carbon atoms and including at least one carbon-carbon double bond. Non-limiting examples of alkenyl groups include ethenyl, 1-propenyl, 2-propenyl (allyl), iso-propenyl, 2-methyl-1-propenyl, 1-butenyl, 2-butenyl and the like. Unless set forth or recited to the contrary, all alkenyl groups described or claimed herein may be straight chain or branched, substituted or unsubstituted.

The term "alkynyl" refers to a hydrocarbon radical containing 2 to 10 carbon atoms and including at least one carbon-carbon triple bond. Non-limiting examples of alkynyl groups include ethynyl, propynyl, butynyl and the like. Unless set forth or recited to the contrary, all alkynyl groups described or claimed herein may be straight chain or branched, substituted or unsubstituted.

The term "alkoxy" refers to an alkyl group attached via an oxygen linkage. Non-limiting examples of such groups are methoxy, ethoxy and propoxy and the like. Unless set forth or recited to the contrary, all alkoxy groups described or claimed herein may be straight chain or branched, substituted or unsubstituted.

The term "haloalkyl" refers to an alkyl group as defined above that is substituted by one or more halogen atoms as defined above. Preferably, the haloalkyl may be monohaloalkyl, dihaloalkyl or polyhaloalkyl including perhaloalkyl. A monohaloalkyl can have one iodine, bromine, chlorine or fluorine atom. Dihaloalkyl and polyhaloalkyl groups can be substituted with two or more of the same halogen atoms or a combination of different halogen atoms. Preferably, a polyhaloalkyl is substituted with up to 12 halogen atoms. Non-limiting examples of a haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl and the like. A perhaloalkyl refers to an alkyl having all hydrogen atoms replaced with halogen atoms. Unless set forth or recited to the contrary, all haloalkyl groups described or claimed herein may be straight chain or branched, substituted or unsubstituted.

The term "haloalkoxy" refers to a haloalkyl, defined herein, group attached via an oxygen linkage. Non-limiting examples of such groups are monohaloalkoxy, dihaloalkoxy or polyhaloalkoxy including perhaloalkoxy. Unless set forth or recited to the contrary, all haloalkoxy group described or claimed herein may be straight chain or branched, substituted or unsubstituted.

The term "hydroxyalkyl" refers to an alkyl group, as defined above that is substituted by one or more hydroxy groups. Preferably, the hydroxyalkyl is monohydroxyalkyl or dihydroxyalkyl. Non-limiting examples of a hydroxyalkyl include 2-hydroxyethyl, 3-hydroxypropyl, 2-hydroxypropyl, and the like. Unless set forth or recited to the contrary, all hydroxyalkyl group described or claimed herein may be straight chain or branched, substituted or unsubstituted.

The term "cycloalkyl" refers to a non-aromatic mono or multicyclic ring system having 3 to 12 carbon atoms, such as cyclopropyl, cyclobutyl, cyclopentyl, cyclohexyl and the like. Examples of multicyclic cycloalkyl groups include, but are not limited to, perhydronaphthyl, adamantyl and norbornyl groups, bridged cyclic groups or spirobicyclic groups, e.g., spiro(4,4)non-2-yl and the like. Unless set forth or recited to the contrary, all cycloalkyl groups described or claimed herein may be substituted or unsubstituted.

The term "cycloalkylene" refers to a saturated divalent cyclic hydrocarbon radical that includes solely carbon and hydrogen atoms in the backbone. In particular, "$C_3$-$C_7$ cycloalkylene" means a saturated divalent cyclic hydrocarbon radical with 3 to 7 carbon atoms e.g. cyclopropylene, cyclobutylene, cyclopentylene, cyclohexylene and the like. Unless set forth or recited to the contrary, all cycloalkylene groups described or claimed herein may be substituted or unsubstituted.

The term "cycloalkenyl" refers to a non-aromatic mono or multicyclic ring system having 3 to 12 carbon atoms and including at least one carbon-carbon double bond, such as cyclopentenyl, cyclohexenyl, cycloheptenyl and the like. Unless set forth or recited to the contrary, all cycloalkenyl groups described or claimed herein may be substituted or unsubstituted.

The term "cycloalkylalkyl" refers to a cycloalkyl group as defined above, directly bonded to an alkyl group as defined above, e.g., cyclopropylmethyl, cyclobutylmethyl, cyclopentylmethyl, cyclohexylmethyl, cyclohexylethyl, etc. Unless set forth or recited to the contrary, all cycloalkylalkyl groups described or claimed herein may be substituted or unsubstituted.

The term "aryl" refers to an aromatic radical having 6- to 14-carbon atoms, including monocyclic, bicyclic and tricyclic aromatic systems, such as phenyl, naphthyl, tetrahydronaphthyl, indanyl, and biphenyl and the like. Unless set forth or recited to the contrary, all aryl groups described or claimed herein may be substituted or unsubstituted.

The term "arylalkyl" refers to an aryl group as defined above directly bonded to an alkyl group as defined above, e.g., —$CH_2C_6H_5$ and —$C_2H_4C_6H_5$. Unless set forth or recited to the contrary, all arylalkyl groups described or claimed herein may be substituted or unsubstituted.

A "carbocyclic ring" or "carbocycle" as used herein refers to a 3- to 10-membered saturated or unsaturated, monocyclic, fused bicyclic, spirocyclic or bridged polycyclic ring containing carbon atoms, which may optionally be substituted, for example, carbocyclic rings include but are not limited to cyclopropyl, cyclobutyl, cyclopentyl, cyclohexyl, cyclopropylene, cyclohexanone, aryl, naphthyl, adamentyl etc. Unless set forth or recited to the contrary, all carbocyclic groups or rings described or claimed herein may be aromatic or non aromatic.

The term "heterocyclic ring" or "heterocyclyl ring" or "heterocyclyl", unless otherwise specified, refers to substituted or unsubstituted non-aromatic 3- to 15-membered ring which consists of carbon atoms and with one or more heteroatom(s) independently selected from N, O or S. The heterocyclic ring may be a mono-, bi- or tricyclic ring system, which may include fused, bridged or spiro ing systems and the nitrogen, carbon, oxygen or sulfur atoms in the heterocyclic ring may be optionally oxidized to various oxidation states. In addition, the nitrogen atom may be optionally quaternized, the heterocyclic ring or heterocyclyl may optionally contain one or more olefinic bond(s), and one or two carbon atoms(s) in the heterocyclic ring or heterocyclyl may be interrupted with —$CF_2$—, —C(O)—, —S(O)—, $S(O)_2$, —C(=N-alkyl)-, or —C(=N-cycloalkyl), etc. In addition heterocyclic ring may also be fused with aromatic ring. Non-limiting examples of heterocyclic rings include azetidinyl, benzopyranyl, chromanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl, tetrahydropyranyl, thiazolinyl, thiazolidinyl, thiamorpholinyl, thiamorpholinyl sulfoxide, thiamorpholinyl sulfone indoline, benzodioxole, tetrahydroquinoline, tetrahydrobenzopyran and the like. The heterocyclic ring may be attached to the main structure at any heteroatom or carbon atom that results in the creation of a stable structure. Unless set forth or recited to the contrary, all heterocyclyl groups described or claimed herein may be substituted or unsubstituted; substituents may be on same or different ring atom.

The term "heteroaryl" unless otherwise specified, refers to a substituted or unsubstituted 5- to 14-membered aromatic heterocyclic ring with one or more heteroatom(s) independently selected from N, O or S. The heteroaryl may be a mono-, bi- or tricyclic ring system. The heteroaryl ring may be attached to the main structure at any heteroatom or carbon atom that results in the creation of a stable structure. Non-limiting examples of a heteroaryl ring include oxazolyl, isoxazolyl, imidazolyl, furyl, indolyl, isoindolyl, pyrrolyl, triazolyl, triazinyl, tetrazolyl, thienyl, thiazolyl, isothiazolyl, pyridyl, pyrimidinyl, pyrazinyl, pyridazinyl, benzofuranyl, benzothiazolyl, benzoxazolyl, benzimidazolyl, benzothienyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl, phthalazinyl and the like. Unless set forth or recited to the contrary, all heteroaryl groups described or claimed herein may be substituted or unsubstituted.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure. Unless set forth or recited to the contrary, all heterocyclylalkyl groups described or claimed herein may be substituted or unsubstituted.

The term "heteroarylalkyl" refers to a heteroaryl ring radical directly bonded to an alkyl group. The heteroarylalkyl radical may be attached to the main structure at any carbon atom in the alkyl group that results in the creation of a stable structure. Unless set forth or recited to the contrary, all heteroarylalkyl groups described or claimed herein may be substituted or unsubstituted.

Unless otherwise specified, the term "substituted" as used herein refers to a group or moiety having one or more substituents attached to the structural skeleton of the group or moiety. Such substituents include, but are not limited to hydroxy, halogen, carboxyl, cyano, nitro, oxo (=O), thio (=S), alkyl, haloalkyl, alkenyl, alkynyl, aryl, arylalkyl, cycloalkyl, cycloalkylalkyl, cycloalkenyl, heteroaryl, heterocyclic ring, heterocyclylalkyl, heteroarylalkyl, —C(O)OR$^x$, —C(O)R$^x$, —C(S)R$^x$, —C(O)NR$^x$R$^y$, —NR$^x$C(O)NR$^y$R$^z$, —N(R$^x$)S(O)R$^y$, —N(R$^x$)S(O)$_2$R$^y$, —NR$^x$R$^y$, —NR$^x$C(O)R$^y$, —NR$^x$C(S)R$^y$, —NR$^x$C(S)NR$^y$R$^z$, —S(O)$_2$NR$^x$R$^y$, —OR$^x$, —OC(O)R$^x$, —OC(O)NR$^x$R$^y$, —R$^x$C(O)OR$^y$, —R$^x$C(O)NR$^y$R$^z$, —R$^x$C(O)R$^y$, —SR$^x$, and —S(O)$_2$R$^x$; wherein each occurrence of R$^x$, R$^y$ and R$^z$ are independently selected from hydrogen, halogen, alkyl, haloalkyl, alkenyl, alkynyl, aryl, arylalkyl, cycloalkyl, cycloalkenyl, heteroaryl, heterocyclic ring, heterocyclylalkyl and heteroarylalkyl. The aforementioned "substituted" groups cannot be further substituted. For example, when the substituent on "substituted alkyl" is "aryl" or "alkenyl", the aryl or alkenyl cannot be substituted aryl or substituted alkenyl, respectively.

The compounds of the present invention may have one or more chiral centers. The absolute stereochemistry at each chiral centre may be 'R' or 'S'. The compounds of the invention include all diastereomers and enantiomers and mixtures thereof. Unless specifically mentioned otherwise, reference to one stereoisomer applies to any of the possible stereoisomers. Whenever the stereoisomeric composition is unspecified, it is to be understood that all possible stereoisomers are included.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. The terms "racemate" or "racemic mixture" refer to a mixture of equal parts of enantiomers.

A "tautomer" refers to a compound that undergoes rapid proton shifts from one atom of the compound to another atom of the compound. Some of the compounds described herein may exist as tautomers with different points of attachment of hydrogen. The individual tautomers as well as mixture thereof are encompassed with compounds of Formula (I).

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof; c) lessening the severity of a disease disorder or condition or at least one of its clinical or subclinical symptoms or (d) relieving the disease, i.e., causing regression of the state, disorder or condition or at least one of its clinical or subclinical symptoms.

The term "modulate" or "modulating" or "modulation" or "modulator" refers to an increase in the amount, quality, or effect of a particular activity or function of the receptor. By way of illustration and not limitation, it includes agonists, partial agonists, allosteric modulators of calcium sensing receptor (CaSR) of the present invention. Such modulation may be contingent on the occurrence of a specific event, such as activation of a signal transduction pathway.

The term "allosteric modulators of calcium-sensing receptor", refers to the ability of a compound that binds to calcium sensing receptors and induces a conformational change that reduces the threshold for calcium sensing receptor activation by the endogenous ligand Ca$^{2+}$ depending on the concentration of the compound exposed to the calcium-sensing receptor.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a disease, disorder, syndrome or condition, is sufficient to cause the effect in the subject which is the purpose of the administration. The "therapeutically effective amount" will vary depending on the compound, the disease and its severity and the age, weight, physical condition and responsiveness of the subject to be treated.

The compound of the invention may form salts. Non-limiting examples of pharmaceutically acceptable salts include salts derived from inorganic bases, salts of organic bases, salts of chiral bases, salts of natural amino acids and salts of non-natural amino acids.

With respect to the overall compounds described by the Formula (I), the invention extends to these stereoisomeric forms and to mixtures thereof. To the extent prior art teaches synthesis or separation of particular stereoisomers, the different stereoisomeric forms of the invention may be separated from one another by a method known in the art, or a given isomer may be obtained by stereo specific or asymmetric synthesis or chiral HPLC (high performance liquid chromatography. Tautomeric forms and mixtures of compounds described herein are also contemplated.

Screening of compounds of invention for calcium sensing receptor (CaSR) modulation activity can be achieved by using various in vitro and in vivo protocols mentioned herein below or methods known in the art.

Pharmaceutical Compositions

The invention relates to pharmaceutical compositions containing the compounds of the Formula (I) disclosed herein. In particular, pharmaceutical compositions containing a therapeutically effective amount of at least one compound of Formula (I) described herein and at least one pharmaceutically acceptable excipient (such as a carrier or diluent). Preferably, the contemplated pharmaceutical compositions include the compound(s) described herein in an amount sufficient to modulate calcium sensing receptor (CaSR) mediated diseases described herein when administered to a subject.

The subjects contemplated include, for example, a living cell and a mammal, including human mammal. The compound of the invention may be associated with a pharmaceutically acceptable excipient (such as a carrier or a diluent) or be diluted by a carrier, or enclosed within a carrier which can be in the form of a capsule, sachet, paper or other container. The pharmaceutically acceptable excipient includes pharmaceutical agent that does not itself induce the production of antibodies harmful to the individual receiving the composition, and which may be administered without undue toxicity.

Examples of suitable carriers or excipients include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, salicylic acid, fatty acids, fatty acid amines, fatty acid monoglycerides and diglycerides, pentaerythritol fatty acid esters, polyoxyethylene, hydroxymethylcellulose and polyvinylpyrrolidone.

The pharmaceutical composition may also include one or more pharmaceutically acceptable auxiliary agents, wetting agents, emulsifying agents, suspending agents, preserving agents, salts for influencing osmotic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions described herein may be prepared by conventional techniques known in the art. For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, caplets, orally disintegrating tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment).

Solid oral formulations include, but are not limited to, tablets, caplets, capsules (soft or hard gelatin), orally disintegrating tablets, dragees (containing the active ingredient in powder or pellet form), troches and lozenges. Tablets, dragees, or capsules having talc and/or a carbohydrate carrier or binder or the like are particularly suitable for oral application. Liquid formulations include, but are not limited to, syrups, emulsions, soft gelatin and sterile injectable liquids, such as aqueous or non-aqueous liquid suspensions or solutions. For parenteral application, particularly suitable are injectable solutions or suspensions formulation.

Liquid formulations include, but are not limited to, syrups, emulsions, suspensions, solutions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as pocketed tablets, capsules, and powders in vials or ampoules. Also, the unit dosage form can be a capsule, tablet, caplet, cachet, or lozenge itself, or it can be the appropriate number of any of these in packaged form.

For administration to subject patients, the total daily dose of the compounds of the invention depends, of course, on the mode of administration. For example, oral administration may require a higher total daily dose, than an intravenous (direct into blood). The quantity of active component in a unit dose preparation may be varied or adjusted from 0.1 mg to 10000 mg according to the potency of the active component or mode of administration.

Suitable doses of the compounds for use in treating the diseases and disorders described herein can be determined by those skilled in the relevant art. Therapeutic doses are generally identified through a dose ranging study in subject based on preliminary evidence derived from the animal studies. Doses must be sufficient to result in a desired therapeutic benefit without causing unwanted side effects for the patient. For example, the daily dosage of the CaSR modulator can range from about 0.1 to about 30.0 mg/kg. Mode of administration, dosage forms, suitable pharmaceutical excipients, diluents or carriers can also be well used and adjusted by those skilled in the art. All changes and modifications are envisioned within the scope of the invention.

Methods of Treatment

In an embodiment, the invention provides compounds and pharmaceutical compositions thereof that are useful in treating, managing or lessening the severity of diseases, disorders, syndromes or conditions modulated by calcium sensing receptor (CaSR). The invention further provides method of treating diseases, disorders, syndromes or conditions modulated by CaSR in a subject in need thereof by administering to the subject a therapeutically effective amount of a compound or a pharmaceutical composition of the invention.

In another aspect of the invention, the methods provided are also useful for diagnosis of conditions that can be treated by modulating CaSR for determining if a patient will be responsible to therapeutic agents.

In another aspect, the invention provides a method for the treatment of diseases, disorders or conditions through modulating CaSR. In this method, a subject in need of such treatment is administered a therapeutically effective amount of a compound of Formula (I) described herein.

The compound and pharmaceutical composition of the present invention is useful to a subject in need of the treatment having a disease, disorder, syndrome or condition characterized by one or more of the following: (a) abnormal calcium ion homeostasis, (b) an abnormal level of a messenger whose production or secretion is affected by the calcium sensing receptor (CaSR) activity or (c) an abnormal level of activity of a messenger whose function is affected by the calcium sensing receptor activity. In one aspect, the patient has a disease, disorder, syndrome or condition characterized by an abnormal level of one or more calcium sensing receptor-regulated components and the compound is active on a CaSR of a cell including parathyroid cell, bone cells (pre-osteoclast, osteoclast, pre-osteoblast, osteoblast), juxtaglomerular kidney cell, kidney messengial cell, glomerular kidney cell, proximal tubule kidney cell, distal tubule kidney cell, cell of the thick ascending limb of Henle's loop and/or collecting duct, parafollicular cell in the thyroid (C-cell), intestinal cell, platelet, vascular smooth muscle cell, gastrointestinal tract cell, pituitary cell or hypothalamic cell. The messenger of the calcium sensing receptor is Calcium.

The compound of Formula (I), being modulators of CaSR, is potentially useful in treating, managing or lessening the severity, morbidity/mortality or complications of diseases, disorders, syndromes or conditions include but are not limited to primary hyperparathyroidism, secondary hyperparathyroidism, tertiary hyperparathyroidism, chronic renal failure (with or without dialysis), chronic kidney disease (with or without dialysis) parathyroid adenoma, parathyroid hyperplasia, parathyroid carcinoma, vascular & valvular calcification, abnormal calcium homeostasis such as hypercalcemia, abnormal phosphorous homeostasis such as hypophosphatemia, bone related diseases or complications arising due to hyperparathyroidism, chronic kidney disease or parathyroid carcinoma, bone loss post renal transplantation, osteitis fibrosa cystica, adynamic bone disease, renal bone diseases, cardiovascular complications arising due to hyperparathyroidism or chronic kidney disease, certain malignancies in which $(Ca^{2+})_e$ ions are abnormally high, cardiac, renal or intestinal dysfunctions, podocyte-related diseases, abnormal intestinal motility, diarrhea, augmenting gastrin or gastric acid secretion to directly or indirectly benefit in atrophic gastritis or to improve absorption of pharmacological compounds, drugs or supplements from gastro-intestinal tract by augmenting gastric acidity.

Primary hyperparathyroidism, is a disorder of one or more of the parathyroid glands, resulting from a hyper function of the parathyroid glands themselves (acquired sporadically or familial) resulting in PTH over secretion which could be due to single or double adenoma, hyperplasia, multigland disease or rarely, carcinoma of the parathyroid glands. As a result, the blood calcium rises to a level that is higher than normal (called hypercalcemia). This elevated calcium level can cause many short-term and long-term complications.

Secondary hyperparathyroidism occurs when a decrease in circulating levels of $Ca^{2+}$ level stimulates PTH secretion. One cause of secondary hyperparathyroidism is chronic renal insufficiency (also referred to as chronic kidney disease or CKD), such as that in renal polycystic disease or chronic pyelonephritis, or chronic renal failure, such as that in hemodialysis patients (also referred to as end stage renal disease or ESRD). Excess PTH may be produced in response to hypocalcemia resulting from low calcium intake, GI disorders, renal insufficiency, vitamin D deficiency, magnesium deficiency and renal hypercalciuria. Tertiary hyperparathyroidism may occur after a long period of secondary hyperparathyroidism and hypercalcemia.

In one aspect, the compound and composition of the present invention can be used in treating, managing or lessening the vascular or valvular calcification in a subject. In one aspect, administration of the compound of the invention retards or reverses the formation, growth or deposition of extracellular matrix hydroxyapatite crystal deposits. In another aspect of the invention, administration of the compound of the invention prevents the formation, growth or deposition of extracellular matrix hydroxyapatite crystal deposits. In one aspect, the compounds of the invention may also be used to prevent or treat atherosclerotic calcification and medial calcification and other conditions characterized by vascular calcification. In one aspect, vascular calcification may be associated with chronic renal insufficiency or end-stage renal disease or excess calcium or PTH itself. In another aspect, vascular calcification may be associated with pre- or post-dialysis or uremia. In a further aspect, vascular calcification may be associated with diabetes mellitus I or II. In yet another aspect, vascular calcification may be associated with a cardiovascular disorder.

Abnormal calcium homeostasis such as hyperparathyroidism related diseases can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hyperparathyroidism.

Abnormal phosphorous homeostasis such as hypophosphatemia can be characterized as described in standard medical textbooks, but not limited to Harrison's Principles of Internal Medicine. The compound and composition of the present invention can be used, in particular, to participate in a reduction of the serum levels in the parathyroid hormone known as PTH: these products could thus be useful for the treatment of diseases such as hypophosphatemia.

In one aspect, the podocyte diseases or disorders treated by methods of the present invention stem from the perturbations in one or more functions of podocytes. These functions of podocytes include: (i) a size barrier to protein; (ii) charge barrier to protein; (iii) maintenance of the capillary loop shape; (iv) counteracting the intraglomerular pressure; (v) synthesis and maintenance of the glomerular basement membrane (GMB); (vi) production and secretion of vascular endothelial growth factor (VEGF) required for the glomerular endothelial cell (GEN) integrity. Such disorders or diseases include but are not limited to loss of podocytes (podocytopenia), podocyte mutation, an increase in foot process width, or a decrease in slit diaphragm length. In one aspect, the podocyte-related disease or disorder can be effacement or a diminution of podocyte density. In one aspect, the diminution of podocyte density could be due to a decrease in a podocyte number, for example, due to apoptosis, detachment, lack of proliferation, DNA damage or hypertrophy.

In one aspect, the podocyte-related disease or disorder can be due to a podocyte injury. In one aspect, the podocyte injury can be due to mechanical stress such as high blood pressure, hypertension, or ischemia, lack of oxygen supply, a toxic substance, an endocrinologic disorder, an infection, a contrast agent, a mechanical trauma, a cytotoxic agent (cis-platinum, adriamycin, puromycin), calcineurin inhibitors, an inflammation (e.g., due to an infection, a trauma, anoxia, obstruction, or ischemia), radiation, an infection (e.g., bacterial, fungal, or viral), a dysfunction of the immune system (e.g., an autoimmune disease, a systemic disease, or IgA nephropathy), a genetic disorder, a medication (e.g., anti-bacterial agent, anti-viral agent, anti-fungal agent, immunosuppressive agent, anti-inflammatory agent, analgestic or anticancer agent), an organ failure, an organ transplantation, or uropathy. In one aspect, ischemia can be sickle-cell anemia, thrombosis, transplantation, obstruction, shock or blood loss. In one aspect, the genetic disorders may include congenital nephritic syndrome of the Finnish type, the fetal membranous nephropathy or mutations in podocyte-specific proteins.

In one aspect, the compounds of the invention can be used for treating abnormal intestinal motilities disorders such as diarrhea. The methods of the invention comprise administering to the subject a therapeutically effective amount of the compounds of Formula I. In a further aspect, diarrhea can be exudative diarrhea, i.e., resulting from direct damage to the small or large intestinal mucosa. This type of diarrhea can be caused by infectious or inflammatory disorders of the gut. In one aspect, exudative diarrhea can be associated with gastrointestinal or abdominal surgery, chemotherapy, radiation treatment, inflammation or toxic traumatic injury. In another aspect, diarrhea can be secretary, means that there is an increase in the active secretion, or there is an inhibition of absorption. There is little to no structural damage. The most common cause of this type of diarrhea is cholera. In another aspect, diarrhea can be due to acceleration of intestinal transit (rapid transit diarrhea). Such condition may occur because the rapid flow-through impairs the ability of the gut to absorb water.

The compound and composition of the present invention can be used, in particular, to participate in an augmenting gastrin or gastric acid secretion to directly or indirectly benefit certain medical conditions such as but not limited to atrophic gastritis or to improve absorption of pharmacological compounds, drugs or supplements from gastro-intestinal tract by augmenting gastric acidity.

All of the patent, patent application and non-patent publications referred to in this specification are incorporated herein by reference in their entireties.

General Methods of Preparation

The compounds described herein may be prepared by techniques known in the art. In addition, the compounds described herein may be prepared by following one or more reaction sequences as depicted in Scheme-1 to Scheme-8. Further, in the following schemes, where specific bases, acids, reagents, solvents, coupling agents, etc., are mentioned, it is understood that other bases, acids, reagents, solvents, coupling agents etc., known in the art may also be used and are therefore included within the scope of the present invention. Variations in reaction conditions, for example, temperature and/or duration of the reaction, which may be used as known in the art are also within the scope of the present invention. All the isomers of the compounds are described in these schemes, unless otherwise specified, are also encompassed within the scope of this invention.

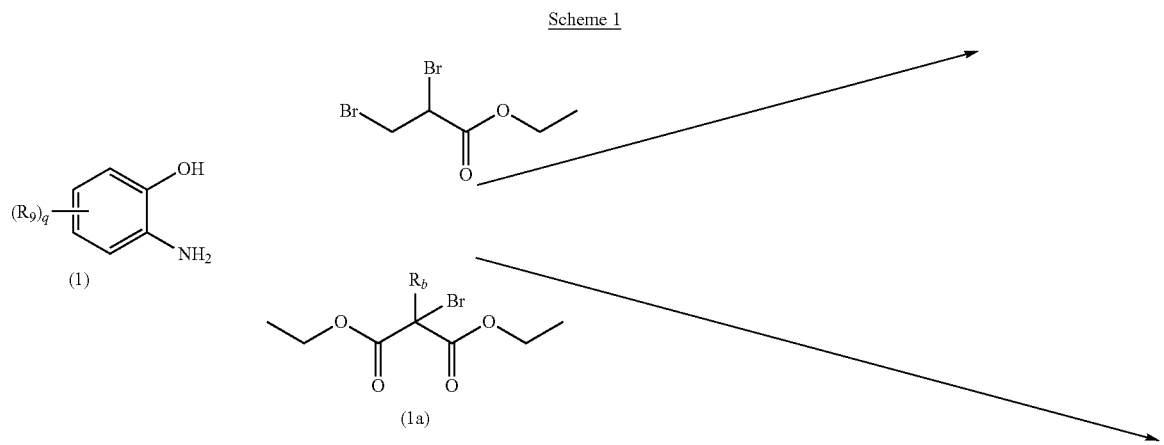

Scheme 1

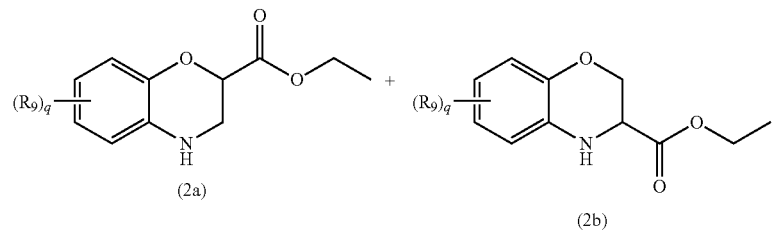

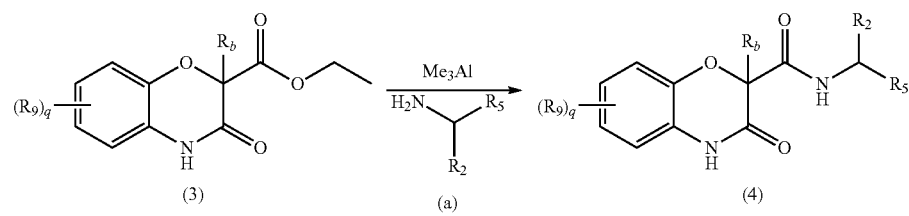

The compound of Formula (4), where $R_b$, $R_2$, $R_5$, $R_9$ and 'q' are as defined herein above can be prepared by following the procedure as depicted in Scheme-1.

The commercially available 2-aminophenol is reacted with ethyl 2,3-dibromo-propionate (*Journal of Heterocyclic Chemistry*, (2001), 38, 221-226) in the presence of base such as sodium carbonate, potassium carbonate or triethylamine to give the corresponding dihydro[1,4]-benzoxazines (2a) and (2b). Alternatively, the commercially available 2-aminophenol is reacted with diethyl 2-bromo-2-methyl malonate in the presence of base such as sodium carbonate, potassium carbonate or triethylamine to give compound of Formula (3). The compound of Formula (3) is further reacted with amine of Formula (a) in the presence of trimethyl aluminium to give compound of Formula (4).

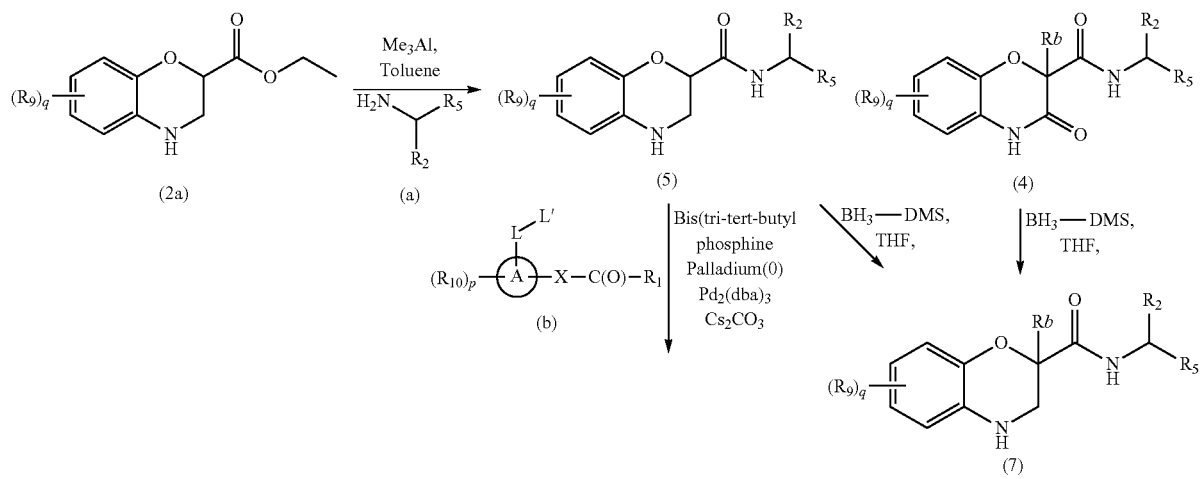

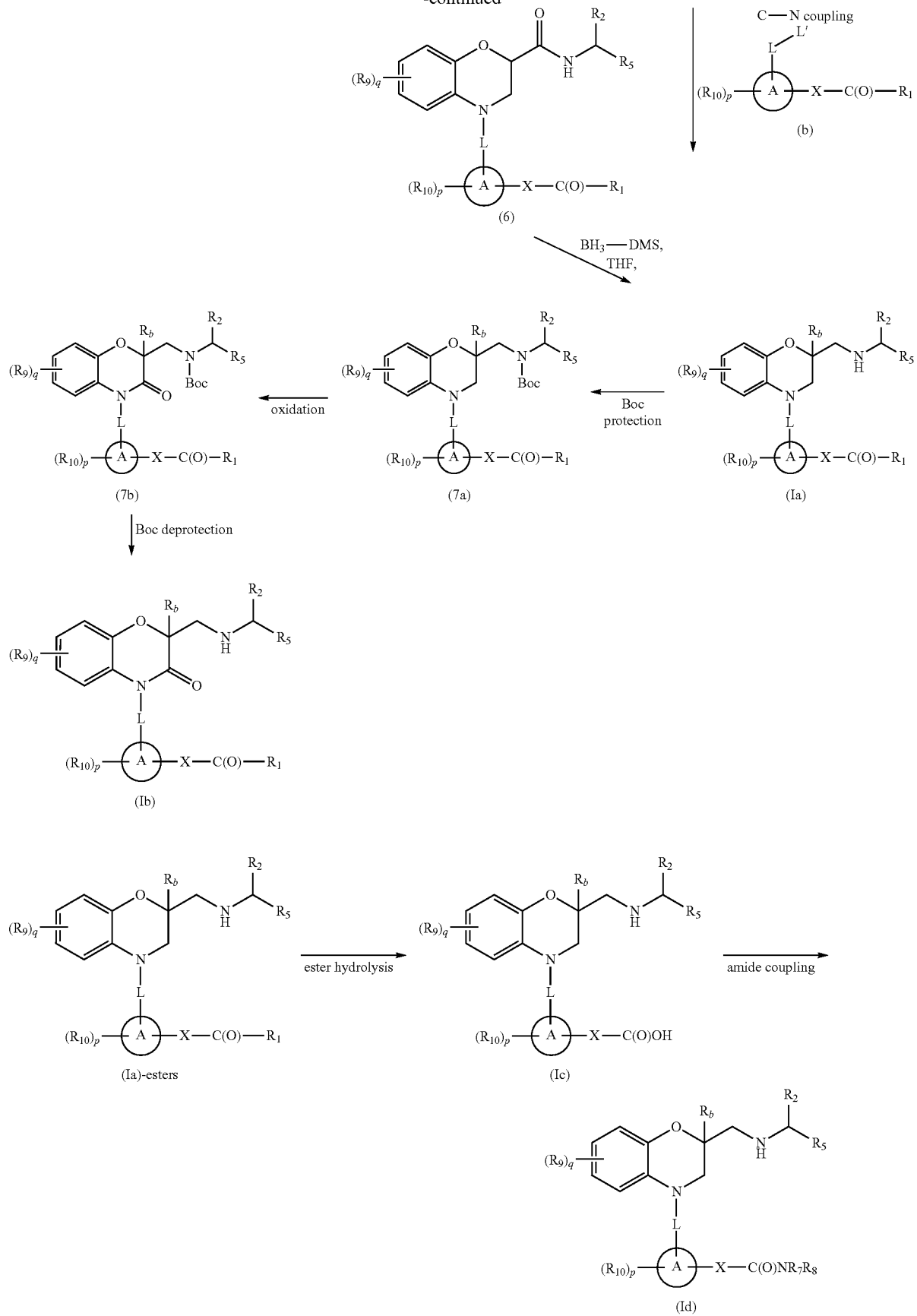

The compound of Formula (Ia), where ring A, L, X, $R_b$, $R_1$, $R_2$, $R_5$, $R_9$, $R_{10}$, 'p' and 'q' are defined herein above, can be prepared by following the procedure as depicted in Scheme-2. The compound of Formula (2a) is reacted with amine of Formula (a) in presence of trimethyl aluminium to obtain compound of Formula (5). This compound of Formula (5) undergoes carbon-nitrogen (C—N) coupling reaction with Formula (b) by following the methods known in the art for example Buchwald coupling reaction (when L is a bond) using suitable reagents known in the art, or the coupling reaction (when L is not a bond) is carried out by using suitable base for example TEA, DIPEA or $K_2CO_3$ etc., and in suitable solvent for example DCM, THF etc., to give compound of Formula (6). This compound of Formula (6) undergoes reduction using suitable reducing agents for example borane-dimethyl sulfide (*Journal of Medicinal Chemistry*, 1998, 46, 3142-3158) complex to give compound of Formula (Ia). This compound of Formula (Ia) undergoes Boc protection on nitrogen then oxidation with suitable oxidizing agent for example $KMnO_4$, in suitable solvent like acetonitrile, acetone; etc., to give compound of Formula (7b), This oxidized compound of Formula (7b) undergoes deprotection to give compound of Formula (Ib), if ester, which can be hydrolyzed to give corresponding acid derivative. Alternatively, the compound of Formula (Ia) is prepared from Formula (4) or Formula (5) by carrying out reduction reaction using suitable reducing agents such as $NaBH_4$, borane-dimethyl sulfide complex, $LiAlH_4$ etc., and in suitable solvent(s). This compound of Formula (7) undergoes carbon-nitrogen (C—N) coupling reaction with Formula (b) by following the methods known in the art for example Buchwald coupling reaction (when L is a bond) using suitable reagents known in the art, or the coupling reaction (when L is not a bond) is carried out by using suitable base for example TEA, DIPEA or $K_2CO_3$ etc., and in suitable solvent for example DCM, THF etc., to give compound of Formula (Ia).

Further, if these compound of formulae (Ia) and (Ib) are esters, can be hydrolyzed to give corresponding acid of Formula (Ic) using suitable base such as NaOH, LiOH, etc., and which further converted to amide of Formula (Id) by reacting with amines using suitable amide coupling agents such as DIPC, DCC, CDI, EDC etc., and the like.

Scheme-3

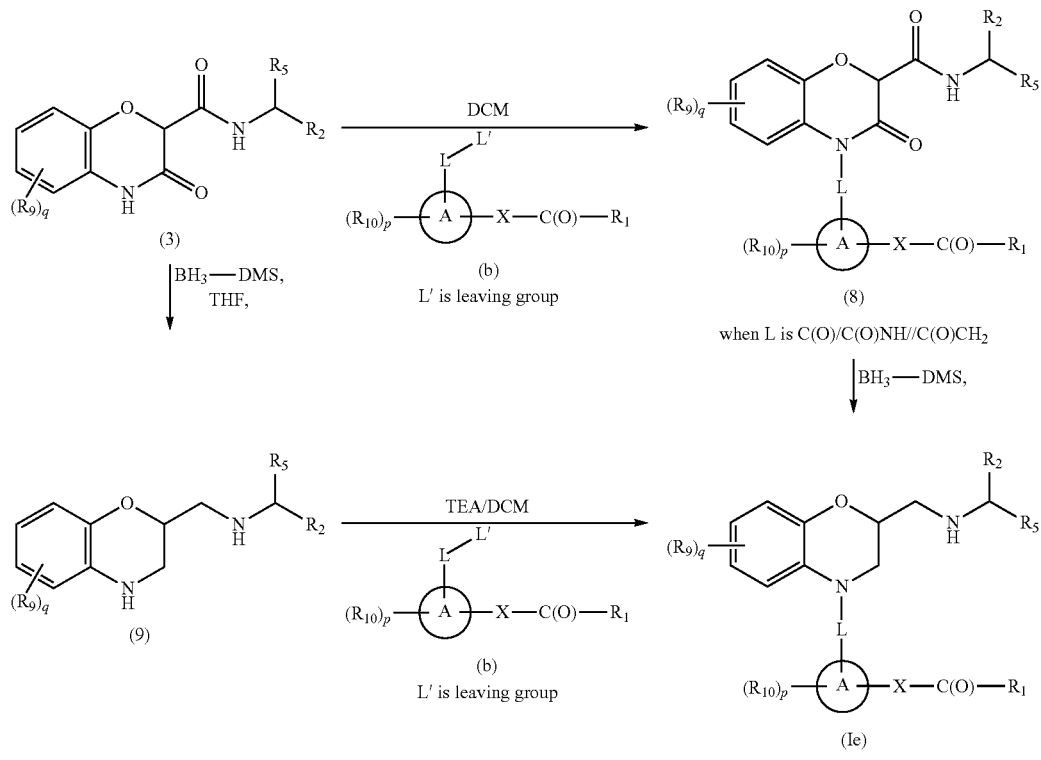

The compound of Formula (3) is reacted with Formula (b) in presence of suitable solvent for example DCM to give compound of Formula (8) which further undergoes reduction reaction using suitable reducing agents such as $NaBH_4$, borane-dimethyl sulfide complex, $LiAlH_4$ etc., (*Journal of Medicinal Chemistry*, (1998), 46, 3142-3158) to give compound of Formula (Ie) where ring A, X, $R_1$, $R_2$, $R_5$, $R_9$, $R_{10}$, 'p' and 'q' are defined herein above. Alternatively compound of Formula (3) undergoes reduction using suitable reducing to give compound of Formula (9) which further carried out C—N coupling reaction by using suitable base like triethyl amine in suitable solvent like DCM to give compound of Formula (Ie).

Scheme 4

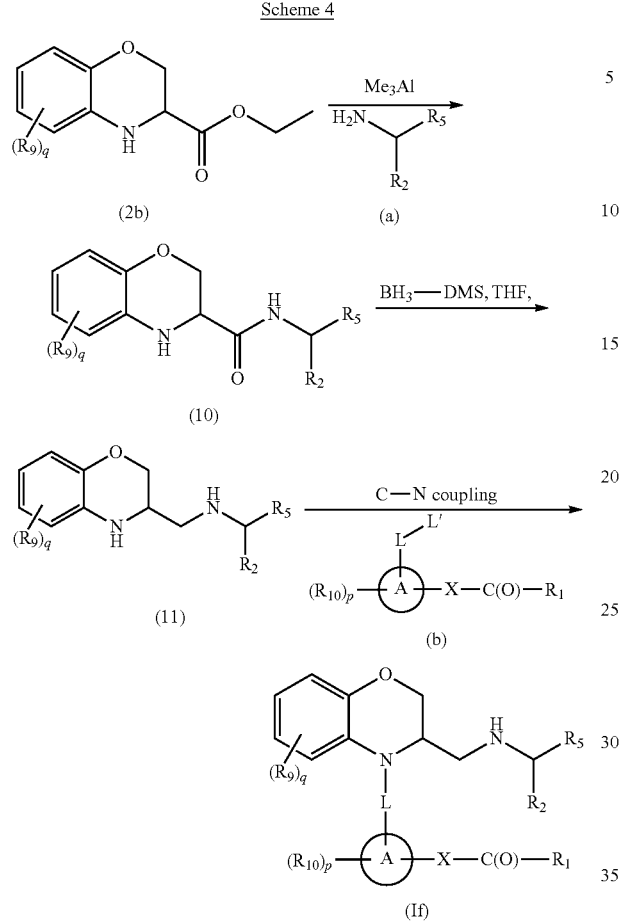

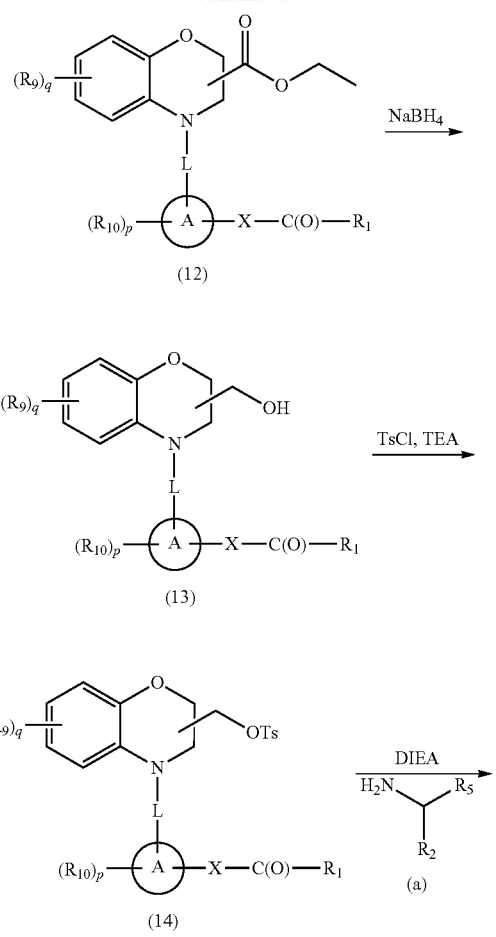

The compound of Formula (2b) is reacted with amine of Formula (a) in presence of trimethyl aluminium in suitable solvent such as toluene, THF etc., to obtain compound of Formula (10). The compound of Formula (15) undergoes reduction using borane-dimethyl sulfide (*Journal of Medicinal Chemistry*, (1998), 46, 3142-3158) to afford compound of Formula (11). This compound of Formula (11) undergoes carbon-nitrogen (C—N) coupling reaction with Formula (b) by following the methods known in the art for example Buchwald coupling reaction (when L is a bond) using suitable reagents known in the art, or the coupling reaction (when L is not a bond) carried out by using suitable base for example TEA, DIPEA or $K_2CO_3$ and in suitable solvent for example DCM, THF etc., to give compound of Formula (If) where ring A, L, X, $R_b$, $R_1$, $R_2$, $R_5$, $R_9$, $R_{10}$, 'p' and 'q' are defined herein above.

Scheme 5

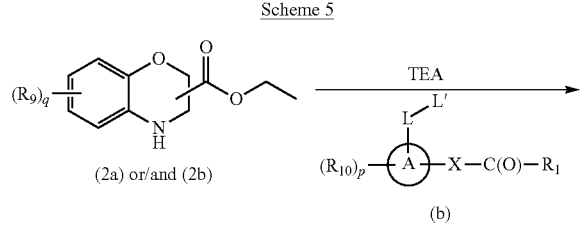

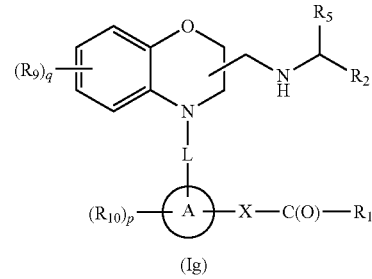

The compound of Formula (2a) or Formula (2b) is coupled with Formula (b) in presence of base for example triethylamine, to give compound of Formula (12). Reduction of the ester group in compound of Formula (12) by using suitable reducing agents for example sodium borohydride in suitable solvent for example alcohols or acetone etc., to afford compound of Formula (13), which further protected with p-toluene sulfonyl chloride in presence of base for example triethylamine to give corresponding O-tosylated compound of Formula (14). This compound of Formula (14) undergoes coupling reaction with amine of Formula (a) in basic conditions such as Hunig's base and in suitable solvent to give compound of Formula (Ig) ring A, X, $R_1$, $R_2$, $R_5$, $R_9$, $R_{10}$, 'p' and 'q' are defined herein above.

Scheme-6

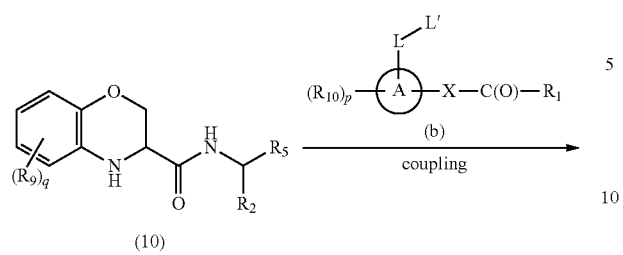

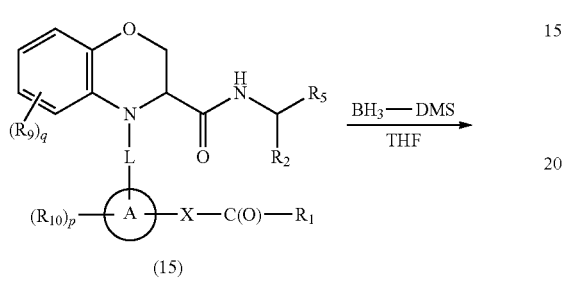

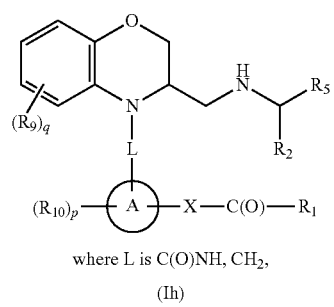

where L is C(O)NH, CH$_2$,
(Ih)

The compound of Formula (10) is reacted with Formula (b) in presence of suitable coupling agents and in suitable solvent to give compound of Formula (15) which further undergoes reduction with borane-dimethyl sulfide complex (*Journal of Medicinal Chemistry*, (1998), 46, 3142-3158) to give compound of Formula (Ih) ring A, X, R$_b$, R$_1$, R$_2$, R$_5$, R$_9$, R$_{10}$, 'p' and 'q' are defined herein above.

Scheme 7

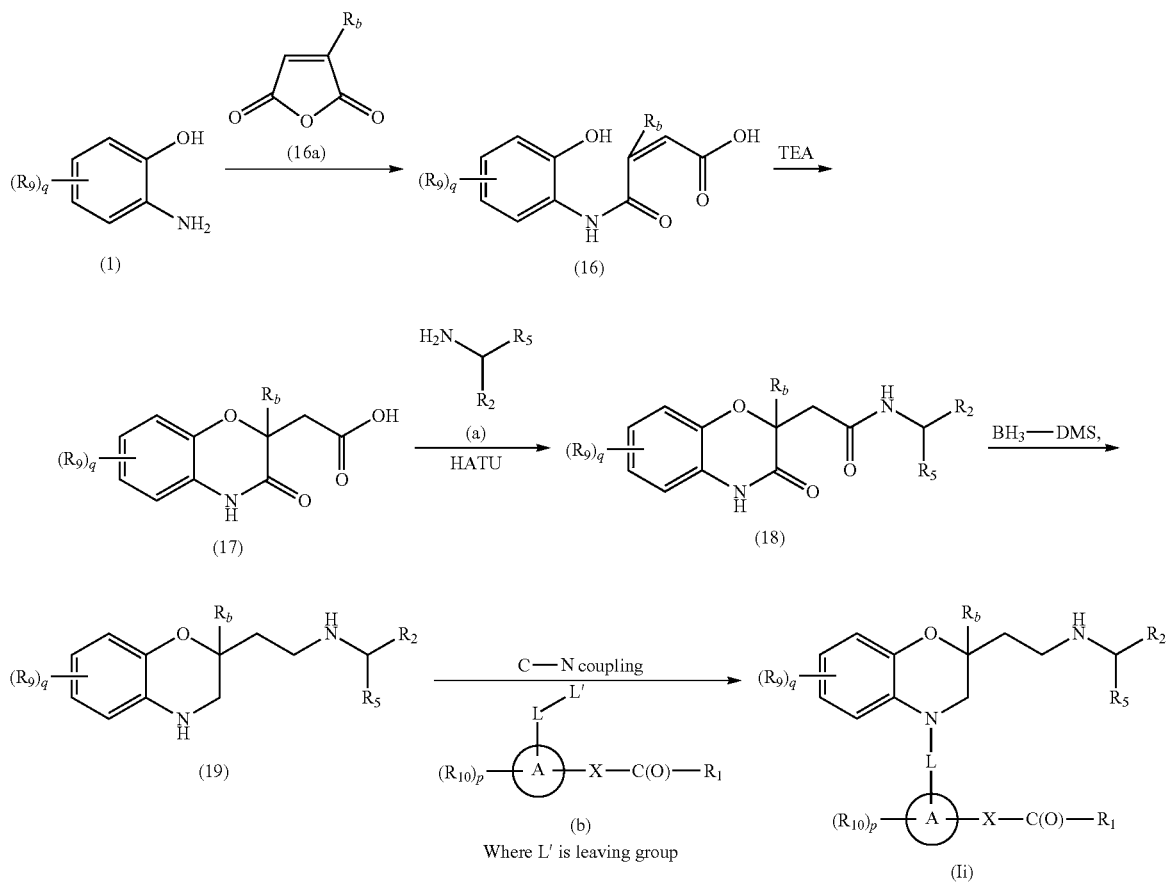

The Commercially available 2-aminophenol is reacted with maleic anhydride of Formula (16a) in suitable solvent for example toluene to give the corresponding 4-((2-hydroxyphenyl)amino)-4-oxobut-2-enoic acid (16). The compound of Formula (16) undergoes cyclisation to give compound of Formula (17) (*Aust. J. Chem.*, 1986, 39, 503-510). The compound of Formula (17) is reacted with Formula (a) in presence of suitable coupling reagent and in suitable solvent to give compound of Formula (18) which further undergoes reduction with borane-dimethyl sulfide complex (*Journal of Medicinal Chemistry*, (1998), 46, 3142-3158) to give compound of Formula (19). The compound of Formula (19) undergoes carbon-nitrogen (C—N) coupling reaction with Formula (b) by following the methods known in the art for example Buchwald coupling reaction (when L is a bond) using suitable reagents known in the art, or the coupling reaction (when L is not a bond) carried out by using suitable base for example TEA, DIPEA or $K_2CO_3$ etc., and in suitable solvent for example DCM, THF etc. to afford compound of Formula (Ii) ring A, L, X, $R_b$, $R_1$, $R_2$, $R_5$, $R_9$, $R_{10}$, 'p' and 'q' are defined herein above. If Formula (Ii) is an ester compound it can be hydrolyzed to give corresponding acid and further converted to corresponding amide by reacting with suitable amine using suitable amide coupling agents known in the art.

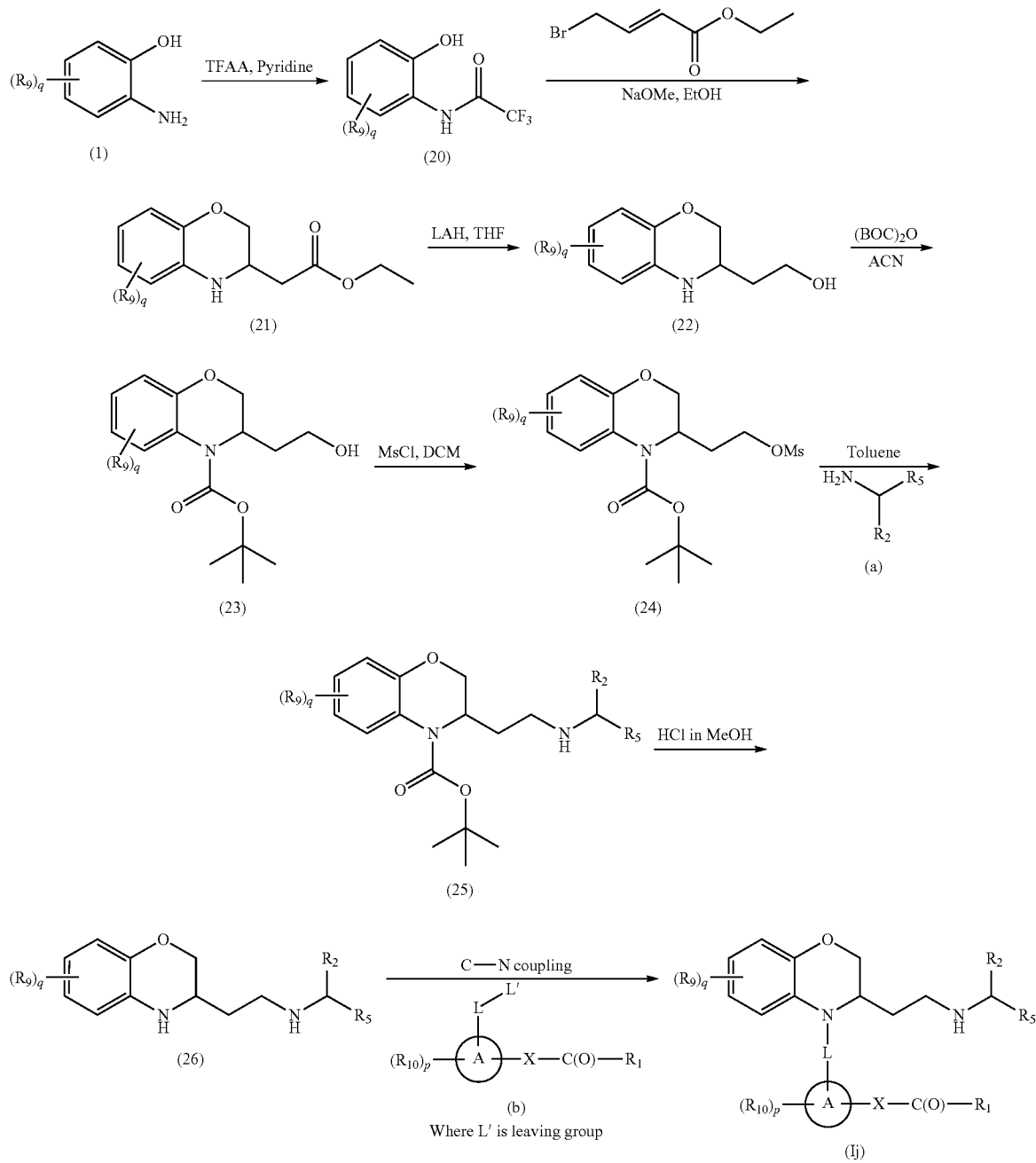

Scheme-8

The compound of Formula (Ij), ring A, L, X, $R_1$, $R_2$, $R_5$, $R_9$, $R_{10}$, 'p' and 'q' are defined herein above, can be prepared by following the procedure as depicted in Scheme-8. The commercially available 2-aminophenol is reacted with trifluoroacetic anhydride in presence of suitable base for example pyridine in suitable solvent for example ether (U.S. Pat. No. 5,550,125). A protected amide of Formula (20) is reacted with 4-bromo 2-butenoate in the presence of suitable base such as sodium methoxide, sodium ethoxide etc., and in suitable solvent to give corresponding ethyl 2-(3,4-dihydro-2H-benzo[b][1,4]oxazin-3-yl)acetate (21). The compound of Formula (21) is further reduced in presence of suitable reducing agents for example lithium aluminium hydride to obtain corresponding alcohol of Formula (22) which is Boc protected using (Boc)$_2$O in suitable solvent to give compound of Formula (23). The hydroxyl group in Formula (23) is protected with methane sulfonyl chloride in presence of triethylamine to give corresponding compound of Formula (24). This compound of Formula (24) undergoes coupling reaction with amine of Formula (a) in basic conditions such as Hunig's base to give compound of Formula (25) followed by deprotection of by using MeOH in HCl to give compound of Formula (26). The compound of Formula (26) undergoes carbon-nitrogen (C—N) coupling reaction with Formula (b) by following the methods known in the art for example Buchwald coupling reaction (when L is a bond) using suitable reagents known in the art, or the coupling reaction (when L is not a bond) carried out by using suitable base for example TEA, DIPEA or $K_2CO_3$ etc., and in suitable solvent for example DCM, THF etc. afford compound of Formula (Ij).

Experimental

The invention is further illustrated by the following examples which are provided merely to be exemplary of the invention and do not limit the scope of the invention. The examples set forth below demonstrate the synthetic procedures for the preparation of the representative compounds. Certain modifications and equivalents will be apparent to those skilled in the art and are intended to be included within the scope of the invention. The aforementioned patents and patent applications are incorporated herein by reference.

Intermediates

Intermediate-1a, 1b

Ethyl 3,4-dihydro-2H-benzo[b][1,4]oxazine-2-carboxylate (1a) and Ethyl 3,4-dihydro-2H-benzo[b][1,4]oxazine-3-carboxylate (1b)

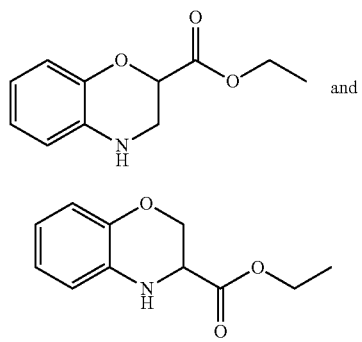

2-Aminophenol (68 g, 0.62 mol) was added to a mixture of (430 g, 3.11 mol) of potassium carbonate in DMF (1 L). The reaction mixture was stirred for 30 min at RT (room temperature) and then added ethyl 2, 3 dibromopropanoate (208 g, 0.80 mol) in dropwise manner. The reaction mixture was heated to 45° C. and further stirred for 15 h at the same temperature. The progress of reaction was monitored by TLC. Reaction mixture was filtered and the filtrate was poured into water. The mixture was extracted with diethyl ether. The organic layer was dried over $Na_2SO_4$ and concentrated to get oily product (108 g). The resultant brown color oily product was purified by flash chromatography on a silica gel column eluted with mixture of 5% ethylacetate in hexane to give compound of 1a (25 g) as an oily mass and compound of 1b was eluted in 3% ethylacetate in hexane as an oil (15 g); (m/z 208.1).

Intermediate-2

N—((R)-1-(3-Methoxyphenyl)ethyl)-3,4-dihydro-2H-benzo[b][1,4]oxazine-2-carboxamide

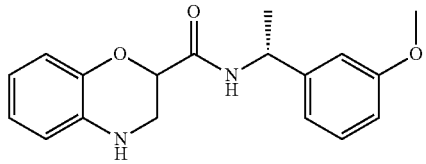 [SMILES: COc1cccc([C@@H](C)NC(=O)C2CNc3ccccc3O2)c1]

(R)-1-(3-Methoxyphenyl)ethanamine (1.46 g, 0.00966 mol) was taken in dry toluene (10 mL) under nitrogen atmosphere. This solution was heated to 50° C. and then added trimethyl aluminium (0.65 mL, 0.0072 mol, 2M solution in toluene). The reaction mixture was stirred for 15 min at the same temperature then slowly added a mixture of Intermediate-1a (1 g, 0.0048 mol) in toluene (10 mL). The reaction mixture was heated to 110° C. and maintained for 5 h. The progress of the reaction was monitored by TLC. The reaction was quenched with dilute HCl and the product extracted into ethylacetate. Organic layer was washed with water followed by brine solution. The organic layers were combined, dried over sodium sulfate and concentrated to get the crude compound. Further this crude compound was purified by flash chromatography by using mixture of ethylacetate/hexane to get the title compound (1.40 g, 92.71%). m/z 313.2.

Intermediate-3

N—((R)-1-(Naphthalen-1-yl)ethyl)-3,4-dihydro-2H-benzo[b][1,4]oxazine-2-carboxamide

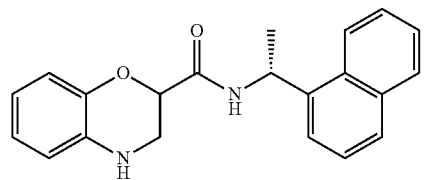 [SMILES: C[C@@H](NC(=O)C1CNc2ccccc2O1)c1cccc2ccccc12]

(R)-1-(Naphthalen-1-yl)ethanamine (1.65 g, 0.0096 mol) was taken in dry toluene (10 mL) under nitrogen atmosphere. This solution was heated to 50° C. and added trimethyl aluminium (0.65 mL, 0.0072 mol, 2M solution in toluene). The reaction mixture was stirred for 15 min at the same temperature then slowly added a mixture of Intermediate-1a (1 g, 0.0048 mol) in toluene (10 mL). The reaction mixture was heated to 110° C. and maintained for 5 h. The reaction progress was monitored by TLC. The reaction was quenched with dilute HCl and the product extracted with ethylacetate. Organic layer was washed with water followed by brine solution. The organic layers were combined, dried over sodium sulfate and concentrated to get the crude compound. Further this crude compound was purified by flash chromatography by using mixture of ethylacetate/hexane to get the title compound (1.45 g, 90.06%). m/z 333.2.

Intermediate-4

(1R)—N-((3,4-dihydro-2H-benzo[b][1,4]oxazin-2-yl)methyl)-1-(naphthalene-1yl) ethanamine

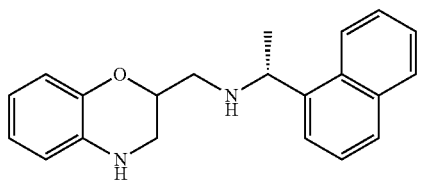 [SMILES: C[C@@H](NCC1CNc2ccccc2O1)c1cccc2ccccc12]

To a stirred solution of Intermediate-3 (6 g, 18.05 mmol) in dry THF (100 mL) borane dimethyl sulphide complex (8.57 ml, 90 mmol, 2M) was added at 0° C. then heated to 70° C. and further maintained for 12 h. Tetrahydrofuran was distilled off under vacuum. The reaction mass was cooled to 0° C. then methanol (15 mL) and dilute HCl (10 mL) were added. Heated the reaction mass to 50° C. and further stirred for 40 minutes at the same temperature to break borane complex. Methanol was distilled off under vacuum. The reaction mixture was cooled to 0° C. and basified with 2M NaOH solution (pH=10). The product was extracted into ethylacetate then the organic layer washed with water followed by brine solution. The organic layer dried over sodium sulphate and concentrated under vacuum to get the crude compound. Further this crude compound was purified by flash chromatography by using mixture of ethylacetate and hexane afforded the title compound as an oily mass (5.12 g, 89%). m/z 319.0.

Intermediate-5

Methyl 4-(2-(((R)-1-(3-methoxyphenyl)ethyl)carbamoyl)-2H-benzo[b][1,4]oxazin-4(3H)-yl)benzoate

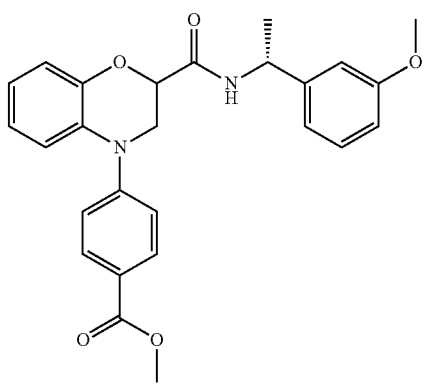 [SMILES: COC(=O)c1ccc(N2CC(C(=O)N[C@H](C)c3cccc(OC)c3)Oc3ccccc32)cc1]

To a mixture of Intermediate-2 (0.3 g, 1.0 mmol), methyl 4-bromobenzoate (0.26 g, 1.21 mmol) and $Cs_2CO_3$ (0.49 g, 1.51 mmol) in toluene (7 mL) was degassed for 15 minutes by purging nitrogen. Then, bis(tri-tert-butyl phosphine palladium (0) (0.026 g, 0.05 mmol) and tris dibenzylidene acetone dipalladium (0) (0.046 g, 0.05 mmol) were added to the reaction mixture. The reaction mixture was heated to 110° C. and further maintained for 20 h at the same temperature. The reaction mixture was cooled to RT and the progress of reaction monitored by TLC. The mixture was diluted with ethylacetate, filtered through celite and concentrated under vacuum to give crude compound. Further crude compound was purified by flash chromatography using a mixture of 15% ethylacetate in hexane to afford the title compound as oily mass (0.28 g 65%). m/z 447.2.

Intermediate-6

Methyl4-(2-(((R)-1-(naphthalen-1-yl)ethyl)carbamoyl)-2H-benzo[b][1,4]oxazin-4(3H)-yl)benzoate

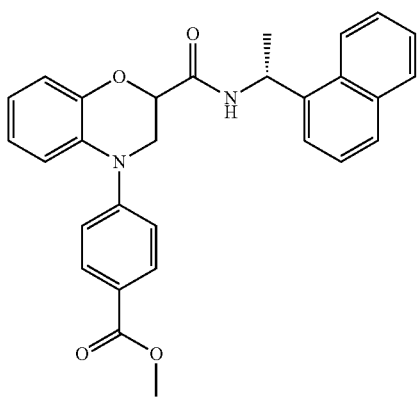 [SMILES: COC(=O)c1ccc(N2CC(C(=O)N[C@H](C)c3cccc4ccccc34)Oc3ccccc32)cc1]

To a mixture of Intermediate-3 (0.3 g, 0.94 mmol), methyl 4-bromobenzoate 0.24 g, 1.13 mmol), $Cs_2CO_3$ (0.46 g, 1.41 mmol) in toluene (7 mL) was degassed for 15 min by purging nitrogen. Then, bis(tri-tert-butylphosphine palladium (0) (0.024 g, 0.047 mmol) and tris dibenzylidene acetone dipalladium (0) (0.043 g, 0.047 mmol) were added to the reaction mixture. The reaction mixture was heated to 110° C. and further maintained for 20 h at the same temperature. The reaction mixture was cooled to RT and the progress of reaction monitored by TLC. The mixture was diluted with ethylacetate, filtered through celite and concentrated under vacuum to give crude compound. Further crude compound was purified by flash chromatography using a mixture of 15% ethylacetate in hexane to afford the title compound as oily mass (0.29 g 81%). m/z 467.1.

Intermediate-7

Ethyl 2-methyl-3-oxo-3,4-dihydro-2H-benzo[b][1,4]oxazine-2-carboxylate

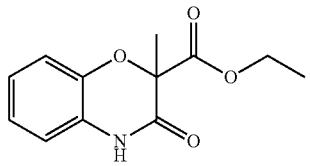 [SMILES: CCOC(=O)C1(C)Oc2ccccc2NC1=O]

2-Aminophenol (1 g, 9.16 mol) was added to a mixture of (1.6 g, 27.5 mmol) of potassium fluoride in DMF (10 mL). The reaction mixture was stirred for 30 min at RT and then added diethyl 2-bromo-2-methyl malonate (3.2 g, 11.91 mmol) in drop wise manner. The reaction mixture was heated to 45° C. and further stirred for 15 h at the same temperature. The progress of reaction was monitored by TLC. Reaction mixture was filtered and the filtrate was poured into water. The mixture was extracted with diethyl ether. The organic layer was dried over $Na_2SO_4$ and concentrated to get oily product. The resulting brown color oily product was purified by flash chromatography on a silica gel column using mixture of ethylacetate/hexane afforded the title compound as an oily mass (0.9 g, 42%). (M+H) (m/z 236.1).

Intermediate-8

2-Methyl-N—((R)-1-(Naphthalen-1-yl)ethyl)-3-oxo-3,4-dihydro-2H-benzo[b][1,4]oxazine-2-carboxamide

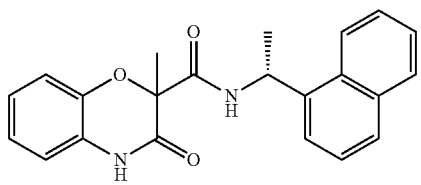 [SMILES: C[C@@H](NC(=O)C1(C)Oc2ccccc2NC1=O)c1cccc2ccccc12]

(R)-1-(Naphthalen-1-yl)ethanamine (0.3 g, 1.81 mmol) was taken in dry toluene (5 mL) under nitrogen atmosphere. This solution was heated to 50° C. and added trimethyl aluminium (0.68 mL, 1.36 mmol, 2M solution in toluene). The reaction mixture was stirred for 15 min at the same temperature then slowly added a mixture of Intermediate-7 (0.2 g, 0.90 mol) in toluene (5 mL). The reaction mixture was heated to 110° C. and maintained for 5 h. The reaction progress was monitored by TLC. The reaction was quenched with dilute HCl and the product extracted with ethylacetate. Organic layer was washed with water followed by brine solution. The organic layers were combined, dried over sodium sulfate and concentrated to get the crude compound. Further this crude compound was purified by flash chromatography using a mixture of ethylacetate/hexane afforded the title compound (0.25 g, 77%). m/z 361.2.

Intermediate-9

(1R)—N-((2-methyl-3,4-dihydro-2H-benzo[b][1,4]oxazin-2yl)methyl)-1-(Naphthalen-1-yl)ethyl)ethanamine

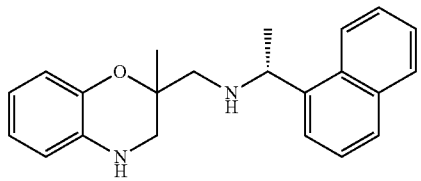 [SMILES: C[C@@H](NCC1(C)CNc2ccccc2O1)c1cccc2ccccc12]

The title compound was prepared by following the similar reduction procedure as described in Intermediate-4 by taking Intermediate-8 and borane dimethyl sulphide complex; m/z 333.5.

Intermediate-10

Ethyl 7-fluoro-3,4-dihydro-2H-benzo[b][1,4]oxazine-2-carboxylate

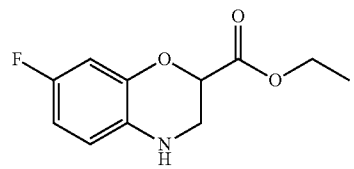 [SMILES: CCOC(=O)C1CNc2ccc(F)cc2O1]

The title compound was prepared by following the similar procedure as described in Intermediate-1a, 1b by taking 5-fluoro-2-amino phenol and ethyl 2, 3 dibromo propanoate; m/z 226.1.

Intermediate-11

7-Fluoro-N—((R)-1-(naphthalen-1-yl)ethyl)-3,4-dihydro-2H-benzo[b][1,4]oxazine-2-carboxamide

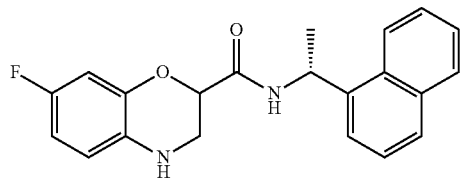 [SMILES: C[C@@H](NC(=O)C1CNc2ccc(F)cc2O1)c1cccc2ccccc12]

The title compound was prepared by following the similar procedure as described in Intermediate-3 by taking Intermediate-10 and (R)-1-(Naphthalen-1-yl)ethanamine; m/z 351.5.

Intermediate-12

(1R)—N-((7-Fluoro-3,4-dihydro-2H-benzo[b][1,4]oxazin-2-yl)methyl)-1-(naphthalen-1-yl)ethanamine

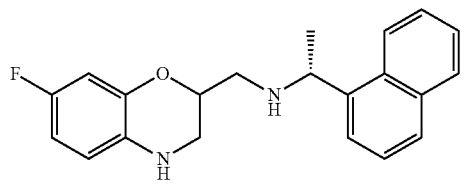 [SMILES: C[C@@H](NCC1CNc2ccc(F)cc2O1)c1cccc2ccccc12]

The title compound was prepared by following the similar reduction procedure as described in Intermediate-4 by taking Intermediate-11 and borane dimethyl sulphide complex; m/z 337.1.

Intermediate-13

Methyl3-(2-(((R)-1-(3-methoxyphenyl)ethyl)carbamoyl)-2H-benzo[b][1,4]oxazin-4(3H)-yl)benzoate

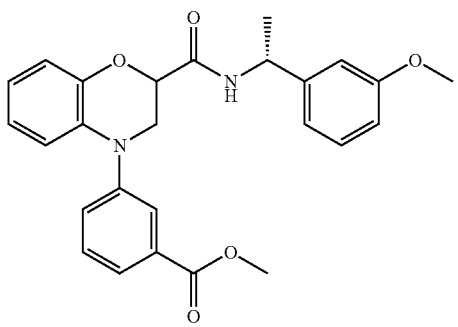 [SMILES: COC(=O)c1cccc(N2CC(C(=O)N[C@H](C)c3cccc(OC)c3)Oc3ccccc32)c1]

The title compound was prepared by following the similar coupling reaction procedure as described in Intermediate-5 by using Intermediate-2 and methyl 3-bromobenzoate. Mass (m/z): 447.2.

Intermediate-14

Methyl3-(2-(((R)-1-(naphthalen-1-yl)ethyl)carbamoyl)-2H-benzo[b][1,4]oxazin-4(3H)-yl)benzoate

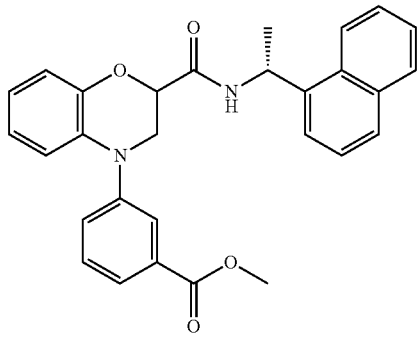 [SMILES: COC(=O)c1cccc(N2CC(C(=O)N[C@H](C)c3cccc4ccccc34)Oc3ccccc32)c1]

The title compound was prepared by following the similar coupling reaction procedure as described in Intermediate-6 by using Intermediate-3 and methyl 3-bromobenzoate; mass (m/z): 467.1.

Intermediate-15

4-((2-Hydroxyphenyl)amino)-4-oxobut-2-enoic acid

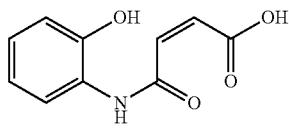 [SMILES: O=C(O)/C=C\C(=O)Nc1ccccc1O]

To a solution of maleic anhydride (8.99 g, 92 mmol) in toluene (100 mL) o-aminophenol (10 g, 92 mmol) was added at room temperature (RT) under stirring. Maintained the reaction mass for 3 h and the resulting solid was filtered to afford the title compound (13 g, 62%); m/z 208.1.

Intermediate-16

2-(3-Oxo-3,4-dihydro-2H-benzo[b][1,4]oxazin-2-yl)acetic acid

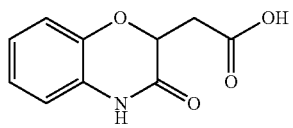 [SMILES: O=C(O)CC1Oc2ccccc2NC1=O]

To a stirred solution of Intermediate-15 (10 g, 48.3 mmol) in 1,4-dioxane (300 mL) triethylamine (20.18 mL, 145 mmol) was added in drop wise manner at RT. The reaction mixture was heated to reflux and further maintained for 12 h. After completion of reaction, solvent was evaporated under vacuum. Reaction mass was acidified with 2N HCl (300 ml) and extracted with ethylacetate (4×500 mL). Organic layer was washed with water, brine, dried over sodium sulfate, concentrated under vacuum to afford the title compound (10 g, 93%); m/z 208.2.

Intermediate-17

N—((R)-1-(Naphthalen-1-yl)ethyl)-2-(3-oxo-3,4-dihydro-2H-benzo[b][1,4]oxazin-2-yl)acetamide

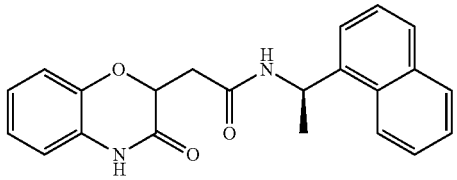 [SMILES: C[C@@H](NC(=O)CC1Oc2ccccc2NC1=O)c1cccc2ccccc12]

To a ice cold solution of Intermediate-16 (9.5 g, 45.9 mmol) in DCM (150 mL), DIPEA (16 mL, 92 mmol) and 2-(1H-7-Azabenzotriazol-1-yl)-1,1,3,3-tetramethyl uronium hexafluorophosphate Methanaminium (HATU) (20.9 g, 55 mmol) were added sequentially. To the reaction mass (R)-1-(naphthalen-1-yl)ethanamine (9.41 g, 55 mmol) in DCM (50 mL) was added slowly by dropping funnel. Reaction mass was then stirred at RT for 16 h. After completion of reaction the solid separated out was filtered and washed with ice cold DCM to get the title compound 12 g (85%); m/z 361.5.

Intermediate-18a, 18b 2-(3,4-Dihydro-2H-benzo[b][1,4]oxazin-2-yl)-N—((R)-1-(naphthalen-1-yl)ethyl) ethanamine

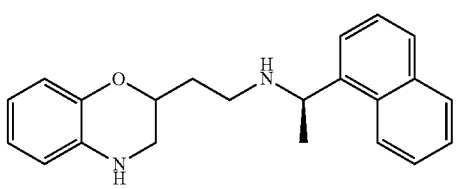 [SMILES: C[C@@H](NCCC1CNc2ccccc2O1)c1cccc2ccccc12]

To a mixture of Intermediate-17 (9 g, 0.75 mmol in dry THF (100 mL) borane dimethyl sulphide complex (39 mL, 78 mmol) was added at 0° C., then heated to 70° C. and maintained for 12 h. Tetrahydrofuran was distilled off under vacuum. Methanol (10 mL) and dilute HCl (15 mL) were added at 0° C. then heated to 50° C. and further stirred for 40 min to break borane complex. Methanol was distilled off under vacuum. The reaction mixture was cooled to 0° C. and basified with 2M NaOH solution [pH=10]. The product was extracted into ethylacetate then the organic layer washed with water followed by brine solution. The organic layer dried over sodium sulfate and concentrated under vacuum to get the racemic compound (7 g. 81%). Further, diastereomers were separated by chiral chromatography; CHIRAL PAK 1D, 250×4.6 MM 5 u; mobile phase: A: hexane/IPA (90:10, % v/v, 0.1% DEA) B: IPA (100%) A:B 80/20% V/V; flow is 1.0 ml/min.

m/z 333.1; a: $^1$H NMR (400 MHz, DMSO-d6): δ 8.27 (d, J=7.6 Hz, 1H), 7.94-7.93 (dd, J=2.4 Hz, J=7.2 Hz, 1H), 7.8 (d, J=8.4 Hz, 1H), 7.68 (d, J=6.4 Hz, 1H), 7.53-7.48 (m, 3H), 6.61 (m, 1H), 6.57-6.51 (m, 2H), 6.41 (m, 1H), 5.68 (bs, 1H), 4.58 (m, 1H), 4.06 (m, 1H), 3.21 (d, 1H), 2.90 (m, 1H), 2.62 (s, 2H), 1.78 (m, 1H), 1.69 (m, 1H), 1.38 (d, J=6.8 Hz, 3H); b: $^1$H NMR (400 MHz, DMSO-d6): δ 8.26 (m, 1H), 7.92 (m, 1H), 7.79 (d, J=8.0 Hz, 1H), 7.71 (d, J=6.4 Hz, 1H), 7.53-7.47 (m, 3H), 6.62 (dt, J=1.6 Hz and J=7.8 Hz, 1H), 6.53 (dt, J=1.2 Hz and J=8.2 Hz, 2H), 6.43 (dt, J=1.6 Hz and J=6.6 Hz, 1H), 5.70 (bs, 1H), 4.63 (m, 1H), 4.06 (m, 1H), 3.29 (d, J=12.0 Hz, 1H), 2.92 (m, 1H), 2.59 (m, 2H), 1.76 (m, 1H), 1.69 (m, 1H), 1.39 (d, J=6.8 Hz, 3H).

Intermediate-19

(Z)-4-((4-Fluoro-2-hydroxyphenyl)amino)-4-oxobut-2-enoic acid

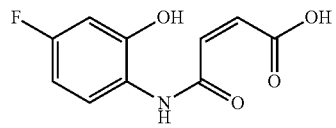 [SMILES: O=C(O)/C=C\C(=O)Nc1ccc(F)cc1O]

The title compound was prepared by following the similar procedure as described in Intermediate-15 by taking 5-fluoro 2-amino phenol and maleic anhydride; m/z 226.1.

Intermediate-20

2-(7-Fluoro-3-oxo-3,4-dihydro-2H-benzo[b][1,4]oxazin-2-yl)acetic acid

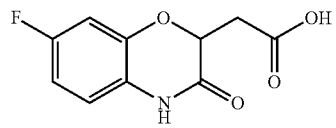 [SMILES: O=C(O)CC1Oc2cc(F)ccc2NC1=O]

The title compound was prepared by following the similar cyclisation procedure as described in Intermediate-16 by taking Intermediate-19 and triethylamine; m/z 226.1.

Intermediate-21

2-(7-Fluoro-3-oxo-3,4-dihydro-2H-benzo[b][1,4]oxazin-2-yl)-N-(1-(naphthalen-1-yl)ethyl)acetamide

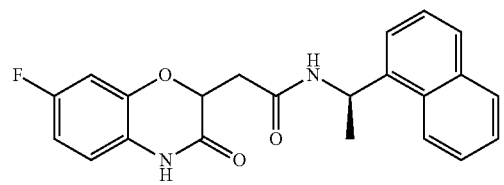 [SMILES: C[C@@H](NC(=O)CC1Oc2cc(F)ccc2NC1=O)c1cccc2ccccc12]

The title compound was prepared by following the similar procedure as described in Intermediate-17 by taking Intermediate-20 and (R)-1-(naphthalen-1-yl)ethanamine; m/z 379.5.

Intermediate-22

2-(7-Fluoro-3,4-dihydro-2H-benzo[b][1,4]oxazin-2-yl)-N-(1-(naphthalen-1 yl)ethyl) ethanamine

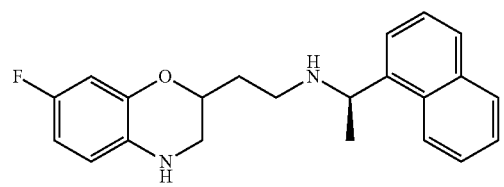 [SMILES: C[C@@H](NCCC1CNc2ccc(F)cc2O1)c1cccc2ccccc12]

The title compound was prepared by following the similar reduction procedure as described in Intermediate-18 by taking Intermediate-21 and borane dimethyl sulphide complex; m/z 351.2.

The below intermediates of 23 to 25 given in Table-1 were prepared in four steps:

Step-1: Reacting a fluoro substituted amino phenol with maleic anhydride by following the similar procedure as described in Intermediate-15;

Step-2: Cyclization of Step-1 intermediate using triethylamine by following the similar procedure as described in Intermediate-16

Step-3: Coupling of Step-2 intermediate with (R)-1-(naphthalen-1-yl)ethanamine by following the similar procedure as described in Intermediate-17

Step-4: Reduction of Step-3 intermediate using borane dimethyl sulphide complex by following the similar procedure as described in Intermediate-18

TABLE 1

| Intermediates | Structure | Chemical Name | Mass (m/z) |
|---|---|---|---|
| 23 | 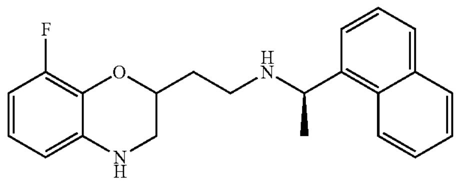 [SMILES: C[C@@H](NCCC1CNc2cccc(F)c2O1)c1cccc2ccccc12] | 2-(8-Fluoro-3,4-dihydro-2H-benzo[b][1,4]oxazin-2-yl)-N-((R)-1-(naphthalen-1-yl)ethyl)ethanamine | 351.2 |
| 24 | 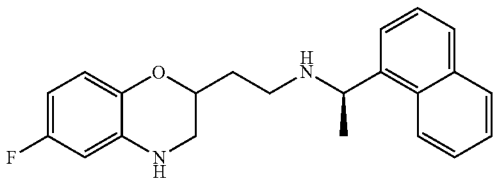 [SMILES: C[C@@H](NCCC1CNc2cc(F)ccc2O1)c1cccc2ccccc12] | 2-(6-Fluoro-3,4-dihydro-2H-benzo[b][1,4]oxazin-2-yl)-N-((R)-1-(naphthalen-1-yl)ethyl)ethanamine | 351.2 |
| 25 | 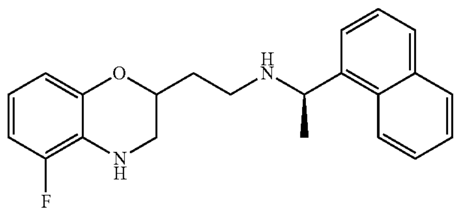 [SMILES: C[C@@H](NCCC1CNc2c(F)cccc2O1)c1cccc2ccccc12] | 2-(5-Fluoro-3,4-dihydro-2H-benzo[b][1,4]oxazin-2-yl)-N-((R)-1-(naphthalen-1-yl)ethyl)ethanamine | 351.2 |

Intermediate-26

(1R)—N-((3,4-dihydro-2H-benzo[b][1,4]oxazin-2-yl)methyl)-1-(4-fluoro-3-methoxy phenyl)ethanamine

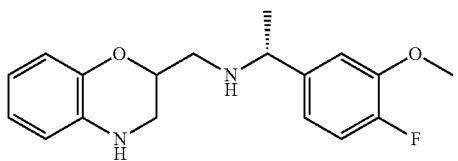 [SMILES: COc1cc([C@@H](C)NCC2CNc3ccccc3O2)ccc1F]

The title compound was prepared by following the similar procedure as described in Intermediate-3 by taking Intermediate-1a and corresponding (R)-1-(4-fluoro-3-methoxyphenyl)ethanamine followed by similar reduction procedure as described in Intermediate-4 by using borane dimethyl sulphide complex; m/z 317.1.

Intermediate-27

4-((2-Hydroxyphenyl)amino)-3-methyl-4-oxobut-2-enoic acid

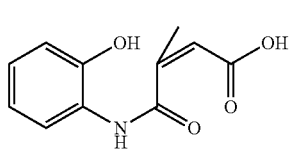 [SMILES: C/C(=C/C(=O)O)C(=O)Nc1ccccc1O]

The title compound was prepared by following the similar procedure as described in Intermediate-15 by taking 2-amino phenol with 3-methylfuran-2,5-dione; m/z 222.1.

Intermediate-28

2-(2-Methyl-3-oxo-3,4-dihydro-2H-benzo[b][1,4]oxazin-2-yl)acetic acid

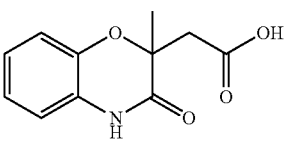 [SMILES: CC1(CC(=O)O)Oc2ccccc2NC1=O]

The title compound was prepared by following the similar cyclization procedure as described in Intermediate-16 by taking Intermediate-27 and triethylamine; m/z 222.1.

Intermediate-29

2-(2-Methyl-3-oxo-3,4-dihydro-2H-benzo[b][1,4]oxazin-2-yl)-N-(1-(naphthalen-1-yl)ethyl)acetamide

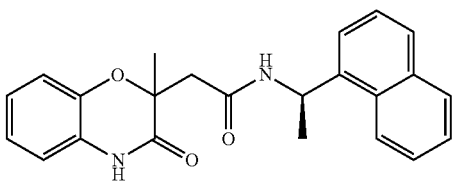 [SMILES: C[C@@H](NC(=O)CC1(C)Oc2ccccc2NC1=O)c1cccc2ccccc12]

The title compound was prepared by following the similar coupling reaction procedure as described in Intermediate-17 by taking Intermediate-28 and (R)-1-(naphthalen-1-yl) ethanamine; m/z 375.5.

Intermediate-30

2-(2-Methyl-3,4-dihydro-2H-benzo[b][1,4]oxazin-2-yl)-N-(1-(naphthalen-1-yl)ethyl) ethanamine

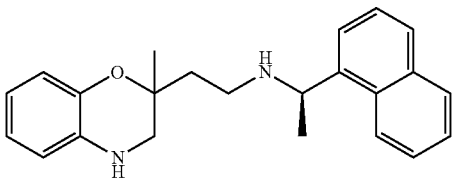 [SMILES: C[C@@H](NCCC1(C)CNc2ccccc2O1)c1cccc2ccccc12]

The title compound was prepared by following the similar reduction procedure as described in Intermediate-18 by taking Intermediate-29 and borane dimethyl sulphide complex; m/z 347.5.

Intermediate-31

2-(3,4-Dihydro-2H-benzo[b][1,4]oxazin-2-yl)-N—((S)-1-(naphthalen-1-yl)ethyl) ethanamine

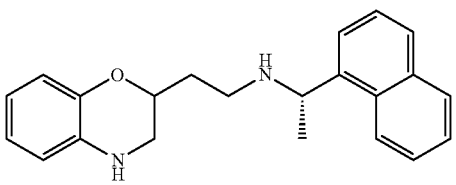 [SMILES: C[C@H](NCCC1CNc2ccccc2O1)c1cccc2ccccc12]

The title compound was prepared in two steps:
Step-1: Condensation reaction of Intermediate-16- with (S)-1-(naphthalen-1-yl) ethanamine by following the similar procedure as described in intermediate-17;
Step-2: Reduction of step-1 intermediate with borane dimethyl complex by following similar procedure as described in Intermediate-18; m/z 333.5.

EXAMPLES

Example-1

Methyl4-(2-((((R)-1-(3-methoxyphenyl)ethyl)amino)methyl)-2H-benzo[b][1,4]oxazin-4(3H)-yl)benzoate hydrochloride

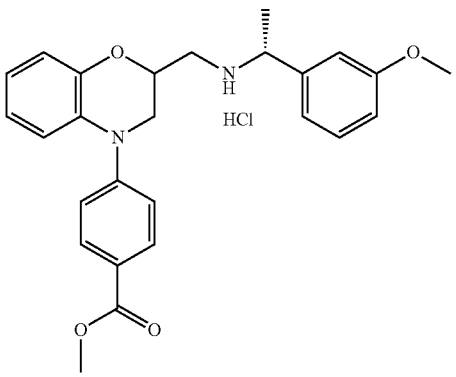 [SMILES: COC(=O)c1ccc(N2CC(CN[C@H](C)c3cccc(OC)c3)Oc3ccccc32)cc1 ; Cl]

To a stirred solution of Intermediate-5 (0.5 g) in dry THF (10 mL) borane dimethyl sulphide complex (0.17 mL) was added at 0° C. then heated to 70° C. and further maintained for 12 h. Tetrahydrofuran was distilled off under vacuum. Methanol (5 mL) and dilute HCl (5 mL) was added at 0° C. then heated to 50° C. and further stirred for 40 minutes to break borane complex. Methanol was distilled off under vacuum. The reaction mixture was cooled to 0° C. and basified with 2M NaOH solution (pH=10]. The product was extracted into ethylacetate then the organic layer washed with water followed by brine solution. The organic layer dried over sodium sulphate and concentrated under vacuum to get the racemic compound. This crude product was purified by flash chromatography using a mixture of 15% ethylacetate/hexane.
Preparation of Hydrochloride Salt(s) of the Amino Examples
Amino compound was dissolved in dry DCM, then slowly added 2M ethereal HCl solution and stirred for 10 min. The solvent was evaporated and the resultant solid washed with diethyl ether followed by n-pentane to give hydrochloride salt of the desired compound (0.3 g, 61.9%).
m/z 433.1; $^1$H NMR (400 MHz, CDCl$_3$): δ9.47 (bs, 1H), 7.9 (m, 2H), 7.32 (m, 1H), 7.23 (m, 2H), 7.13-7.10 (m, 2H), 7.04-7.00 (m, 2H), 6.96-6.94 (m, 2H), 6.81 (m, 1H), 4.43 (m, 1H), 4.05 (m, 1H), 3.82 (m, 3H), 3.53-3.48 (m, 2H), 3.02-3.01 (m, 2H), 1.59 (m, 3H).

Example-2a, 2b

Methyl4-(2-((((R)-1-(naphthalene-1-yl)ethyl)amino)methyl)-2H-benzo[b][1,4]oxazin-4(3H)-yl)benzoate hydrochloride

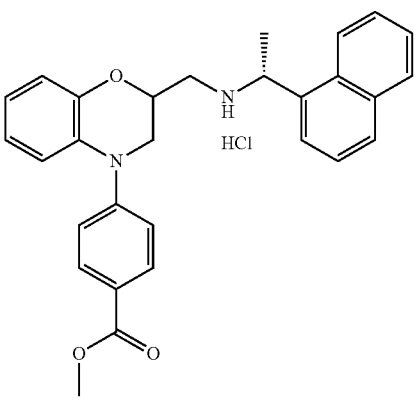 [SMILES: COC(=O)c1ccc(N2CC(CN[C@H](C)c3cccc4ccccc34)Oc3ccccc32)cc1 ; Cl]

The title compound was prepared by following the similar reduction procedure as described in Example-1 by taking Intermediate-6 and borane dimethyl sulphide complex. The diastereomers were separated by flash chromatography using a mixture of 20% ethylacetate/hexane. m/z 453.1;
Further, HCl salts of these isomers were prepared by following the similar HCl salt procedure as described in Example-1.
2a: $^1$H NMR (400 MHz, DMSO-d6): δ 11.60 (bs, 1H), 9.13 (bs, 1H), 8.10 (m, 1H), 7.93-7.82 (m, 3H), 7.65 (d, J=8 Hz, 1H), 7.56-7.45 (m, 3H), 7.16 (m, 1H), 6.86-6.81 (m, 2H), 6.75-666 (m, 3H), 5.20 (m, 1H), 5.01 (m, 1H), 3.89 (s, 3H), 3.55-3.50 (m, 1H), 3.48-3.45 (m, 1H), 3.01 (m, 1H), 2.81 (m, 1H), 2.01 (m, 3H);

2b: $^1$H NMR (400 MHz, DMSO-d6): δ 10.56 (bs, 1H), 8.11 (m, 1H), 7.92-7.90 (m, 2H), 7.86 (d, J=8.4, 1H), 7.80-7.75 (m, 2H), 7.55-7.52 (m, 3H), 6.93-6.84 (m, 4H), 6.79-6.70 (m, 2H), 5.46 (m, 1H), 5.06 (m, 1H), 3.87 (s, 3H), 3.63 (s, 1H), 3.50-3.45 (m, 1H), 3.32 (m, 1H), 3.00 (m, 1H), 2.04 (m, 3H).

Example-3a, 3b

Methyl3-(2-((((R)-1-(3-methoxyphenyl)ethyl)amino)methyl)-2H-benzo[b][1,4]oxazin-4(3H)-yl)benzoate hydrochloride

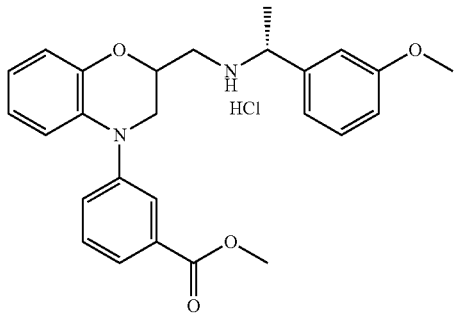 [SMILES: COC(=O)c1cccc(N2CC(CN[C@H](C)c3cccc(OC)c3)Oc3ccccc32)c1 ; Cl]

The title compound was prepared in two steps:
Step-1: To a mixture of Intermediate-2 (0.5 g, 0.96 mmol) and methyl 3-bromo benzoate (0.23 g, 1.06 mmol) Cs$_2$CO$_3$ (0.47 g, 1.44 mmol) in toluene (7 mL) was degassed for 15 minutes by purging nitrogen. Then bis(tri-tert-butyl phosphine palladium(0) (0.025 g, 0.048 mmol) and tris dibenzylideneacetone dipalladium (0) (0.044 g, 0.048 mmol) were added. The reaction mixture was heated to 110° C. and further maintained for 20 h at the same temperature. The reaction mixture was cooled to RT and progress of reaction monitored by TLC. The mixture was diluted with ethylacetate, filtered through celite, and concentrated under vacuum to get the crude compound. Further diastereomers were separated by flash chromatography using a mixture of 15% ethylacetate in hexane to get the title compounds as oily mass, isomer-a and isomer-b (0.18 g, 0.22 g, 80%).
Step-2: To a stirred solution of step-1 isomer-a (0.4 g, 093 mmol) in dry THF (10 mL) borane dimethyl sulphide complex (0.93 mL, 1.86 mmol) was added at 0° C. then heated to 70° C. and further maintained for 12 h. Tetrahydrofuran was distilled off under vacuum. Methanol (5 mL) and dilute HCl (5 mL) was added at 0° C. then heated to 50° C. and further stirred for 40 minutes to break borane complex. Methanol was distilled off under vacuum. The reaction mixture was cooled to 0° C. and basified with 2M NaOH solution (pH=10]. The product was extracted into ethylacetate then the organic layer washed with water followed by brine solution. The organic layer was dried over sodium sulphate and concentrated under vacuum to get the crude product. This crude product was further purified by flash chromatography using a mixture of 15% ethylacetate in hexane. Further hydrochloride salt of this amino compound was prepared by following the similar HCl salt procedure as described in Example-1 (0.25 g, 64.4%). Similarly, Example-3b was prepared by taking isomer-b.

Similarly, Racemic compound of Example-3 was also prepared using the above procedure.

m/z −433.2: Example-3a: $^1$H NMR (400 MHz, CDCl$_3$): δ 9.47 (bs, 1H), 7.9 (m, 2H), 7.32 (m, 1H), 7.23 (m, 2H), 7.13-7.10 (m, 2H), 7.04-7.00 (m, 2H), 6.96-6.94 (m, 2H), 6.81 (m, 1H), 4.43 (m, 1H), 4.05 (m, 1H), 3.82 (m, 3H), 3.53-3.48 (m, 2H), 3.02-3.01 (m, 2H), 1.59 (m, 3H);

Example-3b: $^1$H NMR (400 MHz, CDCl$_3$): δ 7.82 (m, 1H), 7.71-7.69 (m, 1H), 7.38-7.36 (m, 2H), 7.21 (m, 1H), 6.92-6.88 (m, 2H), 6.78-6.85 (m, 2H), 6.79-6.74 (m, 3H), 4.25 (m, 1H), 3.90 (m, 3H), 3.3.79 (m, 3H), 3.78-3.70 (m, 1H), 3.68-3.46 (m, 2H), 2.83-2.62 (m, 2H), 1.36-1.34 (m, 3H);

Example-4

Methyl 3-(2-((((R)-1-(naphthalen-1-yl)ethyl)amino)methyl)-2H-benzo[b][1,4]oxazin-4(3H)-yl)benzoate hydrochloride

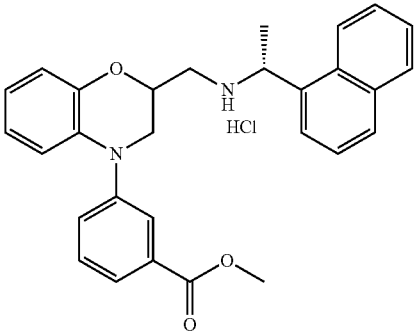 [SMILES: COC(=O)c1cccc(N2CC(CN[C@H](C)c3cccc4ccccc34)Oc3ccccc32)c1 ; Cl]

The title compound was prepared in two steps:
Step-1: To a mixture solution of Intermediate-3 (0.3 g, 0.90 mmol) and methyl 3-bromo benzoate (0.21 g, 0.99 mmol), Cs$_2$CO$_3$ (0.44 g, 1.35 mmol) in toluene (7 mL) was degassed for 15 min by purging nitrogen. Then bis(tri-tert-butylphosphine palladium (0) (0.023 g, 0.045 mmol) and tris dibenzylidene acetone dipalladium (0) (0.041 g, 0.045 mmol) were added. The reaction mixture was heated to 110° C. and further maintained for 20 h at the same temperature. The reaction mixture was cooled to room temperature and progress of reaction monitored by TLC. The mixture was diluted with ethylacetate, filtered through celite and concentrated under vacuum to get crude compound. Further, this crude compound was purified by flash chromatography using a mixture of 15% ethylacetate in hexane afforded the title compound as an oily mass (0.24 g, 81.43%); m/z 410.2
Step-2: To a stirred solution of step-1 intermediate (0.16 g, 0.35 mmol) in dry THF (10 mL) borane dimethyl sulphide complex (0.35 mL, 0.071 mmol) was added at 0° C. then heated to 70° C. and further maintained for 12 h. Tetrahydrofuran was distilled off under vacuum. Methanol (5 mL) and dilute HCl (5 mL) was added at 0° C. then heated to 50° C. and further stirred for 40 minutes to break borane complex. Methanol was distilled off under vacuum. The reaction mixture was cooled to 0° C. and basified with 2M NaOH solution (pH=10]. The product was extracted into ethylacetate then the organic layer washed with water followed by brine solution. The organic layer dried over sodium sulphate and concentrated under vacuum to get the crude compound. This crude compound was purified by flash chromatography using a mixture of 15% ethylacetate in hexane. Further hydrochloride salt of this amino compound was prepared by following the similar HCl salt procedure as described in Example-1 (0.09 g, 61.9%).

m/z 453.21: ¹H NMR (400 MHz, DMSO-D6): δ10.2 (bs, 1H), 9.9 (bs, 1H), 9.57 (bs, 1H), 9.35 (bs, 1H), 8.21 (m, 1H), 8.00-7.99 (m, 3H), 7.70-7.58 (m, 5H), 7.49-7.44 (m, 2H), 7.39 (m, 1H), 6.97-6.85 (m, 1H), 6.83-6.78 (m, 2H), 5.45 (m, 1H), 4.63 (m, 1H), 3.95 (d, J=2 Hz, 1H), 3.83 (s, 3H), 3.54-3.49 (m, 1H), 3.22 (m, 1H), 3.04 (m, 1H), 1.72 (s, 3H)

Example-5

4-(2-((((R)-1-(3-Methoxyphenyl)ethyl)amino)methyl)-2H-benzo[b][1,4]oxazin-4(3H)-yl)benzoic acid

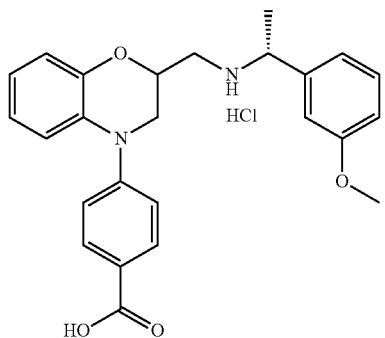 [SMILES: COc1cccc([C@@H](C)NCC2CN(c3ccc(C(=O)O)cc3)c3ccccc3O2)c1 ; Cl]

To a mixture solution of Example-1 (0.2 g, 0.46 mmol) in MeOH (5 mL) and water (2 mL) lithium hydroxide monohydrate was added (0.094 g, 2.31 mmol). The reaction mixture was heated to 80° C. and further maintained for 1 h. The progress of reaction was monitored by TLC. Methanol was distilled off under vacuum and cooled to 0° C. then acidified with dilute HCl solution [pH=3 to 4]. Extract the product with ethyl acetate (10 mL×2), washed with water (5 mL×2) followed by brine solution (5 mL), dried over sodium sulfate and concentrated under vacuum to get solid. Further hydrochloride salt of this amino compound was prepared by following the similar HCl salt procedure as described in Example-1 (0.18 g, 93.46%); m/z 419.32;

¹H NMR (400 MHz, DMSO-D6): δ12.7 (bs, 1H), 9.9 (bs, 1H), 9.6 (bs, 1H), 9.2 (bs, 1H), 7.9 (m, 2H), 7.32 (m, 1H), 7.20-7.15 (m, 3H), 7.10-7.01 (m, 2H), 6.99-6.89 (m, 3H), 6.86-6.81 (m, 1H), 4.52 (m, 1H), 4.41 (m, 1H), 4.03 (m, 1H), 3.72 (m, 3H), 3.54-3.45 (m, 1H), 3.16 (m, 1H), 3.02 (m, 1H), 2.80 (m, 1H), 1.60 (d, J=8 Hz, 3H).

Example-6

4-(2-((((R)-1-(Naphthalen-1-yl)ethyl)amino)methyl)-2H-benzo[b][1,4]oxazin-4(3H)-yl)benzoic acid hydrochloride

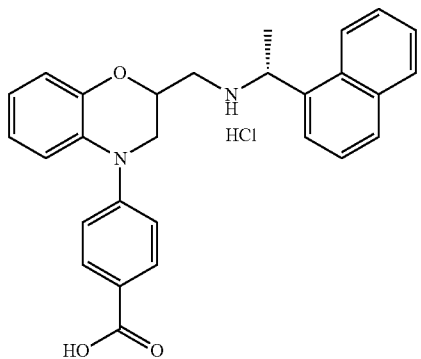 [SMILES: C[C@@H](NCC1CN(c2ccc(C(=O)O)cc2)c2ccccc2O1)c1cccc2ccccc12 ; Cl]

To a solution of racemic compound of Example-2 (0.2 g, 0.44 mmol) in MeOH (5 mL) and water (2 mL) lithium hydroxide monohydrate (0.092 g, 2.31 mmol) was added. The reaction mixture was heated to 50° C. and further maintained for 1 h. The progress of reaction was monitored by TLC. Methanol was distilled off under vacuum then cooled to 0° C. and acidified with dilute HCl solution [pH=3 to 4]. Extracted the product into Ethyl acetate (10 mL×2), washed with water (5 mL×2) followed by brine solution (5 mL), dried over sodium sulfate and concentrated under vacuum to get solid compound. Further, hydrochloride salt of this amino compound was prepared by following the similar HCl salt procedure as described in Example-1. (0.19 g, 98.04%). m/z 439.2;

¹H NMR (400 MHz, DMSO-d6): δ 12.7 (bs, 1H), 10.01 (bs, 1H), 9.8 (bs, 1H), 9.5 (bs, 1H), 9.3 (bs, 1H), 8.2 (m, 1H), 8.03-7.98 (m, 2H), 7.91-7.80 (m, 3H), 7.63-7.58 (m, 3H), 7.20 (m, 1H), 7.09-7.03 (m, 2H), 6.97-6.90 (m, 2H), 6.86-6.83 (m, 1H), 5.43 (m, 1H), 4.59 (m, 1H), 4.05-4.00 (m, 1H), 3.55-3.48 (m, 1H), 3.21 (m, 1H), 3.01 (m, 1H), 1.71 (d, J=6.4 Hz, 3H).

Example-7

4-(2-((((R)-1-(3-Methoxyphenyl)ethyl)amino)methyl)-2H-benzo[b][1,4]oxazin-4(3H)-yl)-N,N-dimethylbenzamide

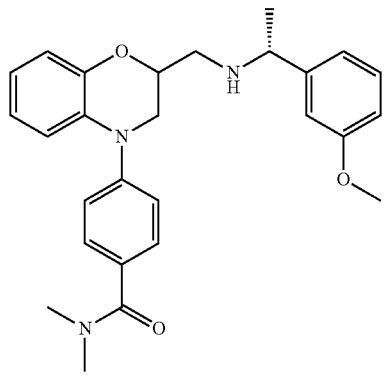 [SMILES: COc1cccc([C@@H](C)NCC2CN(c3ccc(C(=O)N(C)C)cc3)c3ccccc3O2)c1]

To a solution of Example-5 (0.1 g, 0.24 mmol) in dry DMF (5 mL), 1,1'-carbonyldiimidazole (0.048 g, 0.3 mmol) was added. The reaction mixture was stirred at room temperature for 2 hr then added dimethylamine (0.25 mL, 0.48 mmol, 2M solution in THF). The reaction mixture was stirred at room temperature for overnight. The progress of reaction was monitored by TLC. Product extracted with diethyl ether (10 mL×2). Organic layer was washed with water (5 mL) followed by brine (5 mL) solution. The organic layer was dried over sodium sulfate and concentrated under vacuum. This crude compound was purified by preparative HPLC to give title compound of 0.045 g as solid. m/z 446.2.

¹H NMR (400 MHz, DMSO-d6): δ 7.41-7.40 (m, 2H), 7.39-7.16 (m, 3H) 7.06-7.03 (m, 1H), 6.94-6.77 (m, 6H), 4.25 (m, 1H), 3.81 (m, 3H), 3.77 (m, 2H), 3.68-3.46 (m, 1H), 3.46 (m, 6H), 2.80-2.50 (m, 3H), 1.38 (m, 3H)

Example-8

N,N-Dimethyl-4-(2-((((R)-1-(naphthalen-1-yl)ethyl)amino)methyl)-2H-benzo[b][1,4]oxazin-4(3H)-yl)benzamide

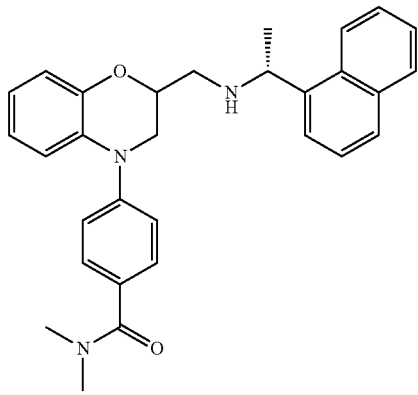 [SMILES: C[C@@H](NCC1CN(c2ccc(C(=O)N(C)C)cc2)c2ccccc2O1)c1cccc2ccccc12]

To a solution of Example-6 (0.1 g, 0.23 mmol) in dry DMF (5 mL), 1,1'-carbonyldiimidazole (0.046 g, 0.29 mmol) was added. The reaction mixture was stirred at RT for 2 hr. Dimethylamine (DEA) in THF 2M (0.23 mL, 0.46 mmol) was added to the reaction mixture. The reaction mixture was stirred at room temperature for overnight. The progress of reaction was monitored by TLC and diluted with diethyl ether and the organic layer washed with water followed by brine solution. The organic layer was dried over sodium sulfate and concentrated under vacuum. The crude compound was purified by preparative HPLC to give title compound of 0.045 g as solid. m/z 466.1;

$^1$H NMR (400 MHz, DMSO-d6): δ 8.2 (m, 1H), 7.9 (m, 1H) 7.75 (m, 1H), 7.74-7.38 (m, 6H), 7.18-7.14 (m, 1H), 7.06-7.04 (m, 1H), 6.85-6.5 (m, 4H), 4.67 (m, 1H), 4.31 (m, 1H), 3.75-3.62 (m, 1H), 3.50-3.45 (m, 1H), 3.06 (m, 6H), 2.91-2.84 (m, 1H), 2.75-2.72 (m, 1H), 1.52 (m, 3H).

Example-9

3-(2-((((R)-1-(3-Methoxyphenyl)ethyl)amino)methyl)-2H-benzo[b][1,4]oxazin-4(3H)-yl)benzoic acid hydrochloride

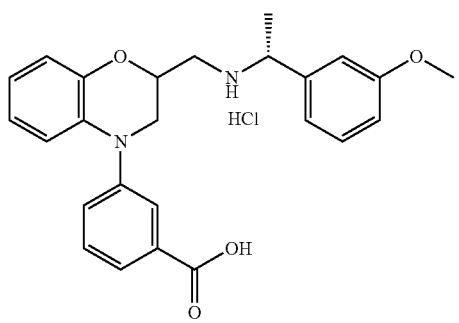 [SMILES: COc1cccc([C@@H](C)NCC2CN(c3cccc(C(=O)O)c3)c3ccccc3O2)c1 ; Cl]

The title compound were prepared by following the similar hydrolysis procedure as described in Example-5 by taking racemic compound of Example-3 and LiOH monohydrate. Further HCl salt was prepared by following the similar HCl salt procedure as described in Example-1.

m/z 419.3. $^1$H NMR (400 MHz, DMSO-d6): δ 10.5 (bs, 1H), 10.1 (bs, 2H), 9.95 (bs, 1H), 7.7 (m, 1H), 7.63 (m, 1H), 7.49-7.44 (m, 1H), 7.41-7.36 (m, 1H), 7.32-7.28 (m, 2H), 7.13-7.08 (m, 1H), 6.96-6.92 (m, 2H), 6.89-6.77 (m, 3H), 5.45 (m, 1H), 4.63 (m, 1H), 4.34 (m, 1H), 4.04-3.92 (m, 1H), 3.14 (m, 1H), 2.92 (m, 1H), 2.76 (m, 1H), 1.63 (d, J=6 Hz, 3H).

Example-10a, 10b

Methyl 3-(3-(2-((((R)-1-(naphthalen-1-yl)ethyl)amino)methyl)-2H-benzo[b][1,4]oxazin-4(3H)-yl)phenyl)propanoate

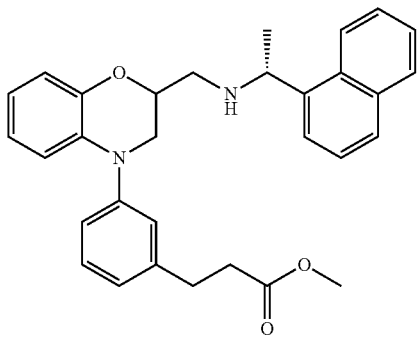 [SMILES: COC(=O)CCc1cccc(N2CC(CN[C@H](C)c3cccc4ccccc34)Oc3ccccc32)c1]

To a mixture solution of Intermediate-4 (0.3 g, 0.94 mmol) and methyl 3-(3-bromophenyl)propanoate (0.16 g, 0.57 mmol)-(0.28 g, 01.13 mmol), Cs$_2$CO$_3$ (0.46 g, 1.41 mmol) in toluene (7 mL) was degassed for 15 min by purging nitrogen. Then, bis(tri-tert-butylphosphine palladium (0) (0.024 g, 0.047 mmol) and tris dibenzylidene acetone dipalladium (0) (0.022 g, 0.047 mmol) were added. The reaction mixture was heated to 110° C. and further maintained for 20 h at the same temperature. The reaction mixture was cooled to RT and progress of reaction monitored by TLC. The mixture was diluted with ethylacetate, filtered through celite and concentrated under vacuum to get the crude product. The diastereomers were separated by flash chromatography using a mixture of 15% ethylacetate in hexane to get Example-10a and Example-10b (0.06 g, 0.09 g 65%) m/z 496.2.

The below Examples of 11 to 39 given in Table-2 were prepared by following the similar procedure as described in Example-10a, 10b by using Intermediate-4 and appropriately substituted halo benzene. Further these diastereomers were separated by flash chromatography using a mixture of ethylacetate/hexane.

TABLE 2

| Example | Structure | Chemical Name | Mass (m/z) |
|---|---|---|---|
| 11 | 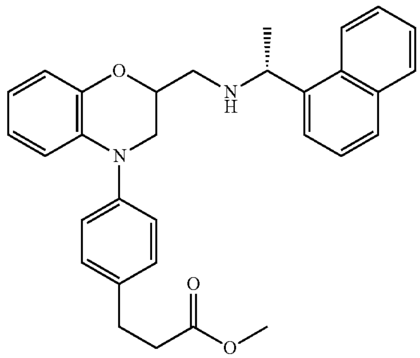 [SMILES: COC(=O)CCc1ccc(N2CC(CN[C@H](C)c3cccc4ccccc34)Oc3ccccc32)cc1] | Methyl 3-(4-(2-((((R)-1-(naphthalen-1-yl)ethyl)amino)methyl)-2H-benzo[b][1,4]oxazin-4(3H)-yl)phenyl)propanoate | 482.2 |
| 12 | 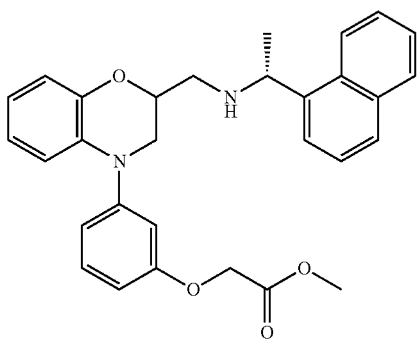 [SMILES: COC(=O)COc1cccc(N2CC(CN[C@H](C)c3cccc4ccccc34)Oc3ccccc32)c1] | Methyl 2-(3-(2-((((R)-1-(naphthalen-1-yl)ethyl)amino)methyl)-2H-benzo[b][1,4]oxazin-4(3H)-yl)phenoxy)acetate | 484.2 |
| 13a, 13b | 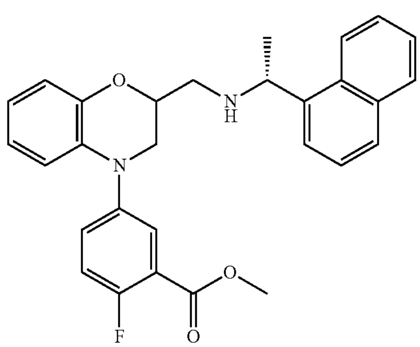 [SMILES: COC(=O)c1cc(N2CC(CN[C@H](C)c3cccc4ccccc34)Oc3ccccc32)ccc1F] | Methyl 2-fluoro-5-(2-((((R)-1-(naphthalen-1-yl)ethyl)amino)methyl)-2H-benzo[b][1,4]oxazin-4(3H)-yl)benzoate | 472.5 |
| 14a, 14b | 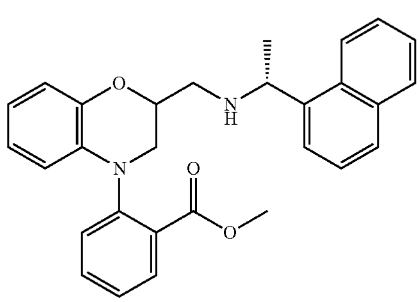 [SMILES: COC(=O)c1ccccc1N1CC(CN[C@H](C)c2cccc3ccccc23)Oc2ccccc21] | Methyl 2-(2-((((R)-1-(naphthalen-1-yl)ethyl)amino)methyl)-2H-benzo[b][1,4]oxazin-4(3H)-yl)benzoate | 454.3 |

TABLE 2-continued

| Example | Structure | Chemical Name | Mass (m/z) |
|---|---|---|---|
| 15 | 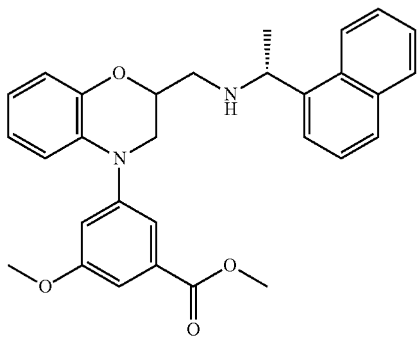 [SMILES: COC(=O)c1cc(OC)cc(N2CC(CN[C@H](C)c3cccc4ccccc34)Oc3ccccc32)c1] | Methyl 3-methoxy-5-(2-((((R)-1-(naphthalen-1-yl)ethyl)amino)methyl)-2H-benzo[b][1,4]oxazin-4(3H)-yl)benzoate | 484.1 |
| 16a, 16b | 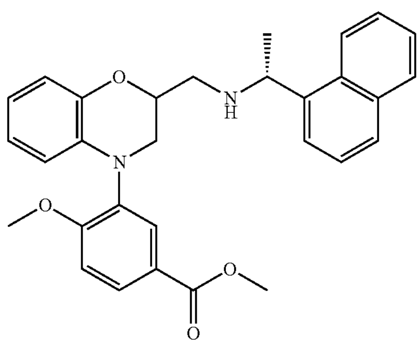 [SMILES: COC(=O)c1ccc(OC)c(N2CC(CN[C@H](C)c3cccc4ccccc34)Oc3ccccc32)c1] | Methyl 4-methoxy-3-(2-((((R)-1-(naphthalen-1-yl)ethyl)amino)methyl)-2H-benzo[b][1,4]oxazin-4(3H)yl)benzoate | 484.1 |
| 17 | 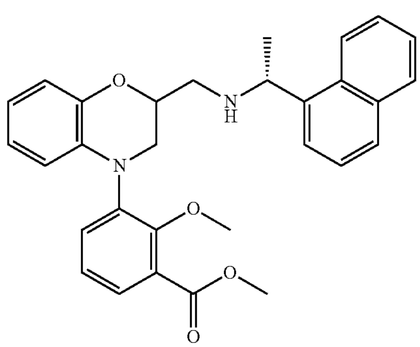 [SMILES: COC(=O)c1cccc(N2CC(CN[C@H](C)c3cccc4ccccc34)Oc3ccccc32)c1OC] | Methyl 2-methoxy-3-(2-((((R)-1-(naphthalen-1-yl)ethyl)amino)methyl)-2H-benzo[b][1,4]oxazin-4(3H)-yl)benzoate | 484.1 |
| 18a, 18b | 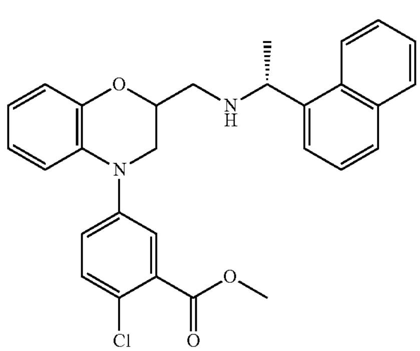 [SMILES: COC(=O)c1cc(N2CC(CN[C@H](C)c3cccc4ccccc34)Oc3ccccc32)ccc1Cl] | 2-chloro-5-(2-((((R)-1-(naphthalen-1-yl)ethyl)amino)methyl)-2H-benzo[b][1,4]oxazin-4(3H)-yl)benzoate | 487.5 |

TABLE 2-continued

| Example | Structure | Chemical Name | Mass (m/z) |
|---------|-----------|---------------|------------|
| 19a, 19b | 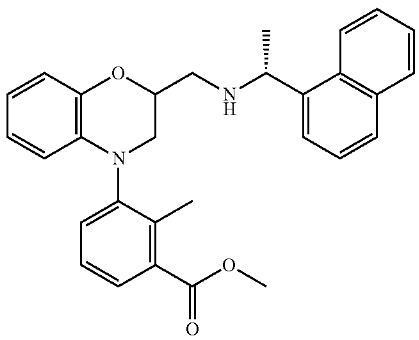 [SMILES: COC(=O)c1cccc(N2CC(CN[C@H](C)c3cccc4ccccc34)Oc3ccccc32)c1C] | Methyl 2-methyl-3-(2-((((R)-1-(naphthalen-1-yl)ethyl) amino) methyl)-2H-benzo[b][1,4]oxazin-4(3H)-yl)benzoate | 468.1 |
| 20 | 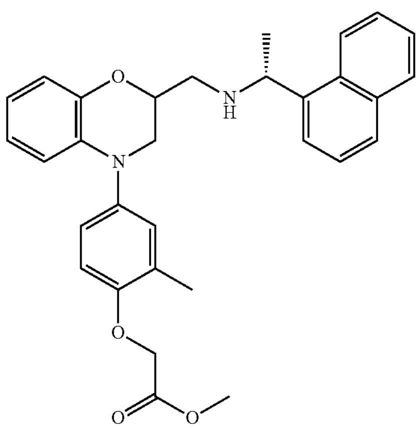 [SMILES: COC(=O)COc1ccc(N2CC(CN[C@H](C)c3cccc4ccccc34)Oc3ccccc32)cc1C] | Methyl 2-(2-methyl-4-(2-((((R)-1-(naphthalen-1-yl)ethyl)amino) methyl)-2H-benzo[b][1,4]oxazin-4(3H)-yl)phenoxy)acetate | 498.1 |
| 21a, 21b | 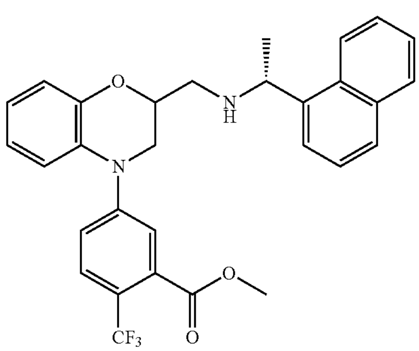 [SMILES: COC(=O)c1cc(N2CC(CN[C@H](C)c3cccc4ccccc34)Oc3ccccc32)ccc1C(F)(F)F] | Methyl 5-(2-((((R)-1-(naphthalen-1-yl) ethyl)amino)methyl)-2H-benzo[b][1,4]oxazin-4(3H)-yl)-2-(trifluoromethyl)benzoate | 522.2 |
| 22 | 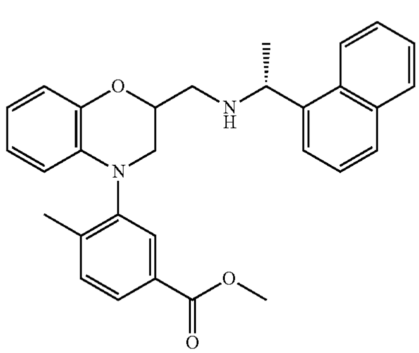 [SMILES: COC(=O)c1ccc(C)c(N2CC(CN[C@H](C)c3cccc4ccccc34)Oc3ccccc32)c1] | Methyl 4-methyl-3-(2-((((R)-1-(naphthalen-1-yl)ethyl)amino) methyl)-2H-benzo[b][1,4]oxazin-4(3H)-yl)benzoate | 466.48 |

TABLE 2-continued

| Example | Structure | Chemical Name | Mass (m/z) |
|---|---|---|---|
| 23a, 23b | 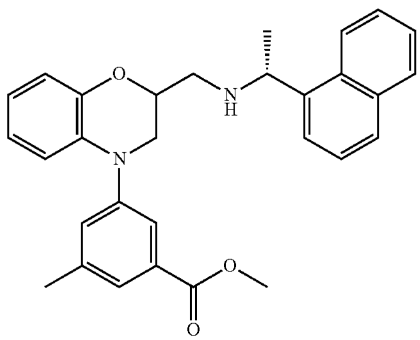 [SMILES: COC(=O)c1cc(C)cc(N2CC(CN[C@H](C)c3cccc4ccccc34)Oc3ccccc32)c1] | Methyl 3-methyl-5-((R)-2-((((R)-1-(naphthalen-1-yl)ethyl)amino)methyl)-2H-benzo[b][1,4]oxazin-4(3H)-yl)benzoate | 468.1 |
| 24a, 24b | 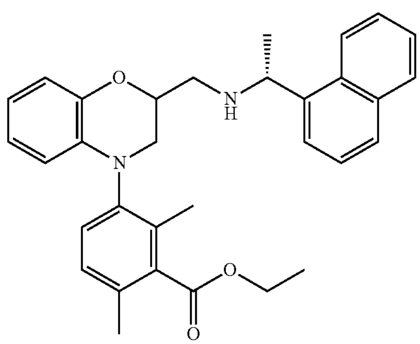 [SMILES: CCOC(=O)c1c(C)ccc(N2CC(CN[C@H](C)c3cccc4ccccc34)Oc3ccccc32)c1C] | Ethyl 2,6-dimethyl-3-(2-((((R)-1-(naphthalen-1-yl)ethyl)amino)methyl)-2H-benzo[b][1,4]oxazin-4(3H)-yl)benzoate | 494.2 |
| 25a, 25b | 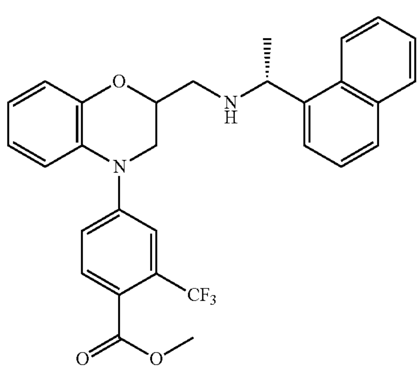 [SMILES: COC(=O)c1ccc(N2CC(CN[C@H](C)c3cccc4ccccc34)Oc3ccccc32)cc1C(F)(F)F] | Methyl 4-(2-((((R)-1-(naphthalen-1-yl)ethyl)amino)methyl)-2H-benzo[b][1,4]oxazin-4(3H)-yl)-2-(trifluoromethyl)benzoate | 521.5 |
| 26b | 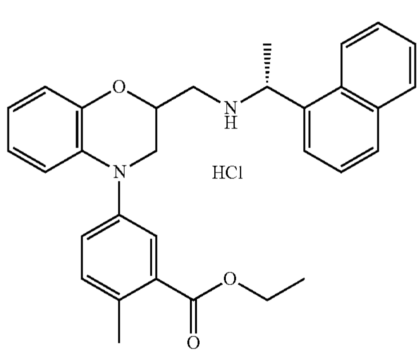 [SMILES: CCOC(=O)c1cc(N2CC(CN[C@H](C)c3cccc4ccccc34)Oc3ccccc32)ccc1C ; Cl] | Ethyl 2-methyl-5-(2-((((R)-1-(naphthalen-1-yl)ethyl)amino)methyl)-2H-benzo[b][1,4]oxazin-4(3H)-yl)benzoate hydrochloride | 481.5 |

TABLE 2-continued

| Example | Structure | Chemical Name | Mass (m/z) |
|---|---|---|---|
| 27a, 27b | 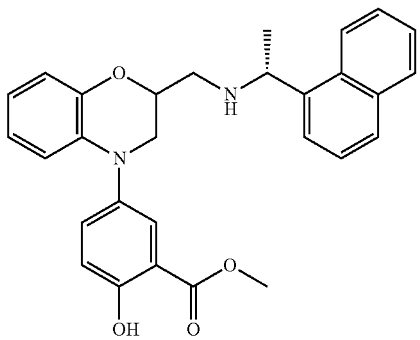 [SMILES: COC(=O)c1cc(N2CC(CN[C@H](C)c3cccc4ccccc34)Oc3ccccc32)ccc1O] | Methyl 2-hydroxy-5-(2-((((R)-1-(naphthalen-1-yl)ethyl)amino)methyl)-2H-benzo[b][1,4]oxazin-4(3H)-yl)benzoate | 467.5 |
| 28a, 28b | 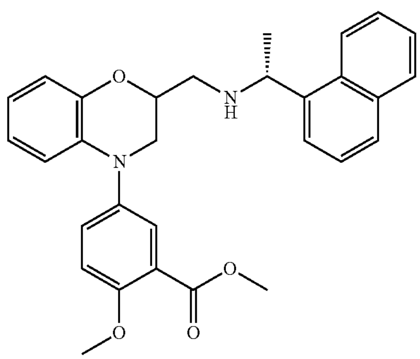 [SMILES: COC(=O)c1cc(N2CC(CN[C@H](C)c3cccc4ccccc34)Oc3ccccc32)ccc1OC] | Methyl 2-methoxy-5-(2-((((R)-1-(naphthalen-1-yl)ethyl)amino)methyl)-2H-benzo[b][1,4]oxazin-4-(3H)-yl)benzoate | 483.5 |
| 29b | 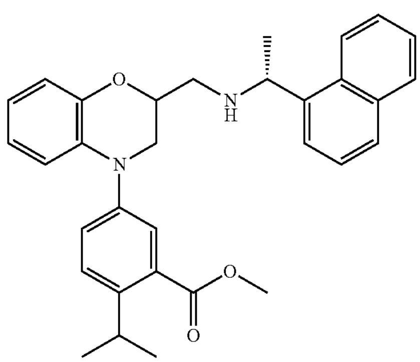 [SMILES: COC(=O)c1cc(N2CC(CN[C@H](C)c3cccc4ccccc34)Oc3ccccc32)ccc1C(C)C] | Methyl 2-isopropyl-5-(2-((((R)-1-(naphthalen-1-yl)ethyl)amino)methyl)-2H-benzo[b][1,4]oxazin-4(3H)-yl)benzoate | 495.5 |
| 30 | 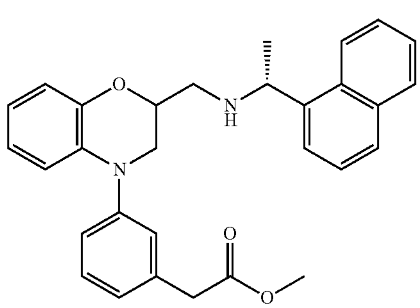 [SMILES: COC(=O)Cc1cccc(N2CC(CN[C@H](C)c3cccc4ccccc34)Oc3ccccc32)c1] | Methyl 2-(3-(2-((((R)-1-(naphthalen-1-yl)ethyl)amino)methyl)-2H-benzo[b][1,4]oxazin-4(3H)-yl)phenyl)acetate | 467.5 |

TABLE 2-continued

| Example | Structure | Chemical Name | Mass (m/z) |
|---|---|---|---|
| 31a, 31b | 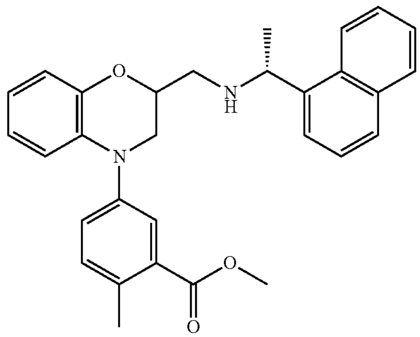 [SMILES: COC(=O)c1cc(N2CC(CN[C@H](C)c3cccc4ccccc34)Oc3ccccc32)ccc1C] | Methyl 2-methyl-5-(2-((((R)-1-(naphthalen-1-yl)ethyl)amino)methyl)-2H-benzo[b][1,4]oxazin-4(3H)-yl)benzoate | 467.5 |
| 32 | 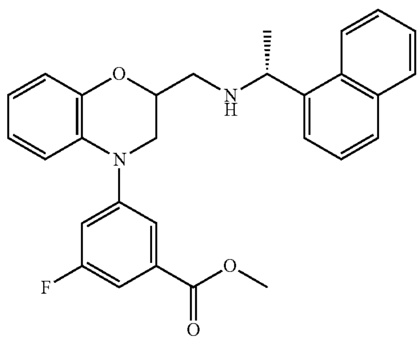 [SMILES: COC(=O)c1cc(F)cc(N2CC(CN[C@H](C)c3cccc4ccccc34)Oc3ccccc32)c1] | 3-Fluoro-5-(2-((((R)-1-(naphthalen-1-yl)ethyl)amino)methyl)-2H-benzo[b][1,4]oxazin-4(3H)-yl)benzoate | 471.5 |
| 33 | 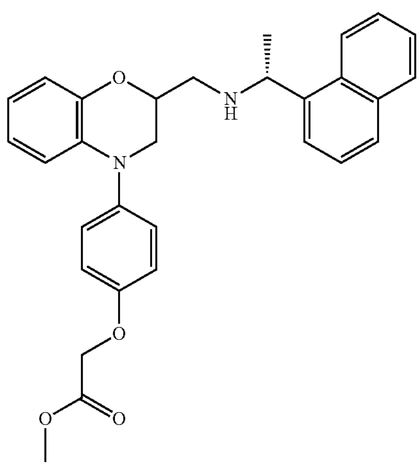 [SMILES: COC(=O)COc1ccc(N2CC(CN[C@H](C)c3cccc4ccccc34)Oc3ccccc32)cc1] | Methyl 2-(4-(2-((((R)-1-(naphthalen-1-yl)ethyl)amino)methyl)-2H-benzo[b][1,4]oxazin-4(3H)-yl)phenoxy)acetate | 483.5 |
| 34a, 34b | 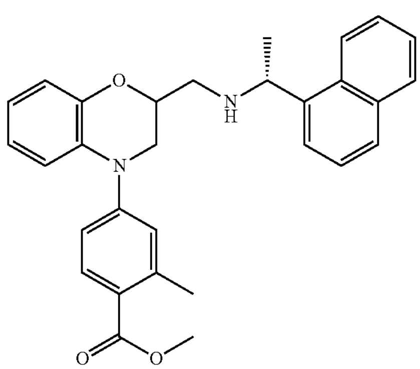 [SMILES: COC(=O)c1ccc(N2CC(CN[C@H](C)c3cccc4ccccc34)Oc3ccccc32)cc1C] | Methyl 2-methyl-4-(2-((((R)-1-(naphthalen-1-yl)ethyl)amino)methyl)-2H-benzo[b][1,4]oxazin-4(3H)-yl)benzoate | 467.5 |

TABLE 2-continued

| Example | Structure | Chemical Name | Mass (m/z) |
|---|---|---|---|
| 35a, 35b | 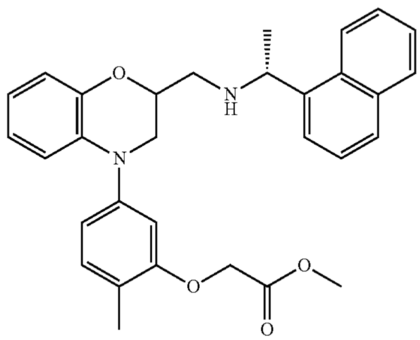 [SMILES: COC(=O)COc1cc(N2CC(CN[C@H](C)c3cccc4ccccc34)Oc3ccccc32)ccc1C] | Methyl 2-(2-methyl-5-(2-((((R)-1-(naphthalen-1-yl)ethyl)amino)methyl)-2H-benzo[b][1,4]oxazin-4(3H)-yl)phenoxy)acetate | 497.2 |
| 36a, 36b | 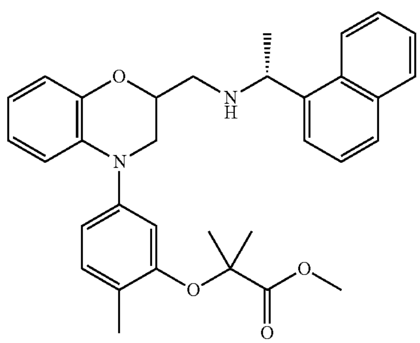 [SMILES: COC(=O)C(C)(C)Oc1cc(N2CC(CN[C@H](C)c3cccc4ccccc34)Oc3ccccc32)ccc1C] | Methyl 2-methyl-2-(2-methyl-5-(2-((((R)-1-(naphthalen-1-yl)ethyl)amino)methyl)-2H-benzo[b][1,4]oxazin-4(3H)-yl)phenoxy)propanoate | 525.5 |
| 37b | 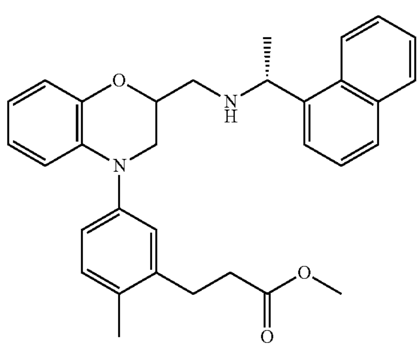 [SMILES: COC(=O)CCc1cc(N2CC(CN[C@H](C)c3cccc4ccccc34)Oc3ccccc32)ccc1C] | Methyl 3-(2-methyl-5-(2-((((R)-1-(naphthalen-1-yl)ethyl)amino)methyl)-2H-benzo[b][1,4]oxazin-4(3H)-yl)phenyl)propanoate | 495.5 |
| 38b | 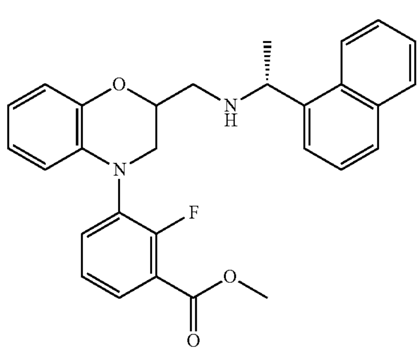 [SMILES: COC(=O)c1cccc(N2CC(CN[C@H](C)c3cccc4ccccc34)Oc3ccccc32)c1F] | Methyl 2-fluoro-3-(2-((((R)-1-(naphthalen-1-yl)ethyl)amino)methyl)-2H-benzo[b][1,4]oxazin-4(3H)-yl)benzoate | 471.2 |

Example-39

Methyl 5-(2-((((R)-1-(3-methoxy phenyl)ethyl)amino)methyl)-2H-benzo[b][1,4]oxazin-4(3H)-yl)-2-methyl benzoate

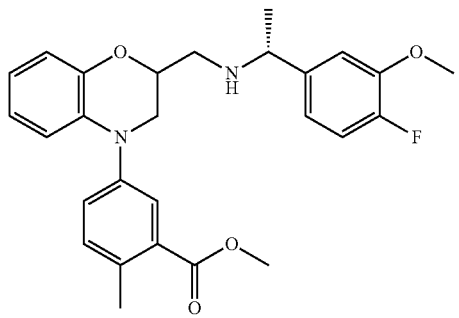 [SMILES: COC(=O)c1cc(N2CC(CN[C@H](C)c3ccc(F)c(OC)c3)Oc3ccccc32)ccc1C]

The title compound was prepared by following the similar procedure as described in Example-10a, 10b by using Intermediate-26 and methyl 5-bromo-2-methylbenzoate. The crude compound obtained was further purified by flash chromatography using a mixture of 15% ethylacetate in hexane to get the title compound. Mass (m/z) 465.2.

Example-40b

Methyl2-methyl-5-(2-((((R)-1-(naphthalen-1-yl)ethyl)amino)methyl)-3-oxo-2H-benzo[b][1,4]oxazin-4(3H)-yl)benzoate

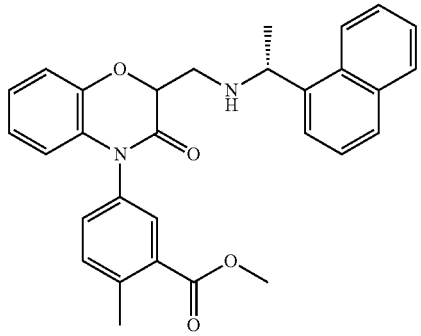 [SMILES: COC(=O)c1cc(N2C(=O)C(CN[C@H](C)c3cccc4ccccc34)Oc3ccccc32)ccc1C]

The title compound was prepared in three steps:

Step 1:—Boc Protection by Using Di-Tert-Butyl Dicarbonate:

To the solution of Example-31b (0.3 g, 0.64 mmol) in acetonitrile (10 mL) was added di-tert-butyl dicarbonate (0.21 g, 0.96 mmol) at 0° C. The reaction was stirred at room temperature for overnight. Reaction was monitored by TLC then the reaction mixture quenched with 10% citric acid. Extracted with Ethyl acetate (10 mL×2), washed with water (15 mL×2) followed by brine solution (5 mL), dried over $Na_2SO_4$, filtered and concentrated to get the crude product. This crude product was further purified by flash chromatography (10% Ethyl acetate:n-hexane) to give the title compound (0.32 g, 88% yield). m/z 567.5.

Step 2: Oxidation:

To a stirred solution of step-1 intermediate (0.120 g, 0.212 mmol) in acetonitrile (10 mL) $KMnO_4$ (0.234 g, 1.482 mmol) and benzyl triethyl ammonium chloride (0.072 g, 0.318 mmol) were added. The reaction was stirred at 85° C. for 20 h. The progress of reaction was monitored by TLC. The reaction mixture was cooled at room temperature. Extracted with Ethyl acetate (10 mL×2), washed with water (15 mL×2) followed by brine solution (5 mL), dried over $Na_2SO_4$, filtered and concentrated to get the crude product. This crude product was further purified by flash chromatography (30% Ethyl acetate: n-hexane) to give the title compound (0.07 g, 56.9%). m/z −581.5.

Step-3: BOC Deprotection

To a solution of step-2 intermediate (0.07 g, 0.12 mmol) was dissolved in DCM (5 mL) and MeOH/HCl (10 mL, 3N). The reaction mixture was stirred at 35° C. for overnight. The progress of reaction was monitored by TLC. The reaction was evaporated under reduced pressure then added saturated $Na_2CO_3$ solution (5 mL). The mixture was extracted with ethylacetate (10 mL×2) and washed with water (5 mL×2) followed by brine solution (5 mL), dried over sodium sulfate, filtered and concentrated under reduced pressure. This was further purified by flash chromatography (15% Ethyl acetate-hexane) to give the title compound (0.02 g, 51.8%). m/z 481.5.

Example-41

3-(2-((((R)-1-(Naphthalen-1-yl)ethyl)amino)methyl)-2H-benzo[b][1,4]oxazin-4(3H)-yl)benzoic acid hydrochloride

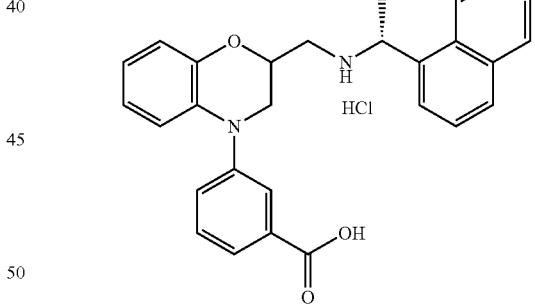

The title compound was prepared by following the similar hydrolysis procedure as described in Example-6 by taking Example-4 using lithium hydroxide monohydrate. m/z 439.2; $^1$H NMR (400 MHz, DMSO-d6): δ 13.15 (bs, 1H), 10.25 (bs, 1H), 9.95 (bs, 1H), 9.6 (bs, 1H), 9.35 (bs, 1H), 8.23 (m, 1H), 8.02-7.95 (m, 3H), 7.70-7.58 (m, 4H), 7.47-7.41 (m, 2H), 7.39 (m, 1H), 6.94-6.78 (m, 3H), 5.45 (m, 1H), 4.63 (m, 1H), 3.95 (d, J=2 Hz, 1H), 3.51 (d, J=2 Hz, 1H), 3.23 (m, 1H), 3.05 (m, 1H), 1.72 (s, 3H).

The below Examples 42 to 47 given Table-3 were prepared by following the similar procedure as described in Example-7 by taking acid compound and appropriate amine. Further, HCl salts were prepared by following the similar HCl salt procedure as described in Example-1.

TABLE 3

| Example | Structure | Acid compound | Mass (m/z) and ¹HNMR |
|---|---|---|---|
| 42 | 4-(2-((((R)-1-(3-methoxyphenyl)ethyl)amino)methyl)-2H-benzo[b][1,4]oxazin-4(3H)-yl)-N-methyl benzamide | Example-5 | m/z 432.3: ¹H NMR (400 MHz, DMSO-d6): δ 8.2 (m, 1H), 7.88 (m, 1H), 7.76-7.73 (m, 1H), 7.71-7.68 (m, 2H), 7.62 (m, 1H), 7.51-7.44 (m, 3H), 7.19-7.15 (m, 2H), 7.09 (m, 1H), 6.94-6.93 (m, 1H), 6.87-6.85 (m, 1H), 6.8 (m, 1H), 4.65 (m, 1H), 4.28 (m, 1H), 3.78-3.70 (m, 1H), 3.66-3.49 (m, 1H), 2.91-2.87 (m, 1H), 2.84-2.74 (m, 1H), 1.52 (m, 3H), |
| 43 | N-methyl-4-(2-((((R)-1-(naphthalen-1-yl)ethyl)amino)methyl)-2H-benzo[b][1,4]oxazin-4(3H)-yl)benzamide | Example-6 | m/z 452.2: ¹H NMR (400 MHz, DMSO-d6): δ 8.2 (m, 1H), 7.88 (m, 1H), 7.76-7.73 (m, 1H), 7.71-7.68 (m, 2H), 7.62 (m, 1H), 7.51-7.44 (m, 3H), 7.19-7.15 (m, 2H), 7.09 (m, 1H), 6.94-6.93 (m, 1H), 6.87-6.85 (m, 1H), 6.8 (m, 1H), 4.65 (m, 1H), 4.28 (m, 1H), 3.78-3.70 (m, 1H), 3.66-3.49 (m, 1H), 2.91-2.87 (m, 1H), 2.84-2.74 (m, 1H), 1.52 (m, 3H) |
| 44 | 3-(2-((((R)-1-(3-methoxyphenyl)ethyl)amino)methyl)-2H-benzo[b][1,4]oxazin-4(3H)-yl)-N-methyl benzamide | Example 9 | m/z 432.3; ¹H NMR (400 MHz, DMSO-d6): δ 8.2 (m, 1H), 7.88 (m, 1H), 7.76-7.73 (m, 1H), 7.71-7.68 (m, 2H), 7.62 (m, 1H), 7.51-7.44 (m, 3H), 7.19-7.15 (m, 2H), 7.09 (m, 1H), 6.94-6.93 (m, 1H), 6.87-6.85 (m, 1H), 6.8 (m, 1H), 4.65 (m, 1H), 4.28 (m, 1H), 3.78-3.70 (m, 1H), 3.66-3.49 (m, 1H), 2.91-2.87 (m, 1H), 2.84-2.74 (m, 1H), 1.52 (m, 3H), |

TABLE 3-continued

| Example | Structure | Acid compound | Mass (m/z) and ¹HNMR |
|---|---|---|---|
| 45 | N-methyl-3-(2-((((R)-1-(naphthalen-1-yl)ethyl)amino)methyl)-2H-benzo[b][1,4]oxazin-4(3H)-yl)benzamide | Example 41 | m/z 452.2; ¹H NMR (400 MHz, DMSO-d6): δ 8.44 (d, J = 3.6 Hz, 1H), 8.25 (t, J = 9.2 Hz, 1H), 7.95 (m, 2H), 7.79 (m, 1H), 7.64-7.63 (m, 1H), 7.59 (m, 1H), 7.52-7.49 (m, 1H), 7.42-7.36 (m, 1H), 7.31 (d, J = 8 Hz, 1H), 7.25 (m, 1H), 7.14-7.00 (m, 1H), 6.94 (m, 2H), 6.82 (m, 1H), 5.41 (m, 1H), 4.62 (m, 1H), 3.91 (d, J = 12 Hz, 1H), 3.59 (m, 2H), 3.53 (m, 3H), 1.68 (s, 3H). |
| 46a, 46b | 3-(2-((((R)-1-(3-methoxyphenyl)ethyl)amino)methyl)-2H-benzo[b][1,4]oxazin-4(3H)-yl)-N,N-dimethyl benzamide hydrochloride | Example 9 | 46a: m/z 446.2; ¹H NMR (400 MHz, DMSO-d$_6$): δ 10.10 (bs, 1H), 9.35 (bs, 1H), 8.22 (m, 1H), 8.02-7.90 (m, 2H), 7.65-7.56 (m, 2H), 7.36 (m, 1H), 7.17-7.06 (m, 2H), 6.95-6.93 (m, 2H), 5.4 (m, 1H), 4.6 (m, 1H), 3.9 (m, 1H), 3.5 (m, 2H), 3.01 (m, 1H), 2.95 (m, 6H), 1.72 (d, J = 6.4 Hz, 3H); 46b: ¹H NMR (400 MHz, DMSO-D6): δ 10.10 (bs, 1H), 9.35 (bs, 1H), 8.22 (m, 1H), 8.02-7.90 (m, 2H), 7.65-7.56 (m, 2H), 7.36 (m, 1H), 7.17-7.06 (m, 2H), 6.95-6.93 (m, 2H), 5.4 (m, 1H), 4.6 (m, 1H), 3.9 (m, 1H), 3.5 (m, 2H), 3.01 (m, 1H), 2.95 (m, 6H), 1.72 (d, J = 6.4 Hz, 3H). |
| 47 | N,N-dimethyl-3-(2-((((R)-1-(naphthalen-1-yl)ethyl)amino)methyl)-2H-benzo[b][1,4]oxazin-4(3H)-yl)benzamide hydrochloride | Example-41 | a: m/z 466.1; ¹H NMR (400 MHz, DMSO-D6): 9.5 (bs, 2H), 7.41 (m, 1H), 7.33 (m, 1H), 7.23-7.21 (m, 1H), 7.13-7.12 (m, 2H), 7.09-7.03 (m, 2H), 6.98-6.95 (m, 2H), 6.90-6.88 (m, 1H), 6.84-6.96 (m, 1H), 4.4 (m, 2H), 3.90-3.86 (m, 1H), 3.49-3.44 (m, 1H), 3.09-3.02 (m, 2H), 2.96-2.91 (m, 6H), 1.60 (d, J = 6.8 Hz, 3H). |

The below Examples 48 to 82 given in Table-4 were prepared by following the similar ester hydrolysis procedure as described in Example-6 by taking corresponding ester compound and lithium hydroxide monohydrate. Further HCl salts were prepared by following the similar Hal salt procedure as described in Example-1.

TABLE 4

| Example | Structure | ester | ¹HNMR |
|---------|-----------|-------|-------|
| 48 | 3-(4-(2-((((R)-1-(naphthalen-1-yl)ethyl) amino)methyl)-2H-benzo [b][1,4]oxazin-4(3H)-yl) phenyl)propanoic acid | Example-11 | m/z 466.2; ¹H NMR (400 MHz, DMSO-D6): δ 8.22 (m, 1H), 7.92-7.89 (m, 1H), 7.78 (d, J = 8.1H), 7.64-7.61 (m, 1H), 7.50-7.44 (m, 3H), 7.23-7.19 (m, 2H), 7.10-7.07 (m, 2H), 6.77-6.71 (m, 2H), 6.67-6.63 (m, 2H), 4.61 (m, 1H), 3.78 (m, 1H), 3.79-3.73 (m, 2H), 3.46-3.35 (m, 2H), 2.81-2.62 (m, 2H), 2.54-2.52 (m, 2H, 1.34 (m, 3H) |
| 49 | 2-(4-(2-((((R)-1-(naphthalen-1-yl)ethyl) amino)methyl)-2H-benzo[b] [1,4]oxazin-4(3H)-yl) phenoxy)aceticacid hydrochloride | Example-33 | m/z 469.1; ¹H NMR (400 MHz, DMSO-D6): δ 13.15 (bs, 1H), 10.3 (bs, 1H), 9.95 (bs, 1H), 9.53 (bs, 1H), 9.35 (bs, 1H), 8.21 (m, 1H), 8.03-7.93 (m, 3H), 7.64-7.55 (m, 3H), 7.11-7.02 (m, 2H), 6.94-6.88 (m, 2H), 6.84-6.82 (m, 1H), 6.72-6.68 (m, 2H), 6.57-6.53 (m, 1H), 5.44 (m, 1H), 4.66 (d, J = 3.6, 2H), 3.74-3.71 (m, 1H), 3.45 (m, 1H), 3.23 (m, 1H), 3.02 (m, 1H), 1.73 (m, 3H) |
| 50 | 2-(3-(2-((((R)-1-(naphthalen-1-yl)ethyl) amino)methyl)-2H-benzo[b] [1,4]oxazin-4(3H)-yl) phenoxy)acetic acid hydrochloride | Example-12 | m/z 468.67; ¹H NMR (400 MHz, DMSO-D6): δ 13.15 (bs, 1H), 10.3 (bs, 1H), 9.95 (bs, 1H), 9.53 (bs, 1H), 9.35 (bs, 1H), 8.21 (m, 1H), 8.03-7.93 (m, 3H), 7.63-7.58 (m, 3H), 7.24-7.17 (m, 1H), 6.94-6.88 (m, 2H), 6.85-6.75 (m, 2H), 6.74-6.65 (m, 2H), 6.60-6.58 (m, 1H), 5.44 (m, 1H), 4.64 (m, 3H), 3.90 (m, 1H), 3.47-3.41 (m, 2H), 3.21 (m, 1H), 1.71 (m, 3H); |

TABLE 4-continued

| Example | Structure | ester | ¹HNMR |
|---|---|---|---|
| 51a, 51b | 2-Fluoro-5-(2-((((R)-1-(naphthalen-1-yl)ethyl)amino)methyl)-2H-benzo[b][1,4]oxazin-4(3H)-yl)benzoic acid hydrochloride | Example-13a, 13b | m/z 457.04; 51a: ¹H NMR (400 MHz, DMSO-D6): δ 13.3 (bs, 1H), 9.85 (bs, 1H), 9.45 (bs, 1H), 8.24 (m, 1H), 8.03-7.98 (m, 2H), 7.93 (d, J = 7.2 Hz, 1H), 7.66-7.58 (m, 4H), 7.44-7.40 (m, 1H), 7.34-7.29 (m, 1H), 6.90-6.88 (m, 1H), 6.83-6.67 (m, 3H), 5.45 (m, 1H), 4.63 (m, 1H), 3.86-3.82 (m, 1H), 3.49-3.44 (m, 2H), 3.24 (m, 1H), 1.72 (d, J = 6.8 Hz, 3H); 51b: ¹H NMR (400 MHz, DMSO-D6): δ 10.01 (bs, 1H), 9.45 (bs, 1H), 8.21 (m, 1H), 8.00-7.90 (m, 3H), 7.64-7.57 (m, 4H), 7.38-7.35 (m, 1H), 7.30-726 (m, 1H), 6.94-6.92 (m, 1H), 6.83-6.74 (m, 3H), 5.45 (m, 1H), 4.59 (m, 1H), 3.86-3.82 (m, 1H), 3.51-3.46 (m, 2H), 3.06-2.94 (m, 1H), 1.70 (d, J = 6.4 Hz, 3H) |
| 52 | 5-(2-((((R)-1-(3-methoxyphenyl)ethyl)amino)methyl)2H-benzo[b][1,4]oxazin-4(3H)-yl)-2-methyl benzoic acid hydrochloride | Example-39 | m/z-451.1; ¹H NMR (400 MHz, DMSO-d6): δ 13.95 (bs, 1H), 9.57 (bs, 1H), 9.44-9.42 (bs, 2H), 9.17 (bs, 1H), 7.59 (m, 1H), 7.42 (d, J = 7.2 Hz, 1H), 7.31-7.23 (m, 3H), 7.06 (m, 1H), 7.69-6.92 (m, 1H), 6.81 (m, 3H), 4.51 (m, 2H), 3.83 (m, 3H), 3.10 (m, 2H), 2.9 (m, 1H), 2.8 (m, 1H), 1.60 (d, J = 6.4 Hz, 3H) |
| 53a, 53b | 2-(2-((((R)-1-(Naphthalen-1-yl)ethyl)amino)methyl)-2H-benzo[b][1,4]oxazin-4(3H)-yl)benzoic acid hydrochloride | Example-14a, 14b | m/z 439.1; 53a: ¹H NMR (400 MHz, DMSO-D6): δ 12.84 (bs, 1H), 9.83 (bs, 1H), 9.54 (bs, 1H), 8.25 (t, J = 8 Hz, 1H), 8.03-7.93 (m, 3H), 7.78 (m, 1H), 7.65-7.56 (m, 4H), 7.32-7.29 (m, 2H), 6.84-6.81 (m, 1H), 6.66 (m, 2H), 5.41 (m, 1H), 4.69 (m, 1H), 3.71 (m, 1H), 3.51 (m, 2H), 1.72 (d, J = 6.4 Hz, 3H). 53b: ¹H NMR (400 MHz, DMSO-D6): δ 12.8 (bs, 1H), 10.1 (bs, 1H), 9.3 (bs, 1H), 8.25 (m, 1H), 8.03-7.95 (m, 2H), 7.92-7.90 (m, 1H), 7.79 (m, 1H), 7.66-7.57 (m, 3H), 7.32-7.28 (m, 2H), 7.08 (m, 1H), 6.89-6.83 (m, 1H), 6.67 (m, 2H), 6.35 (m, 1H), 5.38 (m, 1H), 4.7 (m, 1H), 3.72-3.71 (m, 1H), 3.48 (m, 2H), 1.70 (d, J = 6.0 Hz, 3H). |

TABLE 4-continued

| Example | Structure | ester | ¹HNMR |
|---------|-----------|-------|-------|
| 54 | 3-Methoxy-5-(2-((((R)-1-(naphthalen-1-yl)ethyl)amino)methyl)-2H-benzo[b][1,4]oxazin-4(3H)-yl)benzoic acid hydrochloride | Example-15 | m/z 469.1; ¹H NMR (400 MHz, DMSO-D6): δ 13.15 (bs, 1H), 10.6 (bs, 1H), 10.2 (bs, 1H), 9.8 (bs, 1H), 9.45 (bs, 1H), 8.23 (m, 1H), 8.02-7.95 (m, 3H), 7.63-7.57 (m, 3H), 7.29 (m, 1H), 7.12 (m, 1H), 6.95-6.92 (m, 2H), 6.86-6.79 (m, 3H), 5.45 (m, 1H), 4.66 (m, 1H), 4.03-3.96 (m, 1H), 3.78 (s, 3H), 3.59-3.44 (m, 1H), 3.40 (m, 1H), 3.19 (m, 1H), 3.03 (m, 1H), 1.73 (d, J = 6.4, 3H) |
| 55a | 4-Methoxy-3-(2-((((R)-1-(naphthalen-1-yl)ethyl)amino)methyl)-2H-benzo[b][1,4]oxazin-4(3H)-yl)benzoic acid hydrochloride | Example-16a | m/z 483.2; ¹H NMR (400 MHz, DMSO-D6): δ 10.3 (bs, 1H), 9.9 (bs, 1H), 9.6 (bs, 1H), 9.4 (bs, 1H), 8.22 (m, 1H), 8.02-7.93 (m, 3H), 7.85 (d, J = 2.0, 1H), 7.72-7.69 (m, 1H), 7.63-7.56 (m, 2H), 7.23 (t, J = 2.0 Hz, 1H), 7.01 (m, 1H), 6.91-6.89 (m, 1H), 6.70-6.67 (m, 2H), 6.22 (m, 1H), 5.45 (m, 1H), 4.68 (m, 1H), 3.79 (m, 3H), 3.70 (m, 3H), 3.35-3.34 (m, 1H), 3.11-3.09 (m, 1H), 1.75 (d, J = 10 Hz, 3H). |
| 56b | Methyl 4-methoxy-3-(2-((((R)-1-(naphthalen-1-yl)ethyl)amino)methyl)-2H-benzo[b][1,4]oxazin-4(3H)-yl)benzoate hydrochloride | Example-16b | m/z 483.2; ¹H NMR (400 MHz, DMSO-D6): δ 12.9 (bs, 1H), 10.1 (bs, 1H), 9.9 (bs, 1H), 9.6 (bs, 1H), 9.4 (bs, 1H), 8.22 (m, 1H), 8.02-7.90 (m, 3H), 7.85 (d, J = 2.0, 1H), 7.64-7.57 (m, 3H), 7.22-7.18 (m, 1H), 6.91-6.89 (m, 1H), 6.70-6.68 (m, 2H), 6.23 (m, 1H), 5.45 (m, 1H), 4.66 (m, 1H), 3.71 (m, 4H), 1.72 (d, J = 6.4 Hz, 3H) |

TABLE 4-continued

| Example | Structure | ester | ¹HNMR |
|---|---|---|---|
| 57 | 2-Methoxy-3-(2-((((R)-1-(naphthalen-1-yl)ethyl)amino)methyl)-2H-benzo[b][1,4]oxazin-4(3H)-yl)benzoic acid hydrochloride | Example-17 | m/z 469.1; ¹H NMR (400 MHz, DMSO-D6): δ 12.95 (bs, 1H), 10.5 (bs, 1H), 9.9 (bs, 1H), 9.5 (bs, 1H), 9.3 (bs, 1H), 8.25 (m, 1H), 8.00-7.89 (m, 3H), 7.64-7.56 (m, 3H), 7.52-7.48 (m, 1H), 7.35 (d, J = 1.6 Hz, 1H), 7.21-7.17 (m, 1H) 6.88-6.86 (m, 1H), 6.73-6.71 (m, 2H), 6.4 (m, 1H), 5.45 (m, 1H), 4.65 (m, 1H), 3.71-3.68 (m, 1H), 3.67 (m, 3H), 3.20 (m, 1H), 3.06 (m, 1H), 1.73 (d, J = 6.4 Hz, 3H). |
| 58a, 58b | 2-Methyl-3-(2-((((R)-1-(naphthalen-1-yl)ethyl)amino)methyl)-2H-benzo[b][1,4]oxazin-4(3H)-yl)benzoic acid hydrochloride | Example-19a, 19b | m/z 453.29; 58a: ¹H NMR (400 MHz, DMSO-D6): δ 13 (bs, 1H), 10.01 (bs, 1H), 9.7 (bs, 1H), 8.28 (m, 1H), 8.03-7.96 (m, 3H), 7.67-7.57 (m, 4H), 7.37-7.34 (m, 2H), 6.846.81 (m, 1H), 6.69-6.63 (m, 2H), 5.96-5.94 (m, 1H), 5.45 (m, 1H), 4.8 (m, 1H), 3.7 (d, J = 2.4 Hz, 1H), 3.61-3.58 (m, 1H), 3.53 (m, 1H), 3.42 (m, 1H), 2.33 (s, 3H), 1.73 (d, J = 6.4 Hz, 3H).<br>58b: ¹H NMR (400 MHz, DMSO-D6): δ 13 (bs, 1H), 10.4 (bs, 1H), 9.4 (bs, 1H), 8.24 (m, 1H), 8.03-7.92 (m, 3H), 7.71-7.51 (m, 4H), 7.34-7.28 (m, 2H), 6.91-6.87 (m, 2H), 6.70-6.65 (m, 2H), 6.0-5.96 (m, 1H), 5.45 (m, 1H), 4.77 (m, 1H), 3.71 (m, 1H), 3.62 (d, J = 10 Hz, 1H), 3.48 (m, 1H), 3.08 (d, J = 8.8, Hz, 1H), 2.32 (s, 3H), 1.73 (m, 3H). |
| 59 | 2-(2-Methyl-4-(2-((((R)-1-(naphthalen-1-yl)ethyl)amino)methyl)-2H-benzo[b][1,4]oxazin-4(3H)-yl)phenoxy)acetic acid hydrochloride | Example-20 | m/z 483.3; ¹H NMR (400 MHz, DMSO-D6): δ 13 (bs, 1H), 10.5 (bs, 1H), 9.9 (bs, 1H), 9.6 (bs, 1H), 9.5 (bs, 1H), 8.21 (m, 1H), 8.02-7.96 (m, 3H), 7.63-7.53 (m, 4H), 6.97-6.93 (m, 1H), 6.89 (m, 1H), 6.88-6.76 (m, 2H), 6.70-6.68 (m, 2H), 6.55-6.53 (m, 1H), 5.45 (m, 1H), 4.68 (m, 3H), 3.72 (d, J = 4.8 Hz, 2H), 3.23 (m, 1H), 3.01 (m, 1H), 2.16 (d, J = 10.8 Hz, 3H), 1.73 (d, J = 6.4 Hz, 3H). |

TABLE 4-continued

| Example | Structure | ester | ¹HNMR |
|---|---|---|---|
| 60a, 60b | 5-(2-((((R)-1-(Naphthalen-1-yl)ethyl)amino)methyl)-2H-benzo[b][1,4]oxazin-4(3H)-yl)-2-(trifluoromethyl)benzoic acid hydrochloride | Example-21a, 21b | 60a: m/z 507.19; ¹H NMR (400 MHz, DMSO-D6): δ 13.6 (bs, 1H), 10.2 (bs, 1H), 9.8 (bs, 1H), 8.22 (m, 1H), 8.02-7.95 (m, 3H), 7.72 (d, J = 8 Hz, 1H), 7.63-7.56 (m, 3H), 7.46 (d, J = 2 Hz, 1H), 7.38 (dd, J = 1.6 Hz, J = 8.4 Hz, 1H), 7.13 (d, J = 7.6 Hz, 1H), 6.94-6.92 (m, 2H), 6.87-6.82 (m, 1H), 5.45 (m, 1H), 4.68 (d, J = 7.6 Hz, 1H), 4.13-4.09 (m, 1H), 3.55-3.50 (m, 1H), 3.17 (m, 2H), 1.72 (d, J = 6.8 Hz, 3H). 60b: ¹H NMR (400 MHz, DMSO-D6): δ 13.6 (bs, 1H), 10.6 (bs, 1H), 9.4 (bs, 1H), 8.21 (m, 1H), 8.02-7.95 (m, 3H), 7.63-7.55 (m, 4H), 7.46 (d, J = 2 Hz, 1H), 7.30 (m, 1H), 7.11 (dd, J = 1.2 Hz, J = 8 Hz, 1H), 6.98 (m, 2H), 6.87-6.85 (m, 1H), 5.45 (m, 1H), 4.65 (m, 1H), 4.15-4.11 (m, 1H), 3.55-3.50 (m, 1H), 3.17 (m, 1H), 2.98 (m, 1H), 1.73 (d, J = 6.4 Hz, 3H). |
| 61 | 4-Methyl-3-(2-((((R)-1-(naphthalen-1-yl)ethyl)amino)methyl)-2H-benzo[b][1,4]oxazin-4(3H)-yl)benzoicacid hydrochloride | Example-22 | m/z 452.9; ¹H NMR (400 MHz, DMSO-d₆): δ 12.9 (bs, 1H), 10.01 (bs, 1H), 9.98 (bs, 1H), 9.8 (bs, 1H), 9.4 (bs, 1H), 9.2 (bs, 1H), 8.3 (m, 2H), 7.96-7.88 (m, 4H), 7.80-7.61 (m, 5H), 7.52-7.47 (m, 1H), 6.96-6.89 (m, 2H), 6.73-6.69 (m, 2H), 6.13-6.02 (m, 1H), 5.47 (m, 1H), 4.73 (m, 1H), 3.73-3.57 (m, 1H), 2.22-2.18 (m, 1H), 1.92 (m, 1H). 1.73 (m, 3H). |
| 62a, 62b | 3-Methyl-5-(2-((((R)-1-(naphthalen-1-yl)ethyl)amino)methyl)-2H-benzo[b][1,4]oxazin-4(3H)-yl)benzoic acid hydrochloride | Example-23a, 23b | m/z 453.2; 62a: ¹H NMR (400 MHz, DMSO-D6): δ 13 (bs, 1H), 9.9 (bs, 1H), 9.6 (bs, 1H), 8.25 (d, J = 2.4 Hz, 1H), 8.02-7.92 (m, 3H), 7.63-7.58 (m, 3H), 7.50-7.45 (m, 2H), 7.22 (s, 1H), 6.91-6.81 (m, 4H), 5.45 (m, 1H), 4.61 (m, 1H), 3.92 (dd, J = 2.4 Hz, J = 12.8 Hz, 1H), 3.49-3.44 (m, 1H), 3.28 (m, 2H), 2.32 (s, 3H), 1.72 (d, J = 6.4 Hz, 3H); 62b: ¹H NMR (400 MHz, DMSO-D6): δ 13 (bs, 1H), 10.4 (bs, 1H), 9.4 (bs, 1H), 8.22 (d, J = 8 Hz, 1H), 8.02-7.96 (m, 3H), 7.63-7.56 (m, 3H), 7.48-7.44 (m, 2H), 7.18 (s, 1H), 6.95 (dd, J = 1.6 Hz, J = 8 Hz, 1H), 5.39 (m, 1H), 4.61 (m, 1H), 3.94 (d d, J = 2.4 Hz, J = 12.8 Hz, 1H), 3.50-3.45 (m, 2H), 3.01 (m, 1H), 2.30 (s, 3H), 1.73 (d, J = 6.4 Hz, 3H); |

TABLE 4-continued

| Example | Structure | ester | ¹HNMR |
|---|---|---|---|
| 63a | 2,6-Dimethyl-3-(2-((((R)-1-(naphthalen-1-yl)ethyl)amino)methyl)-2H-benzo[b][1,4]oxazin-4(3H)-yl) benzoic acid hydrochloride | Example-24 | m/z 494.2; ¹H NMR (400 MHz, DMSO-D6): δ 10.3 (bs, 1H), 9.3 (bs, 1H), 8.24 (m, 1H), 8.01-7.97 (m, 1H), 7.93-7.87 (m, 1H), 7.65-7.57 (m, 2H), 7.47 (m, 1H), 7.16-7.08 (m, 1H), 6.69-6.64 (m, 1H), 5.95 (m, 1H), 5.45 (m, 1H), 4.73 (m, 1H ), 4.36-4.31 (m, 2H), 3.71 (m, 1H), 3.58-3.46 (m, 2H), 3.01 (m, 1H), 2.23 (d, J = 12 Hz, 3H), 2.04 (s, 3H), 1.73 (m, 3H), 1.28 (m, 3H). |
| 64a, 64b | 4-(2-((((R)-1-(Naphthalen-1-yl)ethyl)amino)methyl)-2H-benzo[b][1,4]oxazin-4(3H)-yl)-2-(trifluoromethyl)benzoic acid hydrochloride | Example-25a, 25b | m/z 506.56; 64a: ¹H NMR (400 MHz, DMSO-D6): δ 13.2 (bs, 1H), 10.1 (bs, 1H), 9.9 (bs, 1H), 8.24 (d, J = 8 Hz, 1H), 8.02-7.96 (m, 3H), 7.84 (d, J = 8 Hz, 1H), 6.94 (d, J = 4 Hz, 2H), 6.87-6.83 (m, 1H), 5.45 (m, 1H), 4.67 (m, 1H), 4.12 (dd, J = 2.4 Hz, J = 13.2 Hz, 1H), 3.56-3.50 (m, 1H), 3.19 (m, 2H), 1.72 (d, J = 6.4 Hz, 3H)<br>64b: ¹H NMR (400 MHz, DMSO-D6): δ 13.2 (bs, 1H), 10.3 (bs, 1H), 9.35 (bs, 1H), 8.19 (d, J = 7.6 Hz, 1H), 8.02-7.94 (m, 3H), 7.79 (d, J = 8.4 Hz, 1H), 7.61-7.55 (m, 3H), 7.46 (d, J = 2.4 Hz, 1H), 7.36-7.34 (m, 1H), 7.10 (dd, J = 1.2 Hz, J = 8 Hz, 1H), 6.99-6.96 (m, 2H), 6.86 (m, 1H), 5.45 (m, 1H), 4.67 (m, 1H), 4.12 (dd, J = 2.4 Hz, J = 13.6 Hz, 1H), 3.58-3.53 (m, 1H), 3.00 (m, 1H), 1.72 (d, J = 6.4 Hz, 3H). |
| 65b | 2-Isopropyl-5-(2-((((R)-1-(naphthalen-1-yl)ethyl)amino)methyl)-2H-benzo[b][1,4]oxazin-4(3H)-yl) benzoic acid hydrochloride | Example-29b | 65b: m/z 481.11; ¹H NMR (400 MHz, DMSO-D6): δ 12.9 (bs, 1H), 10.10 (bs, 1H), 9.3 (bs, 1H), 8.22 (m, 1H), 8.03-7.96 (m, 2H), 7.94 (d, J = 7.2 Hz, 1H), 7.62-7.56 (m, 3H), 7.38-7.37 (m, 1H), 7.35 (s, 1H), 7.20-6.92 (m, 1H), 6.81-6.77 (m, 3H), 5.41 (m, 1H), 4.59 (m, 1H), 3.88-3.85 (m, 1H), 3.80 (s, 1H), 3.67-3.60 (m, 1H), 3.49-3.44 (m, 2H), 3.05 (m, 1H), 1.71 (d, J = 6.4 Hz, 3H), 1.19 (m, 6H). |

TABLE 4-continued

| Example | Structure | ester | ¹HNMR |
|---|---|---|---|
| 66a, 66b | 2-Hydroxy-5-(2-((((R)-1-(naphthalen-1-yl)ethyl)amino)methyl)-2H-benzo[b][1,4]oxazin-4(3H)-yl)benzoic acid hydrochloride | Example-27a, 27b | 66a: m/z 454.98; ¹H NMR (400 MHz, DMSO-D6): δ 10.01 (bs, 1H), 9.6 (bs, 1H), 8.26 (d, J = 8.4 Hz, 1H), 8.02-7.97 (m, 3H), 7.64-7.54 (m, 3H), 7.38 (dd, J = 2.8 Hz, J = 10.4 Hz, 1H), 7.00 (d, J = 8.8 Hz, 1H), 6.85-6.82 (m, 2H), 6.72-6.70 (m, 2H), 6.56-6.54 (m, 1H), 5.45 (m, 1H), 4.70 (m, 1H), 3.76-3.72 (m, 2H), 3.23 (m, 3H), 1.73 (d, J = 6.8 Hz, 3H); 66b: ¹H NMR (400 MHz, DMSO-D6): δ 10.1 (bs, 1H), 9.3 (bs, 1H), 8.24 (d, J = 8.4 Hz, 1H), 8.02-7.97 (m, 2H), 7.93 (d, J = 6.4 Hz, 1H), 7.64-7.57 (m, 3H), 7.54 (d, J = 1.6 Hz, 1H), 7.33 (dd, J = 2.8 Hz, J = 4 Hz, 1H), 6.97 (d, J = 8.8 Hz, 1H), 6.91-6.88 (m, 1H), 6.74-6.71 (m, 2H), 6.55-6.53 (m, 1H), 5.41 (m, 1H), 4.64 (m, 1H), 3.75-3.72 (m, 1H), 3.08 (m, 2H), 1.73 (d, J = 6.8 Hz, 3H) |
| 67a, 67b | 2-Methoxy-5-(2-((((R)-1-(naphthalen-1-yl)ethyl)amino)methyl)-2H-benzo[b][1,4]oxazin-4(3H)-yl)benzoic acid hydrochloride | Example-28a, 28b | 67a: m/z 469.1; ¹H NMR (400 MHz, DMSO-D6): δ 12.75 (bs, 1H), 10.0 (bs, 1H), 9.6 (bs, 1H), 8.26 (d, J = 8.4 Hz, 1H), 8.02-7.96 (m, 3H), 7.65-7.58 (m, 3H), 7.43 (d, J = 2.8 Hz, 3H), 7.34 (dd, J = 2.8 Hz, J = 8 Hz, 1H) 7.16 (d, J = 8.8 Hz, 1H), 6.85-6.83 (m, 1H), 6.74-6.69 (m, 2H), 6.60-6.58 (m, 1H), 5.45 (m, 1H), 4.70 (m, 1H), 380 (m, 5H), 1.71 (d, J = 6.4 Hz, H); 67b: ¹H NMR (400 MHz, DMSO-D6): δ 10.35 (bs, 1H), 9.4 (bs, 1H), 8.23 (d, J = 8.4 Hz, 1H), 8.02-7.95 (m, 3H), 7.64-7.56 (m, 3H), 7.42 (d, J = 2.8 Hz, 1H), 7.28 (dd, J = 2.8 Hz = 8.8 Hz, 1H), 7.11 (d, J = 8.8 Hz, 1H), 6.90-6.88 (m, 1H), 6.74-6.71 (m, 2H) 6.59-6.55 (m, 1H), 5.41 (m, 1H), 4.64 (m, 1H), 3.80 (m, 4H), 3.01 (m, 1H), 1.71 (s, 3H). |
| 68a, 68b | 3-(3-(2-((((R)-1-(Naphthalen-1-yl)ethyl)amino)methyl)-2H-benzo[b][1,4]oxazin-4(3H)-yl)phenyl)propanoic acid hydrochloride | Example-10a, 10b | 68a: m/z 466.42; a: ¹H NMR (400 MHz, DMSO-D6): δ 12.2 (bs, 1H), 9.7 (bs, 1H), 9.4 (bs, 1H), 8.22 (d, J = 8.4 Hz, 1H), 8.01 (t, J = 9.6, 2H), 7.90 (d, J = 7.2 Hz, 1H), 7.64-7.59 (m, 3H), 7.28 (t, J = 7.6 Hz, 1H), 6.99 (s, 1H), 6.96-6.90 (m, 2H), 6.89-6.83 (m, 1H), 6.78-6.79 (m, 1H), 6.77-6.74 (m, 2H), 5.41 (m, 1H), 4.64 (m, 1H), 3.85-3.81 (m, 1H), 3.48-3.39 (m, 2H), 3.27 (m, 3H), 2.78 (t, J = 8 Hz, 2H), 1.71 (d, J = 6.8 Hz, 3H); 68b: ¹H NMR (400 MHz, DMSO-D6): δ 12.2 (bs, 1H), 10.1 (bs, 1H), 9.3 (bs, 1H), 8.21 (d, J = 8.4 Hz, 1H), 8.02-8.00 (m, 2H), 7.92 (d, J = 7.6 Hz, 1H), 7.63-7.55 (m, 3H), 7.21 (t, J = 7.6 Hz, 1H), 6.99 (s, 1H), 6.94-6.91 (m, 3H), 6.80-6.74 (m, 3H), 5.41 (m, 1H), 4.64 (m, 1H), 3.86-3.82 (m, 1H), 3.49-3.39 (m, 2H), 3.37-3.35 (m, 2H), 3.16 (m, 1H), 3.04-3.02 (m, 2H), 1.72 (d, J = 6.4 Hz, 3H). |

TABLE 4-continued

| Example | Structure | ester | ¹HNMR |
|---|---|---|---|
| 69 | 2-(3-(2-((((R)-1-(Naphthalen-1-yl)ethyl)amino)methyl)-2H-benzo[b][1,4]oxazin-4(3H)-yl)phenyl)acetic acid hydrochloride | Example-30 | m/z 453.04; ¹H NMR (400 MHz, DMSO-D6): δ 12.4 (bs, 1H), 10 (bs, 1H), 9.3 (bs, 1H), 8.21 (m, 1H), 8.03-7.97 (m, 1H), 7.90 (d, J = 7.2 Hz, 2H), 7.63-7.57 (m, 3H), 7.25 (t, J = 8 Hz, 1H), 7.04 (s, 1H), 6.98-6.91 (m, 3H), 6.81-6.74 (m, 3H), 5.41 (m, 1H), 4.64 (m, 1H), 3.86-3.82 (m, 1H), 3.52 (s, 2H), 3.49-3.46 (m, 1H), 3.16-3.04 (m, 2H), 1.71 (d, J = 6.4 Hz, 3H). |
| 70b | 2,6-Dimethyl-3-(2-((((R)-1-(naphthalen-1-yl)ethyl)amino)methyl)-2H-benzo[b][1,4]oxazin-4(3H)-yl)benzoic acid hydrochloride | Example-24b | m/z 466.36; ¹H NMR (400 MHz, DMSO-d6): δ 13.26 (bs, 1H), 10.1 (bs, 1H), 9.3 (bs, 1H), 8.24 (t, J = 11.6 Hz, 1H), 8.04-7.91 (m, 3H), 7.84 (d, J = 7.2 Hz, 1H), 7.70-7.58 (m, 2H), 7.49 (t, J = 7.2 Hz, 1H), 7.16-7.03 (m, 2H), 6.92-6.86 (m, 1H), 6.68 (m, 2H), 5.45 (m, 1H), 4.73 (m, 1H), 4.13 (d, J = 3.2 Hz, 1H), 3.71 (m, 1H), 3.53-3.50 (m, 1H), 3.01 (m, 1H), 2.27 (d, J = 10.4 Hz, 3H), 2.08 (s, 3H), 1.72 (m, 3H). |
| 71a, 71b | 2-Methyl-5-(2-((((R)-1-(naphthalen-1-yl)ethyl)amino)methyl)-2H-benzo[b][1,4]oxazin-4(3H)-yl)benzoic acid hydrochloride | Example-31a, 31b | 71a: m/z 453.1; ¹H NMR (400 MHz, DMSO-d6): δ 12.92 (bs, 1H), 9.77 (bs, 1H), 9.44 (bs, 1H), 8.21 (d, J = 8 Hz, 1H), 8.03-8.00 (m, 2H), 7.92 (d, J = 7.2 Hz, 1H), 7.66-7.58 (m, 4H), 7.30-7.24 (m, 2H), 6.90-6.88 (m, 1H), 6.81 (m, 3H), 5.45 (m, 1H), 4.56 (m, 1H), 3.86-3.82 (m, 1H), 3.2 (m, 2H), 2.49 (s, 3H), 1.71 (d, J = 6.8 Hz, 3H); 71b: ¹H NMR (400 MHz, DMSO-d6): δ 12.9 (bs, 1H), 9.9 (bs, 1H), 9.3 (bs, 1H), 8.21 (m, 1H), 8.03-7.99 (m, 2H), 7.88 (d, J = 7.2 Hz, 1H), 7.65-7.57 (m, 3H), 7.25-7.16 (m, 2H), 6.94 (d, J = 7.6 Hz, 1H), 6.82-6.76 (m, 2H), 5.42 (m, 1H), 4.56 (m, 1H), 3.85-3.81 (m, 1H), 3.50-3.45 (m, 2H), 3.08 (m, 1H), 1.71 (d, J = 6.4 Hz, 3H). |

TABLE 4-continued

| Example | Structure | ester | ¹HNMR |
|---|---|---|---|
| 72 | 3-Fluoro-5-(2-((((R)-1-(naphthalen-1-yl)ethyl)amino)methyl)-2H-benzo[b][1,4]oxazin-4(3H)-yl)benzoic acid hydrochloride | Example-32 | m/z 457.1; ¹H NMR (400 MHz, DMSO-D6): δ 12.35 (bs, 1H), 10.01 (bs, 1H), 9.8 (bs, 1H), 9.5 (bs, 1H), 9.3 (bs, 1H), 8.2 (m, 1H), 8.02-7.96 (m, 2H), 9.92 (d, J = 7.2 Hz, 1H), 7.63-7.57 (m, 3H), 7.53-7.50 (m, 1H), 7.27-7.22 (m, 2H), 7.03-6.96 (m, 1H), 6.93-6.92 (m, 2H), 6.86-6.84 (m, 1H), 5.45 (m, 1H), 4.6 (m, 1H), 4.01 (d, J = 12, 1H), 3.51-3.48 (m, 1H), 3.29 (m, 1H), 3.02 (m, 1H), 1.71 (d, J = 6.8 Hz, 3H). |
| 73a, 73b | 2-Methyl-4-(2-((((R)-1-(naphthalen-1-yl)ethyl)amino)methyl)-2H-benzo[b][1,4]oxazin-4(3H)-yl)benzoic acid hydrochloride | Example-34a, 34b | 73a: m/z 453.1; ¹H NMR (400 MHz, DMSO-D6): δ12.50 (bs, 1H), 9.76 (bs, 1H), 9.46 (bs, 1H), 8.23 (d, J = 8 Hz, 1H), 8.03-7.98 (m, 2H), 7.91 (d, J = 7.2 Hz, 1H), 7.82-7.80 (m, 1H), 7.64-7.59 (m, 2H), 7.08-7.00 (m, 3H), 6.94-6.85 (m, 3H), 5.43 (m, 1H), 4.60 (m, 1H), 4.01 (m, 1H), 3.54-3.50 (m, 1H), 3.22 (m, 2H), 2.49 (s, 3H), 1.71 (d, J = 6.4 Hz, 3H); 73b: ¹H NMR (400 MHz, DMSO-D6): δ 12.50 (bs, 1H), 9.79 (bs, 1H), 9.21 (bs, 1H), 8.20 (d, J = 7.6 Hz, 1H), 8.02-7.96 (m, 2H), 7.84 (d, J = 7.2 Hz, 1H), 7.76 (d, J = 8.8 Hz, 1H), 7.63-7.54 (m, 2H), 7.03-6.81 (m, 5H), 5.40 (m, 1H), 4.55 (m, 1H), 3.97 (d, J = 11.2 Hz, 1H), 3.54-3.50 (m, 1H), 3.01 (m, 2H), 2.44 (s, 3H), 1.70 (d, J = 6.4 Hz, 3H). |
| 74b | 2-Fluoro-3-(2-((((R)-1-(naphthalen-1yl)ethyl)amino)methyl)-2H-benzo[b][1,4]oxazin-4(3H)-yl)benzoic acid hydrochloride | Example-38b | m/z 456.9: ¹H NMR (400 MHz, DMSO-d6): δ 13.4 (bs, 1H), 10.35 (bs, 1H), 9.45 (bs, 1H), 8.23 (d, J = 8 Hz, 1H), 8.02-7.98 (m, 3H), 7.69 (t, J = 6.4 Hz, 1H), 7.65-7.56 (m, 3H), 7.45 (t, J = 6.8 Hz, 1H), 7.27 (t, J = 8 Hz, 1H), 6.91 (dd, J = 2 Hz = 7.6 Hz, 1H), 6.77-6.74 (m, 2H), 6.38 (d, J = 7.2 Hz, 1H), 5.40 (d, J = 5.6 Hz, 1H), 4.72 (s, 1H), 3.78 (d, J = 10.8 Hz, 1H), 3.59-3.50 (m, 2H), 3.09 (s, 2H), 1.72 (d, J = 6.8 Hz, 3H) |

TABLE 4-continued

| Example | Structure | ester | ¹HNMR |
|---|---|---|---|
| 75a, 75b | 2-Chloro-5-(2-((((R)-1-(naphthalen-1-yl)ethyl)amino)methyl)-2H-benzo[b][1,4]oxazin-4(3H)-yl)benzoic acid hydrochloride | Example-18a, 18b | 75a: m/z 473.1: ¹H NMR (400 MHz, DMSO-d6): δ 13.5 (bs, 1H), 9.9 (bs, 1H), 9.5 (bs, 1H), 8.22 (s, 1H), 7.97-7.80 (m, 2H), 7.79 (d, J = 7.2 Hz, 1H), 7.64-7.58 (m, 3H), 7.43-7.50 (m, 2H), 7.27 (d, J = 2.8 Hz, 1H), 6.92-6.78 (m, 4H), 5.39-5.38 (m, 1H), 4.57-4.5 (m, 1H), 3.44-3.24 (m, 2H), 3.22-3.20 (m, 2H), 1.68 (d, J = 6.4 Hz, 3H); 75b: ¹H NMR (400 MHz, DMSO-d6): δ 13.5 (bs, 1H), 10.2 (bs, 1H), 9.35 (bs, 1H), 8.22 (s, 1H), 7.97-7.80 (m, 2H), 7.79 (d, J = 7.2 Hz, 1H), 7.64-7.58 (m, 3H), 7.43-7.50 (m, 2H), 7.27 (d, J = 2.8 Hz, 1H), 6.92-6.78 (m, 4H), 5.39-5.38 (m, 1H), 4.57-4.5 (m, 1H), 3.44-3.24 (m, 2H), 3.22-3.20 (m, 2H), 1.68 (d, J = 6.4 Hz, 3H); |
| 76a, 76b | 2-(2-Methyl-5-(2-((((R)-1-(naphthalen-1-yl)ethyl)amino)methyl)-2H-benzo[b][1,4]oxazin-4(3H)-yl)phenoxy)acetic acid hydrochloride | Example-35a, 35b | 76a: m/z 483.3; ¹H NMR (400 MHz, DMSO-d6): δ 9.8 (bs, 1H), 9.7 (bs, 1H), 8.25 (d, J = 8 Hz, 1H), 8.02-7.98 (m, 2H), 7.93 (d, J = 7.2 Hz, 1H), 7.63-7.58 (m, 3H), 7.13 (d, J = 7.6 Hz, 1H), 6.89 (m, 1H), 6.77-6.74 (m, 3H), 6.67-6.63 (m, 2H), 5.43 (m, 1H), 4.72 (m, 3H), 3.78 (m, 2H), 3.46-3.41 (m, 1H), 3.16-3.04 (m, 1H), 2.16 (s, 3H), 1.72 (d, J = 6.4 Hz, 3H); 76b: ¹H NMR (400 MHz, DMSO-d6): δ 9.6 (bs, 1H), 9.3 (bs, 1H), 8.25 (d, J = 8 Hz, 1H), 8.03-7.98 (m, 2H), 7.89-7.81 (m, 1H), 7.64-7.60 (m, 3H), 7.13 (d, J = 8 Hz, 1H), 7.05-6.86 (m, 1H), 6.79-6.74 (m, 3H), 6.66-6.63 (m, 3H), 6.54 (m, 2H), 5.41 (m, 1H), 4.65 (s, 2H), 4.58 (m, 1H), 3.79 (m, 2H), 2.15 (s, 3H), 1.69 (s, 3H). |
| 77a, 77b | 2-Methyl-2-(2-methyl-5-(2-((((R)-1-(naphthalen-1-yl)ethyl)amino)methyl)-2H-benzo[b][1,4]oxazin-4(3H)-yl)phenoxy)propanoic acid hydrochloride | Example-36a, 36b | 77a: m/z 511.2; ¹H NMR (400 MHz, DMSO-d6): δ 13.01 (bs, 1H), 9.9 (bs, 1H), 9.5 (bs, 1H), 8.26 (d, J = 8 Hz, 1H), 8.01 (t, J = 8.8 Hz, 2H), 7.92 (d, J = 6.8 Hz, 1H), 7.66-7.58 (m, 3H), 7.16 (d, J = 8 Hz, 1H), 6.86-6.84 (m, 1H), 6.75-6.70 (m, 3H), 6.67 (m, 1H), 6.53 (m, 1H), 5.44 (m, 1H), 4.6 (m, 1H), 3.75 (m, 1H), 3.42 (m, 1H), 3.26 (m, 2H), 2.12 (s, 3H), 1.71 (d, J = 6.4 Hz, 3H), 1.49 (m, 6H); 77b: ¹H NMR (400 MHz, DMSO-D6): δ 13 (bs, 1H), 9.9 (bs, 1H), 9.3 (bs, 1H), 8.23 (d, J = 8 Hz, 1H), 8.03-7.97 (m, 2H), 7.89 (d, J = 7.2 Hz, 1H), 7.66-7.58 (m, 3H), 7.12 (d, J = 8 Hz, 1H), 6.91-6.89 (m, 1H), 6.76-6.8 (m, 3H), 6.61 (m, 1H), 6.53 (m, 1H), 5.43 (m, 1H), 4.6 (m, 1H), 3.74 (m, 1H), 3.07 (m, 2H), 2.11 (s, 3H), 1.71 (d, J = 6.8 Hz, 3H), 1.48 (m, 6H) |

TABLE 4-continued

| Example | Structure | ester | ¹HNMR |
|---|---|---|---|
| 78b | 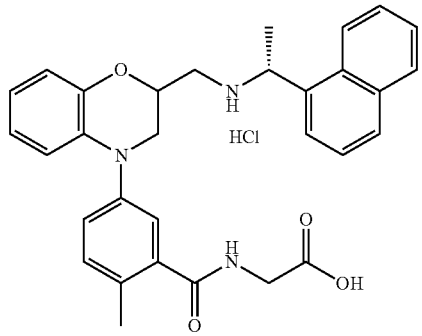<br>3-(2-Methyl-5-(2-((((R)-1-(naphthalen-1-yl)ethyl)amino)methyl)-2H-benzo[b][1,4]oxazin-4(3H)-yl)phenyl)propanoic acid hydrochloride | Example 37b | 78a: m/z 481.11; ¹H NMR (400 MHz, DMSO-D6): 12.2 (bs, 1H), 9.8 (bs, 1H), 9.3 (bs, 1H), 8.23 (d, J = 8.4 Hz, 1H), 8.03-7.97 (m, 2H), 7.85 (d, J = 7.6 Hz, 1H), 7.65-7.58 (m, 3H), 7.08 (d, J = 8 Hz, 1H), 6.93-6.90 (m, 1H), 6.82-6.69 (m, 3H), 5.40 (m, 1H), 4.54 (m, 1H), 3.76-3.45 (m, 1H), 3.44-3.42 (m, 3H), 3.01 (m, 2H), 2.76-2.72 (m, 2H), 2.44 (m, 2H), 1.71 (d, J = 6.4 Hz, 3H). |

Example-79b 2-(2-Methyl-5-(2-((((R)-1-(naphthalen-1-yl)ethyl)amino)methyl)-2H-benzo[b][1,4]oxazin-4(3H)-yl)benzamido)acetic acid hydrochloride

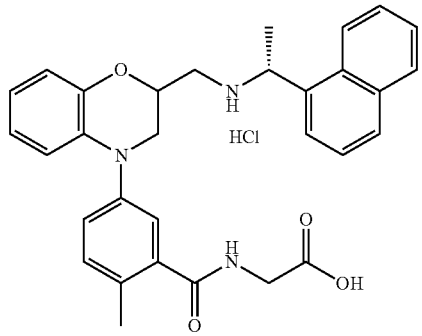 [SMILES: Cc1ccc(N2CC(CN[C@H](C)c3cccc4ccccc34)Oc3ccccc32)cc1C(=O)NCC(=O)O ; Cl]

The title compound was prepared in two steps.

Step-1: Example-71b was reacted with methyl 2-aminoacetate following the similar as described in Example-8.

Step-2: Step-1 compound was hydrolyzed by following the similar procedure as in Example-6 by using LiOH monohydrate.

m/z 510.2; ¹H NMR (400 MHz, DMSO-D6): δ 12.6 (bs, 1H), 10.05 (bs, 1H), 9.30 (bs, 1H), 8.58 (t, J=6 Hz, 1H), 8.23 (d, J=8, 1H), 8.03-7.90 (m, 3H), 7.65-7.56 (m, 3H), 7.17-7.13 (m, 1H), 7.04-7.01 (m, 1H), 6.93-6.92 (m, 1H), 6.81-6.73 (m, 2H), 5.45 (m, 1H), 4.67 (m, 1H), 3.85 (m, 3H), 3.01 (m, 1H), 2.41 (s, 3H), 1.72 (m, 3H).

Example-80

Methyl 2-methyl-5-(2-(2-(((S)-1-(naphthalen-1-yl)ethyl)amino)ethyl)-2H-benzo[b][1,4]oxazin-4(3H)-yl)benzoate

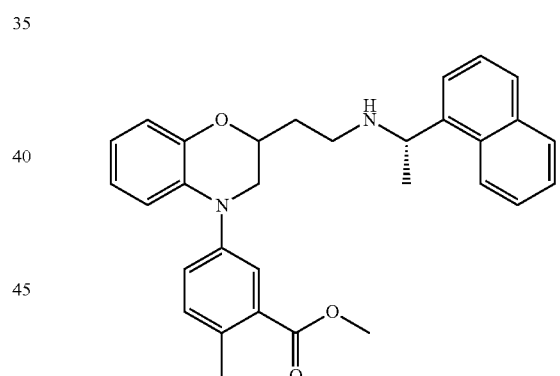

Intermediate-31 (0.15 g, 0.45 mmol) and methyl 5-bromo-2-methylbenzoate (0.12 g, 054 mmol), Cs₂CO₃ (0.22 g, 0.68 mmol) were added in toluene (7 mL) and degassed for 15 min by purging nitrogen. Then, bis(tri-tert-butylphosphine palladium (0) (0.012 g, 0.023 mmol) and tris dibenzylidene acetone dipalladium (0) (0.021 g, 0.023 mmol) were added. The reaction mixture was heated to 110° C. and further maintained for 20 h at the same temperature. The reaction mixture was cooled to room temperature and progress of reaction monitored by TLC. The mixture was diluted with ethylacetate, filtered through celite and concentrated under vacuum to get the crude product. The crude product was purified by flash chromatography using a mixture of 20% ethylacetate in hexane (0.14 g, 64%). m/z 481.2.

Example-81

Methyl 3-((2-((((R)-1-(naphthalen-1-yl)ethyl)amino)methyl)-2H-benzo[b][1,4]oxazin-4(3H)-yl)methyl)benzoate

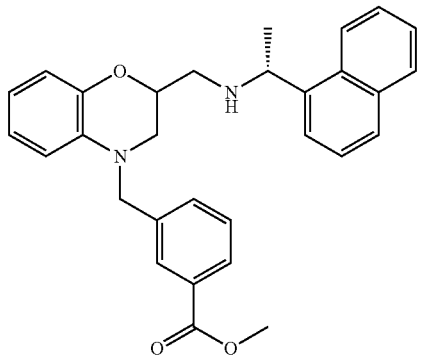 [SMILES: COC(=O)c1cccc(CN2CC(CN[C@H](C)c3cccc4ccccc34)Oc3ccccc32)c1]

Methyl 3-((2-(((R)-1-(naphthalen-1-yl)ethyl)carbamoyl)-2H-benzo[b][1,4]oxazin-4(3H)-yl)methyl)benzoate Step-1: Intermediate-3 (0.7 g, 2.1 mmol) was dissolved in DMF (5 mL) and cooled to 0° C. To this solution $K_2CO_3$ (0.58 g, 4.21 mmol) was added and stirred for 15 min then methyl 3-(bromomethyl)benzoate (0.72 g, 3.16 mmol) was added slowly. The reaction mixture was allowed to RT and further stirred for 20 h. The progress of reaction was monitored by TLC. The mixture was diluted with Ethyl acetate. Organic layer was washed with water followed by brine solution. The organic layer was dried over sodium sulfate and concentrated to get crude compound. This was further purified by flash chromatography using a mixture of ethyl acetate/hexane as eluent to give title compound as an oily mass (0.8 g, 80%). m/z 480.10.

Step 2: Methyl 3-((2-((((R)-1-(naphthalen-1-yl)ethyl)amino)methyl)-2H-benzo[b][1,4]oxazin-4(3H)-yl)methyl)benzoate The title compound was prepared by following the similar coupling procedure as described in Example-1, by taking step-1 intermediate. m/z −467.5.

Example-82

3-((2-((((R)-1-(Naphthalen-1-yl)ethyl)amino)methyl)-2H-benzo[b][1,4]oxazin-4(3H)-yl)methyl)benzoic acid hydrochloride

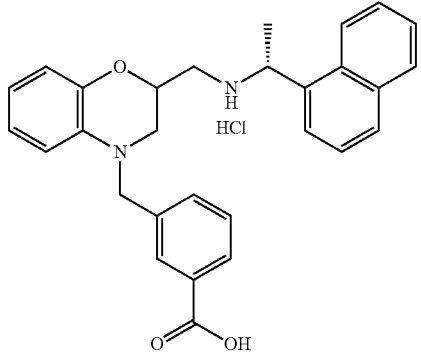 [SMILES: C[C@@H](NCC1CN(Cc2cccc(C(=O)O)c2)c2ccccc2O1)c1cccc2ccccc12 ; Cl]

The title compound was prepared by following the similar hydrolysis procedure as described in Example-6, by taking Example-81.
m/z 453.1; $^1$H NMR (400 MHz, DMSO-d6): δ 12.95 (bs, 1H), 10.3 (bs, 1H), 9.9 (bs, 1H), 9.6 (bs, 1H), 9.35 (bs, 1H), 8.24 (m, 1H), 8.03-7.93 (m, 3H), 7.85-7.80 (m, 2H), 7.65-7.57 (m, 3H), 7.45-7.40 (m, 2H), 6.85-6.82 (m, 1H), 6.77-6.72 (m, 1H), 6.69-6.67 (m, 1H), 6.60-6.59 (m, 1H), 5.44 (m, 1H), 4.64 (m, 1H), 4.54-4.48 (m, 2H), 3.46 (m, 1H), 3.22-3.19 (m, 2H), 3.04 (m, 1H), 1.72 (d, J=6.4 Hz, 3H);

Example-83

Methyl 5-(7-fluoro-2-((((R)-1-(naphthalen-1-yl)ethyl)amino)methyl)-2H-benzo[b][1,4]oxazin-4(3H)-yl)-2-methylbenzoate

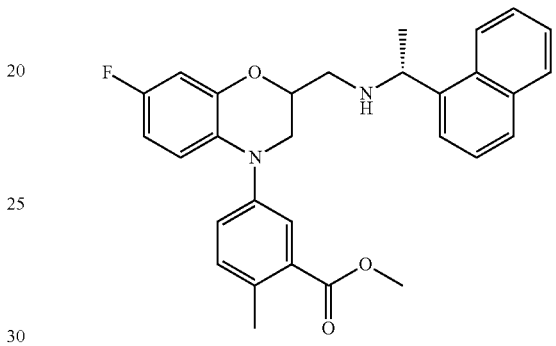

The title compound was prepared by following the similar coupling reaction procedure as described in Example-10a, 10b by taking Intermediate-12 and methyl 5-bromo-2-methylbenzoate. Further, the compound was purified by flash chromatography using a mixture of 15% ethylacetate in hexane. m/z 485.1.

Example-84

5-(7-Fluoro-2-((((R)-1-(naphthalen-1-yl)ethyl)amino)methyl)-2H-benzo[b][1,4]oxazin-4(3H)-yl)-2-methyl benzoic acid hydrochloride

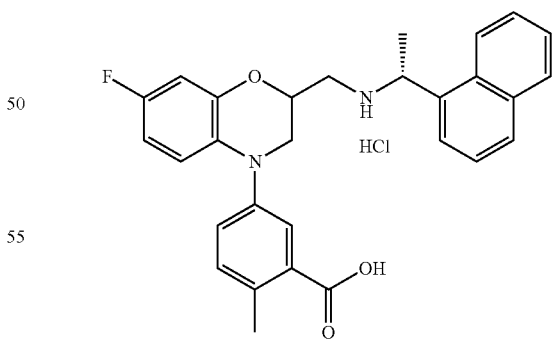

The title compound was prepared by following the similar hydrolysis procedure as described in Example-6a, 6b by taking Example-83.
m/z 471.1; $^1$H NMR (400 MHz, DMSO-D6): δ 12.95 (bs, 1H), 10.5 (bs, 1H), 10.13 (bs, 1H), 9.78 (bs, 1H), 9.42 (bs, 1H), 8.25 (m, 1H), 8.02-7.96 (m, 3H), 7.63-7.53 (m, 4H), 7.27-7.18 (m, 1H), 7.14-7.12 (m, 1H), 6.78-6.75 (m, 2H), 6.67-6.62 (m, 1H), 5.45 (m, 1H), 4.67 (m, 1H), 3.90-3.85 (m, 1H), 3.46-3.40 (m, 3H), 3.20 (m, 1H), 3.06 (m, 1H), 1.73 (d, J=6.4 Hz, 3H).

Example-85a, 85b

Methyl 2-methyl-5-(2-methyl-2-((((R)-1-(naphthalen-1-yl)ethyl)amino)methyl)-2H-benzo[b][1,4]oxazin-4(3H)-yl)benzoate

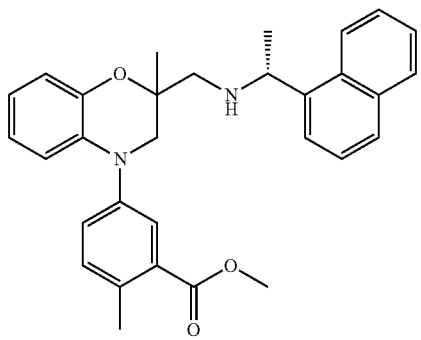 [SMILES: COC(=O)c1cc(N2CC(C)(CN[C@H](C)c3cccc4ccccc34)Oc3ccccc32)ccc1C]

The title compound was prepared by following the similar coupling reaction procedure as described in Example-10a, 10b by taking Intermediate-9 and methyl 5-bromo-2-methylbenzoate. Further diastereomers were separated by using flash chromatography using a mixture of 15% ethylacetate in hexane. m/z 482.2.

Example-86a, 86b

2-Methyl-5-(2-methyl-2-((((R)-1-(naphthalen-1-yl)ethyl)amino)methyl)-2H-benzo[b][1,4]oxazin-4(3H)-yl)benzoic acid hydrochloride

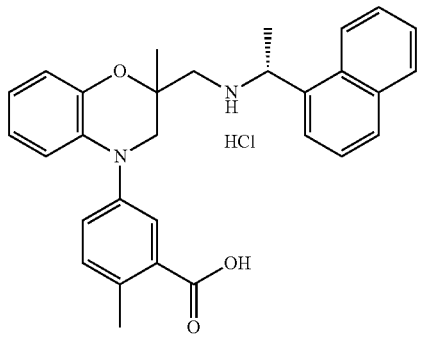 [SMILES: Cc1ccc(N2CC(C)(CN[C@H](C)c3cccc4ccccc34)Oc3ccccc32)cc1C(=O)O ; Cl]

The title compound was prepared by following the similar hydrolysis procedure as described in Example-6a, 6b by taking Example-85a. Further HCl salt of this amino compound was prepared by following the similar HCl salt procedure as described in Example-1.

Example-86a: m/z 466.36; $^1$H NMR (400 MHz, DMSO-d6): δ12.95 (bs, 1H), 9.65 (bs, 1H), 9.25 (bs, 1H), 8.12 (m, 1H), 8.02-7.96 (m, 3H), 7.63-7.57 (m, 4H), 7.25 (d, J=8.4, 1H), 7.17-7.14 (m, 1H), 6.87-6.85 (m, 1H), 6.80-6.72 (m, 3H), 5.35 (m, 1H), 3.71 (d, J=12.8, 1H), 3.56 (m, 1H), 3.40 (m, 3H), 3.29 (m, 1H), 3.06 (m, 1H), 2.47 (s, 3H), 1.73 (d, J=6.8 Hz, 3H);

Similarly, Example-86b was prepared from Example-85b by following the similar procedure as described in Example-6a, 6b.

Example-86b: $^1$H NMR (400 MHz, DMSO-d6): δ 12.95 (bs, 1H), 10.10 (bs, 1H), 8.85 (bs, 1H), 8.13 (d, J=8 Hz, 1H), 8.01 (d, J=1.6 Hz, 1H), 7.85 (d, J=8 Hz, 1H), 7.74 (d, J=7.2, 1H), 7.60-7.56 (m, 2H), 7.35 (d, J=2.4 Hz, 1H), 7.25 (t, J=7.6 Hz, 1H), 6.93 (dd, J=1.2 Hz, J=8.0 Hz, 1H), 6.85-6.81 (m, 2H), 3.71 (d, J=12.8, 1H), 6.70 (t, J=7.2 Hz, 1H), 6.60 (dd, J=1.2 Hz, J=1.2 Hz, 1H), 5.35 (m, 1H), 3.64 (m, 1H), 3.40 (m, 3H), 3.18 (m, 1H), 2.79 (m, 1H), 2.38 (s, 3H), 1.73 (d, J=6.4 Hz, 3H).

Example-87b

2-Methyl-5-(2-((((R)-1-(naphthalen-1-yl)ethyl)amino)methyl)-3-oxo-2H-benzo[b][1,4]oxazin-4(3H)-yl)benzoic acid hydrochloride

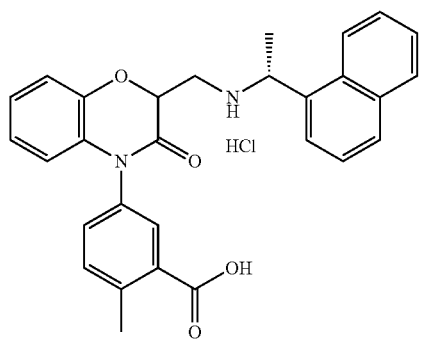 [SMILES: Cc1ccc(N2C(=O)C(CN[C@H](C)c3cccc4ccccc34)Oc3ccccc32)cc1C(=O)O ; Cl]

To a solution of Example-40b (0.050 g, 0.10 mmol) in MeOH (5 mL), THF (5.00 mL) and water (0.5 mL) lithium hydroxide monohydrate (0.075 g, 0.3 μmol) were added. The reaction mixture was heated to 50° C. and further maintained for 2 h. The progress of reaction was monitored by TLC. The reaction mixture was concentrated under vacuum then cooled to 0° C. and acidified with dilute HCl solution [pH=3 to 4]. The product was extracted into Ethyl acetate (10 mL×2), washed with water (5 mL×2) followed by brine solution (5 mL), dried over sodium sulfate and concentrated under vacuum to get solid compound. Further HCl salt of this amino compound was prepared by following the similar HCl salt procedure as described in Example-1. (0.03 g, 61.8% yield).

m/z 466.1; $^1$H NMR (400 MHz, CDCl$_3$): δ 8.17 (d, J=7.2, 1H), 7.89 (d, J=7.6, 2H), 7.78-7.68 (m, 2H), 7.55-7.46 (m, 3H), 7.37 (d, J=7.6, 1H), 7.03-6.95 (m, 2H), 6.82 (m, 1H), 6.35 (m, 1H), 4.95 (m, 1H), 3.26 (m, 1H), 2.65 (m, 2H), 1.61 (m, 3H), 1.30 (m, 3H).

Example-88a, 88b

Methyl 2-methyl-5-(2-(2-(((R)-1-(naphthalen-1-yl)ethyl)amino)ethyl)-2H-benzo[b][1,4]oxazin-4(3H)-yl)benzoate

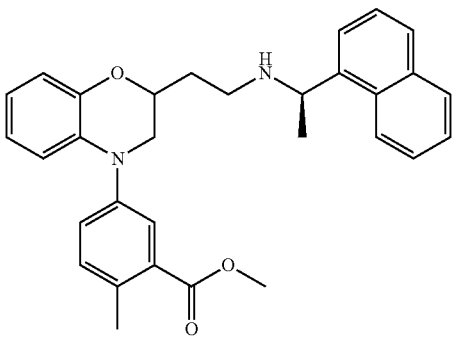 [SMILES: COC(=O)c1cc(N2CC(CCN[C@H](C)c3cccc4ccccc34)Oc3ccccc32)ccc1C]

Racemic mixture of Intermediate-18 (0.35 g, 1.05 mmol) and methyl 5-bromo-2-methylbenzoate (0.29 g, 1.26 mmol), $Cs_2CO_3$ (0.52 g, 1.58 mmol) were added in toluene (7 mL) and degassed for 15 min by purging nitrogen. Then, bis(tri-tert-butylphosphine palladium (0) (0.027 g, 0.053 mmol) and tris dibenzylidene acetone dipalladium (0) (0.048 g, 0.053 mmol) were added. The reaction mixture was heated to 110° C. and further maintained for 20 hr at the same temperature. The reaction mixture was cooled to room temperature and progress of reaction monitored by TLC. The mixture was diluted with ethylacetate, filtered through celite and concentrated under vacuum to get the crude product. The crude product was purified by flash chromatography using a mixture of 20% ethylacetate in hexane (0.18 g, 86%). Diastereomers were separated by chiral chromatography (CHIRAL ID 250×4.6 5 u) solvent:- Hexane/IPA (90/10), B=IPA A: B 70/30% V/V. m/z 481.2;

Example-88a: ($t_R$=6.06), $^1$H NMR (400 MHz, $CDCl_3$): δ 8.17 (d, J=7.2 Hz, 1H), 7.89 (d, J=9.6 Hz, 1H), 7.78-7.68 (m, 2H), 7.65 (d, J=6.8 Hz, 1H), 7.50-7.48 (m, 2H), 7.28-7.26 (m, 2H), 7.22 (d, J=8.4 Hz, 1H), 6.86-6.82 (m, 2H), 6.77-6.73 (m, 2H) 4.71 (m, 1H), 4.3 (m, 1H), 3.88 (s, 3H), 3.67-3.65 (m, 1H), 3.47-3.42 (m, 1H), 2.86-2.79 (m, 2H), 2.57 (s, 3H), 1.95-1.89 (m, 1H), 1.83-1.78 (m, 1H), 1.52 (d, J=6.4 Hz, 3H).

Example-88b: ($t_R$=7.06), m/z=481.2; $^1$H NMR (400 MHz, $CDCl_3$): δ 8.2 (d, J=7.2 Hz, 1H), 7.88 (d, J=9.6 Hz, 1H), 7.78-7.68 (m, 2H), 7.62 (d, J=6.8 Hz, 1H), 7.50-7.48 (m, 2H), 7.46-7.42 (m, 1H), 7.24-7.21 (m, 2H), 6.87-6.83 (m, 2H), 6.77-6.73 (m, 2H), 4.68-4.63 (m, 1H), 4.35-4.33 (m, 1H), 3.88 (s, 3H), 3.60-3.50 (m, 1H), 3.42-3.37 (m, 1H), 2.86-2.75 (m, 2H), 2.58 (s, 3H), 1.99-1.93 (m, 1H), 1.79-1.73 (m, 1H), 1.52 (d, J=6.4 Hz, 3H)

The below Examples 89 to 113 given in Table-5 were prepared by following the similar procedure as described in Example-88a, 88b by taking Intermediate-18a and appropriately substituted halo benzene.

TABLE 5

| Example | Structure | Chemical Name | Mass m/z |
|---|---|---|---|
| 89a | 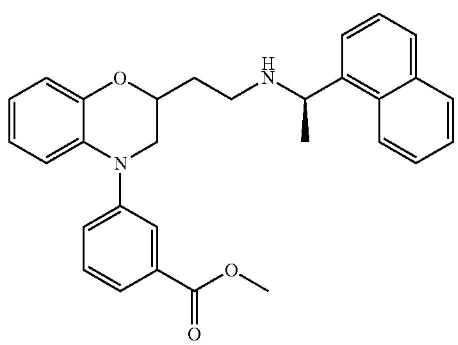 [SMILES: COC(=O)c1cccc(N2CC(CCN[C@H](C)c3cccc4ccccc34)Oc3ccccc32)c1] | Methyl-3-(2-(2-(((R)-1-(naphthalen-1-yl) ethyl) amino) ethyl)-2H-benzo[b][1,4]oxazin-4(3H)-yl) benzoate | 467.1 |
| 90a | 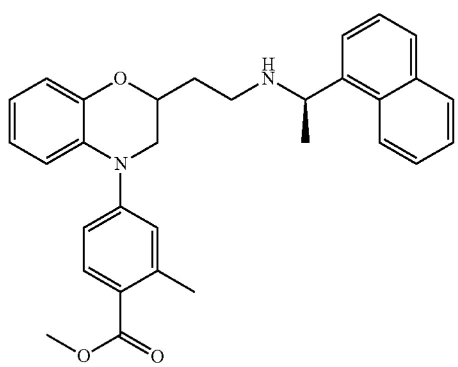 [SMILES: COC(=O)c1ccc(N2CC(CCN[C@H](C)c3cccc4ccccc34)Oc3ccccc32)cc1C] | Methyl 2-methyl-4-(2-(2-(((R)-1-(naphthalen-1-yl) ethyl) amino) ethyl)-2H-benzo [b][1,4]oxazin-4(3H)-yl) benzoate | 481.2 |

TABLE 5-continued

| Example | Structure | Chemical Name | Mass m/z |
|---|---|---|---|
| 91a | 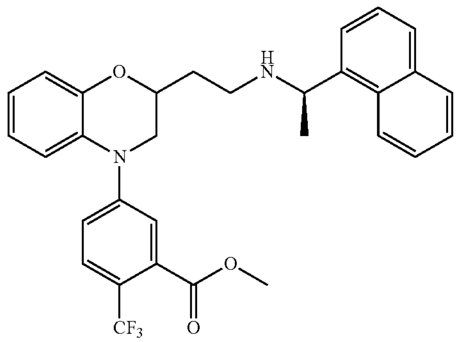 [SMILES: COC(=O)c1cc(N2CC(CCN[C@H](C)c3cccc4ccccc34)Oc3ccccc32)ccc1C(F)(F)F] | Methyl 5-(2-(2-(((R)-1-(naphthalen-1-yl)ethyl) amino) ethyl)-2H-benzo [b] [1,4] oxazin-4 (3H) yl)-2-(trifluoromethyl) benzoate | 535.5 |
| 92a | 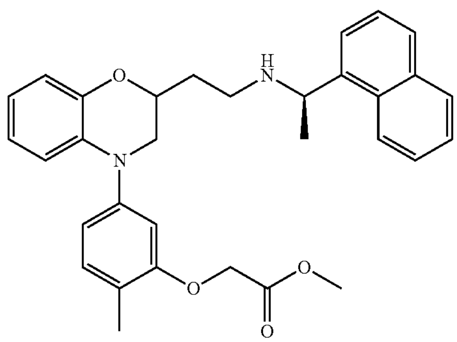 [SMILES: COC(=O)COc1cc(N2CC(CCN[C@H](C)c3cccc4ccccc34)Oc3ccccc32)ccc1C] | Methyl2-(2-methyl-5-(2-(2-(((R)-1-(naphthalen-1-yl) ethyl)amino) ethyl)-2H-benzo [b][1,4] oxazin-4(3H)-yl) phenoxy) acetate | 511.5 |
| 93a | 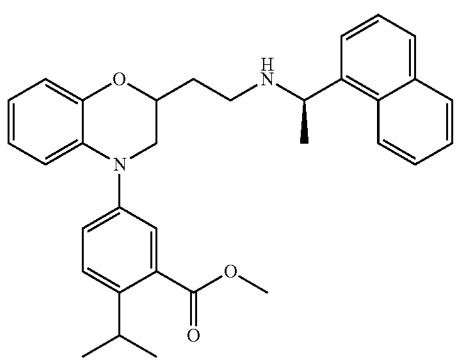 [SMILES: COC(=O)c1cc(N2CC(CCN[C@H](C)c3cccc4ccccc34)Oc3ccccc32)ccc1C(C)C] | Methyl 2-isopropyl-5-(2-(2-(((R)-1-(naphthalen-1-yl) ethyl) amino) ethyl)-2H-benzo [b] [1,4]oxazin-4(3H)-yl) benzoate | 509.5 |
| 94a | 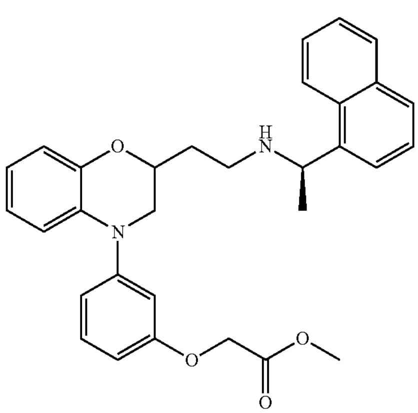 [SMILES: COC(=O)COc1cccc(N2CC(CCN[C@H](C)c3cccc4ccccc34)Oc3ccccc32)c1] | Methyl 2-(3-(2-(2-(((R)-1 (naphthalen-1-yl)ethyl) amino) ethyl)-2H-benzo[b] [1,4] oxazin-4(3H)-yl) phenoxy) acetate | 497.1 |

TABLE 5-continued
| Example | Structure | Chemical Name | Mass m/z |
|---|---|---|---|
| 95a | 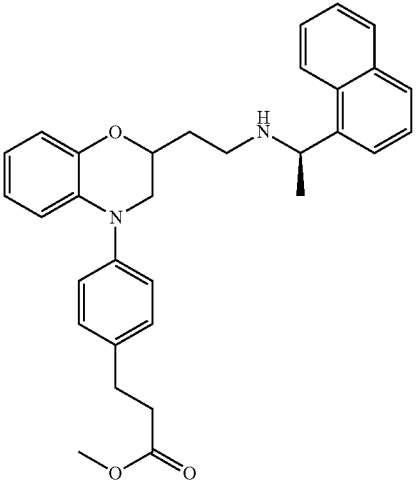 [SMILES: COC(=O)CCc1ccc(N2CC(CCN[C@H](C)c3cccc4ccccc34)Oc3ccccc32)cc1] | Methyl 3-(4-(2-(2-(((R)-1-(naphthalen-1-yl)ethyl) amino)ethyl)-2H-benzo [b] [1,4]oxazin-4(3H)-yl) phenyl) propanoate | 495.5 |
| 96a | 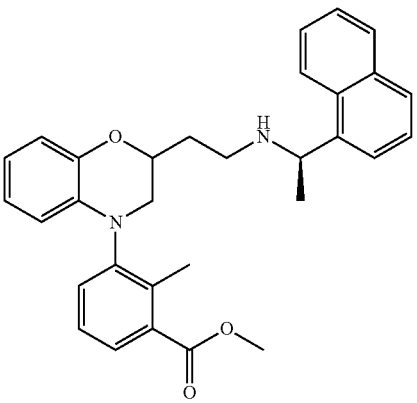 [SMILES: COC(=O)c1cccc(N2CC(CCN[C@H](C)c3cccc4ccccc34)Oc3ccccc32)c1C] | Methyl 2-methyl-3-(2-(2-(((R)-1-(naphthalen-1-yl) ethyl) amino) ethyl)-2H-benzo [b] [1,4] oxazin-4(3H)-yl) benzoate | 481.2 |
| 97a | 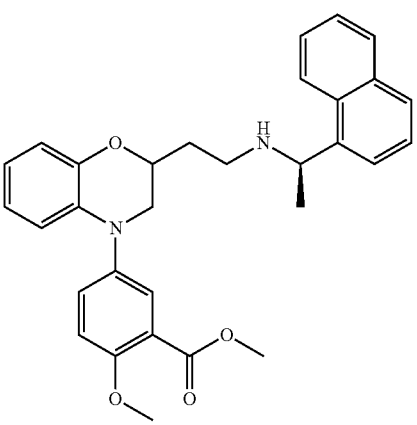 [SMILES: COC(=O)c1cc(N2CC(CCN[C@H](C)c3cccc4ccccc34)Oc3ccccc32)ccc1OC] | Methyl 2-methoxy-5-(2-(2-(((R)-1-(naphthalen-1-yl) ethyl) amino) ethyl)-2H-benzo [b][1,4] oxazin-4(3H)-yl) benzoate | 497.2 |

TABLE 5-continued

| Example | Structure | Chemical Name | Mass m/z |
|---|---|---|---|
| 98a | 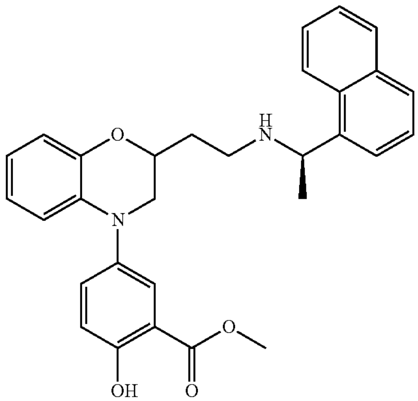 [SMILES: COC(=O)c1cc(N2CC(CCN[C@H](C)c3cccc4ccccc34)Oc3ccccc32)ccc1O] | Methyl 2-hydroxy-5-(2-(2-(((R)-1-(naphthalen-1-yl) ethyl) amino) ethyl)-2H-benzo[b][1,4]oxazin-4(3H)-yl) benzoate | 483.2 |
| 99a | 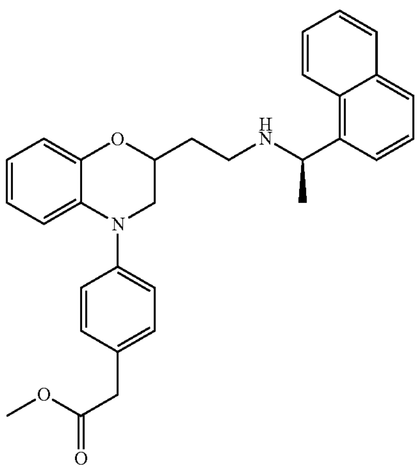 [SMILES: COC(=O)Cc1ccc(N2CC(CCN[C@H](C)c3cccc4ccccc34)Oc3ccccc32)cc1] | Methyl 2-(4-(2-(2-(((R)-1-(naphthalen-1-yl)ethyl) amino) ethyl)-2H-benzo[b][1,4]oxazin-4(3H)-yl)phenyl) acetate | 481.5 |
| 100a | 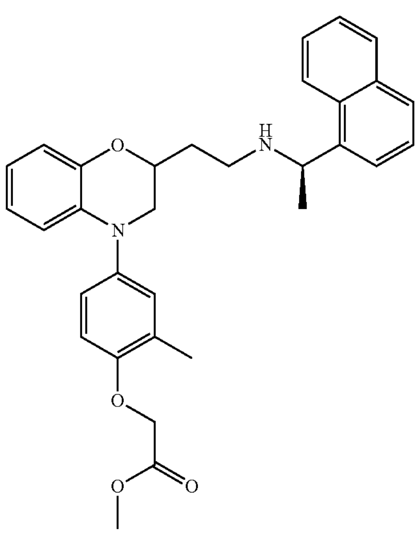 [SMILES: COC(=O)COc1ccc(N2CC(CCN[C@H](C)c3cccc4ccccc34)Oc3ccccc32)cc1C] | Methyl 2-(2-methyl-4-(2-(2-(((R)-1-(naphthalen-1-yl) ethyl) amino) ethyl)-2H-benzo[b][1,4]oxazin-4(3H)-yl)phenoxy)acetate | 511.5 |

TABLE 5-continued
| Example | Structure | Chemical Name | Mass m/z |
|---|---|---|---|
| 101a | 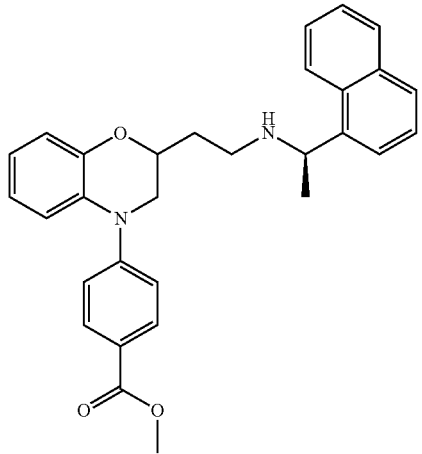 [SMILES: COC(=O)c1ccc(N2CC(CCN[C@H](C)c3cccc4ccccc34)Oc3ccccc32)cc1] | Methyl 4-(2-(2-(((R)-1-(naphthalen-1-yl)ethyl)amino)ethyl)-2H-benzo [b][1,4] oxazin-4(3H)-yl) benzoate | 467.5 |
| 102a | 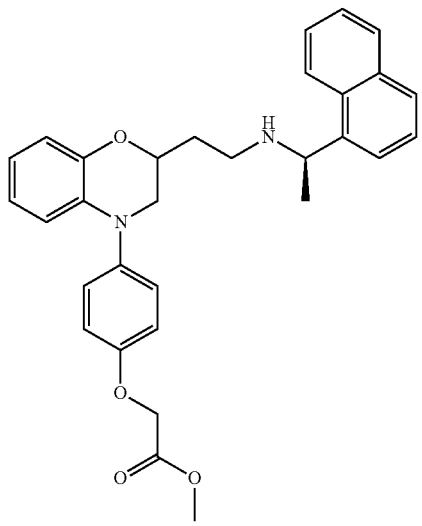 [SMILES: COC(=O)COc1ccc(N2CC(CCN[C@H](C)c3cccc4ccccc34)Oc3ccccc32)cc1] | Methyl 2-(4-(2-(2-(((R)-1-(naphthalen-1-yl)ethyl)amino)ethyl)-2H-benzo [b][1,4]oxazin-4(3H)-yl) phenoxy)acetate | 497.5 |
| 103a | 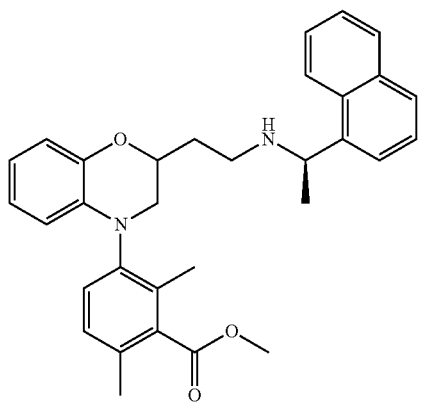 [SMILES: COC(=O)c1c(C)ccc(N2CC(CCN[C@H](C)c3cccc4ccccc34)Oc3ccccc32)c1C] | Methyl 2,6-dimethyl-3-(2-(2-(((R)-1-(naphthalen-1-yl)ethyl)amino) ethyl)-2H-benzo [b][1,4]oxazin-4(3H)-yl) benzoate | 495.2 |

TABLE 5-continued

| Example | Structure | Chemical Name | Mass m/z |
|---|---|---|---|
| 104a | 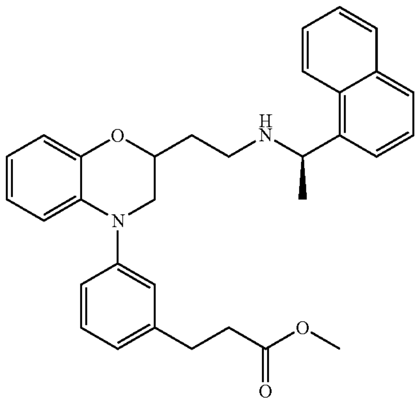 [SMILES: COC(=O)CCc1cccc(N2CC(CCN[C@H](C)c3cccc4ccccc34)Oc3ccccc32)c1] | Methyl 3-(3-(2-(2-(((R)-1-(naphthalen-1-yl)ethyl)amino)ethyl)-2H-benzo [b][1,4]oxazin-4(3H)-yl) phenyl) propanoate | 495.5 |
| 105a | 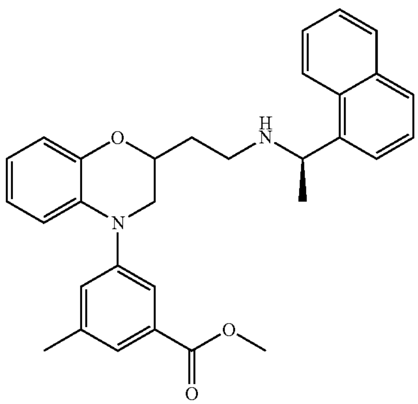 [SMILES: COC(=O)c1cc(C)cc(N2CC(CCN[C@H](C)c3cccc4ccccc34)Oc3ccccc32)c1] | Methyl 3-methyl-5-(2-(2-(((R)-1-(naphthalen-1-yl)ethyl)amino)ethyl)-2H-benzo[b][1,4]oxazin-4(3H)-yl)benzoate | 481.1 |
| 106a | 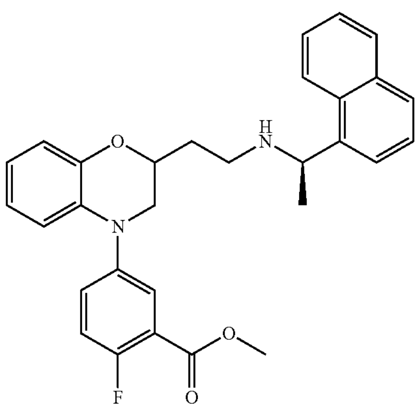 [SMILES: COC(=O)c1cc(N2CC(CCN[C@H](C)c3cccc4ccccc34)Oc3ccccc32)ccc1F] | Methyl 2-fluoro-5-(2-(2-(((R)-1-(naphthalen-1-yl)ethyl)amino)ethyl)-2H-benzo[b][1,4]oxazin-4(3H)-yl)benzoate | 485.1 |
| 107a | 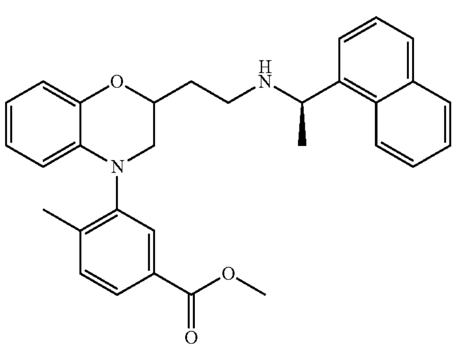 [SMILES: COC(=O)c1ccc(C)c(N2CC(CCN[C@H](C)c3cccc4ccccc34)Oc3ccccc32)c1] | Methyl 4-methyl-3-(2-(2-(((R)-1-(naphthalen-1-yl)ethyl)amino)ethyl)-2H-benzo[b][1,4]oxazin-4(3H)-yl)benzoate | 481.5 |

TABLE 5-continued

| Example | Structure | Chemical Name | Mass m/z |
|---|---|---|---|
| 108a | 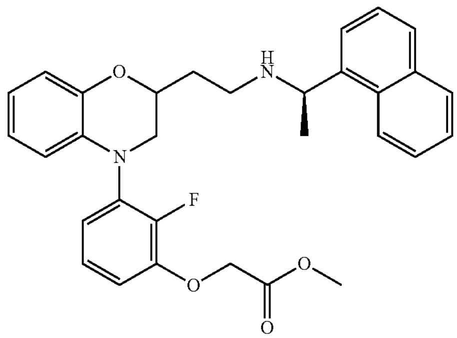 [SMILES: COC(=O)COc1cccc(N2CC(CCN[C@H](C)c3cccc4ccccc34)Oc3ccccc32)c1F] | Methyl 2-(2-fluoro-3-(2-(2-(((R)-1-(naphthalen-1-yl)ethyl)amino)ethyl)-2H-benzo[b][1,4]oxazin-4(3H)-yl)phenoxy)acetate | 515.2 |
| 109a | 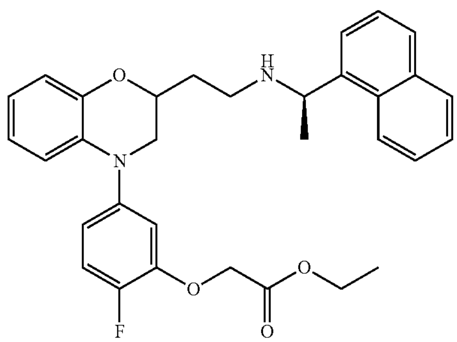 [SMILES: CCOC(=O)COc1cc(N2CC(CCN[C@H](C)c3cccc4ccccc34)Oc3ccccc32)ccc1F] | Ethyl 2-(2-fluoro-5-(2-(2-(((R)-1-(naphthalen-1-yl)ethyl)amino)ethyl)-2H-benzo[b][1,4]oxazin-4(3H)-yl)phenoxy)acetate | 529.2 |
| 110a | 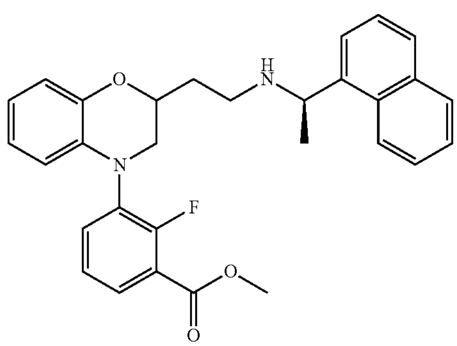 [SMILES: COC(=O)c1cccc(N2CC(CCN[C@H](C)c3cccc4ccccc34)Oc3ccccc32)c1F] | Methyl 2-fluoro-3-(2-(2-(((R)-1-(naphthalen-1-yl) ethyl)amino)ethyl)-2H-benzo[b][1,4]oxazin-4(3H)-yl)benzoate | 485.5 |
| 111a | 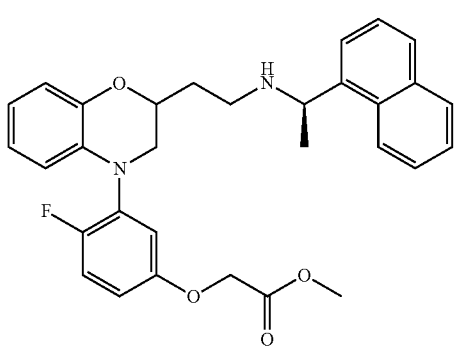 [SMILES: COC(=O)COc1ccc(F)c(N2CC(CCN[C@H](C)c3cccc4ccccc34)Oc3ccccc32)c1] | Methyl 2-(4-fluoro-3-(2-(2-(((R)-1-(naphthalen-1-yl)ethyl)amino)ethyl)-2H-benzo[b][1,4]oxazin-4(3H)-yl)phenoxy)acetate | 515.2 |

TABLE 5-continued

| Example | Structure | Chemical Name | Mass m/z |
|---|---|---|---|
| 112a | 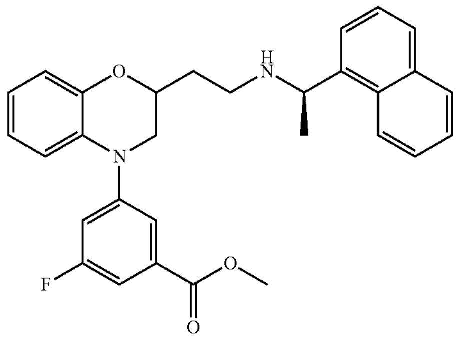 [SMILES: COC(=O)c1cc(F)cc(N2CC(CCN[C@H](C)c3cccc4ccccc34)Oc3ccccc32)c1] | Methyl 3-fluoro-5-(2-(2-(((R)-1-(naphthalen-1-yl)ethyl)amino)ethyl)-2H-benzo[b][1,4]oxazin-4(3H)-yl)benzoate | 485.5 |
| 113a | 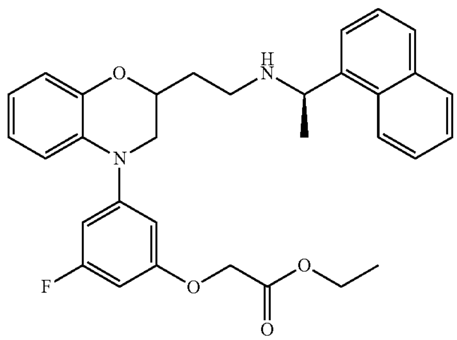 [SMILES: CCOC(=O)COc1cc(F)cc(N2CC(CCN[C@H](C)c3cccc4ccccc34)Oc3ccccc32)c1] | Ethyl 2-(3-fluoro-5-(2-(2-(((R)-1-(naphthalen-1-yl)ethyl)amino)ethyl)-2H-benzo[b][1,4]oxazin-4(3H)-yl)phenoxy)acetate | 529.2 |

Example-114a, 114b

Methyl 2-methyl-5-(2-methyl-2-(2-(((R)-1-(naphthalen-1-yl)ethyl)amino)ethyl)-2H-benzo[b][1,4]oxazin-4(3H)-yl)benzoic acid hydrochloride

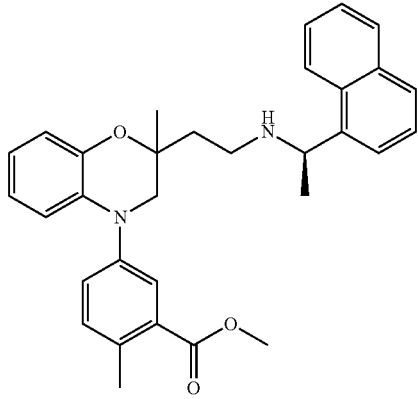 [SMILES: COC(=O)c1cc(N2CC(C)(CCN[C@H](C)c3cccc4ccccc34)Oc3ccccc32)ccc1C]

The title compound was prepared by following the similar coupling reaction procedure as described in Example-88a, 88b by taking Intermediate-30 and methyl 5-bromo-2-methylbenzoate. Further, diastereomers were separated by using chiral chromatography, Phenomenex-CELL-1, 250 mm×4.6, 5µ Flow: 1.0 ml/min;

mobile Phase: A=n-hexane:IPA (90:10% v/v, 0.1% DEA) B=MeOH:EtOH (1:1) A:B=95/5% v/v. m/z 495.05.

Example-115a, 115b

Methyl 5-(7-fluoro-2-(2-(((R)-1-(naphthalen-1-yl)ethyl)amino)ethyl)-2H-benzo[b][1,4]oxazin-4(3H)-yl)-2-methylbenzoate

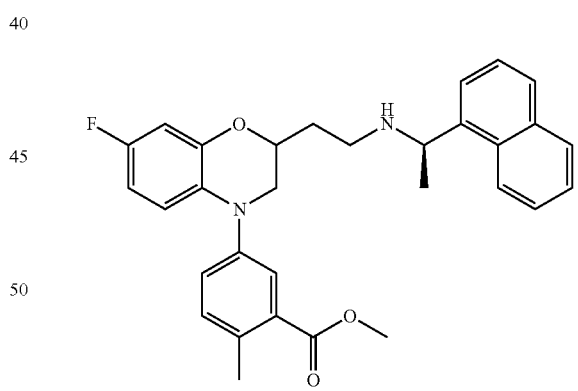

The title compound was prepared by following the similar procedure as described in Example-88a, 88b by taking Intermediate-22 and methyl 5-bromo-2-methylbenzoate. Further, diastereomers were separated by using chiral chromatography column: CHIRAL PAK 1D, 250×4.6 MM 5 u Mobile Phase: A: hexane/IPA (90:10, % v/v, 0.1% DEA) B: IPA (100%) A:B 90/10% v/v: flow is 1.0 ml/min m/z 498.36.

The below Examples 116 to 132 given in Table-6 were prepared by following the similar procedure as described in Example-88a, 88b by taking appropriate intermediate and appropriately substituted halobenzene. Further diastereomers were separated by using chiral preparative HPLC; column: CHIRAL PAK 1C, 250×4.65 u mobile Phase: A=hexane/IPA (90:10, % v/v, 0.1% DEA) B=IPA (100%) A:B 70/30% V/V, flow is 1.0 ml/min or Column: CHIRAL PAK 1D, 250×4.6 MM 5 u. Mobile Phase: A: hexane/IPA (90:10, % v/v, 0.1% DEA) B: IPA (100%) A:B 90/10% v/v Flow is 1.0 ml/min

TABLE 6

| Example | Structure | Chemical Name | Intermediate | Mass m/z |
|---|---|---|---|---|
| 116a,116b | 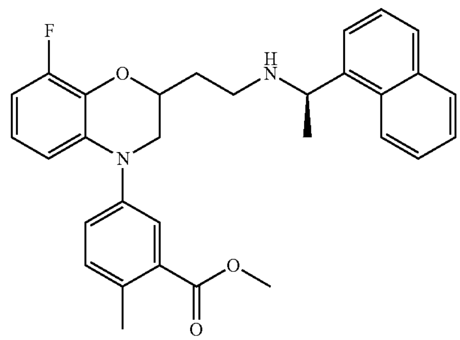 | Methyl 5-(8-fluoro-2-(2-(((R)-1-(naphthalen-1-yl) ethyl) amino) ethyl)-2H-benzo[b] [1,4] oxazin-4(3H)-yl)-2-methyl benzoate | 23 | 499.2 |
| 117a,117b | 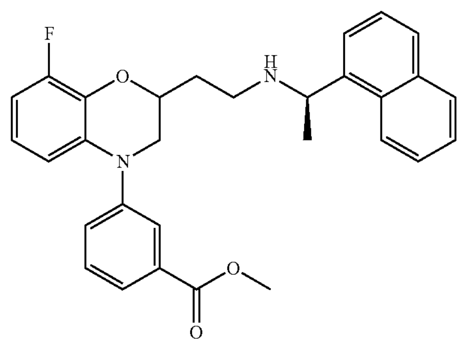 | Methyl 3-(8-fluoro-2-(2-(((R)-1-(naphthalen-1-yl)ethyl) amino) ethyl)-2H-benzo[b] [1,4] oxazin-4(3H)-yl) benzoate | 23 | 485.2 |
| 118a,118b | 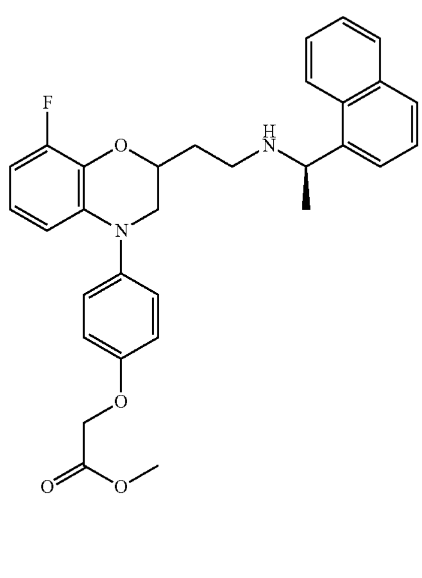 [SMILES: COC(=O)COc1ccc(N2CC(CCN[C@H](C)c3cccc4ccccc34)Oc3c(F)cccc32)cc1] | Methyl 2-(4-(8-fluoro-2-(2-(((R)-1-(naphthalen-1-yl)ethyl)amino)ethyl)-2H-benzo[b][1,4]oxazin-4(3H)-yl)phenoxy)acetate | 23 | 515.2 |

TABLE 6-continued

| Example | Structure | Chemical Name | Intermediate | Mass m/z |
|---------|-----------|---------------|--------------|----------|
| 119a,119b | 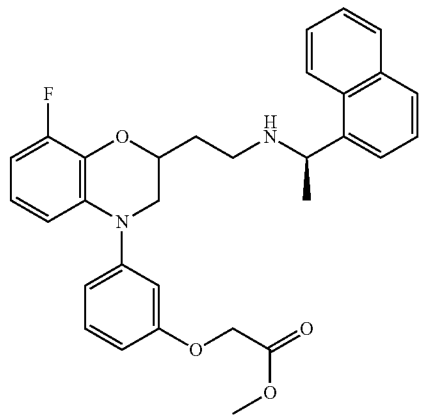 [SMILES: COC(=O)COc1cccc(N2CC(CCN[C@H](C)c3cccc4ccccc34)Oc3c(F)cccc32)c1] | Methyl 2-(3-(8-fluoro-2-(2-(((R)-1-(naphthalen-1-yl)ethyl)amino)ethyl)-2H-benzo[b][1,4]oxazin-4(3H)-yl)phenoxy)acetate | 23 | 515.2 |
| 120a,120b | 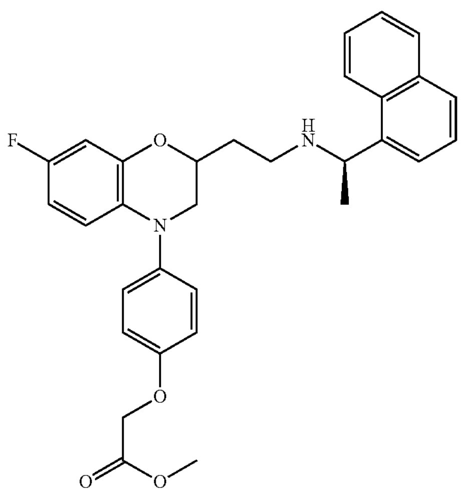 [SMILES: COC(=O)COc1ccc(N2CC(CCN[C@H](C)c3cccc4ccccc34)Oc3cc(F)ccc32)cc1] | Methyl 2-(4-(7-fluoro-2-(2-(((R)-1-(naphthalen-1-yl)ethyl)amino)ethyl)-2H-benzo[b][1,4]oxazin-4(3H)-yl)phenoxy)acetate | 22 | 515.2 |
| 121a,121b | 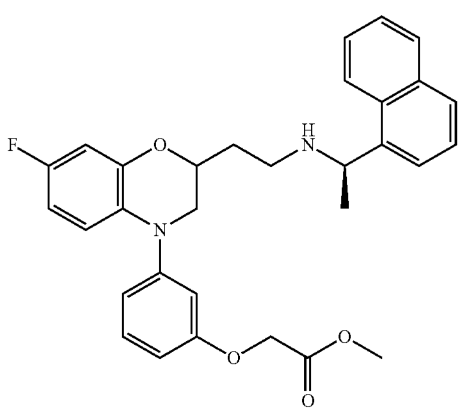 [SMILES: COC(=O)COc1cccc(N2CC(CCN[C@H](C)c3cccc4ccccc34)Oc3cc(F)ccc32)c1] | Methyl 2-(3-(7-fluoro-2-(2-(((R)-1-(naphthalen-1-yl)ethyl)amino)ethyl)-2H-benzo[b][1,4]oxazin-4(3H)-yl)phenoxy)acetate | 22 | 515.2 |

TABLE 6-continued

| Example | Structure | Chemical Name | Intermediate | Mass m/z |
|---|---|---|---|---|
| 122a,122b | 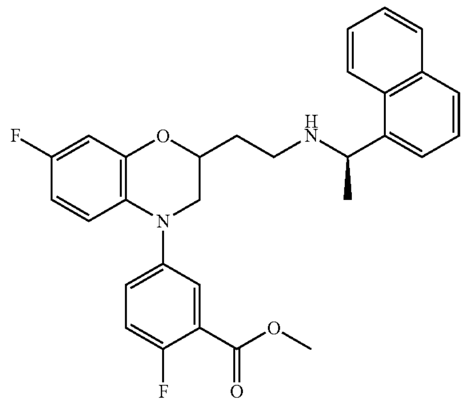 [SMILES: COC(=O)c1cc(N2CC(CCN[C@H](C)c3cccc4ccccc34)Oc3cc(F)ccc32)ccc1F] | Methyl 2-fluoro-5-(7-fluoro-2-(2-(((R)-1-(naphthalen-1-yl)ethyl)amino)ethyl)-2H-benzo[b][1,4]oxazin-4(3H)-yl)benzoate | 22 | 503.1 |
| 123a,123b | 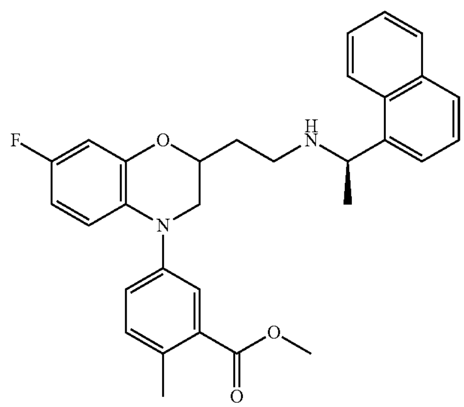 [SMILES: COC(=O)c1cc(N2CC(CCN[C@H](C)c3cccc4ccccc34)Oc3cc(F)ccc32)ccc1C] | Methyl 5-(7-fluoro-2-(2-(((R)-1-(naphthalen-1-yl)ethyl)amino)ethyl)-2H-benzo[b][1,4]oxazin-4(3H)-yl)-2-methyl benzoate | 22 | 499.2 |
| 124a,124b | 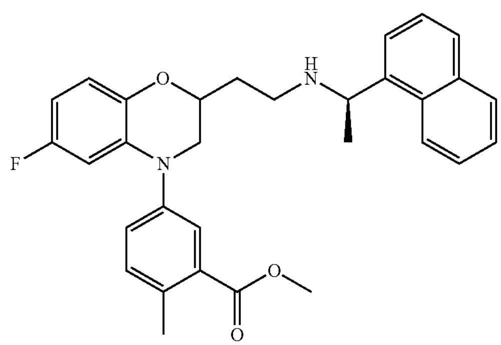 [SMILES: COC(=O)c1cc(N2CC(CCN[C@H](C)c3cccc4ccccc34)Oc3ccc(F)cc32)ccc1C] | Methyl 5-(6-fluoro-2-(2-(((R)-1-(naphthalen-1-yl)ethyl)amino)ethyl)-2H-benzo[b][1,4]oxazin-4(3H)-yl)-2-methyl benzoate | 24 | 499.1 |
| 125a,125b | 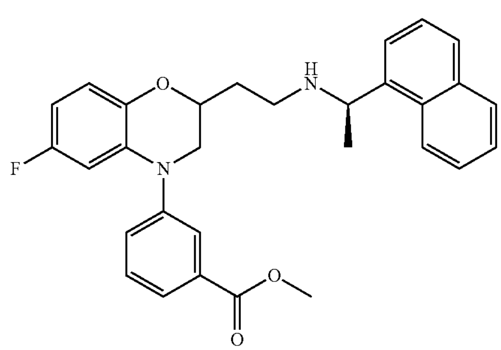 [SMILES: COC(=O)c1cccc(N2CC(CCN[C@H](C)c3cccc4ccccc34)Oc3ccc(F)cc32)c1] | Methyl 3-(6-fluoro-2-(2-(((R)-1-(naphthalen-1-yl)ethyl)amino)ethyl)-2H-benzo[b][1,4]oxazin-4(3H)-yl)benzoate | 24 | 485.2 |

TABLE 6-continued

| Example | Structure | Chemical Name | Intermediate | Mass m/z |
|---|---|---|---|---|
| 126a,126b | 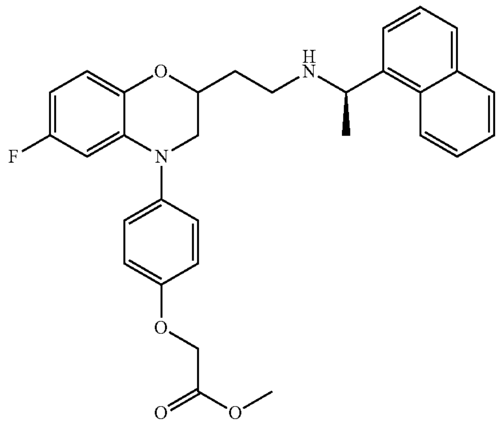 [SMILES: COC(=O)COc1ccc(N2CC(CCN[C@H](C)c3cccc4ccccc34)Oc3ccc(F)cc32)cc1] | Methyl 2-(4-(6-fluoro-2-(2-(((R)-1-(naphthalen-1-yl)ethyl)amino)ethyl)-2H-benzo[b][1,4]oxazin-4(3H)-yl)phenoxy)acetate | 24 | 515.2 |
| 127a,127b | 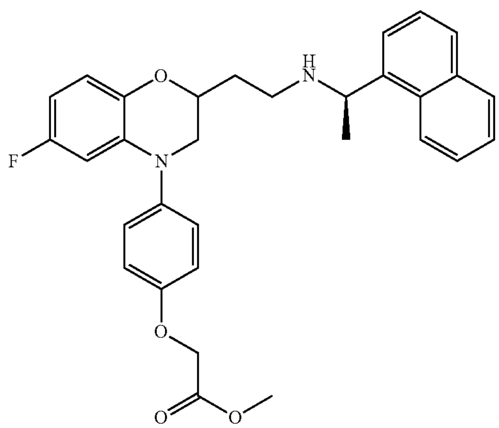 [SMILES: COC(=O)COc1ccc(N2CC(CCN[C@H](C)c3cccc4ccccc34)Oc3ccc(F)cc32)cc1] | Methyl 2-(4-(6-fluoro-2-(2-(((R)-1-(naphthalen-1-yl)ethyl)amino)ethyl)-2H-benzo[b][1,4]oxazin-4(3H)-yl)phenoxy)acetate | 24 | 515.2 |
| 128a,128b | 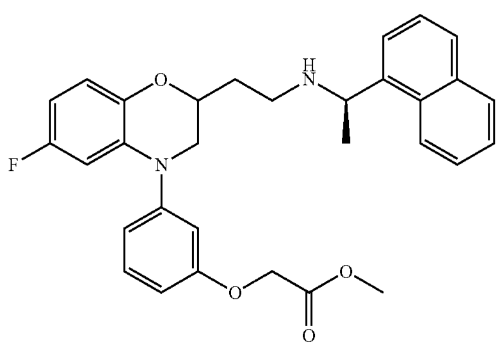 [SMILES: COC(=O)COc1cccc(N2CC(CCN[C@H](C)c3cccc4ccccc34)Oc3ccc(F)cc32)c1] | Methyl 2-(3-(6-fluoro-2-(2-(((R)-1-(naphthalen-1-yl)ethyl)amino)ethyl)-2H-benzo[b][1,4]oxazin-4(3H)-yl)phenoxy)acetate | 24 | 515.2 |
| 129a,129b | 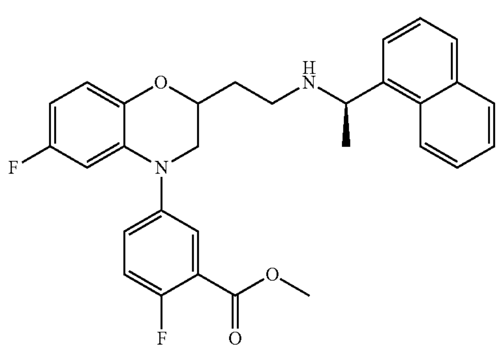 [SMILES: COC(=O)c1cc(N2CC(CCN[C@H](C)c3cccc4ccccc34)Oc3ccc(F)cc32)ccc1F] | Methyl 2-fluoro-5-(6-fluoro-2-(2-(((R)-1-(naphthalen-1-yl)ethyl)amino)ethyl)-2H-benzo[b][1,4]oxazin-4(3H)-yl)benzoate | 24 | 503.2 |

TABLE 6-continued

| Example | Structure | Chemical Name | Intermediate | Mass m/z |
|---------|-----------|---------------|--------------|----------|
| 130a,130b | 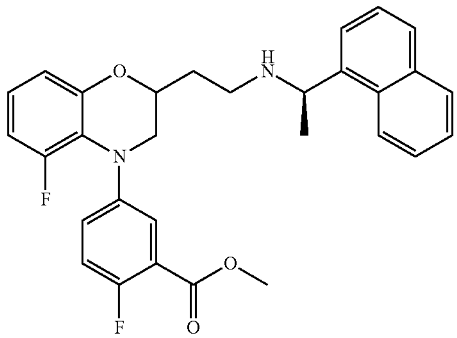 [SMILES: COC(=O)c1cc(N2CC(CCN[C@H](C)c3cccc4ccccc34)Oc3cccc(F)c32)ccc1F] | Methyl 2-fluoro-5-(5-fluoro-2-(2-(((R)-1-(naphthalen-1-yl)ethyl)amino)ethyl)-2H-benzo[b][1,4]oxazin-4(3H)-yl)benzoate | 25 | 503.2 |
| 131a,131b | 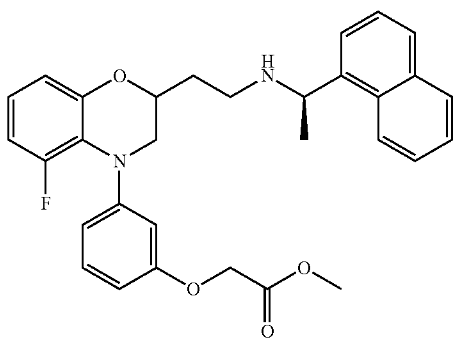 [SMILES: COC(=O)COc1cccc(N2CC(CCN[C@H](C)c3cccc4ccccc34)Oc3cccc(F)c32)c1] | Methyl 2-(3-(5-fluoro-2-(2-(((R)-1-(naphthalen-1-yl)ethyl)amino)ethyl)-2H-benzo[b][1,4]oxazin-4(3H)-yl)phenoxy)acetate | 25 | 515.2 |
| 132a,132b | 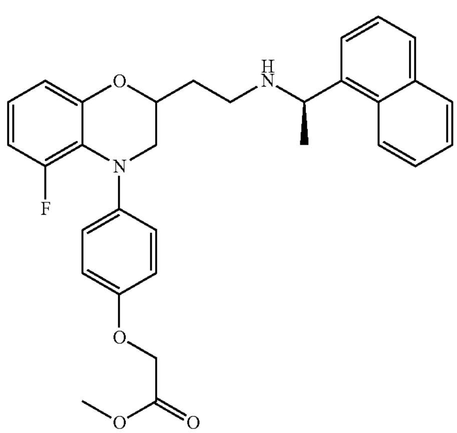 [SMILES: COC(=O)COc1ccc(N2CC(CCN[C@H](C)c3cccc4ccccc34)Oc3cccc(F)c32)cc1] | Methyl 2-(4-(5-fluoro-2-(2-(((R)-1-(naphthalen-1-yl)ethyl)amino)ethyl)-2H-benzo[b][1,4]oxazin-4(3H)-yl)phenoxy)acetate | 25 | 515.2 |

Example-133a, 133b

2-Methyl-5-(2-(2-(((R)-1-(naphthalen-1-yl)ethyl)amino)ethyl)-2H-benzo[b][1,4]oxazin-4(3H)-yl) benzoic acid hydrochloride

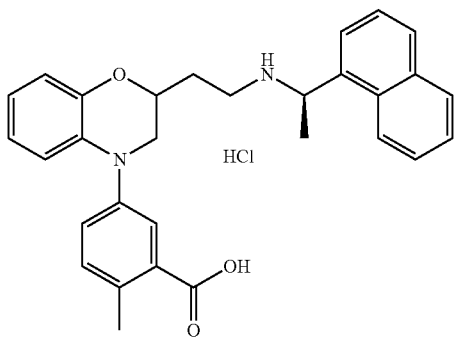 [SMILES: Cc1ccc(N2CC(CCN[C@H](C)c3cccc4ccccc34)Oc3ccccc32)cc1C(=O)O ; Cl]

To a solution of Example-88a (1.2 g, 2.5 mmol) in MeOH (10 mL), THF (10 mL) and water (1 mL) lithium hydroxide monohydrate (0.52 g, 12.48 mmol) was added. The reaction mixture was heated to 80° C. and further maintained for 2 h. The progress of reaction was monitored by TLC. The reaction mixture was concentrated under vacuum then cooled to 0° C. and acidified with dilute HCl solution [pH=3 to 4]. Extracted the product into Ethyl acetate (10 mL×2), washed with water (5 mL×2) followed by brine solution (5 mL), dried over sodium sulfate and concentrated under vacuum to get solid. Further HCl salt of this amino compound was prepared by following the similar HCl salt procedure as described in Example-1 (1.15 g, 92% yield). m/z 467.4.

Similarly, Example-133b was prepared from Example-88b by using this procedure.

Example-133a: m/z 467.4: $^1$H NMR (400 MHz, DMSO-d6): δ13.0 (bs, 1H), 9.6 (bs, 1H), 9.1 (bs, 1H), 8.24 (d, J=8.0 Hz, 1H), 8.01 (t, J=7.6 Hz, 2H), 7.87 (d, J=6.8 Hz, 1H), 7.70-7.58 (m, 4H), 7.29 (s, 2H), 6.80-6.73 (m, 4H), 5.3 (m, 1H), 4.28 (m, 1H), 3.73 (m, 1H), 3.68 (m, 1H), 3.26-3.21 (m, 1H), 3.0 (m, 1H), 2.5 (s, 3H), 2.04-1.99 (m, 2H), 1.66 (d, J=6.8 Hz, 3H);

Example-133b: $^1$H NMR (400 MHz, DMSO-d$_6$): δ 13.0 (bs, 1H), 9.6 (bs, 1H), 9.1 (bs, 1H), 8.24 (d, J=8.0 Hz, 1H), 7.87 (d, J=7.6 Hz, 1H), 7.70-7.58 (m, 4H), 7.30-7.28 (m, 2H), 6.77-6.70 (m, 4H), 5.3 (m, 1H), 4.28 (m, 1H), 3.40 (m, 2H), 3.26-3.14 (m, 1H), 3.096-3.04 (m, 1H), 2.45 (s, 3H), 2.0-1.96 (m, 2H), 1.64 (d, J=6.8 Hz, 3H).

The below Examples 134 to 158 given in Table-7 were prepared by following the similar ester hydrolysis procedure as described in Example-133a, 133b by using appropriate acid ester intermediate. Further HCl salts of these amino compounds were prepared by following the similar HCl salt procedure as described in Example-1.

TABLE 7

| Example | Structure | Ester | Mass (m/z) and 1H NMR |
|---|---|---|---|
| 134a<br><br>2-Melhyl-4-(2-(2-(((R-1-(naphthalen-1-yl)ethyl)amino)ethyl)-2H-benzo[b][1,4]oxazin-4(3H)-yl) benzoic acid hydrochloride | | Example-90a | 134a: m/z 467.4; $^1$H NMR (400 MHz, DMS0-D6): δ 12.5 (bs, 1H), 9.8 (bs, 1 H), 9.1 (bs, 1H), 8.24 (d, J = 8.8 Hz, 1H), 8.03 (t, 2H), 7.88-7.81 (m, 2H), 7.64-7.64 (m, 3H), 7.08-7.06 (m, 3H), 6.83 6.77 (m, 3H), 5.3 (m, 1H), 4.26 (m, 1H), 3.87 (m, 2H), 3.55 (s, 3H), 3.09 (m, 2H), 2.08 (m, 2H), 1.64-1.63 (d, J = 6.8 Hz, 3H) |

TABLE 7-continued

| Example | Structure | Ester | Mass (m/z) and 1H NMR |
|---|---|---|---|
| 135a | 5-(2-(2-(((R)-1-(Naphthalen-1-yl)ethyl)amino)ethyl)-2H-benzo[b][1,4]oxazin-4(3H)-yl)-2-(trifluoro methyl)benzoic acid hydrochloride | Example-91a | 135a: m/z 521.2; $^1$H NMR (400 MHz, DMSO-D6): δ 13.5 (bs, 1H), 9.8 (bs, 1H), 9.1 (bs, 1H), 8.22 (d, J = 8.4 Hz, 1H), 8.03 (t, J = 8.0 Hz, 2H), 7.88-7.81 (d, J = 7.2 Hz, 2H), 7.644-7.64 (m, 3H), 7.085-7.058 (m, 3H), 6.83-6.77 (m, 3H), 5.3 (m, 1H), 4.26 (m, 1H), 3.26 (m, 2H), 3.09 (m, 2H), 2.08 (m, 2H), 1.64-1.63 (d, J = 6.8 Hz, 3H); |
| 136a, 136b | 2-(2-Methyl-5-(2-(2-(((R)-1-(naphthalenlyl)ethyl)amino)ethyl)2Hbenzo[b][1,4]oxazin-4(3H)-yl)phenoxy)acetic acid hydrochloride | Example-92a, 92b | 136a: m/z 497.1 $^1$H NMR (400 MHz, DMSO-D6): δ 12.9 (bs, 1H), 9.7 (bs, 1H), 9.15 (bs, 1H), 8.26 (d, J = 8.4 Hz, 1H), 8.01 (t, J = 9.2 Hz, 2H), 7.91 (d, J = 6.8 Hz, 1H), 7.66-7.58 (m, 3H), 7.13 (d, J = 8.8 Hz, 1H), 6.78-6.76 (m, 1H), 6.72-6.99 (m, 5H), 5.37 (m, 1H), 4.67 (m, 2H), 4.26 (m, 1H), 3.69-3.66 (m, 1H), 3.21-3.16 (m, 1H), 3.03(m, 1H), 2.16 (m, 3H), 2.08 (m, 1H), 2.03 (m, 2H), 1.67 (d, J = 6.8 Hz, 3H); <br> 136b: $^1$H NMR (400 MHz, DMSO-D6): δ 9.97 (bs, 1H), 9.25 (bs, 1H), 8.25 (d, J = 8.4 Hz, 1H), 8.03-7.95 (m, 2H), 7.6 5-7.58 (m, 3H), 7.13 (d, J = 8.8 Hz, 1H), 6.78-6.74 (m, 1H), 6.72-6.71 (m, 5H), 5.34 (m, 1H), 4.67 (m, 2H), 4.27 (m, 1H), 3.69-3.66 (m, 4H), 3.24 (m, 2H), 3.10 (m, 1H), 2.15 (m, 3H), 1.69 (d, J = 6.4 Hz, 3H) |
| 137a | 2-Isopropyl-5-(2-(2-(((R)-1-(naphthalen-1-yl)ethyl)amino)ethyl)-2H-benzo[b][1,4]oxazin-4(3H)-yl)benzoic acid hydrochloride | Example-93a | m/z 495.2: $^1$H NMR (400 MHz, DMSO-D6): δ 13.01 (bs, 1H), 9.97 (bs, 1H). 9.25 (bs, 1H), 8.25 (d, J = 8.4 Hz, 1H), 8.02-7.96 (m, 3H), 7.70-7.57 (m, 3H), 7.44-7.41 (m, 2H), 7.33-7.31 (m, 1H), 6.86-6.79 (m, 1H), 6.76-6.73 (m, 3H), 5.34 (m, 1H), 4.26 (m, 1H), 3.75-3.68 (m, 1H), 3.67-3.61 (m, 1H), 3.23 (m, 1H), 3.08 (m, 1H), 2.08-2.05 (m, 2H), 1.68 (d, J = 6.4 Hz, 3H), 1.17 (d, J = 6.8 Hz, 6H), 3.08 (t, J = 7.2 Hz, 1H). |

TABLE 7-continued

| Example | Structure | Ester | Mass (m/z) and 1H NMR |
|---|---|---|---|
| 138a | 2-(3-(2-(2-(((R)-1-(Naphthalen-1-yl)ethyl)amino)ethyl)-2H-benzo[b][1,4]oxazin-4(3H)-yl)phenoxy)aceticacid hydrochloride | Example-94a | 138a: m/z 483.1 $^1$HNMR (400 MHz, DMSO-d6): δ 13.03 (bs, 1H), 9.69 (bs, 1H), 9.13 (bs, 1H), 8.24 (d, J = 8 Hz, 1H), 8.0-7.98 (m, 3H), 7.91-7.58 (m, 3H), 7.24 (t, J = 8 Hz, 1H), 6.89 (d, J = 5.2 Hz, 1H ), 6.79-6.61 (m, 4H), 6.59 (d, J = 2 Hz, 1H), 5.34 (d, J = 5.61 Hz, 1H), 4.65 (s, 2H), 4.26 (d, J = 6 Hz, 1H), 3.74 (d, J = 10 Hz, 2H), 3.23.19 (m, 2H), 2.03 (d, J = 7.2 Hz, 2H), 1.67 (d, J = 6.8 Hz, 3H). |
| 139a | 3-(4-(2-(2-(((R)-1-(Naphlhalen-1-yl)ethyl)amino)ethyl)-2H-benzo[b][1,4]oxazin-4(3H)-yl)phenyl)propanoic acid hydrochloride | Example-95a | 139a: m/z 481.1 $^1$H NMR (400 MHz, DMSO-d6): δ 12.2 (bs, 1H), 9.7 (bs, 1H), 9.15 (bs, 1H), 8.21 (d, J = 8.4 Hz, 1H), 8.03-7.98 (m, 2H), 7.78 (d, J = 6.8 Hz 1H), 7.65-7.58 (m, 3H), 7.21 (d, J = 8.4 Hz, 2H), 7.09 (d, J = 8.4 Hz 2H), 6.74-6.67 (m, 4H), 5.33 (d, J = 6.8 Hz, 1H), 4.25(d, J = 7.2 Hz, 1H), 3.70 (d, J = 2 Hz, 1H), 3.39-3.36 (m, 1H), 3.3-3.27 (m, 3H), 3.26-3.24 (m, 2H), 2.79 (t, J = 7.2 Hz, 2H), 2.02 (t, J = 7.2 Hz, 2H), 1.67 (d, J = 6.8 Hz, 3H). |

TABLE 7-continued

| Example | Structure | Ester | Mass (m/z) and 1H NMR |
|---|---|---|---|
| 140a | 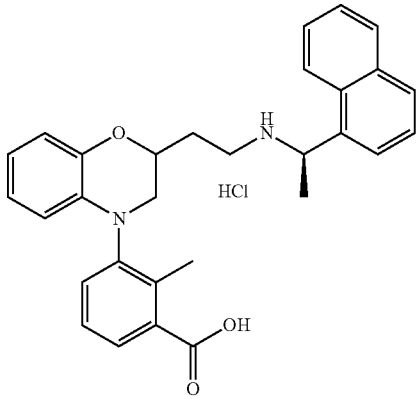 [SMILES: Cc1c(C(=O)O)cccc1N1CC(CCN[C@H](C)c2cccc3ccccc23)Oc2ccccc21 ; Cl]<br>2-Methyl-3-(2-(2-(((R)-1-(naphthalen-1-yl)ethyl)amino)ethyl)-2H-benzo[b][1,4]oxazin-4(3H)-yl) benzoic acid hydrochloride | Example-96a | 140a: m/z 467.2: $^1$H NMR (400 MHz, DMSO-d6): δ 9.78 (bs, 1H), 9.2 (bs, 1H), 8.26-8.20 (m, 1H), 8.03-7.89 (m, 2H), 7.95-7.90 (m, 1H), 7.73-7.6 (m, 4H), 7.42-7.35 (m, 2H), 6.71-6.58 (m, 3H), 5.9 8 (dd, J = 7.6 and J = 8 Hz, 1H), 5.37-5.3 6 (m, 1H), 4.49-4.1 (m, 1H), 3.35-3.5 6 (m, 1H), 3.42-3.38 (m, 1H), 3.34-3.33 (m, 1H), 3.4-3.11 (m, 1H), 2.25 (s, 3H), 2.32-2.07 (m, 2H), 1.63 (d, J = 6.4 Hz, 3H). |
| 141a | 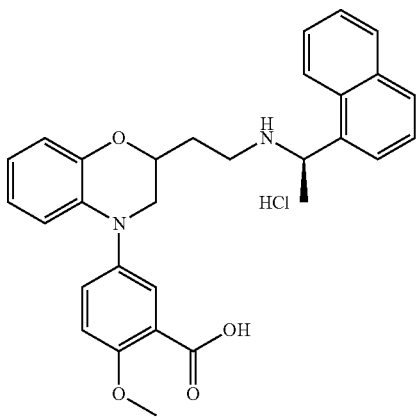 [SMILES: COc1ccc(N2CC(CCN[C@H](C)c3cccc4ccccc34)Oc3ccccc32)cc1C(=O)O ; Cl]<br>2-Methoxy-5-(2-(2-(((R)-1-(naphthalen-1-yl)ethyl)amino) ethyl)-2H-benzo[b][1,4]oxazin-4(3H)-yl) benzoic acid hydrochloride | Example-97a | 141a: m/z 483.05: $^1$HNMR (400 MHz, DMSO-d6): δ 9.8 (bs, 1H), 9.4 (bs, 1H), 8.25 (d, J = 8.4 Hz, 1H), 8.03-8.0 (m, 2H), 7.93 (d, J = 7.2 Hz, 1H), 7.65-7.58 (m, 3H), 7.45 d, J = 2.8 Hz, 1H), 7.37-7.35 (m, 1H, 7.16-7.14 (m, 1H), 6.73-6.64 (m, 3H), 6.59-6.58 (m, 1H), 5.85-5.33 (m, 1H), 4.30-4.28 (m, 1H), 3.81 (s, 3H), 3.62-3.60 (m, 1H), 3.27-3.23 (m, 3H), 3.09-3.07 (m, 1H, 2.08-2.03 (m, 1H), 1.68 (d, J = 6.4 Hz, 3H) |

TABLE 7-continued

| Example | Structure | Ester | Mass (m/z) and 1H NMR |
|---|---|---|---|
| 142a | 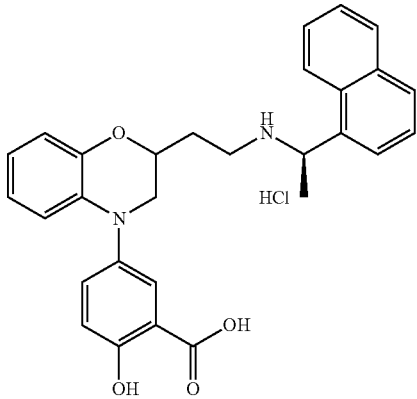 [SMILES: C[C@@H](NCCC1CN(c2ccc(O)c(C(=O)O)c2)c2ccccc2O1)c1cccc2ccccc12 ; Cl]<br>2-Hydroxy-5-(2-(2-(((R)-1-(naphthalen-1-yl)ethyl)amino)ethyl)-2H-benzo[b][1,4]oxazin-4(3H)-yl) benzoic acid hydrochloride | Example-98a | 142a: m/z 468.48 $^1$H NMR (400 MHz, DMS0-d6): δ 9.5 (bs, 1H), 9.0 (bs, 1H), 8.25 (d, J = 8.4 Hz, 2H), 8.04-7.99 (m, 2H), 7.82 (d, J = 7.2 Hz 1H), 7.67-7.59 (m, 3H), 7.40 (d, J = 2.8 Hz 1H), 7.03 (d, J = 8.8 Hz 1H), 6.73-6.64 (m, 3H), 6.59-6.58 (m, 1H), 585-533 (m, 1H), 4.30-4.28 (m, 1H), 3.62-3.60 (m, 1H), 3.27-3.23 (m, 3H), 3.09-3.07 (m, 1H), 2.0 8-2.03 (m, 2H), 1.68 (d, J = 6.4 Hz, 3H) |
| 143a | 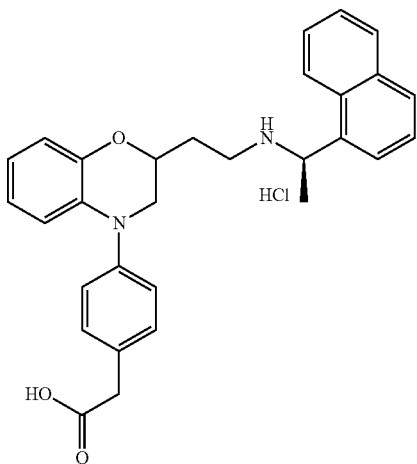 [SMILES: C[C@@H](NCCC1CN(c2ccc(CC(=O)O)cc2)c2ccccc2O1)c1cccc2ccccc12 ; Cl]<br>2-(4-(2-(2-(((R)-1-(Naphthalen-1-yl)ethyl) amino)ethyl)-2H-benzo[b][1,4]oxazin-4(3H)-yl)phenyl) acetic acid hydrochloride | Example-99a | 143a: m/z 467.2 $^1$HNMR (400 MHz, DMSO-d6): δ 12.2 (bs, 1H), 9.7 (bs, 1H), 9.15 (bs, 1H), 8.24 (d, J = 8.4 Hz,1H), 8.03-7.98 (m, 2H), 7.86 (d, J = 6.8 Hz, 1H), 7.65-7.53 (m, 3H), 7.24 (d, J = 8.4 Hz, 2H), 7.14 (d, J = 8.4 Hz, 2H), 6.81-6.78 (m, 1H), 6.76-6.69 (m, 3H), 5.35-5.34 (m, 1H), 4.25 (d, J = 7.2 Hz, 1H), 3.73 (d, J = 2 Hz, 1H), 3.54 (s, 2H), 3.39-3.34 (m, 1H), 3.34-3.24 (m, 1H, 3.14-3.08 (m, 1H), 2.03-2.01 (m, 2H), 1.67 (d, J = 6.8 Hz, 3H). |

TABLE 7-continued

| Example | Structure | Ester | Mass (m/z) and 1H NMR |
|---|---|---|---|
| 144a | 2-(2-Methyl-4-(2-(2-(((R)-1-(naphlhalen-1-yl)ethyl)amino)ethyl)-2H-benzo[b][1,4]oxazin-4(3H)-yl)phenoxy)aceticacid hydrochloride | Example-100a | 144a m/z 496.69 $^1$H NMR (400 MHz, DMSO-d6): δ 13.03 (bs, 1H), 9.69 (bs, 1H), 9.10 (bs, 1H), 8.24 (d, J = 8 Hz, 1H), 8.0-7.98 (m, 2H), 7.87 (d, J = 6.8 Hz 1H), 7.66-7.60 (m, mH), 7.04-7.03 (m, 1H), 6.98-6.95 (m, 1H), 6.83 (d, J = 8.8 Hz 1H), 6.71-6.63 (m, 2H), 6.55 (dd, J = 2 Hz and J = 8 Hz, 1H), 5.36-5.33 (m, 1H), 4.69 (s, 2H), 4.28 (d, J = 6 Hz, 1H), 3.61 (d, J = 2.4 Hz 1H), 3.35-3.20 (m, 2H), 3.21-3.16 (m, 2H), 2.18 (s, 3H), 2.04-1.98 (m, 2H), 1.67 (d, J = 6.8 Hz, 3H). |
| 145a | 4-(2-(2-(((R)-1-(Naphthalen-1-yl)elhyl)amino)ethyl)-2H-benzo[b][1,4]oxazin-4(3H)-yl)benzoicacid hydrochloride | Example-101a | 145a: m/z 452.98: $^1$H NMR (400 MHz, DMSO-d6): δ 12.7 (bs, 1H), 9.7 (bs, 1H), 9.15 (bs, 1H), 8.21 (d, J = 8.4 Hz, 1H), 8.03-7.98 (m, 2H), 7.91-7.86 (m, 3H), 7.65-7.58 (m, 3H), 7.25 (d, J = 8.4 Hz, 2H), 7.11-7.09 (m, 1H), 6.8 7-6.77 (m, 3H), 5.34-5.32 (m, 1H), 4.29-4.27 (m, 1H), 3.89 (d, J = 2Hz, 1H), 3.39-3.36 (m, 1H), 3.3-3.27 (m, 1H), 3.16-3.06 (m, 1H), 2.04-1.99 (m, 2 H), 1.67 (d, J = 6.8 Hz, 3H). |

TABLE 7-continued

| Example | Structure | Ester | Mass (m/z) and 1H NMR |
|---|---|---|---|
| 146a | 3-(2-(2-(((R)-1-(Naphthalen-1-yl)ethyl)amino)ethyl)-2H-benzo[b][1,4]oxazin-4(3H)-yl)benzoic acid hydrochloride | Example-89a | 146a: m/z 452.98: ¹H NMR(400 MHz, DMSO-d6): δ 13.06 (bs, 1H), 9.87 (bs, 1H), 9.25 (bs, 1H), 8.24 (d, J = 8.4 Hz, 1H), 8.02-7.93 (m, 3H), 7.7 4 (s, 1H), 7.64-7.57 (m, 4H), 7.48-7.43 (m, 2H), 6.88-6.86 (m, 1H), 6.77-6.73 (m, 3H), 5-34 (d, J = 5.6 Hz, 1H), 4.28 (d, J = 6.4 Hz 1H), 3.80-3.77 (m, 1H), 3.46-3.08 (m, 3H), 2.08-1.98 (m, 2H), 1.65 (d, J = 6.4 Hz, 3H). |
| 147a | 2-(4-(2-(2-(((R)-1-(Naphthalen-1-yl)ethyl)amino)ethyl)-2H-benzo[b][1,4]oxazin-4(3H)-yl)phenoxy)aceticacid hydrochloride | Example-102a | 147a: m/z 483.05 ¹H NMR (400 MHz DMSO-d6): δ 13.03 (bs, 1H), 9.69 (bs, 1H), 9.20 (bs, 1H), 8.24 (d, J = 8 Hz, 1H), 8.03-8.01 (m, 2H), 7.90 (d, J = 6.8 Hz, 1H), 7.64-7.60 (m, 3H), 7.18-7.12 (m, 2H), 6.95-6.92 (m, 2H), 6.71-6.62 (m, 3H), 6.65-6.54 (m, 1H), 5.36-5.34 (m, 1H), 4.67 (s, 2H), 4.30-4.28 (m, 1H), 3.61 (dd, J = 2 and J = 12.4 Hz, 1H), 3.33-3.24 (m, 2H), 3.11-3.09 (m, 1H), 2.07-2.02 2H), (m, 1.67 (d, J = 6.4 Hz, 3H). |

TABLE 7-continued

| Example | Structure | Ester | Mass (m/z) and 1H NMR |
|---------|-----------|-------|------------------------|
| 148a | 2,6-Dimethyl-3-(2-(2-(((R)-1-(naphthalen-1-yl)ethyl)amino)ethyl)-2H-benzo[b][1,4]oxazin-4(3H)-yl) benzoic acid hydrochloride | Example-103a | 148a: m/z 481.1: $^1$H NMR (400 MHz, DMSO-d6): δ 13.30 (bs, 1H), 9.78 (bs, 1H), 9.20 (bs, 1H), 8.27 (d, J = 8.4 Hz 1H), 8.03-7.95 (m, 2H), 7.95-7.90 (m, 1H), 7.66-7.60 (m, 3H), 7.18-7.15 (m, 2H), 6.70-6.56 (m, 3H), 6.05-5.93 (m, 1H), 5.34 (d, J = 5.6 Hz, 1H), 4.38 (d, J = 6.4 Hz, 1H), 3.57-3.33 (m, 3H), 3.26-3.10 (m, 2H), 2.25 (s, 3H), 2.10-2.01 (m, 4H), 1.68 (d, J = 6.4 Hz, 3H). |
| 149a | 3-(3-(2-(2-(((R)-1-(Naphthalen-1-yl)ethyl)amino)ethyl)-2H-benzo[b][1,4]oxazin-4(3H)-yl) phenyl)propanoicacid hydrochloride | Example-104a | 149a; m/z 48.11: $^1$H NMR (40 MHz, DMSO-d6): δ 12.23 (bs, 1H), 9.85 (bs, 1H), 9.23 (bs, 1H), 8.18 (d, J = 8 Hz, 1H), 8.02-7.93 (m, 3H), 7.63-7.60 (m, 3H) 7.25 (t, J = 8 Hz, 1H), 7.03 (s, 1H), 6.98 (d, J = 8 Hz, 1H), 6.92 (d, J = 7.6 Hz, 1H), 6.80-6.78 (m, 1H), 6.73-6.69 (m, 3H), 5.33-5.28 (m, 1H), 4.24-4.23 (m, 1H), 3.67 (d, J = 12.4 Hz, 1H), 3.38-3.33 (m, 2H), 3.24-3.23 (m, 1H), 3.14-3.07 (m, 1H), 2.78-2.75 (m, 2H), 2.55-2.53 (m, 1H), 2.07-2.02 (m, 2H), 1.6 (d, J = 6.8 Hz, 3H). |

TABLE 7-continued

| Example | Structure | Ester | Mass (m/z) and 1H NMR |
|---------|-----------|-------|------------------------|
| 150a, 150b | 2-Methyl-5-(2-methyl-2-(2-(((R)-1-(naphthalen-1-yl)ethyl)amino)ethyl)-2H-benzo[b][1,4]oxazin-4(3H)-yl)benzoicacid hydrochloride | Example-114a | 150a: m/z 481.6 ¹HNMR (400 MHz, DMSO-d6) δ 12.98 (bs, 1H), 9.8 (bs, 1H), 9.3 (bs, 1H), 8.20 (d, J = 8.4 Hz, 1H), 8.01-7.95 (m, 2H), 7.87 (d, J = 7.2 Hz, 1H), 7.68 (s, 1H), 7.65-7.55 (m, 3H), 6.81-6.69 (m, 4H), 5.31(d, J = 6 Hz, 1H), 3.51-3.41 (m, 4H), 3.13-2.98 (m, 2H), 2.4 (s, 4 Hz, 3H), 2.13 (d, J = 4 Hz, 1H), 2.0 (t, J = 8.4 Hz, 1H), 1.63 (d, J = 6.4 Hz, 3H), 1.25 (s, 3H)<br>150b: m/z 481.6 ¹H-NMR (400 MHz, DMSO-d6): δ 12.98 (bs, 1H), 9.8 (bs, 1H), 9.3 (bs, 1H), 8.20 (d, J = 8.4 Hz, 1H), 8.01-7.95 (m, 2H), 7.87 (d, J = 7.2 Hz, 1H), 7.68 (s, 1H), 7.65-7.55 (m, 3H), 6.81-6.69 (m, 4H), 5.31 (d, J = 6 Hz, 1H), 3.51-3.41 (m, 4H), 3.13-2.98 (m, 2H), 2.4 (s, J = 8.4 Hz, 3H), 2.13 (d, J = 4 Hz, 1H), 2.0 (t, J = 8.4 Hz, 1H), 1.63 (d, J = 6.4 Hz, 3H), 1.25 (s, 3H). |
| 151a | 3-Methyl-5-(2-(2-(((R)-1-(naphlhalen-1-yl)ethyl)amino)ethyl)-2H-benzo[b][1,4]oxazin-4(3H)-yl) benzoicacid hydrochloride | Example-105a | m/z = 467.2; ¹H NMR (400 DMSO-U6): δ 12.9 (bs, 1H), 9.8 (bs, 1H), 9.4 (bs, 1H), 8.25(d, J = 8.4 Hz, 1H), 8.03-8.0 (m, 2H), 7.93 (d, J = 7.2 Hz, 1H), 7.65-7.60 (m, 3H), 7.56-7.54 (m, 1H), 7.45 (d, J = 2.8 Hz, 1H), 7.21 (m, 1H), 6.87-6.84 (m, 1H), 6.77-6.58 (m, 3H), 5.25 (m, 1H), 4.30-4.28 (m, 1H), 3.62-3.60 (m, 1H), 3.27-3.23 (m, 3H), 3.09-3.07 (m, 1H), 2.33 (s, 3H), 2.08-2.03 (m, 1H), 1.68 (d, J = 6.4 Hz, 3H). |

TABLE 7-continued

| Example | Structure | Ester | Mass (m/z) and 1H NMR |
|---|---|---|---|
| 152a | 2-Fluoro-5-(2-(2-(((tf)-1-(naphthalen-1-yl)ethyl) amino)ethyl)-2//-benzo[/>][1,4]oxazin-4(3//)-yl) benzoic acid hydrochloride | Example-106a | m/z 471.2; $^1$H NMR (400 MHz, DMSO-d6: δ 12 (bs, 1H), 9.5 (bs, 1H), 9.0 (bs, 1H), 8.21 (d, J = 8.4 Hz, 1H), 8.04-7.99 (m, 2H), 7.82 (d, J = 7.2 Hz 1H), 7.67 (d, J = 7.61 Hz, 1H), 7.65-7.57 (m, 3H), 7.46-7.43 (m, 1H), 7.32-7.29 (m, 1H), 6.74 (m, 4H), 5.34-5.29 (m, 1H), 4.26-4.24 (m, 1H), 3.41-3.38 (m, 1H), 3.73-3.69 (m, 1H), 3.45-3.4 3 (m, 1H), 3.30-3.26 (m, 1H), 3.10-3.08 (m, 1H), 2.09-1.98 (m, 1H), 1.68 (d, J = 6.4 Hz, 3H). |
| 153a | 4-Methyl-3-(2-(2-(((R)-1-(naphlhalen-1-yl)ethyl)amino)ethyl)-2H-benzo[b][1,4]oxazin-4(3H)-yl)benzoic acid hydrochloride | Example-107a | m/z = 467.2; $^1$H NMR (400 MHz, DMSO-d6): δ 12.8 (bs, 1H), 9.7 (bs, 1H), 9.15 (bs, 1H), 8.23-8.21 (m, 1H), 8.02 (t, J = 7.6 Hz, 2H), 7.86-7.84 (m, 1H), 7.82-7.90 (m, 2H), 7.65-7.53 (m, 3H), 7.47-7.42 (m, 1H), 6.72-6.59 (m, 3H), 5.97 (m, 1H), 5.35-5.34 (m, 1H), 4.25 (d, J = 7.2 Hz, 1H), 3.73-3.70 (m, 1H), 3.39-3.34 (m, 1H), 3.34-3.24 (m, 1H), 3.14-3.08 (m, 1H), 3.12 (s, 3H), 2.03-2.01 (m, 2H), 1.67 (d, J = 6.8 Hz, 3H) |
| 154a | 2-(2-Fluoro-3-(2-(2-(((R)-1-(naphthalen-1-yl)ethyl)amino)ethyl)-2H-benzo[b][1,4]oxazin-4(3H)-yl)phenoxy)acetic acid hydrochloride | Example-108a | m/z = 501.1: $^1$H NMR (400 MHz, DMS0-d6): δ 13.1 (bs, 1H), 9.9 (bs, 1H), 9.2 (bs, 1H), 8.26 (d, J = 8.4 Hz, 1H), 8.03-7.93 (m, 3H), 7.65-7.58 (m, 3H), 7.14 (t, J = 8.0 Hz, 1H), 6.93-6.89 (m, 2H), 6.73-6.51 (m, 3H), 6.40-6.38 (m, 1H), 5.35-5.34 (m, 1H), 4.80 (s, 2H), 4.35-4.33 (m, 1H), 3.65-3.35 (m, 2H), 3.39-3.34 (m, 2H), 2.13-2.08 (m, 2H), 1.67 (d, J = 6.8 Hz, 3H). |

TABLE 7-continued

| Example | Structure | Ester | Mass (m/z) and 1H NMR |
|---|---|---|---|
| 155a | 2-(2-Fluoro-5-(2-(2-(((R)-1-(naphthalen-1-yl)ethyl)amino)ethyl)-2H-benzo[b][1,4]oxazin-4(3H)-yl)phenoxy)acetic acid hydrochloride | Example-109a | m/z = 501.1; $^1$H NMR (400 MHz, DMSO-d6): δ 13.1 (bs, 1H), 9.9 (bs, 1H), 9.2 (bs, 1H), 8.22 (d, J = 8.4 Hz, 1H), 8.02 (t, J = 8 Hz, 2H), 7.87 (d, J = 6.8 Hz, 1H), 7.63-7.59 (m, 3H), 7.20 (t, J = 8.8 Hz, 1H), 6.90 (d, J = 6.4 Hz, 1H), 6.74 (m, 5H), 5.33-5.31 (m, 1H), 4.84 (s, 2H), 4.25-4.23 (m, 1H), 3.66-3.60 (m, 2H), 3.22-3.08 (m, 2H), 2.03 (d, J = 6.41 Hz, 2H), 1.67 (d, J = 6.8 Hz, 3H). |
| 156a | 2-Fluoro-3-(2-(2-(((R)-1-(naphlhalen-1-yl)ethyl)amino)ethyl)-2H-benzo[6][1,4]oxazin-4(3H)-yl) benzoic acid hydrochloride | Example-110a | m/z = 471.2: $^1$H NMR (400 MHz, DMSO-d6): δ 13.12 (bs, 1H), ) 9.9 (bs, 1H), 9.1 (bs, 1H), 8.24 (d, J = 8.4 Hz, 1H), 8.03 (t, J = 8 Hz), 2H), 7.94 (d, J = 7.2 Hz, 1H), 7.71 (d, J = 6.4 Hz, 1H), 7.65-7.57 (m, 4H), 7.35 (d, J = 7.2 Hz, 1H), 6.75-5.58 (m, H), 6.38-6.36 (m, 1H), 5.37-5.34 (m, 1H), 4.36-4.34 (m, 1H), 3.41-3.38 (m, 1H), 3.73-3.69 (m, 1H), 3.45-3.43 (m, 1H), 3.10-3.08 (m, 1H), 2.11-2.07 (m, 2H), 1.68 (d, J = 6.4 Hz, 3H). |
| 157a | 2-(4-Fluoro-3-(2-(2-(((R)-1-(naphthalen-1-yl)elhyl)amino)ethyl)-2H-benzo[b][1,4]oxazin-4(3H)-yl)phenoxy)acetic acid hydrochloride | Example-111a | m/z = 501.1; $^1$H NMR (400 MHz, DMSO-d6): δ 13.0 (bs, 1H), 9.7 (bs, 1H), 9.0 (bs, 1H), 8.12 (d, J = 8.4 Hz, 1H), 7.99 (t, J = 7.61 Hz, 2H), 7.69 (d, J = 6.8 Hz, 1H), 7.61-7.56 (m, 3H), 7.19 (t, J = 8.8 Hz, 1H), 6.77-6.72 (m, 2H), 6.69-6.62 (m, 3H), 6.37-6.35 (m, 1H), 5.27-5.24 (m, 1H), 4.24-4.22 (m, 1H), 3.56-3.54 (m, 1H), 3.42-3.38 (m, 3H), 3.22-3.19 (m, 1H), 3.06-3.02 (m, 1H), 2.00 (d, J = 6.4 Hz, 2H), 1.67 (d, J = 6.8 Hz. |

TABLE 7-continued

| Example | Structure | Ester | Mass (m/z) and 1H NMR |
|---|---|---|---|
| 158a | 3-Fluoro-5-(2-(2-(((R)-1-(naphthalen-1-yl)elhyl)amino)ethyl)-2H-benzo[b][1,4]oxazin-4(3H)-yl)benzoic acid hydrochloride | Example-112a | m/z = 471.2; $^1$H-NMR (400 MHz, DMSO-d6): δ 13.1 (bs, 1H), 10.0 (bs, 1H), 9.3 (bs, 1H), 8.22 (d, J = 8.4 Hz, 1H), 8.02 (t, J = 8.4 Hz, 2H), 7.84-7.83 (m, 1H),7.64-7.57 (m, 4H), 7.29-7.25 (m, 2H), 7.036 (d, J = 7.6 Hz, 1H), 6.87-6.77 (m, 2H), 5.37-5.34 (m, 1H), 4.26-4.24 (m, 1H), 3.85-3-78 (m, 1H), 3.72-3.70 (m, 1H), 3.44-3.42 (m, 1H), 3.10-3.08 (m, 1H), 2.10-2.07 (m, 2H), 1.68 (d, J = 6.4 Hz, 3H). |

The below Examples 159 to 172 given in Table-8 were prepared by following the similar ester hydrolysis procedure as described in Example-133a, 133b by using appropriate ester compound. Further HCl salt of this amino compound was prepared by following the similar HCl salt procedure as described in Example-1.

TABLE 8

| Example | Structure | Ester Example | Mass(m/z) and 1H NMR |
|---|---|---|---|
| 159a 159b | 5-(8-Fluoro-2-(2-(((R)-1-(naphthalen-1-yl)elhyl)amino)elhyl)-2H-benzo[b][1,4]oxazin-4(3H)-yl)-2-methylbenzoic acid hydrochloride | | 159a: m/z 485.1 $^1$H NMR (400 MHz, DMSO-D6): δ 13.0 (bs, 1H), 9.6 (bs, 1H), 9.1 (bs, 1H), 8.26 (d, J = 8 Hz, 1H), 8.03-7.98 (m, 2H), 7.86 (d, J = 6.8 Hz, 1H), 7.65-7.58 (m, 3H), 7.32 (m, 2H), 6.71-6.65 (m, 2H), 6.76 (m, 1H), 5.36 (m, 1H), 4.36 (m, 1H), 3.78-3.74 (m, 1H), 3.50-3.40 (m, 1H), 3.38-3.35 (m, 1H), 3.2 (m, 2H), 3.16 (m, 1H), 2.08 (m, 3H), 1.67 (d, J = 6.4 Hz, 3H); 159b: $^1$H NMR (400 MHz, DMSO-D6): δ 13.0 (bs, 1H), 9.7 (bs, 1H), 9.2 (bs, 1H), 8.26 (d, J = 8 Hz, 1H), 8.03-7.98 (m, 2H), 7.89 (d, J = 6.8 Hz, 1H), 7.66-7.58 (m, 3H), 7.32 (m, 2H), 6.71-6.64 (m, 2H), 6.55 (m, 1H), 5.38 (m, 1H), 4.37 (m1H), 3.77-3.73 (m, 1H), 3.51-3.35 (m, 1H), 3.22 (m, 2H), 3.16 (m, 1H), 3.04 (m, 1H), 2.08 (m, 3H), 1.66 (d, J = 6.4 Hz, 3H). |

TABLE 8-continued

| Example | Structure | Ester Example | Mass(m/z) and 1H NMR |
|---|---|---|---|
| 160a 160b | 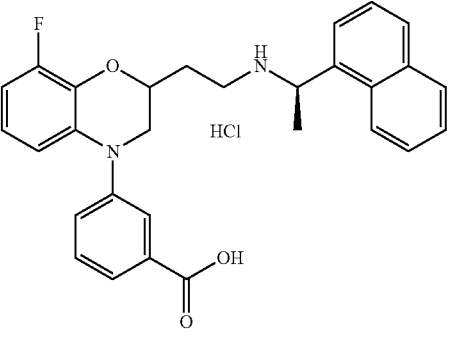 [SMILES: C[C@@H](NCCC1CN(c2cccc(C(=O)O)c2)c2cccc(F)c2O1)c1cccc2ccccc12 ; Cl] 3-(8-Fluoro-2-(2-(((R)-1-(naphthalen-1-yl)ethyl)amino)ethyl)-2H-benzo[b][1,4]oxazin-4(3H)-yl)benzoic acid hydrochloride | 117a, 117b | 160a: m/z 471.1 $^1$H NMR (400 MHz, DMSO-D6): δ 13.1 (bs, 1H), 9.7 (bs, 1H), 9.2 (bs, 1H), 8.26 (d, J = 8 Hz, 1H), 8.03-7.98 (m, 2H), 7.88 (d, J = 6.8 Hz, 1H), 7.76 (m, 1H), 7.69-7.58 (m, 4H), 7.53-7.47 (m, 2H), 6.77 (m, 3H), 5.36 (m, 1H), 4.39 (m, 1H), 3.84-3.81 (m, 1H), 3.54-3.51 (m, 1H), 3.22 (m, 1H), 3.16 (m, 1H), 2.10-2.06 (m, 2H), 1.67 (d, J = 6.4 Hz, 3H); 160b: $^1$H NMR (400 MHz, DMSO-D6): δ 13.1 (bs, 1H), 9.6 (bs, 1H), 9.15 (bs, 1H), 8.26 (d, J = 8 Hz, 1H), 8.03-7.98 (m, 2H), 7.88 (d, J = 6.8 Hz, 1H), 7.77 (m, 1H), 7.69-7.59 (m, 4H), 7.54-7.49 (m, 2H), 6.72-6.62 (m, 3H), 5.39 (m, 1H), 4.37 (m, 1H), 3.84-3.80 (m, 1H), 3.55-3.50 (m, 1H), 3.23 (m, 1H), 3.16 (m, 1H), 2.08-2.03 (m, 2H), 1.66 (d, J = 6.4 Hz, 3H). |
| 161a 161b | 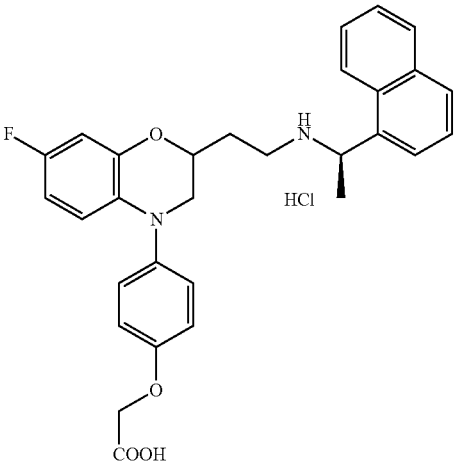 [SMILES: C[C@@H](NCCC1CN(c2ccc(OCC(=O)O)cc2)c2ccc(F)cc2O1)c1cccc2ccccc12 ; Cl] 2-(4-(7-Fluoro-2-(2-(((R)-1-(naphthalen-1-yl)ethyl)amino)ethyl)-2H-benzo[b][1,4]oxazin-4(3H)-yl)phenoxy)aceticacid hydrochloride | 120a, 120b | 161a: m/z 501.2;: $^1$HNMR (400 MHz, DMSO-d6): δ 13.02 (bs, 1H), 9.73 (bs, 1H), 9.18 (bs, 1H), 8.25 (d, J = 8.4 Hz, 1H), 8.03-7.90 (m, 3H), 7.66-7.58 (m, 3H), 7.12 m, 2H), 6.93 (m, 2H), 6.58-6.53 (m, 3H), 5.35 (m, 1H), 4.66 (s, 2H), 4.31 (m, 1H), 3.61 (m, 1H), 3.37-2.99 (m, 3H), 2.04 (m, 2H), 1.67 (d, J = 6.8 Hz, 3H); 161b: m/z 501.2: $^1$H NMR(400 MHz, DMSO-d6): δ 13.02 (bs, 1H), 9.20 (bs, 1H), 9.07 (bs, 1H), 8.25 (d, J = 8 Hz, 1H), 8.03-7.86 (m, 3H), 7.64-7.60 (m, 3H), 7.11-7.09 (m, 2H), 6.94-6.91 (m, 2H), 6.61-6.53 (m, 3H), 5.33 (m, 1H), 4.66 (s, 2H), 4.31 (m, 1H), 3.61 (m, 1H), 3.34-3.08 (m, 3H), 2.01 (m, 2H), 1.66 (d, J = 6.8 Hz, 3H); |

TABLE 8-continued

| Example | Structure | Ester Example | Mass(m/z) and 1H NMR |
|---|---|---|---|
| 162a 162b | 2-(3-(7-Fluoro-2-(2-(((R)-1-(naphthalan-1-yl)ethyl)amino)ethyl)-2H-benzo[b][1,4]oxazin-4(3H)-yl)phenoxy) aceticacid hydrochloride | 121a, 121b | m/z 501.1; 162a: $^1$H NMR (400 MHz, DMSO-d6): δ 13.02 (bs, 1H), 9.73 (bs, 1H), 9.18 (bs, 1H), 8.24 (d, J = 8.4 Hz, 1H), 8.03-7.89 (m, 3H), 7.65-7.58 (m, 3H), 7.23 (t, J = 8.0 Hz, 1H), 6.89 (dd, J = 7.6 and J = 8.8 Hz 1H), 6.76-6.69 (m, 2H), 6.65-6.57 (m, 3H), 5.33 (m, 1H), 4.65 (s, 2H), 4.27 (m, 1H), 3.76 (m, 1H), 3.38-3.02 (m, 3H), 1.95 (m, 2H), 1.63 (d, J = 6.8 Hz, 3H); 162b: $^1$H NMR (400 MHz, DMSO-d6): δ 13.02 (bs, 1H), 9.20 (bs, 1H), 9.07 (bs, 1H), 8.24 (d, J = 8 Hz, 1H), 8.03-7.90 (m, 3H), 7.66-7.58 (m, 3H), 7.24 (t, J = 8.0 Hz, 1H), 6.88 (dd, J = 5.6 and J = 9.6 Hz 1H), 6.77-6.70 (m, 2H), 6.61-6.56 (m, 3H), 5.34 (m, 1H), 4.65 (s, 2H), 4.27 (m, 1H), 3.76 (m, 1H), 3.36-3.03 (m, 3H), 2.01 (m, 2H), 1.66 (d, J = 6.4 Hz, 3H); |
| 163a 163b | 5-(7-Fluoro-2-(2-(((R)-1-(naphthalen-1-yl)ethyl)amino)ethyl)-2H-benzo[b][1,4]oxazin-4(3H)-yl)-2-methylbenzoic acid hydrochloride | 123a, 123b | m/z 485.11; 163a: $^1$H NMR (400 MHz, DMSO-d6): δ 12.93 (bs, 1H), 9.73 (bs, 1H), 9.18 (bs, 1H), 8.24 (d, J = 8.4 Hz, 1H), 8.03-7.90 (m, 3H), 7.65-7.58 (m, 4H), 7.29-7.24 (m, 2H), 6.79 (dd, J = 5.6 and J = 8.8 Hz 1H), 6.66-6.58 (m, 2H), 5.33 (m, 1H), 4.29 (m, 1H), 3.73 (m, 1H), 3.39-3.07 (m, 3H), 2.47 (s, 3H), 2.04 (m, 2H), 1.67 (d, J = 6.8 Hz, 3H); 163b: $^1$HNMR (400 MHz, DMSO-d6): δ 13.38 (bs, 1H), 9.65 (bs, 1H), 9.16 (bs, 1H), 8.25 (d, J = 8.4 Hz, 1H), 8.03-7.98 (m, 2H), 7.89 (d, J = 6.8 Hz, 1H), 7.66-7.58 (m, 4H), 7.30-7.25 (m, 2H), 6.77 (m, 1H), 6.63-6.57 (m, 2H), 5.34 (m, 1H), 4.28 (m, 1H), 3.71 (m, 1H), 3.42-3.01 (m, 3H), 2.47 (s, 3H), 2.03 (m, 2H), 1.66 (d, J = 6.8 Hz, 3H); |

TABLE 8-continued

| Example | Structure | Ester Example | Mass(m/z) and 1H NMR |
|---|---|---|---|
| 164a 164b | 2-(4-(8-Fluoro-2-(2-(((R)-1-(naphthalen-1-yl)ethyl)amino)ethyl)-2H-benzo[b][1,4]oxazin-4(3H)-yl)phenoxy)aceticacid hydrochloride | 118a, 118b | 164a: m/z 501.2; $^1$H NMR (400 MHz, DMS0-d6): δ 13.02 (bs, 1H), 9.73 (bs, 1H), 9.18 (bs, 1H), 8.26 (d, J = 8.4 Hz, 1H ), 8.03-7.98 (m, 2H), 7.88 (d, J = 7.2 Hz, 1H), 7.65-7.60 (m, 3H), 7.17 (m, 2H), 6.96 (m,2H), 6.65-6.53 (m, 2H), 6.32 (d, J = 8.0 Hz, 1H), 5.35 (m, 1H), 4.68 (s, 2H), 4.37-4.36 (m, 1H), 3.67 (d, J = 12.4 Hz, 1H), 3.44-3.34 (m, 3H), 3.11-3.09 (m, 1H), 2.10-2.05 (m, 2H), 1.67 (d, J = 6.8 Hz, 3H); 164b: $^1$HNMR (400 MHz, DMSO-d6): δ 13.02 (bs, 1H), 9.80 (bs, 1H), 9.25 (bs, 1H), 8.26 (d, J = 8.4 Hz, 1H), 8.03-8.00 (m, 2H), 7.95 (d, J = 6.8 Hz, 1H), 7.64-7.58 (m, 3H), 7.18-7.16 (m, 2H), 6.97-6.95 (m, 2H), 6.63-6.54 (m, 2H), 6.32 (d, J = 8.4 Hz, 1H), 5.35 (m, 1H), 4.68 (s, 2H), 4.38-4.37 (m, 1H), 3.67-3.64 (d, J = 12.8 Hz, 1H), 3.44-3.34 (m, 2H), 3.22-3.03 (m, 1H), 2.12-2.06 (m, 2H), 1.67 (d, J = 6.8 Hz, 3H). |
| 165a 165b | 2-(3-(8-Fluoro-2-(2-(((R)-1-(naphthalen-1-yl)ethyl)amino)ethyl)-2H-benzo[b][1,4]oxazin-4(3H)-yl)phenoxy)aceticacid hydrochloride | 119a, 119b | 165a: m/z 501.1; $^1$H NMR (400 MHz, DMSO-d6): δ 13.02 (bs, 1H), 9.73 (bs, 1H), 9.18 (bs, 1H), 8.24 (d, J = 8.4 Hz, 1H), 8.02-7.98 (m, 3H), 7.90 (d, J = 7.2 Hz, 1H), 7.66-7.58 (m, 3H),7.28 (t, J = 8.0 Hz, 1H), 6.83-6.77 (m, 2H), 6.69-6.62 (m, 3H), 5.38 (m, 1H), 4.66 (s, 2H), 4.36-4.34 (m, 1H), 3.79-3.75 (m, 1H), 3.49-3.44 (m, 1H), 3.25-3.01 (m, 2H), 2.08-2.05 (m, 2H), 1.65 (d, J = 6.8 Hz, 3H); 165b: m/z: 501; $^1$H NMR (400 MHz, DMSO- d6): δ 13.02 (bs, 1H), 9.73 (bs, 1H), 9.18 (bs, 1H), 8.24 (d, J = 8.0 Hz, 1H), 8.03-7.98 (m, 3H), 7.89 (d, J = 6.8 Hz, 1H), 7.65-7.58 (m, 3H), 7.29 (t, J = 8.0 Hz, 1H), 6.82-6.76 (m, 2H), 6.69-6.63 (m, 3H), 5.36 (m, 1H), 4.66 (s, 2H), 4.35-4.33 (m, 1H), 3.79-3.76 (m, 1H), 3.48-3.43 (m, 1H), 3.30-3.10 (m, 2H), 2.09-1.98 (m, 2H), 1.65 (d, J = 6.4 Hz, 3H). |

TABLE 8-continued

| Example | Structure | Ester Example | Mass(m/z) and 1H NMR |
|---|---|---|---|
| 166a 166b | 5-(6-Fluoro-2-(2-(((R)-1-(naphthalan-1-yl)ethyl)amino)ethyl)-2H-benzo[b][1,4]oxazin-4(3H)-yl)-2-methylbenzoicacid hydrochloride | 124a, 124b | m/z: 485.11: 166a: $^1$H NMR (400 MHz, DMSO-d6): δ 8.25 (d, J = 8.4 Hz, 1H), 8.03-7.98 (m, 2 H), 7.89-7.87 (m, 1H), 7.68-7.58 (m, 4H), 7.37-7.33 (m, 2H), 6.73-6.70 (m, 1H), 6.51-6.44 (m, 2H), 5.37-5.35 (m, 1H), 4.29-4.27 (m, 1H), 3.72-3.68 (m, 1H), 3.47-3.30 (m, 4H), 3.00-3.01 (m, 1H), 2.05-2.00 (m, 2H), 1.67-1.65 (m, 3H) 166b: $^1$H NMR (400 MHz DMSO-d6): δ 8.24 (d, J = 8.4 Hz, 1H), 8.03-7.94 (m, 3 H), 7.66-7.57 (m, 4H), 7.34-7.33 (m, 2 H), 6.74-6.70 (m, 1H), 6.51-6.43 (m, 2 H), 5.34-5.32 (m, 1H), 4.29-4.27 (m, 1 H), 3.72-3.68 (m, 1H), 3.47-3.42 (m, 1H), 3.43-3.30 (m, 4H), 2.51-2.49 (m, 1 H), 2.05-2.00 (m, 2H), 1.67-1.65 (m, 3 H) |
| 167a 167b | 3-(6-Fluoro-2-(2-(((R)-1-(naphthalen-1-yl)ethyl)amino)ethyl)-2H-benzo[b][1,4]oxazin-4(3H)-yl)benzoic acid | 125a, 125b | (m/z): 471.04 167a: $^1$H NMR (400 MHz, DMSO-d6): δ 8.23 (d, J = 8.4 Hz, 1H), 8.03-7.98 (m, 2H), 7.87-7.85 (m, 1H), 7.77-7.76 (m, 1H), 1.12-1.69 (m, 1H), 7.64-7.55 (m, 2H), 7.53-7.49 (m, 2H), 6.77-6.74 (m, 1H), 6.57-6.51 (m, 2H), 4.30-4.28 (m, 1H), 3.78-3.75 (m, 1H), 3.49-3.44 (m, 2H), 3.29-3.26 (m, 1H), 3.17-3.16 (m, 1H), 2.08-2.00 (m, 2H), 1.67-1.65 (m, 3H); 167b: $^1$H NMR (400 MHz, DMSO-d6): δ 8.23 (d, J = 8.4Hz, 1H), 8.03-7.98 (m, 1H), 7.87-7.85 (m, 1H), 7.77-7.76 (m, 1H), 7.72-7.69 (m, 1H), 7.64-7.55 (m, 2H), 7.53-7.49 (m, 2H), 6.77-6.74 (m, 1H), 6.57-6.51 (m, 2H), 5.36-5.359 (m, 1H), 4.30-4.28 (m, 1H), 3.78-3.75 (m, 1H), 3.50-3.45 (m, 2H), 3.29-3.22 (m, 1H), 3.01-3.03 (m, 1H), 2.08-2.01 (m, 2H), 1.67-1.66 (m, 3H) |
| 168a 168b | 2-(4-(6-Fluoro-2-(2-(((R)-1-(naphthalen-1-yl)ethyl)amino)ethyl)-2H-benzo[b][1,4]oxazin-4(3H)yl)phenoxy)acetic acid | 126a, 126b | m/z: 501.1: 168a: $^1$H-NMR (400 MHz, DMSO-d6): δ 8.25 (d, J = 8 Hz, 1H), 8.04-7.99 (m, 2 H), 7.83-7.81 (m, 1H), 7.66-7.59 (m, 3H), 7.33-7.29 (m, 1H), 6.87-6.70 (m, 4 H), 6.56-6.51 (m, 2H), 5.36-5.34 (m, 1H), 4.68-4.64 (m, 1H), 4.28-4.26 (m, 1H), 3.74-3.71 (m, 2H), 3.03-2.91 (m, 2H), 2.01-1.91 (m, 2H), 1.67-1.65 (m, 3H) 168b: $^1$H NMR (400 MHz, DMSO-d6 ) δ 8.25 (d, J = 8 Hz, 1H), 8.03-7.99 (m, 2 H), 7.86-7.84 (m, 1H), 7.66-7.58 (m, 3 H), 7.33-7.28 (m, 1H), 6.87-6.69 (m, 4 H), 6.53-6.50 (m, 2H), 5.36-5.34 (m, 1 H), 4.68-4.64 (m, 1H), 4.28-4.26 (m, 1 H), 3.73-3.70 (m, 2H), 3.15-3.01 (m, 2H), 2.01-1.91 (m, 2H), 1.68-1.66 (m, 3H); |

TABLE 8-continued

| Example | Structure | Ester Example | Mass(m/z) and 1H NMR |
|---|---|---|---|
| 169a 169b | 2-(3-(6-Fluoro-2-(2-(((R)-1-(naphthalen-1-yl)ethyl)amino)ethyl)-2H-benzo[b][1,4]oxazin-4(3H)-yl)phenoxy)aceticacid hydrochloride | 128a, 128b | m/z: 500.69: 169a: $^1$H NMR (400 MHz, DMSO-d6): δ 8.24 (d, J = 8 Hz, 1H), 8.03-7.99 (m, 2 H), 7.92-7.90 (m, 1H), 7.64-7.60 (m, 3H), 7.19-7.16 (m, 2H), 6.98-6.96 (m, 2H), 6.69-6.66 (m, 2H), 6.42-6.37 (m, 1H), 6.19-6.16 (m, 1H), 5.29-5.28 (m, 1H), 4.69 (m, 1H), 4.30-4.28 (m, 1H), 3.57-3.53 (m, 2H), 3.38-3.30 (m, 2H), 3.20-3.05 (m, 2H), 1.98-1.96 (m, 2H), 1.65-1.63 (m, 3H); 169b: $^1$H NMR (400 MHz, DMSO-d6): δ 8.24 (d, J = 8 Hz, 1H), 8.03-7.98 (m, 2H), 7.94-7.93 (m, 1H), 7.66-7.58 (m, 3 H), 7.21-7.18 (m, 2H), 6.99-6.97 (m, 2 H), 6.68-6.64 (m, 2H), 6.40-6.35 (m, 1H), 6.19-6.16 (m, 1H), 5.37-5.35 (m, 1H), 4.69 (m, 1H), 4.30-4.28 (m, 1H), 3.63-3.59 (m, 2H), 3.45-3.35 (m, 2H), 3.25-3.03 (m, 2H), 2.08-1.98 (m, 2H), 1.68-1.67 (m, 3H) |
| 170a 170b | 2-Fluoro-5-(5-fluoro-2-(2-(((R)-1-(naphthalen-1-yl)ethyl)amino)ethyl)-2H-benzo[b][1,4]oxazin-4(3H)-yl)benzoicacid hydrochloride | 130a, 130b | (m/z): 489.11: 170a: $^1$H NMR (400 MHz, DMSO-d6): δ 9.397-9.396 (d, J = 8 Hz, 1H), 8.987-8.986 (m, 1H), 8.245-8.244 (m, 1H), 8.024-7.827 (m, 2 H), 7.623-7.622 (m, 1H), 7.270-7.269 (m, 2H), 7.003-7.002 (m, 2H), 6.88-6.77 (m, 2H), 6.466-6.465 (m, 2H), 5.43-5.34 (m, 1H), 4.19-3.72 (m, 2H), 2.96-3.11 (m, 2H), 1.966-1.965 (m, 2H), 1.661-1.660 (m, 3H); 170b: $^1$H NMR (400 MHz, DMSO-d6): δ 8.24 (d, J = 8 Hz, 1H), 8.034-8.011 (m, 2H), 7.86-7.84 (m, 1H), 7.690-7.60 (m, 4H), 7.53-7.50 (m, 1H), 7.395-7.345 (m, 1H), 6.76-6.72 (m, 1H), 6.54-6.49 (m, 1H), 6.44-6.41 (m, 1H), 5.34-5.34 (m, 1H), 3.72-3.44 (m, 1H), 3.41-3.23 (m, 3H), 3.091-3.090 (m, 1H), 1.99-1.97 (m, 2H), 1.67-1.65 (m, 3H) |
| 171a 171b | 2-(3-(5-Fluoro-2-(2-(((R)-1-(Naphthalen-1-yl)ethyl)amino)ethyl)-2H-benzo[b][1,4]oxazin-4(3H)-yl)phenoxy)aceticacid hydrochloride | 131a, 131b | m/z. 500.69: 171a: $^1$NMR (400 MHz, DMSO-d6) δ 8.25-8.23 (d, J = 8.4 1H), 8.03-7.98 (t, J = 7.2 Hz,, 2H), 7.84-7.82 (d, J = 6.8 1H), 7.65-7.58 (m, 3H), 7.18-7.14 (m, 1H), 7.02-6.96 (m, 1H), 6.78-6.71 (m, 2H), 6.52-6.25 (m, 3H), 5.23 (bs, 1H), 4.61 (s, 2H ), 4.06-4.08 (m, 1H), 3.38-3.35 (m, 2H), 3.28-3.21 (m, 2H), 3.08-3.01 (m, 1H), 1.99-1.95 (m, 2H), 1.66-1.64 (d, J = 6.8 Hz, 3H), 171b: $^1$H NMR (400 MHz, DMSO-d6): δ 8.25-8.23 (d, J = 8.0, 1H), 8.03-7.95 (t, J = 7.2 Hz,, 2H), 7.84-7.82 (d, J = 7.2 Hz, 1H, 7.66-7.58 (m, 3H), 7.18-7.13 (m, 1H), 7.01-6.95 (m, 1H), 6.78-6.73 (m, 2H), 6.75-6.69 (m, 2H), 6.67-6.59 (m, 3H), 5.35 (bs, 1H), 4.61 (s, 2H), 4.08 (m, 2H), 3.39-3.30 (m, 1H), 3.28-3.23 (m, 1H), 1.95-1.92 (m, 2H), 1.65-1.64 (d, J = 6.8 Hz, 3H). |

TABLE 8-continued

| Example | Structure | Ester Example | Mass(m/z) and 1H NMR |
|---|---|---|---|
| 172a 172b | 2-(4-(5-Fluoro-2-(2-(((R)-1-(naphlhalen-1-yl)ethyl)amino)ethyl)-2H-benzo[b][1,4]oxazin-4(3H)-yl)phenoxy)aceticacid hydrochloride | 132a, 132b | m/z: 501.2: 172a: $^1$H NMR (400 MHz, DMSO- d6): δ 8.25-8.22 (d J = 8.4, 1H), 8.03-7.98 (m, 2H), 7.84 (d, J = 7.2, 1H), 7.64-7.60 (m, 3H), 6.96-6.81 (m, 5H,), 6.75-6.69 (m, 2H), 5.31 (bs, 1H,), 4.60 (s, 2H), 4.00-3.99 (m, 2H), 3.21-3.19 (m, 2H), 3.10-3.07 (m, 2H), 1.92-1.90 (m, 2H), 1.64 (d, J = 6.8 Hz, 3H). 172b: $^1$H NMR (400 MHz, DMSO-d6): δ 8.25 (d, 1H), 8.03-7.98 (m, 2H), 7.84 (d, 1H,), 7.66-7.58 (m, 3H), 6.94-6.81(m, 5H), 6.69-6.67 (m, 2H), 5.35 (bs, 1H), 4.61 (s, 2H), 3.75-4.00 (t, J = 7.2 Hz, H), 3.61 (d, 1H), 3.25-3.21 (m, 2H), 3.04-3.02 (m, 2H), 1.99-1.97 J = 6.8Hz, (m, 2H), 1.65 (d, 3H) |

Example 173a

Methyl 2-methyl-5-((2-(2-(((R)-1-(naphthalen-1-yl)ethyl)amino)ethyl)-2H-benzo[b][1,4]oxazin-4(3H)-yl)methyl)benzoate

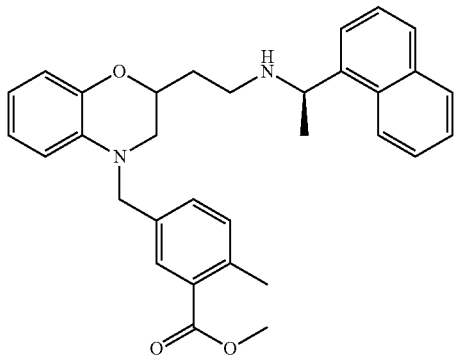 [SMILES: COC(=O)c1cc(CN2CC(CCN[C@H](C)c3cccc4ccccc34)Oc3ccccc32)ccc1C]

To the stirred solution of Intermediate-18a (0.17 g, 0.511 mmol) in added TEA (0.107 mL, 0.767 mmol) at 0° C. to stirred at 45° C. for 48 h. Reactions progress was monitored by TLC. Reaction mixture diluted by water and extracted into DCM then the organic layer washed with water followed by brine solution. The organic layer dried over sodium sulphate and concentrated under vacuum to get crude compound. The crude product purified by flash chromatography using a mixture of 20% ethylacetate in hexane to afford the title compound (0.09 g, 35.6% yield) m/z −495.2.

The below Examples 174 to 176 given Table-9 were prepared by following the similar procedure as described in Example-173a by using Intermediate-18a and appropriately substituted benzyl halide.

TABLE 9

| Example | Structure | Ester | Mass (m/z) |
|---|---|---|---|
| 174a | 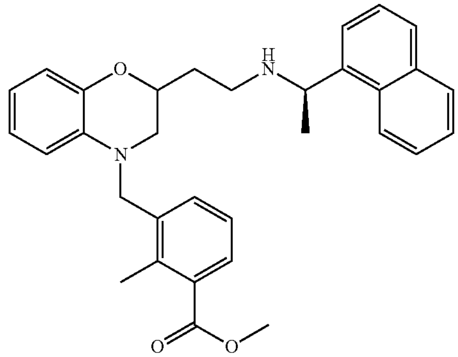 [SMILES: COC(=O)c1cccc(CN2CC(CCN[C@H](C)c3cccc4ccccc34)Oc3ccccc32)c1C] | Methyl2-methyl-3-((2-(2-(((R)-1-(naphthalen-1-yl)ethyl)amino)ethyl)-2H-benzo[b][1,4]oxazin-4(3H)-yl)methyl)benzoate | 495.1 |

TABLE 9-continued

| Example | Structure | Ester | Mass (m/z) |
|---|---|---|---|
| 175a | 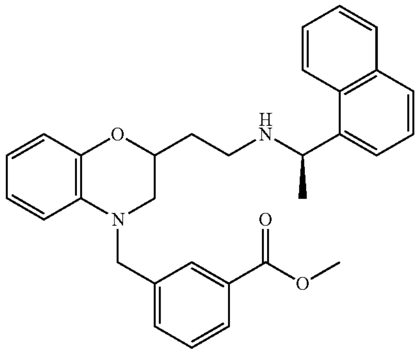 [SMILES: COC(=O)c1cccc(CN2CC(CCN[C@H](C)c3cccc4ccccc34)Oc3ccccc32)c1] | Methyl 3-((2-(2-(((R)-1-(naphthalen-1-yl)ethyl)amino)ethyl)-2H-benzo[b][1,4]oxazin-4(3H)-yl)methyl) benzoate | 481.2 |
| 176a | 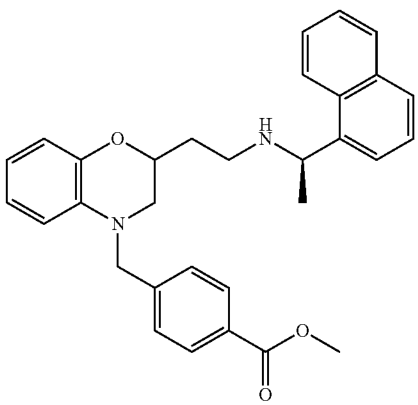 [SMILES: COC(=O)c1ccc(CN2CC(CCN[C@H](C)c3cccc4ccccc34)Oc3ccccc32)cc1] | Methyl 4-((2-(2-(((R)-1-(naphthalen-1-yl)ethyl)amino)ethyl)-2H-benzo[b][1,4]oxazin-4(3H)-yl)methyl)benzoate | 481.2 |

Example 177a

2-Methyl-5-((2-(2-(((R)-1-(naphthalen-1-yl)ethyl)amino)ethyl)-2H-benzo[b][1,4]oxazin-4(3H)-yl)methyl)benzoic acid hydrochloride

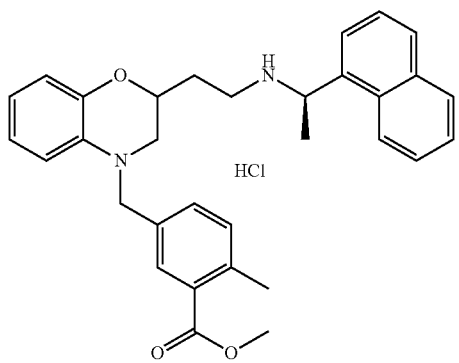 [SMILES: COC(=O)c1cc(CN2CC(CCN[C@H](C)c3cccc4ccccc34)Oc3ccccc32)ccc1C ; Cl]

To a solution of Example-173a (0.09 g, 0.18 mmol) in MeOH (15 mL), THF (5 mL) and water (0.5 mL) lithium hydroxide monohydrate (0.013 g, 0.55 mmol) was added. The reaction mixture was heated to 80° C. and further maintained for 2 h. The progress of reaction was monitored by TLC. The reaction mixture was concentrated under vacuum then cooled to 0° C. and acidified with dilute HCl solution [pH=3 to 4]. Extracted the product into Ethyl acetate (10 mL×2), washed with water (5 mL×2) followed by brine solution (5 mL), dried over sodium sulfate and concentrated under vacuum to get solid compound. Further HCl salt of this amino compounds were prepared by following the similar HCl salt procedure as described in Example-1 (0.057 g, 65.2% yield). (m/z) 481.11;

$^1$H NMR (400 MHz, DMSO-d6): δ 8.24 (d, 1H), 8.03-7.98 (m, 3H), 7.73 (d, 1H), 7.64-7.59 (m, 3H), 7.34-7.32 (d, 1H), 7.24-7.22 (d, 1H), 6.69-6.53 (m, 3H), 6.53-6.51 (m, 1H), 5.34-5.32 (q, 1H), 4.5-4.46 (m, 4H), 4.25-4.23 (m, 2H), 3.38-3.34 (m, 1H), 3.21-3.15 (m, 2H), 2.51-2.43 (S, 3H), 2.05-1.98 (m, 2H), 1.69-1.68 (d, 3H).

The below Examples 178 to 180 given in Table-10 were prepared by following the similar ester hydrolysis procedure as described in Example-177 by using appropriate ester intermediate. Further HCl salts of these amino compounds were prepared by following the similar HCl salt procedure as described in Example-1.

TABLE 10

| Example | Structure | Ester | Mass (m/z) and ¹H NMR |
|---|---|---|---|
| 178a |  2-Methyl-3-((2-(2-(((R)-1-(naphthalen-1-yl)ethyl)amino)ethyl)-2H-benzo[b] [1,4]oxazin-4(3H)-yl)methyl) benzoic acid hydrochloride | 174a | m/z 467.2; ¹H NMR (400 MHz, DMSO-d6): δ 13.38 (bs, 1H), 9.73 (bs, 1H), 9.18 (bs, 1H), 8.25 (d, J = 8.4 Hz, 1H), 8.01 (t, J = 9.2 Hz, 2H), 7.93 (d, J = 7.2 Hz, 1H), 7.86-7.81 (m, 2H), 7.66-7.58 (m, 3H), 7.51 (d, J = 7.6 Hz, 1H), 7.45 (t, J = 7.6 Hz, 1H), 6.71-6.62 (m, 3H), 6.52 (t, J = 8.0 Hz, 1H), 5.36 (m, 1H), 4.52 (q, J = 16.4 Hz, 2H), 4.26 (m, 1H), 3.39-3.08 (m, 4H), 2.04 (m, 2H), 1.68 (d, J = 6.8 Hz, 3H); |
| 179a |  3-((2-(2-(((R)-1-(Naphthalen-1-yl)ethyl) amino)ethyl)-2H-benzo [b][1,4]oxazin-4(3H)-yl)methyl) benzoic acid hydrochloride | 175a | m/z 467.2; ¹H NMR (400 MHz, DMSO-d6): δ 13.38 (bs, 1H), 9.73 (bs, 1H), 9.18 (bs, 1H), 8.25 (d, J = 8.4 Hz, 1H), 8.01 (t, J = 9.2 Hz, 2H), 7.93 (d, J = 7.2 Hz, 1H), 7.86-7.81 (m, 2H), 7.66-7.58 (m, 3H), 7.51 (d, J = 7.6 Hz, 1H), 7.45 (t, J = 7.6 Hz, 1H), 6.71-6.62 (m, 3H), 6.52 (t, J = 8.0 Hz, 1H), 5.36 (m, 1H), 4.52 (q, J = 16.4 Hz, 2H), 4.26 (m, 1H), 3.39-3.08 (m, 4H), 2.04 (m, 2H), 1.68 (d, J = 6.8 Hz, 3H); |
| 180a |  4-((2-(2-(((R)-1-(Naphthalen-1-yl)ethyl)amino)ethyl)-2H-benzo[b] [1,4] oxazin-4(3H)-yl) methyl) benzoic acid hydrochloride | 176a | m/z 467.2; ¹H NMR (400 MHz, DMSO-d6): δ 13.38 (bs, 1H), 9.73 (bs, 1H), 9.18 (bs, 1H), 8.25 (d, J = 8.4 Hz, 1H), 8.03-7.88 (m, 5H), 7.66-6.52 (m, 3H), 7.39 (d, J = 8.4 Hz, 2H), 6.70-7.52 (m, 4H), 5.34 (m, 1H), 4.52 (q, J = 17.2 Hz, 2H), 4.28 (m, 1H), 3.40-3.07 (m, 4H), 2.04 (m, 2H), 1.68 (d, J = 6.8 Hz, 3H); |

Example-181

2-Methyl-5-(2-(2-(((S)-1-(naphthalen-1-yl)ethyl)amino)ethyl)-2H-benzo[b][1,4]oxazin-4(3H)-yl)benzoicacid hydrochloride

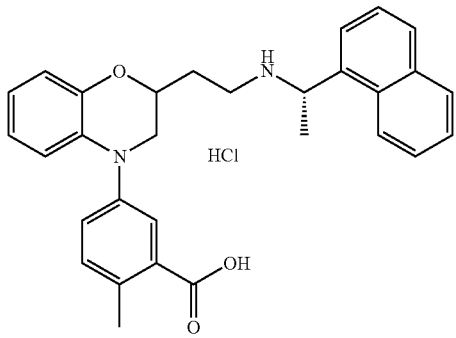 [SMILES: Cc1ccc(N2CC(CCN[C@@H](C)c3cccc4ccccc34)Oc3ccccc32)cc1C(=O)O ; Cl]

The title compound was prepared following the similar hydrolysis procedure as described in Example-133a, 133b by taking Example-80 and LiOH monohydrate.

m/z 467.4; $^1$H NMR (400 MHz, DMSO-D6): δ12.9 (bs, 1H), 9.86 (bs, 1H), 9.26 (bs, 1H), 8.26 (d, J=8.4 Hz, 1H), 8.03-7.94 (m, 3H), 7.65-7.58 (m, 4H), 7.29 (s, 2H), 6.79-6.77 (m, 1H), 6.74-6.70 (m, 3H), 5.36-5.34 (m, 1H), 4.28-4.25 (m, 1H), 3.80-3.69 (m, 1H), 3.40-3.38 (m, 1H), 3.26-3.21 (m, 1H) 3.0-2.98 (m, 1H), 2.5 (s, 3H), 2.04-1.99 (m, 2H), 1.64-1.63 (d, J=6.8 Hz, 3H).

Example-182a, 182b

2-Fluoro-5-(6-fluoro-2-(2-(((R)-1-(naphthalen-1-yl)ethyl)amino)ethyl)-2H-benzo[b][1,4]oxazin-4(3H)-yl)benzoic acid hydrochloride

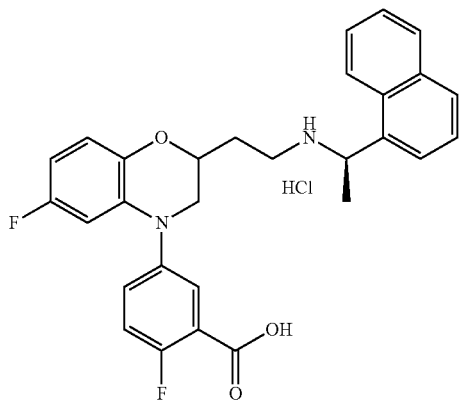 [SMILES: C[C@@H](NCCC1CN(c2ccc(F)c(C(=O)O)c2)c2cc(F)ccc2O1)c1cccc2ccccc12 ; Cl]

The title compound of Example-182a was prepared by following the similar ester hydrolysis procedure as described in Example-133a, 133b by using Example-129a and LiOH monohydrate. Similarly, Example-182b was prepared from Example-129b.

m/z: 489.11;

$^1$H NMR (400 MHz, DMSO-d6): δ8.24 (d, J=8 Hz, 1H), 8.034-8.011 (m, 2H), 7.86-7.84 (m, 1H), 7.690-7.60 (m, 4H), 7.53-7.50 (m, 1H), 7.395-7.345 (m, 1H), 6.76-6.72 (m, 1H), 6.54-6.49 (m, 1H), 6.44-6.41 m, 1H), 5.343-5.342 (m, 1H), 3.72-3.44 (m, 1H), 3.41-3.23 (m, 3H), 3.091-3.090 (m, 1H), 1.99-1.97 (m, 2H), 1.67-1.65 (m, 3H).

b: $^1$H NMR (400 MHz, DMSO-d6): 8.243 (d, J=8 Hz, 1H), 8.02-7.98 (m, 2H), 7.81-7.80 (m, 1H), 7.67-7.58 (m, 4H), 7.53-7.51 (m, 1H), 7.39-7.34 (m, 1H), 6.73-6.70 (m, 1H), 6.52-6.47 (m, 1H), 6.43-6.40 (m, 1H), 5.35-5.33 (m, 1H), 4.28-4.26 (m, 1H), 3.70-3.67 (m, 2H), 3.45-3.40 (m, 1H), 3.27-3.20 (m, 2H), 2.01-1.99 (m, 2H), 1.66-1.64 (m, 3H).

Example-183a, 183b

2-Fluoro-5-(7-fluoro-2-(2-(((R)-1-(naphthalen-1-yl)ethyl)amino)ethyl)-2H-benzo[b][1,4]oxazin-4(3H)-yl)benzoic acid hydrochloride

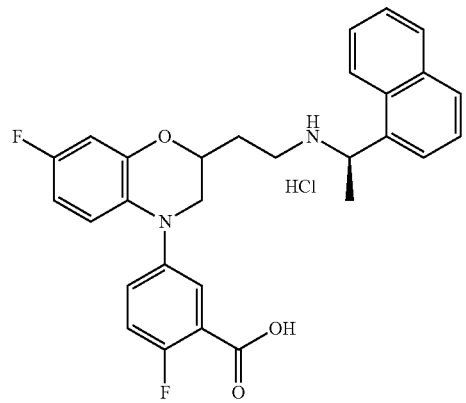 [SMILES: C[C@@H](NCCC1CN(c2ccc(F)c(C(=O)O)c2)c2ccc(F)cc2O1)c1cccc2ccccc12 ; Cl]

The title compound of Example-183a was prepared by following the similar ester hydrolysis procedure as described in Example-133a, 133b by using Example-122a and LiOH monohydrate.

Similarly, Example-183b was prepared from Example-122b.

m/z 489.2; a: $^1$H NMR (400 MHz, DMSO-d6): δ 13.38 (bs, 1H), 9.73 (bs, 1H), 9.18 (bs, 1H), 8.24 (d, J=8.4 Hz, 1H), 8.03-7.91 (m, 3H), 7.65-7.58 (m, 4H), 7.42 (m, 1H), 7.31 (dd, J=9.2 & J=10.4 Hz 1H), 6.77 (dd, J=6.0 & J=9.2 Hz 1H), 6.67-6.59 (m, 2H), 5.33 (m, 1H), 4.30 (m, 1H), 3.73 (m, 1H), 3.40-3.07 (m, 3H), 2.04 (m, 2H), 1.67 (d, J=6.8 Hz, 3H);

b: $^1$H NMR (400 MHz, DMSO-d6): δ 13.38 (bs, 1H), 9.73 (bs, 1H), 9.18 (bs, 1H), 8.25 (d, J=8.4 Hz, 1H), 8.03-7.87 (m, 3H), 7.66-7.59 (m, 4H), 7.44 (m, 1H), 7.32 (t, J=10.4 Hz, 1H), 6.78 (m, 1H), 6.64-6.60 (m, 2H), 5.36 (m, 1H), 4.29 (m, 1H), 3.73 (m, 1H), 3.41-2.98 (m, 3H), 2.01 (m, 2H), 1.66 (d, J=6.4 Hz, 3H);

The following Examples 184 to 221 given in Table-11a and Table-11b are prepared by following the similar procedure as described in Example-88a, 88b by taking appropriate halo benzene (ester) followed by ester hydrolysis using LiOH monohydrate by following the procedure as described in Example-133a, 133b by taking appropriately substituted intermediates further hydrochloride salt is prepared as described in Example-1.

TABLE 11a

| Sr. No | Structure | Starting Intermediate |
|---|---|---|
| 184 | 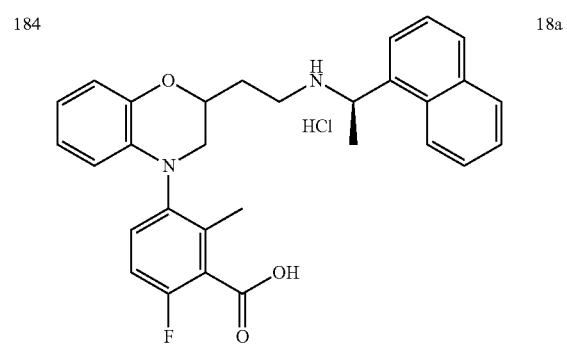<br>6-Fluoro-2-methyl-3-(2-(2-(((R)-1-(naphthalen-1-yl)ethyl)amino)ethyl)-2H-benzo[b][1,4]oxazin-4(3H)-yl)benzoic acid hydrochloride | 18a |
| 185 | 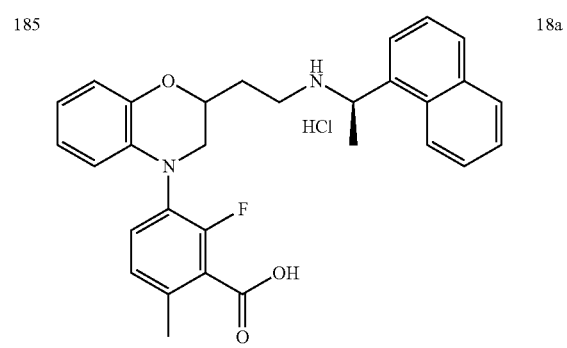<br>2-Fluoro-6-methyl-3-(2-(2-(((R)-1-(naphthalen-1-yl)ethyl)amino)ethyl)-2H-benzo[b][1,4]oxazin-4(3H)-yl)benzoic acid hydrochloride | 18a |
| 186 | 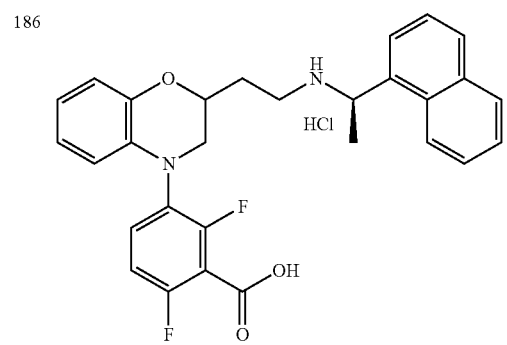 [SMILES: C[C@@H](NCCC1CN(c2ccc(F)c(C(=O)O)c2F)c2cc(F)ccc2O1)c1cccc2ccccc12 ; Cl]<br>2,6-Difluoro-3-(2-(2-(((R)-1-(naphthalen-1-yl)ethyl)amino) ethyl)-2H-benzo[b] [1,4]oxazin-4 (3H)-yl) benzoic acid hydrochloride | 18a |
| 187 | 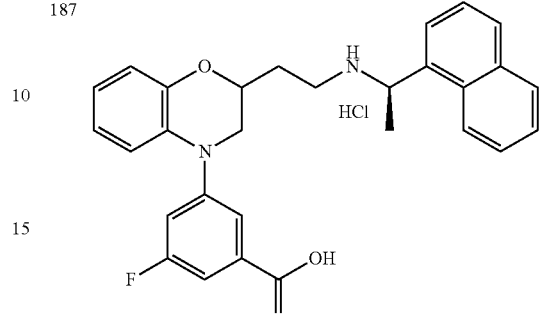<br>3-Fluoro-5-(2-(2-(((R)-1-(naphthalen-1-yl)ethyl)amino)ethyl)-2H-benzo[b] [1,4]oxazin-4(3H)-yl) benzoic acid hydrochloride | 18a |
| 188 | 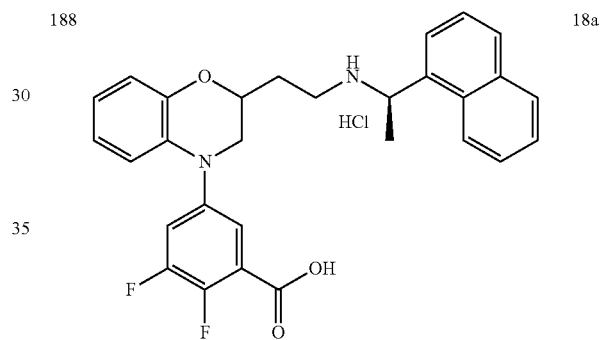<br>2,3-Difluoro-5-(2-(2-(((R)-1-(naphthalen-1-yl) ethyl) amino) ethyl)-2H-benzo[b] [1,4]oxazin-4 (3H)-yl)benzoic acid hydrochloride | 18a |
| 189 | 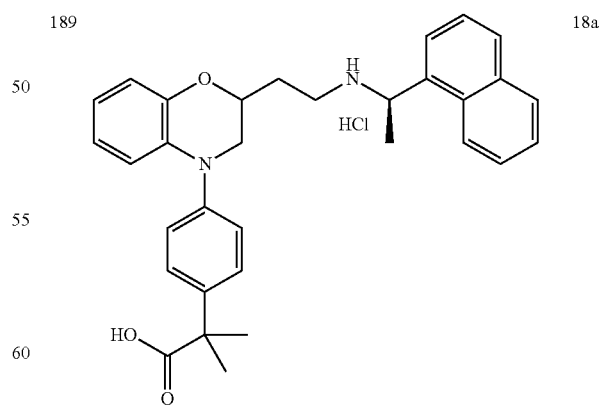<br>2-Methyl-2-(4-(2-(2-(((R)-1-(naphthalen-1-yl)ethyl)amino)ethyl)-2H-benzo[b][1,4]oxazin-4(3H)-yl)phenyl)propanoic acid hydrochloride | 18a |

TABLE 11a-continued

| Sr. No | Structure | Starting Intermediate |
|---|---|---|
| 190 | 2,4-Difluoro-5-(2-(2-(((R)-1-(naphthalen-1-yl)ethyl)amino)ethyl)-2H-benzo[b][1,4]oxazin-4 (3H)-yl)benzoic acid hydrochloride | 18a |
| 191 | 3-(2-Fluoro-5-(2-(2-(((R)-1-(naphthalen-1-yl) ethyl)amino)ethyl)-2H-benzo[b] [1,4] oxazin-4 (3H)-yl)phenyl) propanoic acid hydrochloride | 18a |
| 192 | 3-(2-Fluoro-3-(2-(2-(((R)-1-(naphthalen-1-yl) ethyl)amino)ethyl)-2H-benzo[b][1,4] oxazin-4 (3H)-yl)phenyl)propanoic acid hydrochloride | 18a |
| 193 | 3-(3-Fluoro-5-(2-(2-(((R)-1-(naphthalen-1-yl) ethyl)amino)ethyl)-2H-benzo[b] [1,4]oxazin-4 (3H)-yl)phenyl) propanoic acid hydrochloride | 18a |
| 194 | 3-(4-Fluoro-3-(2-(2-(((R)-1-(naphthalen-1-yl)ethyl)amino)ethyl)-2H-benzo[b][1,4]oxazin-4 (3H)-yl)phenyl)propanoic acid hydrochloride | 18a |
| 195 | 2-(3-Fluoro-4-(2-(2-(((R)-1-(naphthalen-1-yl) ethyl)amino)ethyl)-2H-benzo[b][1,4]oxazin-4 (3H)-yl)phenoxy)acetic acid hydrochloride | 18a |

TABLE 11a-continued

| Sr. No | Structure | Starting Intermediate |
|---|---|---|
| 196 | 2-(2-Fluoro-4-(2-(2-(((R)-1-(naphthalen-1-yl) ethyl)amino) ethyl)-2H-benzo[b] [1,4]oxazin-4 (3H)-yl)phenoxy) acetic acid hydrochloride | 18a |
| 197 | 2-(3-Methyl-4-(2-(2-(((R)-1-(naphthalen-1-yl)ethyl)amino) ethyl)-2H-benzo[b][1,4]oxazin-4 (3H)-yl)phenoxy) acetic acid hydrochloride | 18a |
| 198 | 2-(2-Methyl-5-(2-(2-(((R)-1-(naphthalen-1-yl) ethyl)amino) ethyl)-2H-benzo[b] [1,4] oxazin-4 (3H)-yl)phenoxy) acetic acid hydrochloride | 18a |
| 199 | 2-(2-Methyl-3-(2-(2-(((R)-1-(naphthalen-1-yl) ethyl)amino) ethyl)-2H-benzo[b][1,4] oxazin-4 (3H)-yl)phenoxy)acetic acid hydrochloride | 18a |
| 200 | 2-(3-Methyl-5-(2-(2-(((R)-1-(naphthalen-1-yl)ethyl)amino) ethyl)-2H-benzo[b][1,4]oxazin-4 (3H)-yl)phenoxy)acetic acid hydrochloride | 18a |
| 201 | 2-(4-Methyl-3-(2-(2-(((R)-1-(naphthalen-1-yl)ethyl)amino) ethyl)-2H-benzo[b][1,4] oxazin-4 (3H)-yl)phenoxy)acetic acid hydrochloride | 18a |

TABLE 11a-continued

| Sr. No | Structure | Starting Intermediate |
|---|---|---|
| 202 | 2-Methyl-2-(3-(2-(2-(((R)-1-(naphthalen-1-yl)ethyl)amino)ethyl)-2H-benzo[b][1,4]oxazin-4 (3H)-yl)phenyl)propanoic acid hydrochloride | 18a |
| 203 | 1-(3-(2-(2-(((R)-1-(Naphthalen-1-yl)ethyl) amino)ethyl)-2H-benzo [b][1,4]oxazin-4(3H)-yl) phenyl) cyclopropanecarboxylic acid hydrochloride | 18a |
| 204 | 1-(4-(2-(2-(((R)-1-(Naphthalen-1-yl)ethyl)amino)ethyl)-2H-benzo [b][1,4]oxazin-4(3H)-yl)phenyl) cyclopropanecarboxylic acid hydrochloride | 18a |

TABLE 11b

| Sr. No | Structure | Starting Intermediate |
|---|---|---|
| 205 | 6-Fluoro-3-(8-fluoro-2-(2-(((R)-1-(naphthalen-1-yl)ethyl)amino)ethyl)-2H-benzo[b][1,4]oxazin-4(3H)-yl)-2-methyl benzoic acid hydrochloride | 23 |
| 206 | 2-Fluoro-3-(8-fluoro-2-(2-(((R)-1-(naphthalen-1-yl)ethyl)amino)ethyl)-2H-benzo[b][1,4]oxazin-4(3H)-yl)-6-methyl benzoic acid hydrochloride | 23 |
| 207 | 2,6-Difluoro-3-(8-fluoro-2-(2-(((R)-1-(naphthalen-1-yl)ethyl)amino)ethyl)-2H-benzo[b][1,4]oxazin-4(3H)-yl) benzoic acid hydrochloride | 23 |

TABLE 11b-continued

| Sr. No | Structure | Starting Intermediate |
|---|---|---|
| 208 | 3-Fluoro-5-(8-fluoro-2-(2-(((R)-1-(naphthalen-1-yl)ethyl)amino)ethyl)-2H-benzo[b][1,4]oxazin-4(3H)-yl) benzoic acid hydrochloride | 23 |
| 209 | 2-Fluoro-5-(8-fluoro-2-(2-(((R)-1-(naphthalen-1-yl)ethyl)amino)ethyl)-2H-benzo[b][1,4]oxazin-4(3H)-yl) benzoic acid | 23 |
| 210 | 6-Fluoro-3-(7-fluoro-2-(2-(((R)-1-(naphthalen-1-yl)ethyl)amino)ethyl)-2H-benzo[b][1,4]oxazin-4(3H)-yl)-2-methyl benzoic acid hydrochloride | 22 |
| 211 | 2-Fluoro-3-(7-fluoro-2-(2-(((R)-1-(naphthalen-1-yl)ethyl)amino)ethyl)-2H-benzo[b][1,4]oxazin-4(3H)-yl)-6-methyl benzoic acid hydrochloride | 22 |
| 212 | 2,6-Difluoro-3-(7-fluoro-2-(2-(((R)-1-(naphthalen-1-yl)ethyl)amino)ethyl)-2H-benzo[b][1,4]oxazin-4(3H)-yl)benzoic acid hydrochloride | 22 |
| 213 | 3-Fluoro-5-(7-fluoro-2-(2-(((R)-1-(naphthalen-1-yl)ethyl)amino)ethyl)-2H-benzo[b][1,4]oxazin-4(3H)-yl) benzoic acid hydrochloride | 22 |
| 214 | 6-Fluoro-3-(6-fluoro-2-(2-(((R)-1-(naphthalen-1-yl)ethyl)amino)ethyl)-2H-benzo[b][1,4]oxazin-4(3H)-yl)-2-methylbenzoic acid hydrochloride | 24 |

TABLE 11b-continued

| Sr. No | Structure | Starting Intermediate |
|---|---|---|
| 215 | 2-Fluoro-3-(6-fluoro-2-(2-(((R)-1-(naphthalen-1-yl)ethyl)amino)ethyl)-2H-benzo[b][1,4]oxazin-4(3H)-yl)-6-methyl benzoic acid hydrochloride | 24 |
| 216 | 2,6-Difluoro-3-(6-fluoro-2-(2-(((R)-1-(naphthalen-1-yl)ethyl)amino)ethyl)-2H-benzo[b][1,4]oxazin-4(3H)-yl)benzoic acid hydrochloride | 24 |
| 217 | 3-Fluoro-5-(6-fluoro-2-(2-(((R)-1-(naphthalen-1-yl)ethyl)amino)ethyl)-2H-benzo[b][1,4]oxazin-4(3H)-yl)benzoic acid hydrochloride | 24 |
| 218 | 6-Fluoro-3-(5-fluoro-2-(2-(((R)-1-(naphthalen-1-yl)ethyl)amino)ethyl)-2H-benzo[b][1,4]oxazin-4(3H)-yl)-2-methyl benzoic acid hydrochloride | 25 |
| 219 | 2-Fluoro-3-(5-fluoro-2-(2-(((R)-1-(naphthalen-1-yl)ethyl)amino)ethyl)-2H-benzo[b][1,4]oxazin-4(3H)-yl)-6-methyl benzoic acid hydrochloride | 25 |
| 220 | 2,6-Difluoro-3-(5-fluoro-2-(2-(((R)-1-(naphthalen-1-yl)ethyl)amino)ethyl)-2H-benzo[b][1,4]oxazin-4(3H)-yl)benzoic acid hydrochloride | 25 |

TABLE 11b-continued

| Sr. No | Structure | Starting Intermediate |
|---|---|---|
| 221 | ![structure] 3-Fluoro-5-(5-fluoro-2-(2-(((R)-1-(naphthalen-1-yl)ethyl)amino)ethyl)-2H-benzo[b][1,4]oxazin-4(3H)-yl)benzoic acid hydrochloride | 25 |

Pharmacological Activity

Certain illustrative compounds within the scope of the invention are screened for CaSR activity according to the procedure given below. The screening of the compounds may also be carried by other methods and procedures known to skilled in the art.

In-Vitro Assay Method of Calcimemtics Through Modulation of Calcium Sensing Receptor (CaSR):

The ability of the compounds to modulate Calcium sensing receptor is determined by measuring an increase in intracellular calcium $[Ca^{2+}]_i$. Stably transfected HEK293 cells expressing hCaSR_pTriEx-3 hygro vector are developed. Cells are grown overnight on a 96-well plate to 80% confluency in Ham's F12 containing 20% FBS at 37° C., 5% $CO_2$. Subsequently, cells are washed extensively with 20 mM HEPES buffer containing 126 mM NaCl, 1 mM $MgCl_2$ and 4 mM KCl to remove serum components that might interfere with the assay. Cells are loaded with calcium sensing Fluo4NW dye in HEPES base buffer containing 0.1% BSA and 1 mg/ml glucose for 30 minutes to measure changes in intracellular calcium. The activities of the compounds are measured in FLIPR using 0.3 mM $CaCl_2$ in 20 mM HEPES base buffer. The effectiveness of the compound to modulate receptor activity is determined by calculating the $EC_{50}$ responses for that compound in an 8-point assay and plotted using GraphPad Prism 5.

The compounds prepared were tested using the above assay procedure and the results obtained are given below. The $EC_{50}$ (nM) values of few representative compounds are set forth in Table-12.

Activity data has been given in Table-12 for representative compounds.

TABLE 12

| Example number | $EC_{50}$ Range |
|---|---|
| 31b, 64b, 66b, 70b, , 71b, 73b, 76a, 79b, 133a, 133b, , 135a, 138a, 139a, 141a, 144a, 148a, 160a, 161a, 164a, 166a, 167a, 168a, 169a, 171a, 171b, 172a, 172b, 177a | less than 20 nM |
| 2b, 24b, 31a, 41, 50, 51b, 58a, 58b, 60a, 66a, 84, 87b, 159a, 167b | between 20-50 nM |
| 2a, 6, 48, 54, 55a, 62a, 62b, 67b, 68a, 68b, 69, 72, 75b, 77a, 86a, 86b, 134a, 137a, 143a | between 50-200 nM |

Through the use of above described assay method, compounds were found to exhibit agonistic activity thus to be particularly well suited for the treatment of the diseases or disorders as described herein above.

All patents, patent applications and publications cited in this application are hereby incorporated by reference in their entirety for all purposes to the same extent as if each individual patent, patent application or publication were so individually denoted.

Although certain embodiments and examples have been described in detail above, those having ordinary skill in the art will clearly understand that many modifications are possible in the embodiments and examples without departing from the teachings thereof. All such modifications are intended to be encompassed within the below claims of the invention.

The invention claimed is:

1. A compound of Formula (I):

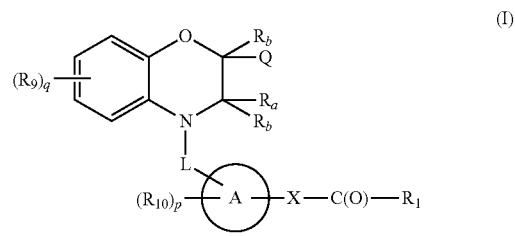

wherein,

Q is

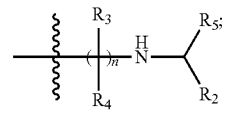

$R_a$ is hydrogen, halogen or alkyl;

$R_b$ is selected from hydrogen, alkyl, and haloalkyl;

or $R_a$ and $R_b$ together attached on the same carbon form C(O);

L is a bond or —$CR_cR_d$—;

ring A is phenyl;

$R_c$ and $R_d$ are independently selected from hydrogen, halogen, and alkyl;

X is selected from a bond, —$(CR_eR_f)_m$—, —O—, —O$(CR_eR_f)_m$—, —$(CR_eR_f)_m$O—, —C(O)$(CR_eR_f)_m$—, —C(O)$NR_7$—, —C(O)$NR_7(CR_eR_f)_m$—, -cycloalkylene-, and —O-cycloalkylene-;

$R_e$ and $R_f$, which may be same or different at each occurrence, are independently selected from hydrogen, halogen, alkyl, haloalkyl and cycloalkyl; or $R_e$ and $R_f$ together with the carbon atom to which they are attached, may form a 3 to 7 membered saturated carbocyclic ring;

$R_1$ is —$OR_6$ or —$NR_7R_8$;

$R_2$ is substituted or unsubstituted aryl;

R$_3$ and R$_4$ are independently selected from hydrogen, halogen, alkyl, haloalkyl, and cycloalkyl;
R$_5$ is alkyl or haloalkyl;
R$_6$ is hydrogen or alkyl;
R$_7$ and R$_8$ are independently selected from hydrogen, alkyl, cycloalkyl cycloalkylalkyl and aryl;
R$_9$, which may be same or different at each occurrence, is independently selected from halogen, cyano, alkyl, haloalkyl, and cycloalkyl;
R$_{10}$, which may be same or different at each occurrence, is independently selected from halogen, cyano, alkyl, alkenyl, alkynyl, haloalkyl, hydroxyalkyl, —OR$_6$, —C(O)R$_6$, —NR$_7$C(O)R$_6$, —S(O)$_{0-2}$R$_6$, —S(O)$_2$NR$_7$R$_8$, and —NR$_7$S(O)$_2$R$_6$;
'm' is an integer ranging from 1 to 3, both inclusive;
'n' is an integer ranging from 1 to 3, both inclusive;
'p' is an integer ranging from 0 to 2, both inclusive; and
'q' is an integer ranging from 0 to 1, both inclusive;
or pharmaceutically acceptable salt thereof.

2. The compound of claim 1, having the Formula (II):

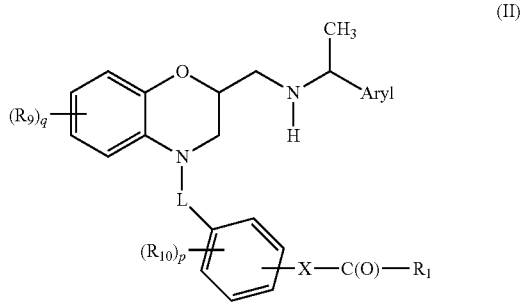

(II)

wherein,
L is a bond, or —CR$_c$R$_d$;
Aryl is substituted or unsubstituted phenyl or substituted or unsubstituted naphthyl, wherein the phenyl is substituted with halogen, alkyl, haloalkyl, alkoxy or haloalkoxy;
R$_c$, R$_d$, X, R$_1$, R$_9$, R$_{10}$, 'p' and 'q' are as defined claim 1;
or pharmaceutically acceptable salt thereof.

3. The compound of claim 1, having the Formula (III):

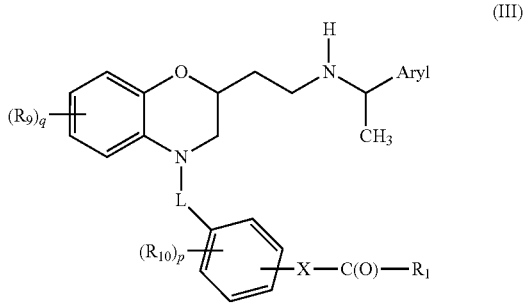

(III)

wherein,
L is a bond or CR$_c$R$_d$;
Aryl is substituted or unsubstituted phenyl or substituted or unsubstituted naphthyl, wherein the phenyl is substituted with halogen, alkyl, haloalkyl, alkoxy or haloalkoxy;
R$_c$, R$_d$, X, R$_1$, R$_9$, R$_{10}$, 'p' and 'q' are as defined in claim 1;
or pharmaceutically acceptable salt thereof.

4. The compound of claim 1, wherein Q is

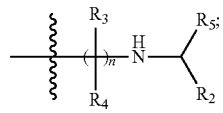

R$_3$ and R$_4$ are hydrogen; 'n' is 1 or 2; R$_2$ is phenyl or naphthyl wherein the phenyl is substituted with halogen, alkyl, haloalkyl, alkoxy or haloalkoxy; R$_5$ is alkyl; R$_a$ is hydrogen; and R$_b$ is hydrogen or alkyl.

5. The compound of claim 1, wherein X is selected from a bond, —(CR$_e$R$_f$)$_m$, —O(CR$_e$R$_f$)$_m$—, —C(O)(CR$_e$R$_f$)$_m$—, —C(O)NR$_7$— and —C(O)NR$_7$(CR$_e$R$_f$)$_m$—; wherein R$_e$ and R$_f$ may be same or different and are independently selected from hydrogen, halogen, alkyl, haloalkyl and cycloalkyl; or R$_e$ and R$_f$, together form a 3 to 7 membered saturated carbocyclic ring; R$_7$ is hydrogen or alkyl; and 'm' is 1 or 2.

6. The compound of claim 1, wherein R$_1$ is —OR$_6$, wherein R$_6$ is hydrogen or alkyl.

7. The compound of claim 1, wherein R$_1$ is —NR$_7$R$_8$, wherein R$_7$ and R$_8$ are hydrogen, alkyl or cycloalkyl.

8. The compound of claim 1, wherein X is selected from a bond, —(CR$_e$R$_f$)$_m$, —C(O)(CR$_e$R$_f$)$_m$—, —C(O)NR$_7$— and —C(O)NR$_7$(CR$_e$R$_f$)$_m$—; wherein R$_e$ and R$_f$ may be same or different and are independently selected from hydrogen, halogen, alkyl, haloalkyl and cycloalkyl; or R$_e$ and R$_f$, together form a 3 to 7 membered saturated carbocyclic ring; 'm' is 1 or 2; and R$_1$ is —OR$_6$ or —NR$_7$R$_8$ wherein R$_6$ is hydrogen or alkyl; R$_7$ and R$_8$ are hydrogen, alkyl, or cycloalkyl.

9. The compound of claim 1, wherein R$_{10}$ is selected from halogen, cyano, alkyl, haloalkyl, hydroxyalkyl, —OR$_6$, —C(O)R$_6$, —NR$_7$R$_8$, —NR$_7$C(O)R$_6$, —S(O)$_2$NR$_7$R$_8$, and —NR$_7$S(O)$_2$R$_6$; wherein R$_6$ is hydrogen or alkyl; R$_7$ and R$_8$ are independently selected from hydrogen, alkyl, cycloalkyl, and aryl; and 'p' is 0 to 2.

10. The compound of claim 1, wherein Q is

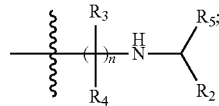

R$_a$ is hydrogen; R$_b$ is hydrogen or alkyl;
L is a bond, or —CR$_c$R$_d$;
ring A is phenyl;
R$_c$ and R$_d$ are independently selected from hydrogen, halogen, and alkyl;
X is selected from a bond, —(CR$_e$R$_f$)$_m$-, —O—, —O(CR$_e$R$_f$)$_m$—, —(CR$_e$R$_f$)$_m$O—, —C(O)(CR$_e$R$_f$)$_m$—, —C(O)NR$_7$—, and —C(O)NR$_7$(CR$_e$R$_f$)$_m$—;
R$_e$ and R$_f$, which may be same or different at each occurrence, are independently selected from hydrogen, halogen, alkyl, haloalkyl and cycloalkyl; or R$_e$ and R$_f$, together with the carbon atom to which they are attached, form a 3 to 7 membered saturated carbocyclic ring;
R$_1$ is —OR$_6$ or —NR$_7$R$_8$;
R$_2$ is phenyl or naphthyl, wherein the phenyl is substituted with halogen, alkyl, haloalkyl, alkoxy or haloalkoxy;
R$_3$ and R$_4$ are hydrogen;
R$_5$ is alkyl;

R₆ is hydrogen or alkyl;

R₇ and R₈ are hydrogen or alkyl;

R₉ is independently selected from halogen, cyano, alkyl, haloalkyl, and cycloalkyl;

R₁₀, which may be same or different at each occurrence, is independently selected from halogen, cyano, alkyl, haloalkyl, hydroxyalkyl, —OR₆, —C(O)R₆, —NR₇R₈, —NR₇C(O)R₆, and —(O)₂NR₇R₈;

'm' is 1 to 3; 'n' is 1 to 3; 'p' is 0 to 2; 'q' is 0 to 1; or pharmaceutically acceptable salt thereof.

11. The compound of claim 1, wherein the pharmaceutically acceptable salt is hydrochloride salt.

12. A compound which is selected from:

Methyl 4-(2-((((R)-1-(3-methoxyphenyl)ethyl)amino) methyl)-2H-benzo[b] [1,4]oxazin-4(3H)-yl)benzoate hydrochloride;

Methyl 4-(2-((((R)-1-(naphthalene-1-yl)ethyl)amino) methyl)-2H-benzo[b][1,4]oxazin-4(3H)-yl)benzoate hydrochloride;

Methyl 3-(2-((((R)-1-(3-methoxyphenyl)ethyl)amino) methyl)-2H-benzo[b][1,4] oxazin-4(3H)-yl)benzoate hydrochloride;

Methyl 3-(2-((((R)-1-(naphthalen-1-yl)ethyl)amino) methyl)-2H-benzo[b][1,4]oxazin-4(3H)-yl)benzoate hydrochloride;

4-(2-((((R)-1-(3-Methoxyphenyl) ethyl) amino) methyl)-2H-benzo[b][1,4]oxazin-4 (3H)-yl)benzoic acid;

4-(2-((((R)-1-(Naphthalen-1-yl)ethyl) amino)methyl)-2H-benzo[b][1,4]oxazin-4(3H)-yl)benzoic acid hydrochloride;

4-(2-((((R)-1-(3-Methoxyphenyl) ethyl) amino) methyl)-2H-benzo[b][1,4]oxazin-4 (3H)-yl)-N,N-dimethylbenzamide;

N,N-Dimethyl-4-(2-((((R)-1-(naphthalen-1-yl)ethyl) amino) methyl)-2H-benzo[b] [1,4]oxazin-4(3H)-yl) benzamide;

3-(2-((((R)-1-(3-Methoxyphenyl)ethyl)amino)methyl)-2H-benzo[b] [1,4]oxazin-4(3H)-yl)benzoic acid hydrochloride;

Methyl-3-(3-(2-((((R)-1-(naphthalen-1-yl)ethyl)amino) methyl)-2H-benzo[b][1,4] oxazin-4(3H)-yl)phenyl) propanoate;

Methyl 3-(4-(2-((((R)-1-(naphthalen-1-yl) ethyl) amino) methyl)-2H-benzo [b] [1,4]oxazin-4(3H)-yl) phenyl) propanoate;

Methyl 2-(3-(2-((((R)-1-(naphthalen-1-yl)ethyl) amino) methyl)-2H-benzo[b] [1,4]oxazin-4(3H)-yl) phenoxy) acetate;

Methyl 2-fluoro-5-(2-((((R)-1-(naphthalen-1-yl) ethyl) amino) methyl)-2H-benzo [b] [1,4] oxazin-4(3H)-yl) benzoate;

Methyl 2-(2-((((R)-1-(naphthalen-1-yl) ethyl) amino) methyl)-2H-benzo [b][1,4]oxazin-4(3H)-yl) benzoate;

Methyl 3-methoxy-5-(2-((((R)-1-(naphthalen-1-yl) ethyl) amino) methyl)-2H-benzo [b][1,4] oxazin-4(3H)-yl) benzoate;

Methyl 4-methoxy-3-(2-((((R)-1-(naphthalen-1-yl) ethyl) amino)methyl)-2H-benzo[b] [1,4]oxazin-4(3H)yl)benzoate;

Methyl 2-methoxy-3-(2-((((R)-1-(naphthalen-1-yl)ethyl) amino) methyl)-2H-benzo[b] [1,4] oxazin-4(3H)-yl) benzoate;

2-chloro-5-(2-((((R)-1-(naphthalen-1-yl)ethyl) amino) methyl)-2H-benzo [b][1,4]oxazin-4(3H)-yl)benzoate;

Methyl 2-methyl-3-(2-((((R)-1-(naphthalen-1-yl)ethyl) amino) methyl)-2H-benzo [b] [1,4] oxazin-4(3H)-yl) benzoate;

Methyl 2-(2-methyl-4-(2-((((R)-1-(naphthalen-1-yl) ethyl)amino) methyl)-2H-benzo[b][1,4] oxazin-4(3H)-yl) phenoxy)acetate;

Methyl 5-(2-((((R)-1-(naphthalen-1-yl) ethyl) amino) methyl)-2H-benzo [b][1,4]oxazin-4(3H)-yl)-2-(trifluoromethyl) benzoate;

Methyl 3-methyl-5-((R)-2-((((R)-1-(naphthalen-1-yl) ethyl) amino)methyl)-2H-benzo[b] [1,4] oxazin-4(3H)-yl) benzoate;

Ethyl 2,6-dimethyl-3-(2-((((R)-1-(naphthalen-1-yl) ethyl) amino) methyl)-2H-benzo[b] [1,4]oxazin-4(3H)-yl) benzoate;

Methyl 4-(2-((((R)-1-(naphthalen-1-yl) ethyl) amino) methyl)-2H-benzo [b][1,4]oxazin-4(3H)-yl)-2-(trifluoro methyl) benzoate;

Ethyl 2-methyl-5-(2-((((R)-1-(naphthalen-1-yl)ethyl) amino) methyl)-2H-benzo[b] [1,4]oxazin-4(3H)-yl) benzoate hydrochloride;

Methyl 2-hydroxy-5-(2-((((R)-1-(naphthalen-1-yl) ethyl) amino) methyl)-2H-benzo[b][1,4] oxazin-4(3H)-yl) benzoate;

Methyl 2-methoxy-5-(2-((((R)-1-(naphthalen-1-yl) ethyl) amino) methyl)-2H-benzo [b] [1,4] oxazin-4-(3H)-yl) benzoate;

Methyl 2-isopropyl-5-(2-((((R)-1-(naphthalen-1-yl)ethyl) amino) methyl)-2H-benzo[b] [1,4]oxazin-4(3H)-yl) benzoate;

Methyl 2-(3-(2-((((R)-1-(naphthalen-1-yl)ethyl) amino) methyl)-2H-benzo [b] [1,4]oxazin-4(3H)-yl) phenyl) acetate;

Methyl 2-methyl-5-(2-((((R)-1-(naphthalen-1-yl)ethyl) amino)methyl)-2H-benzo [b][1,4] oxazin-4(3H)-yl) benzoate;

3-Fluoro-5-(2-((((R)-1-(naphthalen-1-yl)ethyl) amino) methyl)-2H-benzo [b][1,4] oxazin-4(3H)-yl) benzoate;

Methyl 2-(4-(2-((((R)-1-(naphthalen-1-yl)ethyl)amino) methyl)-2H-benzo [b][1,4]oxazin-4(3H)-yl) phenoxy) acetate;

Methyl 2-methyl-4-(2-((((R)-1-(naphthalen-1-yl)ethyl) amino) methyl)-2H-benzo[b] [1,4]oxazin-4(3H)-yl) benzoate;

Methyl 2-(2-methyl-5-(2-((((R)-1-(naphthalen-1-yl) ethyl) amino) methyl)-2H-benzo [b][1,4] oxazin-4 (3H)-yl) phenoxy) acetate;

Methyl 2-methyl-2-(2-methyl-5-(2-((((R)-1-(naphthalen-1-yl) ethyl) amino)methyl)-2H-benzo[b] [1,4]oxazin-4 (3H)-yl) phenoxy) propanoate;

Methyl 3-(2-methyl-5-(2-((((R)-1-(naphthalen-1-yl) ethyl) amino)methyl)-2H-benzo[b] [1,4]oxazin-4(3H)-yl)phenyl)propanoate;

Methyl 2-fluoro-3-(2-((((R)-1-(naphthalen-1-yl)ethyl) amino) methyl)-2H-benzo[b] [1,4] oxazin-4(3H)-yl) benzoate;

Methyl 5-(2-((((R)-1-(3-methoxy phenyl) ethyl) amino) methyl)-2H-benzo[b] [1,4] oxazin-4(3H)-yl)-2-methyl benzoate;

Methyl 2-methyl-5-(2-((((R)-1-(naphthalen-1-yl)ethyl) amino)methyl)-3-oxo-2H-benzo[b][1,4]oxazin-4(3H)-yl)benzoate;

3-(2-((((R)-1-(Naphthalen-1-yl)ethyl)amino)methyl)-2H-benzo[b][1,4]oxazin-4(3H)-yl)benzoic acid hydrochloride;

4-(2-((((R)-1-(3-methoxyphenyl) ethyl)amino)methyl)-2H-benzo[b][1,4] oxazin-4(3H)-yl)-N-methyl benzamide;

N-methyl-4-(2-((((R)-1-(naphthalen-1-yl) ethyl)amino) methyl)-2H-benzo[b][1,4] oxazin-4(3H)-yl) benzamide;

3-(2-((((R)-1-(3-methoxyphenyl) ethyl)amino)methyl)-2H-benzo[b][1,4] oxazin-4(3H)-yl)-N-methyl benzamide;

N-methyl-3-(2-((((R)-1-(naphthalen-1-yl) ethyl)amino) methyl)-2H-benzo [b][1,4]oxazin-4(3H)-yl) benzamide;

3-(2-((((R)-1-(3-methoxyphenyl) ethyl)amino) methyl)-2H-benzo[b][1,4] oxazin-4(3H)-yl)-N,N-dimethyl benzamide hydrochloride;

N,N-dimethyl-3-(2-((((R)-1-(naphthalen-1-yl)ethyl) amino) methyl)-2H-benzo[b] [1,4]oxazin-4(3H)-yl) benzamide hydrochloride;

3-(4-(2-((((R)-1-(naphthalen-1-yl)ethyl) amino) methyl)-2H-benzo [b] [1,4]oxazin-4(3H)-yl) phenyl)propanoic acid;

2-(4-(2-((((R)-1-(naphthalen-1-yl) ethyl) amino)methyl)-2H-benzo[b] [1,4]oxazin-4(3H)-yl) phenoxy)aceticacid hydrochloride;

2-(3-(2-((((R)-1-(naphthalen-1-yl) ethyl) amino)methyl)-2H-benzo[b] [1,4]oxazin-4(3H)-yl) phenoxy)acetic acid hydrochloride;

2-Fluoro-5-(2-((((R)-1-(naphthalen-1-yl) ethyl) amino) methyl)-2H-benzo [b] [1,4] oxazin-4(3H)-yl) benzoic acid hydrochloride;

5-(2-((((R)-1-(3-methoxyphenyl) ethyl)amino) methyl) 2H-benzo[b] [1,4] oxazin-4 (3H)-yl)-2-methyl benzoic acid hydrochloride;

2-(2-((((R)-1-(Naphthalen-1-yl) ethyl)amino)methyl)-2H-benzo [b][1,4]oxazin-4(3H)-yl) benzoic acid hydrochloride;

3-Methoxy-5-(2-((((R)-1-(naphthalen-1-yl) ethyl) amino) methyl)-2H-benzo [b][1,4] oxazin-4(3H)-yl) benzoic acid hydrochloride;

4-Methoxy-3-(2-((((R)-1-(naphthalen-1-yl)ethyl) amino) methyl)-2H-benzo[b] [1,4]oxazin-4(3H)-yl) benzoic acid hydrochloride;

Methyl 4-methoxy-3-(2-((((R)-1-(naphthalen-1-yl) ethyl) amino)methyl)-2H-benzo [b] [1,4]oxazin-4(3H)-yl) benzoate hydrochloride;

2-Methoxy-3-(2-((((R)-1-(naphthalen-1-yl)ethyl) amino) methyl)-2H-benzo[b] [1,4]oxazin-4(3H)-yl) benzoic acid hydrochloride;

2-Methyl-3-(2-((((R)-1-(naphthalen-1-yl) ethyl) amino) methyl)-2H-benzo [b][1,4] oxazin-4(3H)-yl) benzoic acid hydrochloride;

2-(2-Methyl-4-(2-((((R)-1-(naphthalen-1-yl)ethyl) amino) methyl)-2H-benzo [b][1,4] oxazin-4(3H)-yl) phenoxy)acetic acid hydrochloride;

5-(2-((((R)-1-(Naphthalen-1-yl)ethyl)amino)methyl)-2H-benzo[b][1,4]oxazin-4(3H)-yl)-2-(trifluoro methyl) benzoic acid hydrochloride;

3-Methyl-5-(2-((((R)-1-(naphthalen-1-yl)ethyl)amino) methyl)-2H-benzo[b][1,4]oxazin-4(3H)-yl)benzoic acid hydrochloride;

2,6-Dimethyl-3-(2-((((R)-1-(naphthalen-1-yl)ethyl) amino)methyl)-2H-benzo[b] [1,4]oxazin-4(3H)-yl) benzoic acid hydrochloride;

4-(2-((((R)-1-(Naphthalen-1-yl)ethyl)amino)methyl)-2H-benzo[b][1,4]oxazin-4(3H)-yl)-2-(trifluoro methyl) benzoic acid hydrochloride;

2-Isopropyl-5-(2-((((R)-1-(naphthalen-1-yl) ethyl) amino) methyl)-2H-benzo [b] [1,4] oxazin-4(3H)-yl) benzoic acid hydrochloride;

2-Hydroxy-5-(2-((((R)-1-(naphthalen-1-yl)ethyl) amino) methyl)-2H-benzo [b][1,4] oxazin-4(3H)-yl) benzoic acid hydrochloride;

2-Methoxy-5-(2-((((R)-1-(naphthalen-1-yl)ethyl) amino) methyl)-2H-benzo [b][1,4] oxazin-4(3H)-yl) benzoic acid hydrochloride;

3-(3-(2-((((R)-1-(Naphthalen-1-yl)ethyl) amino)methyl)-2H-benzo [b][1,4]oxazin-4(3H)-yl) phenyl)propanoic acid hydrochloride;

2-(3-(2-((((R)-1-(Naphthalen-1-yl)ethyl) amino)methyl)-2H-benzo [b][1,4]oxazin-4(3H)-yl) phenyl)acetic acid hydrochloride;

2,6-Dimethyl-3-(2-((((R)-1-(naphthalen-1-yl)ethyl) amino) methyl)-2H-benzo [b][1,4] oxazin-4(3H)-yl) benzoic acid hydrochloride;

2-Methyl-5-(2-((((R)-1-(naphthalen-1-yl)ethyl) amino methyl)-2H-benzo [b][1,4]oxazin-4(3H)-yl) benzoic acid hydrochloride;

3-Fluoro-5-(2-((((R)-1-(naphthalen-1-yl)ethyl) amino) methyl)-2H-benzo [b][1,4] oxazin-4(3H)-yl) benzoic acid hydrochloride;

2-Methyl-4-(2-((((R)-1-(naphthalen-1-yl)ethyl) amino) methyl)-2H-benzo [b][1,4]oxazin-4(3H)-yl) benzoic acid hydrochloride;

2-fluoro-3-(2-((((R)-1-(naphthalen-1yl)ethyl) amino) methyl)-2H-benzo [b][1,4]oxazin-4(3H)-yl) benzoic acid hydrochloride;

2-chloro-5-(2-((((R)-1-(naphthalen-1-yl)ethyl) amino) methyl)-2H-benzo [b][1,4]oxazin-4(3H)-yl) benzoic acid hydrochloride;

2-(2-Methyl-5-(2-((((R)-1-(naphthalen-1-yl)ethyl) amino) methyl)-2H-benzo [b][1,4]oxazin-4(3H)-yl) phenoxy) acetic acid hydrochloride;

2-Methyl-2-(2-methyl-5-(2-((((R)-1-(naphthalen-1-yl) ethyl) amino)methyl)-2H-benzo[b] [1,4]oxazin-4(3H)-yl)phenoxy) propanoic acid hydrochloride;

3-(2-Methyl-5-(2-((((R)-1-(naphthalen-1-yl) ethyl) amino)methyl)-2H-benzo [b][1,4] oxazin-4(3H)-yl) phenyl) propanoic acid hydrochloride;

2-(2-Methyl-5-(2-((((R)-1-(naphthalen-1-yl)ethyl) amino)methyl)-2H-benzo [b] [1,4] oxazin-4(3H)-yl) benzamido)acetic acid hydrochloride;

Methyl 2-methyl-5-(2-2-((((S)-1-(naphthalen-1-yl)ethyl) amino)ethyl)-2H-benzo[b] [1,4]oxazin-4 (3H)-yl)benzoate;

Methyl 3-((2-((((R)-1-(naphthalen-1-yl)ethyl)amino) methyl)-2H-benzo[b][1,4]oxazin-4(3H)-yl)methyl) benzoate;

3-((2-((((R)-1-(Naphthalen-1-yl)ethyl)amino)methyl)-2H-benzo[b][1,4]oxazin-4(3H)-yl)methyl)benzoic acid hydrochloride;

Methyl5-(7-fluoro-2-((((R)-1-(naphthalen-1-yl) ethyl) amino) methyl)-2H-benzo[b] [1,4]oxazin-4(3H)-yl)-2-methylbenzoate;

5-(7-Fluoro-2-((((R)-1-(naphthalen-1-yl)ethyl)amino) methyl)-2H-benzo[b][1,4] oxazin-4(3H)-yl)-2-methyl benzoic acid hydrochloride;

Methyl 2-methyl-5-(2-methyl-2-((((R)-1-(naphthalen-1-yl) ethyl) amino) methyl)-2H-benzo [b][1,4]oxazin-4 (3H)-yl)benzoate;

2-Methyl-5-(2-methyl-2-((((R)-1-(naphthalen-1-yl)ethyl) amino)methyl)-2H-benzo[b] [1,4]oxazin-4(3H)-yl) benzoic acid hydrochloride;

2-Methyl-5-(2-((((R)-1-(naphthalen-1-yl)ethyl) amino) methyl)-3-oxo-2H-benzo[b] [1,4]oxazin-4(3H)-yl)benzoic acid hydrochloride;

Methyl 2-methyl-5-(2-(2-(((R)-1-(naphthalen-1-yl)ethyl) amino)ethyl)-2H-benzo [b] [1,4]oxazin-4(3H)-yl)benzoate;

Methyl-3-(2-(2-(((R)-1-(naphthalen-1-yl) ethyl) amino) ethyl)-2H-benzo[b][1,4]oxazin-4(3H)-yl) benzoate;

Methyl2-methyl-4-(2-(2-(((R)-1-(naphthalen-1-yl) ethyl) amino) ethyl)-2H-benzo [b] [1,4]oxazin-4(3H)-yl) benzoate;

Methyl 5-(2-(2-(((R)-1-(naphthalen-1-yl)ethyl) amino) ethyl)-2H-benzo [b] [1,4] oxazin-4 (3H) yl)-2-(trifluoro methyl) benzoate;

Methyl2-(2-methyl-5-(2-(2-(((R)-1-(naphthalen-1-yl) ethyl)amino) ethyl)-2H-benzo [b][1,4] oxazin-4(3H)-yl) phenoxy) acetate;

Methyl 2-isopropyl-5-(2-(2-(((R)-1-(naphthalen-1-yl) ethyl) amino) ethyl)-2H-benzo [b] [1,4]oxazin-4(3H)-yl) benzoate;

Methyl 2-(3-(2-(2-(((R)-1 (naphthalen-1-yl)ethyl) amino) ethyl)-2H-benzo[b] [1,4] oxazin-4(3H)-yl) phenoxy) acetate;

Methyl 3-(4-(2-(2-(((R)-1-(naphthalen-1-yl)ethyl) amino) ethyl)-2H-benzo [b] [1,4]oxazin-4(3H)-yl) phenyl) propanoate;

Methyl2-methyl-3-(2-(2-(((R)-1-(naphthalen-1-yl) ethyl) amino) ethyl)-2H-benzo [b][1,4] oxazin-4(3H)-yl) benzoate;

Methyl 2-methoxy-5-(2-(2-(((R)-1-(naphthalen-1-yl) ethyl) amino) ethyl)-2H-benzo [b][1,4] oxazin-4(3H)-yl) benzoate;

Methyl 2-hydroxy-5-(2-(2-(((R)-1-(naphthalen-1-yl) ethyl) amino) ethyl)-2H-benzo [b][1,4]oxazin-4(3H)-yl) benzoate;

Methyl 2-(4-(2-(2-(((R)-1-(naphthalen-1-yl)ethyl) amino) ethyl)-2H-benzo[b][1,4] oxazin-4(3H)-yl)phenyl) acetate;

Methyl 2-(2-methyl-4-(2-(2-(((R)-1-(naphthalen-1-yl) ethyl) amino) ethyl)-2H-benzo [b][1,4]oxazin-4(3H)-yl)phenoxy)acetate;

Methyl 4-(2-(2-(((R)-1-(naphthalen-1-yl)ethyl) amino) ethyl)-2H-benzo[b] [1,4] oxazin-4(3H)-yl) benzoate;

Methyl 2-(4-(2-(2-(((R)-1-(naphthalen-1-yl)ethyl) amino) ethyl)-2H-benzo [b] [1,4]oxazin-4(3H)-yl) phenoxy) acetate;

Methyl 2,6-dimethyl-3-(2-(2-(((R)-1-(naphthalen-1-yl) ethyl)amino) ethyl)-2H-benzo [b][1,4]oxazin-4(3H)-yl) benzoate;

Methyl 3-(3-(2-(2-(((R)-1-(naphthalen-1-yl)ethyl) amino) ethyl)-2H-benzo [b] [1,4]oxazin-4(3H)-yl) phenyl) propanoate;

Methyl 3-methyl-5-(2-(2-(((R)-1-(naphthalen-1-yl)ethyl) amino)ethyl)-2H-benzo[b] [1,4]oxazin-4(3H)-yl)benzoate;

Methyl 2-fluoro-5-(2-(2-(((R)-1-(naphthalen-1-yl)ethyl) amino)ethyl)-2H-benzo[b] [1,4]oxazin-4(3H)-yl)benzoate;

Methyl 4-methyl-3-(2-(2-(((R)-1-(naphthalen-1-yl)ethyl) amino)ethyl)-2H-benzo[b][1,4]oxazin-4(3H)-yl)benzoate;

Methyl 2-(2-fluoro-3-(2-(2-(((R)-1-(naphthalen-1-yl) ethyl)amino) ethyl)-2H-benzo[b][1,4]oxazin-4(3H)-yl) phenoxy)acetate;

Ethyl 2-(2-fluoro-5-(2-(2-(((R)-1-(naphthalen-1-yl)ethyl) amino)ethyl)-2H-benzo[b] [1,4]oxazin-4(3H)-yl) phenoxy)acetate;

Methyl 2-fluoro-3-(2-(2-(((R)-1-(naphthalen-1-yl) ethyl) amino)ethyl)-2H-benzo [b] [1,4]oxazin-4(3H)-yl)benzoate;

Methyl 2-(4-fluoro-3-(2-(2-(((R)-1-(naphthalen-1-yl) ethyl)amino)ethyl)-2H-benzo[b][1,4]oxazin-4(3H)-yl) phenoxy)acetate;

Methyl 3-fluoro-5-(2-(2-(((R)-1-(naphthalen-1-yl)ethyl) amino)ethyl)-2H-benzo[b] [1,4]oxazin-4(3H)-yl)benzoate;

Ethyl 2-(3-fluoro-5-(2-(2-(((R)-1-(naphthalen-1-yl)ethyl) amino)ethyl)-2H-benzo[b] [1,4]oxazin-4(3H)-yl) phenoxy)acetate;

Methyl 2-methyl-5-(2-methyl-2-(2-(((R)-1-(naphthalen-1-yl)ethyl)amino) ethyl)-2H-benzo[b][1,4]oxazin-4 (3H)-yl) benzoic acid hydrochloride;

Methyl 5-(7-fluoro-2-(2-(((R)-1-(naphthalen-1-yl)ethyl) amino)ethyl)-2H-benzo[b] [1,4]oxazin-4(3H)-yl)-2-methylbenzoate;

Methyl 5-(8-fluoro-2-(2-(((R)-1-(naphthalen-1-yl) ethyl) amino) ethyl)-2H-benzo[b] [1,4] oxazin-4(3H)-yl)-2-methyl benzoate;

Methyl3-(8-fluoro-2-(2-(((R)-1-(naphthalen-1-yl)ethyl) amino) ethyl)-2H-benzo[b] [1,4] oxazin-4(3H)-yl) benzoate;

Methyl 2-(4-(8-fluoro-2-(2-(((R)-1-(naphthalen-1-yl) ethyl)amino)ethyl)-2H-benzo[b][1,4]oxazin-4(3H)-yl) phenoxy)acetate;

Methyl 2-(3-(8-fluoro-2-(2-(((R)-1-(naphthalen-1-yl) ethyl)amino)ethyl)-2H-benzo[b][1,4]oxazin-4(3H)-yl) phenoxy)acetate;

Methyl 2-(4-(7-fluoro-2-(2-(((R)-1-(naphthalen-1-yl) ethyl)amino)ethyl)-2H-benzo[b][1,4]oxazin-4(3H)-yl) phenoxy)acetate;

Methyl 2-(3-(7-fluoro-2-(2-(((R)-1-(naphthalen-1-yl) ethyl)amino)ethyl)-2H-benzo[b][1,4]oxazin-4(3H)-yl) phenoxy)acetate;

Methyl 2-fluoro-5-(7-fluoro-2-(2-(((R)-1-(naphthalen-1-yl)ethyl) amino)ethyl)-2H-benzo [b][1,4]oxazin-4 (3H)-yl)benzoate;

Methyl 5-(7-fluoro-2-(2-(((R)-1-(naphthalen-1-yl) ethyl) amino)ethyl)-2H-benzo[b][1,4]oxazin-4 (3H)-yl)-2-methyl benzoate;

Methyl 5-(6-fluoro-2-(2-(((R)-1-(naphthalen-1-yl) ethyl) amino)ethyl)-2H-benzo[b][1,4]oxazin-4 (3H)-yl)-2-methyl benzoate;

Methyl 3-(6-fluoro-2-(2-(((R)-1-(naphthalen-1-yl)ethyl) amino)ethyl)-2H-benzo[b][1,4]oxazin-4(3H)-yl)benzoate;

Methyl 2-(4-(6-fluoro-2-(2-(((R)-1-(naphthalen-1-yl) ethyl)amino) ethyl)-2H-benzo[b][1,4]oxazin-4 (3H)-yl)phenoxy)acetate;

Methyl 2-(4-(6-fluoro-2-(2-(((R)-1-(naphthalen-1-yl) ethyl)amino) ethyl)-2H-benzo[b][1,4]oxazin-4 (3H)-yl)phenoxy)acetate;

Methyl 2-(3-(6-fluoro-2-(2-(((R)-1-(naphthalen-1-yl) ethyl)amino) ethyl)-2H-benzo[b][1,4]oxazin-4 (3H)-yl)phenoxy)acetate;

Methyl 2-fluoro-5-(6-fluoro-2-(2-(((R)-1-(naphthalen-1-yl)ethyl) amino)ethyl)-2H-benzo [b][1,4]oxazin-4 (3H)-yl) benzoate;

Methyl 2-fluoro-5-(5-fluoro-2-(2-(((R)-1-(naphthalen-1-yl)ethyl) amino)ethyl)-2H-benzo[b] [1,4]oxazin-4 (3H)-yl) benzoate;

Methyl 2-(3-(5-fluoro-2-(2-(((R)-1-(naphthalen-1-yl) ethyl)amino) ethyl)-2H-benzo[b][1,4]oxazin-4 (3H)-yl)phenoxy)acetate;

Methyl 2-(4-(5-fluoro-2-(2-(((R)-1-(naphthalen-1-yl) ethyl)amino) ethyl)-2H-benzo[b][1,4]oxazin-4(3H)-yl) phenoxy)acetate;

2-Methyl-5-(2-(2-(((R)-1-(naphthalen-1-yl) ethyl) amino) ethyl)-2H-benzo [b] [1,4] oxazin-4(3H)-yl) benzoic acid hydrochloride;

2-Methyl-4-(2-(2-(((R)-1-(naphthalen-1-yl)ethyl) amino) ethyl)-2H-benzo [b] [1,4]oxazin-4(3H)-yl) benzoic acid hydrochloride;

5-(2-(2-(((R)-1-(Naphthalen-1-yl)ethyl) amino)ethyl)-2H-benzo [b][1,4]oxazin-4(3H)-yl)-2-(trifluoro methyl) benzoic acid hydrochloride;

2-(2-Methyl-5-(2-(2-(((R)-1-(naphthalen1yl) ethyl) amino)ethyl)2Hbenzo[b] [1,4] oxazin-4(3H)-yl) phenoxy) acetic acid hydrochloride;

2-Isopropyl-5-(2-(2-(((R)-1-(naphthalen-1-yl)ethyl) amino)ethyl)-2H-benzo[b] [1,4]oxazin-4(3H)-yl) benzoic acid hydrochloride;

2-(3-(2-(2-(((R)-1-(Naphthalen-1-yl)ethyl) amino)ethyl)-2H-benzo[b] [1,4]oxazin-4(3H)-yl) phenoxy)aceticacid hydrochloride;

3-(4-(2-(2-(((R)-1-(Naphthalen-1-yl)ethyl) amino)ethyl)-2H-benzo [b] [1,4]oxazin-4(3H)-yl) phenyl)propanoic acid hydrochloride;

2-Methyl-3-(2-(2-(((R)-1-(naphthalen-1-yl)ethyl) amino) ethyl)-2H-benzo[b] [1,4]oxazin-4(3H)-yl) benzoic acid hydrochloride;

2-Methoxy-5-(2-(2-(((R)-1-(naphthalen-1-yl) ethyl) amino) ethyl)-2H-benzo [b] [1,4]oxazin-4(3H)-yl) benzoic acid hydrochloride;

2-Hydroxy-5-(2-(2-(((R)-1-(naphthalen-1-yl)ethyl) amino)ethyl)-2H-benzo[b] [1,4]oxazin-4(3H)-yl) benzoic acid hydrochloride;

2-(4-(2-(2-(((R)-1-(Naphthalen-1-yl)ethyl) amino) ethyl)-2H-benzo [b] [1,4]oxazin-4(3H)-yl) phenyl) acetic acid hydrochloride;

2-(2-Methyl-4-(2-(2-(((R)-1-(naphthalen-1-yl)ethyl) amino)ethyl)-2H-benzo[b] [1,4]oxazin-4(3H)-yl) phenoxy)aceticacid hydrochloride;

4-(2-(2-(((R)-1-(Naphthalen-1-yl)ethyl)amino)ethyl)-2H-benzo [b][1,4]oxazin-4(3H)-yl)benzoicacid hydrochloride;

3-(2-(2-(((R)-1-(Naphthalen-1-yl)ethyl)amino)ethyl)-2H-benzo [b][1,4]oxazin-4(3H)-yl) benzoic acid hydrochloride;

2-(4-(2-(2-(((R)-1-(Naphthalen-1-yl)ethyl) amino)ethyl)-2H-benzo [b] [1,4] oxazin-4(3H)-yl) phenoxy)aceticacid hydrochloride;

2,6-Dimethyl-3-(2-(2-(((R)-1-(naphthalen-1-yl)ethyl) amino) ethyl)-2H-benzo[b] [1,4]oxazin-4(3H)-yl) benzoic acid hydrochloride;

3-(3-(2-(2-(((R)-1-(Naphthalen-1-yl)ethyl) amino)ethyl)-2H-benzo[b] [1,4]oxazin-4(3H)-yl) phenyl)propanoicacid hydrochloride;

2-Methyl-5-(2-methyl-2-(2-(((R)-1-(naphthalen-1-yl) ethyl)amino)ethyl)-2H-benzo[b][1,4]oxazin-4(3H)-yl) benzoicacid hydrochloride;

3-Methyl-5-(2-(2-(((R)-1-(naphthalen-1-yl)ethyl) amino) ethyl)-2H-benzo [b][1,4]oxazin-4(3H)-yl) benzoicacid hydrochloride;

2-Fluoro-5-(2-(2-(((R)-1-(naphthalen-1-yl)ethyl) amino) ethyl)-2H-benzo[b] [1,4]oxazin-4(3H)-yl) benzoic acid hydrochloride;

4-Methyl-3-(2-(2-(((R)-1-(naphthalen-1-yl)ethyl)amino) ethyl)-2H-benzo[b][1,4]oxazin-4(3H)-yl)benzoic acid hydrochloride;

2-(2-Fluoro-3-(2-(2-(((R)-1-(naphthalen-1-yl) amino)ethyl)-2H-benzo[b][1,4]oxazin-4(3H)-yl)phenoxy)acetic acid hydrochloride;

2-(2-Fluoro-5-(2-(2-(((R)-1-(naphthalen-1-yl)ethyl) amino)ethyl)-2H-benzo[b][1,4]oxazin-4(3H)-yl)phenoxy)acetic acid hydrochloride;

2-Fluoro-3-(2-(2-(((R)-1-(naphthalen-1-yl)ethyl) amino)ethyl)-2H-benzo[b] [1,4]oxazin-4(3H)-yl) benzoic acid hydrochloride;

2-(4-Fluoro-3-(2-(2-(((R)-1-(naphthalen-1-yl)ethyl) amino)ethyl)-2H-benzo[b][1,4]oxazin-4(3H)-yl)phenoxy)acetic acid hydrochloride;

3-Fluoro-5-(2-(2-(((R)-1-(naphthalen-1-yl)ethyl)amino) ethyl)-2H-benzo[b][1,4]oxazin-4(3H)-yl)benzoic acid hydrochloride;

5-(8-Fluoro-2-(2-(((R)-1-(naphthalen-1-yl)ethyl) amino) ethyl)-2H-benzo [b][1,4]oxazin-4(3H)-yl)-2-methylbenzoic acid hydrochloride;

3-(8-Fluoro-2-(2-(((R)-1-(naphthalen-1-yl) ethyl) amino) ethyl)-2H-benzo [b] [1,4]oxazin-4(3H)-yl) benzoic acid hydrochloride;

2-(4-(7-Fluoro-2-(2-(((R)-1-(naphthalen-1-yl)ethyl) amino)ethyl)-2H-benzo[b][1,4] oxazin-4(3H)-yl) phenoxy)aceticacid hydrochloride;

2-(3-(7-Fluoro-2-(2-(((R)-1-(naphthalen-1-yl)ethyl) amino)ethyl)-2H-benzo[b][1,4] oxazin-4(3H)-yl)phenoxy) aceticacid hydrochloride;

5-(7-Fluoro-2-(2-(((R)-1-(naphthalen-1-yl)ethyl) amino) ethyl)-2H-benzo [b] [1,4] oxazin-4(3H)-yl)-2-methylbenzoic acid hydrochloride;

2-(4-(8-Fluoro-2-(2-(((R)-1-(naphthalen-1-yl)ethyl) amino)ethyl)-2H-benzo[b] [1,4] oxazin-4(3H)-yl) phenoxy)aceticacid hydrochloride;

2-(3-(8-Fluoro-2-(2-(((R)-1-(naphthalen-1-yl)ethyl) amino)ethyl)-2H-benzo[b][1,4]oxazin-4(3H)-yl) phenoxy)aceticacid hydrochloride;

5-(6-Fluoro-2-(2-(((R)-1-(naphthalen-1-yl)ethyl) amino) ethyl)-2H-benzo [b][1,4]oxazin-4(3H)-yl)-2-methylbenzoicacid hydrochloride;

3-(6-Fluoro-2-(2-(((R)-1-(naphthalen-1-yl)ethyl) amino) ethyl)-2H-benzo [b][1,4]oxazin-4(3H)-yl) benzoic acid;

2-(4-(6-Fluoro-2-(2-(((R)-1-(naphthalen-1-yl)ethyl) amino)ethyl)-2H-benzo[b][1,4] oxazin-4(3H)yl)phenoxy)acetic acid;

2-(3-(6-Fluoro-2-(2-(((R)-1-(naphthalen-1-yl)ethyl) amino)ethyl)-2H-benzo[b][1,4] oxazin-4(3H)-yl) phenoxy)acetic acid hydrochloride;

2-Fluoro-5-(5-fluoro-2-(2-(((R)-1-(naphthalen-1-yl) ethyl)amino)ethyl)-2H-benzo[b][1,4] oxazin-4(3H)-yl) benzoic acid hydrochloride;

2-(3-(5-Fluoro-2-(2-(((R)-1-(Naphthalen-1-yl)ethyl) amino)ethyl)-2H-benzo [b][1,4] oxazin-4(3H)-yl) phenoxy)acetic acid hydrochloride;

2-(4-(5-Fluoro-2-(2-(((R)-1-(naphthalen-1-yl)ethyl) amino)ethyl)-2H-benzo[b][1,4] oxazin-4(3H)-yl) phenoxy)acetic acid hydrochloride;

Methyl 2-methyl-5-((2-(2-(((R)-1-(naphthalen-1-yl) ethyl)amino)ethyl)-2H-benzo[b] [1,4]oxazin-4(3H)-yl) methyl)benzoate;

Methyl2-methyl-3-((2-(2-(((R)-1-(naphthalen-1-yl) ethyl)amino)ethyl)-2H-benzo[b][1,4]oxazin-4(3H)-yl) methyl)benzoate;

Methyl 3-((2-(2-(((R)-1-(naphthalen-1-yl)ethyl) amino) ethyl)-2H-benzo[b] [1,4]oxazin-4(3H)-yl)methyl) benzoate;

Methyl 4-((2-(2-(((R)-1-(naphthalen-1-yl)ethyl) amino) ethyl)-2H-benzo[b] [1,4]oxazin-4(3H)-yl) methyl)benzoate;

2-Methyl-5-((2-(2-(((R)-1-(naphthalen-1-yl)ethyl)amino) ethyl)-2H-benzo[b][1,4] oxazin-4(3H)-yl)methyl)benzoic acid hydrochloride;
2-Methyl-3-((2-(2-(((R)-1-(naphthalen-1-yl)ethyl)amino) ethyl)-2H-benzo[b] [1,4] oxazin-4(3H)-yl) methyl) benzoic acid hydrochloride;
3-((2-(2-(((R)-1-(Naphthalen-1-yl) ethyl) amino)ethyl)-2H-benzo [b][1,4] oxazin-4(3H)-yl) methyl) benzoic acid hydrochloride;
4-((2-(2-(((R)-1-(Naphthalen-1-yl) ethyl)amino)ethyl)-2H-benzo [b] [1,4] oxazin-4(3H)-yl) methyl) benzoic acid hydrochloride;
2-Methyl-5-(2-(2-(((S)-1-(naphthalen-1-yl)ethyl) amino) ethyl)-2H-benzo[b][1,4] oxazin-4(3H)-yl)benzoic acid hydrochloride;
2-Fluoro-5-(6-fluoro-2-(2-(((R)-1-(naphthalen-1-yl) ethyl)amino)ethyl)-2H-benzo[b] [1,4]oxazin-4(3H)-yl) benzoic acid hydrochloride;
2-Fluoro-5-(7-fluoro-2-(2-(((R)-1-(naphthalen-1-yl) ethyl)amino)ethyl)-2H-benzo[b] [1,4]oxazin-4(3H)-yl) benzoic acid hydrochloride;
6-Fluoro-2-methyl-3-(2-(2-(((R)-1-(naphthalen-1-yl) ethyl)amino)ethyl)-2H-benzo[b][1,4]oxazin-4(3H)-yl) benzoic acid hydrochloride;
2-Fluoro-6-methyl-3-(2-(2-(((R)-1-(naphthalen-1-yl) ethyl)amino)ethyl)-2H-benzo[b][1,4]oxazin-4(3H)-yl) benzoic acid hydrochloride;
2,6-Difluoro-3-(2-(2-(((R)-1-(naphthalen-1-yl)ethyl) amino)ethyl)-2H-benzo[b][1,4]oxazin-4(3H)-yl)benzoic acid hydrochloride;
3-Fluoro-5-(2-(2-(((R)-1-(naphthalen-1-yl)ethyl)amino) ethyl)-2H-benzo[b][1,4]oxazin-4(3H)-yl)benzoic acid hydrochloride;
2,3-Difluoro-5-(2-(2-(((R)-1-(naphthalen-1-yl)ethyl) amino)ethyl)-2H-benzo[b][1,4]oxazin-4(3H)-yl)benzoic acid hydrochloride;
2-Methyl-2-(4-(2-(2-(((R)-1-(naphthalen-1-yl)ethyl) amino)ethyl)-2H-benzo[b][1,4]oxazin-4(3H)-yl)phenyl)propanoic acid hydrochloride;
2,4-Difluoro-5-(2-(2-(((R)-1-(naphthalen-1-yl)ethyl) amino)ethyl)-2H-benzo[b][1,4]oxazin-4(3H)-yl)benzoic acid hydrochloride;
3-(2-Fluoro-5-(2-(2-(((R)-1-(naphthalen-1-yl)ethyl) amino)ethyl)-2H-benzo[b][1,4]oxazin-4(3H)-yl)phenyl)propanoic acid hydrochloride;
3-(2-Fluoro-3-(2-(2-(((R)-1-(naphthalen-1-yl)ethyl) amino)ethyl)-2H-benzo[b][1,4]oxazin-4(3H)-yl)phenyl)propanoic acid hydrochloride;
3-(3-Fluoro-5-(2-(2-(((R)-1-(naphthalen-1-yl)ethyl) amino)ethyl)-2H-benzo[b][1,4]oxazin-4(3H)-yl)phenyl)propanoic acid hydrochloride;
3-(4-Fluoro-3-(2-(2-(((R)-1-(naphthalen-1-yl)ethyl) amino)ethyl)-2H-benzo[b][1,4]oxazin-4(3H)-yl)phenyl)propanoic acid hydrochloride;
2-(3-Fluoro-4-(2-(2-(((R)-1-(naphthalen-1-yl)ethyl) amino)ethyl)-2H-benzo[b][1,4]oxazin-4(3H)-yl)phenoxy)acetic acid hydrochloride;
2-(2-Fluoro-4-(2-(2-(((R)-1-(naphthalen-1-yl)ethyl) amino)ethyl)-2H-benzo[b][1,4]oxazin-4(3H)-yl)phenoxy)acetic acid hydrochloride;
2-(3-Methyl-4-(2-(2-(((R)-1-(naphthalen-1-yl)ethyl) amino)ethyl)-2H-benzo[b][1,4]oxazin-4(3H)-yl)phenoxy)acetic acid hydrochloride;
2-(2-Methyl-5-(2-(2-(((R)-1-(naphthalen-1-yl)ethyl) amino)ethyl)-2H-benzo[b][1,4]oxazin-4(3H)-yl)phenoxy)acetic acid hydrochloride;
2-(2-Methyl-3-(2-(2-(((R)-1-(naphthalen-1-yl)ethyl) amino)ethyl)-2H-benzo[b][1,4]oxazin-4(3H)-yl)phenoxy)acetic acid hydrochloride;
2-(3-Methyl-5-(2-(2-(((R)-1-(naphthalen-1-yl)ethyl) amino)ethyl)-2H-benzo[b][1,4]oxazin-4(3H)-yl)phenoxy)acetic acid hydrochloride;
2-(4-Methyl-3-(2-(2-(((R)-1-(naphthalen-1-yl)ethyl) amino)ethyl)-2H-benzo[b][1,4]oxazin-4(3H)-yl)phenoxy)acetic acid hydrochloride;
2-Methyl-2-(3-(2-(2-(((R)-1-(naphthalen-1-yl)ethyl) amino)ethyl)-2H-benzo[b][1,4]oxazin-4(3H)-yl)phenyl)propanoic acid hydrochloride;
1-(3-(2-(2-(((R)-1-(Naphthalen-1-yl)ethyl)amino)ethyl)-2H-benzo[b][1,4]oxazin-4(3H)-yl)phenyl)cyclopropanecarboxylic acid hydrochloride;
1-(4-(2-(2-(((R)-1-(Naphthalen-1-yl)ethyl)amino)ethyl)-2H-benzo[b][1,4]oxazin-4(3H)-yl)phenyl)cyclopropanecarboxylic acid hydrochloride;
6-Fluoro-3-(8-fluoro-2-(2-(((R)-1-(naphthalen-1-yl) ethyl)amino)ethyl)-2H-benzo[b][1,4]oxazin-4(3H)-yl)-2-methylbenzoic acid hydrochloride;
2-Fluoro-3-(8-fluoro-2-(2-(((R)-1-(naphthalen-1-yl) ethyl)amino)ethyl)-2H-benzo[b][1,4]oxazin-4(3H)-yl)-6-methylbenzoic acid hydrochloride;
2,6-Difluoro-3-(8-fluoro-2-(2-(((R)-1-(naphthalen-1-yl) ethyl)amino)ethyl)-2H-benzo[b][1,4]oxazin-4(3H)-yl) benzoic acid hydrochloride;
3-Fluoro-5-(8-fluoro-2-(2-(((R)-1-(naphthalen-1-yl) ethyl)amino)ethyl)-2H-benzo[b][1,4]oxazin-4(3H)-yl) benzoic acid hydrochloride;
2-Fluoro-5-(8-fluoro-2-(2-(((R)-1-(naphthalen-1-yl) ethyl)amino)ethyl)-2H-benzo[b][1,4]oxazin-4(3H)-yl) benzoic acid;
2,6-Difluoro-3-(7-fluoro-2-(2-(((R)-1-(naphthalen-1-yl) ethyl)amino)ethyl)-2H-benzo[b][1,4]oxazin-4(3H)-yl) benzoic acid hydrochloride;
3-Fluoro-5-(7-fluoro-2-(2-(((R)-1-(naphthalen-1-yl) ethyl)amino)ethyl)-2H-benzo[b][1,4]oxazin-4(3H)-yl) benzoic acid hydrochloride;
6-Fluoro-3-(6-fluoro-2-(2-(((R)-1-(naphthalen-1-yl) ethyl)amino)ethyl)-2H-benzo[b][1,4]oxazin-4(3H)-yl)-2-methylbenzoic acid hydrochloride;
2-Fluoro-3-(6-fluoro-2-(2-(((R)-1-(naphthalen-1-yl) ethyl)amino)ethyl)-2H-benzo[b][1,4]oxazin-4(3H)-yl)-6-methylbenzoic acid hydrochloride;
2, 6-Difluoro-3-(6-fluoro-2-(2-(((R)-1-(naphthalen-1-yl) ethyl)amino)ethyl)-2H-benzo[b][1,4]oxazin-4(3H)-yl) benzoic acid hydrochloride;
3-Fluoro-5-(6-fluoro-2-(2-(((R)-1-(naphthalen-1-yl) ethyl)amino)ethyl)-2H-benzo[b][1,4]oxazin-4(3H)-yl) benzoic acid hydrochloride;
6-Fluoro-3-(5-fluoro-2-(2-(((R)-1-(naphthalen-1-yl) ethyl)amino)ethyl)-2H-benzo[b][1,4]oxazin-4(3H)-yl)-2-methylbenzoic acid hydrochloride;
2-Fluoro-3-(5-fluoro-2-(2-(((R)-1-(naphthalen-1-yl) ethyl)amino)ethyl)-2H-benzo[b][1,4]oxazin-4(3H)-yl)-6-methylbenzoic acid hydrochloride;
2, 6-Difluoro-3-(5-fluoro-2-(2-(((R)-1-(naphthalen-1-yl) ethyl)amino)ethyl)-2H-benzo[b][1,4]oxazin-4(3H)-yl) benzoic acid hydrochloride; and
3-Fluoro-5-(5-fluoro-2-(2-(((R)-1-(naphthalen-1-yl) ethyl)amino)ethyl)-2H-benzo[b][1,4]oxazin-4(3H)-yl) benzoic acid hydrochloride;
or pharmaceutically acceptable salts thereof or stereoisomers thereof.

13. A pharmaceutical composition comprising one or more compounds of Formula (I) according to claim 1, and one or more pharmaceutically acceptable excipients.

14. A method of treating a disease associated with the modulation of CaSR receptor in a subject in need thereof by administering to the subject a therapeutically effective amount of a compound of claim 1 or a pharmaceutically acceptable salt thereof where the disease is hyperparathyroidism.

15. A process for the preparation of compound of Formula (Ia) and (Ic):

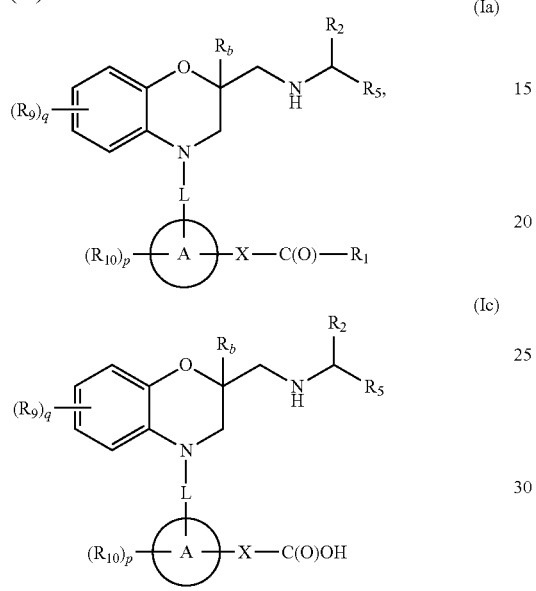

wherein ring A, L, $R_b$, X, $R_1$, $R_2$, $R_5$, $R_9$, $R_{10}$, 'p' and 'q' are as defined in claim 1;

the process comprising:

a) coupling of compound of Formula (5) with Formula (b) where L' is leaving group, to get compound of Formula (6);

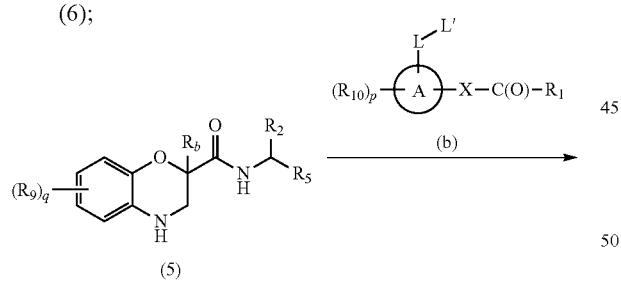

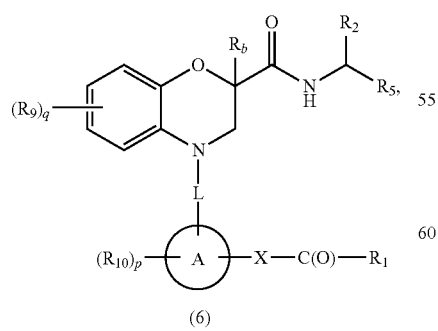

b) reducing a compound of Formula (6) using suitable reducing agents to get compound of Formula (Ia);

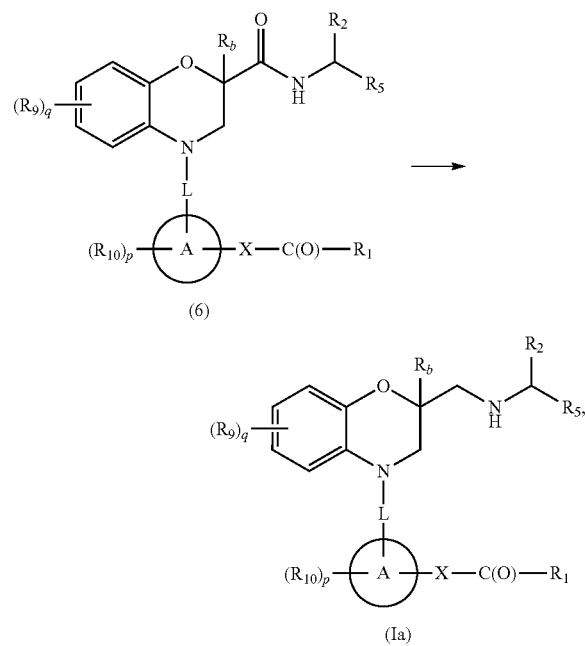

or c) reducing a compound of Formula (5) using suitable reducing agent to get compound of Formula (7);

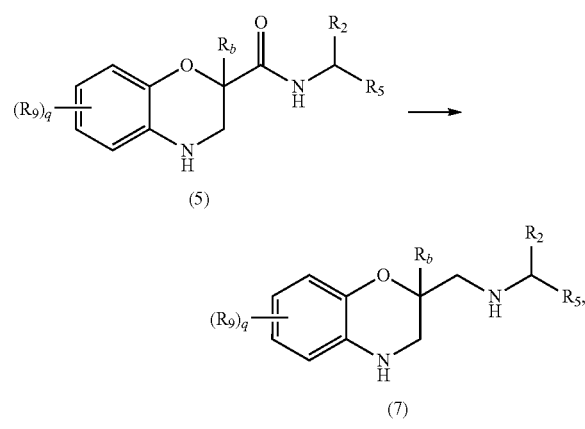

d) coupling of compound of Formula (7) with formula (b) where L' is leaving group, to give compound of Formula (Ia);

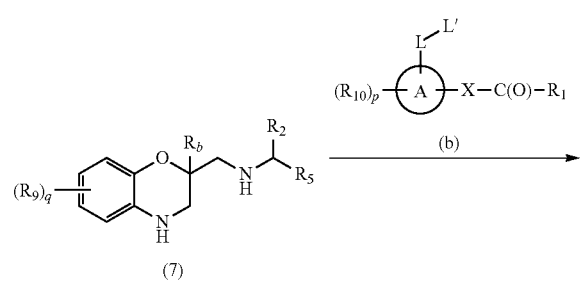

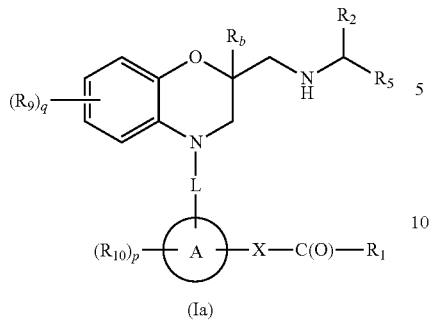

(Ia)

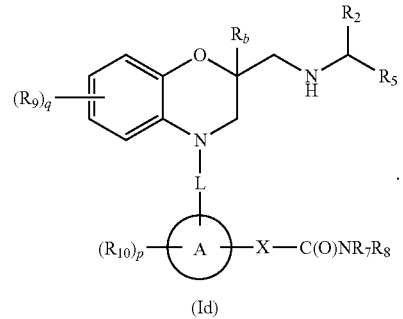

(Id)

e) hydrolyzing the compound of Formula (Ia) when $R_1$ is $OR_6$ and $R_6$ is alkyl, to give compound of Formula (Ic);

16. A process for the preparation of compound of Formula (Ii):

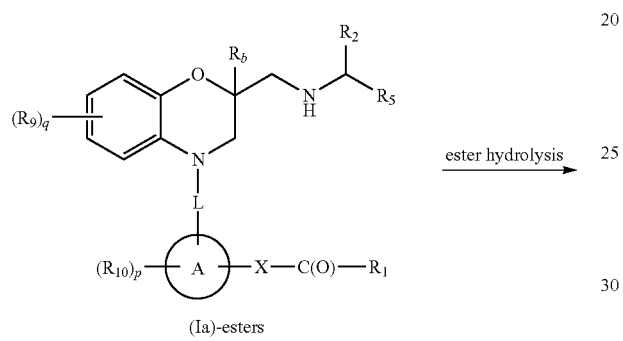

(Ia)-esters ester hydrolysis

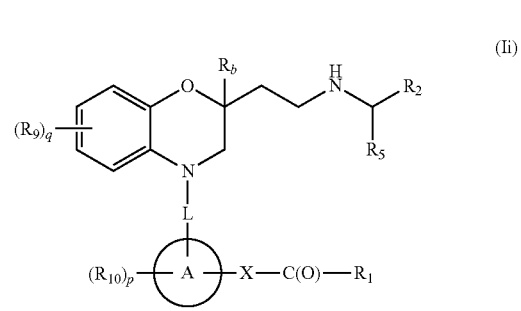

(Ii)

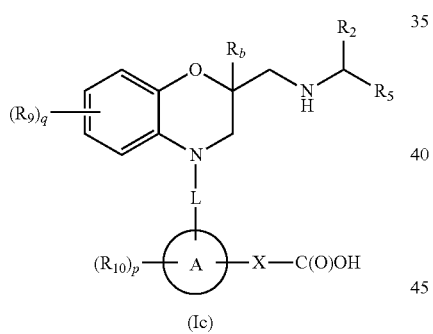

(Ic)

f) optionally, reacting acid compound of Formula (Ic) with suitable amine to give compound of Formula (Id)

wherein ring A, L, $R_b$, X, $R_1$, $R_2$, $R_5$, $R_9$, $R_{10}$, 'p' and 'q' are as defined in claim 1;

a) reducing the compound of Formula (18) to give compound of Formula (19) using suitable reducing agent

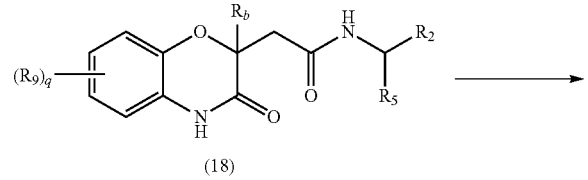

(18)

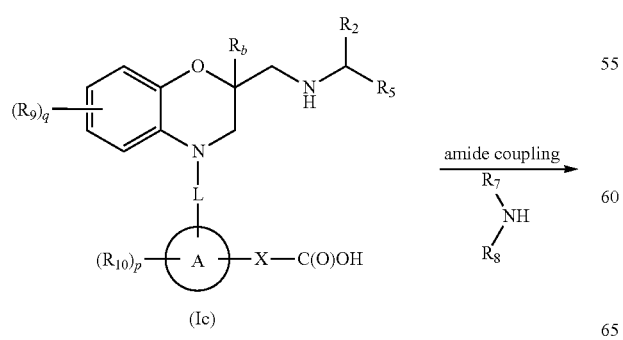

(Ic)

amide coupling $\underset{R_8}{\overset{R_7}{\diagdown}}NH$

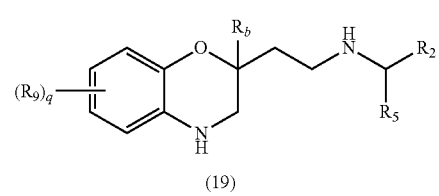

(19)

b) coupling of compound of Formula (19) with Formula (b) where L' is leaving group, to give compound of Formula (Ii);

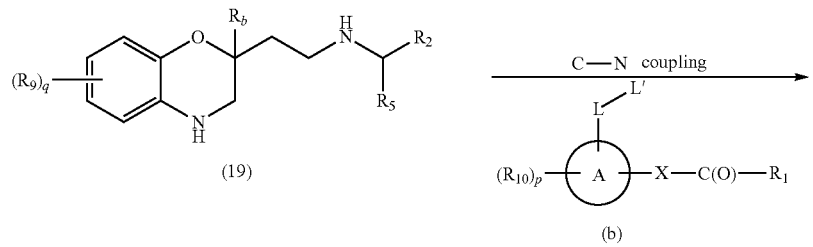

(19)

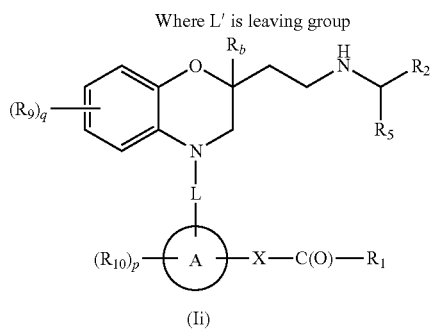

(b)

Where L' is leaving group (Ii)

c) hydrolyzing the compound of Formula (Ii) when $R_1$ is $OR_6$ and $R_6$ is alkyl, to give corresponding acid;

d) optionally, coupling of acid with suitable amine to give corresponding amide.

17. A compound which is 2-Methyl-5-((R)-2-((((R)-1-(naphthalen-1-yl)ethyl)amino)methyl)-2H-benzo[b][1,4]oxazin-4(3H)-yl)benzoic acid hydrochloride or stereoisomers thereof.

18. A compound which is 2-Methyl-5-((S)-2-(2-(((R)-1-(naphthalen-1-yl)ethyl)amino)ethyl)-2H-benzo[b][1,4]oxazin-4(3H)-yl)benzoic acid hydrochloride or stereoisomers thereof.

19. A compound which is 3-((S)-2-(2-((R)-1-(Naphthalen-1-yl)ethyl)amino)ethyl)-2H-benzo[b][1,4]oxazin-4-(3H)-yl)benzoic acid hydrochloride or stereoisomers thereof.

20. A compound which is 2,6-Dimethyl-3-((S)-2-(2-((R)-1-(naphthalen-1-yl)ethyl)amino)ethyl)-2H-benzo[b][1,4]oxazin-4(3H)-yl)benzoic acid hydrochloride or stereoisomers thereof.

21. The method of claim 14, wherein the hyperparathyroidism is primary hyperparathyroidism, secondary hyperparathyroidism, or tertiary hyperparathyroidism.

22. The method of claim 16, wherein the suitable reducing agent comprises $BH_3$ in dimethyl sulfoxide.

* * * * *